United States Patent
Chiron et al.

(10) Patent No.: US 11,692,039 B2
(45) Date of Patent: Jul. 4, 2023

(54) MULTIFUNCTIONAL NATURAL KILLER (NK) CELL ENGAGERS BINDING TO NKP46 AND CD123

(71) Applicants: INNATE PHARMA, Marseilles (FR); SANOFI, Paris (FR)

(72) Inventors: Marielle Chiron, Paris (FR); Angela Virone-Oddos, Paris (FR); Laurent Gauthier, Marseilles (FR)

(73) Assignees: INNATE PHARMA; SANOFI

( * ) Notice: Subject to any disclaimer, the term of this patent is extended or adjusted under 35 U.S.C. 154(b) by 0 days.

(21) Appl. No.: 17/566,142

(22) Filed: Dec. 30, 2021

(65) Prior Publication Data

US 2022/0213202 A1 Jul. 7, 2022

Related U.S. Application Data

(60) Provisional application No. 63/256,950, filed on Oct. 18, 2021.

(30) Foreign Application Priority Data

Dec. 31, 2020 (EP) .................................... 20306717

(51) Int. Cl.
| | |
|---|---|
| C07K 16/28 | (2006.01) |
| A61K 39/395 | (2006.01) |
| A61P 35/02 | (2006.01) |
| A61K 39/00 | (2006.01) |

(52) U.S. Cl.
CPC ........ *C07K 16/2866* (2013.01); *A61K 39/395* (2013.01); *A61K 39/3955* (2013.01); *A61P 35/02* (2018.01); *C07K 16/2896* (2013.01); *A61K 2039/505* (2013.01); *C07K 2317/31* (2013.01); *C07K 2317/52* (2013.01); *C07K 2317/565* (2013.01); *C07K 2317/64* (2013.01)

(58) Field of Classification Search
None
See application file for complete search history.

(56) References Cited

U.S. PATENT DOCUMENTS

| | | | |
|---|---|---|---|
| 5,288,931 A * | 2/1994 | Chang | C07K 1/1133 530/825 |
| 6,177,078 B1 | 1/2001 | Lopez | |
| 6,733,743 B2 | 5/2004 | Jordan | |
| 7,112,660 B1 * | 9/2006 | Domingues | A61P 37/08 424/85.2 |
| 7,220,829 B2 | 5/2007 | Rossjohn et al. | |
| 7,435,549 B1 | 10/2008 | Kufer et al. | |
| 7,651,678 B2 | 1/2010 | Jordan | |
| 7,919,089 B2 | 4/2011 | Kufer et al. | |
| 8,492,119 B2 | 7/2013 | Tawara et al. | |
| 8,535,669 B2 | 9/2013 | Vairo et al. | |
| 8,569,461 B2 | 10/2013 | Panousis | |
| 8,609,149 B2 | 12/2013 | Callahan et al. | |
| 8,790,645 B2 | 7/2014 | Kufer et al. | |
| 8,852,551 B2 | 10/2014 | Jordan | |
| 9,155,802 B2 | 10/2015 | Pedersen et al. | |
| 9,217,039 B2 | 12/2015 | Pedersen et al. | |
| 9,394,370 B2 | 7/2016 | Tawara et al. | |
| 9,540,441 B2 | 1/2017 | Tawara et al. | |
| 9,683,048 B2 | 6/2017 | Freeman et al. | |
| 9,758,585 B2 | 9/2017 | Vairo et al. | |
| 9,815,898 B2 | 11/2017 | Freeman et al. | |
| 9,850,310 B2 | 12/2017 | Gaudet et al. | |
| 9,879,087 B2 | 1/2018 | Desander et al. | |
| 9,944,709 B2 | 4/2018 | Galetto | |
| 10,005,832 B2 | 6/2018 | Yoshida et al. | |
| 10,047,161 B2 | 8/2018 | Panousis | |
| 10,113,003 B2 | 10/2018 | Gauthier et al. | |
| 10,155,818 B2 | 12/2018 | Seibert et al. | |
| 10,179,817 B2 | 1/2019 | Sagert et al. | |
| 10,221,246 B2 | 3/2019 | Pedersen et al. | |
| 10,280,226 B2 | 5/2019 | Seibert et al. | |
| 10,508,150 B2 | 12/2019 | Jordan | |
| 10,519,234 B2 | 12/2019 | Gauthier et al. | |

(Continued)

FOREIGN PATENT DOCUMENTS

| | | |
|---|---|---|
| CN | 105367657 A | 3/2016 |
| EP | 1161453 A1 | 12/2001 |

(Continued)

OTHER PUBLICATIONS

Vidarsson et al, Frontiers in Immunology, 2014, vol. 5, article 521, pp. 1-17.*
Wang et al, Protein Cell 2018, vol. 9, No. 1, pp. 63-73.*
Tokuriki et al., 2009, Curr. Opin. Struc. Biol. 19:596-604.*
Bhattacharya et al. (2017, PLoS ONE 12(3): e0171355.*
Ulloa-Aguirre et al. (2004, Traffic 5:821-837).*
Bernier et al. (2004, Curr. Opin. Pharmacol. 4:528-533).*
Alaoui-Ismaili (2009, Cytokine Growth Factor Rev. 20(5-6):501-7).*
Guo et al. (2004, PNAS USA 101(25):9205-10).*
Lazar et al, (PNAS, 2006, vol. 103, No. 11, pp. 4005-4010).*
Cai et al, (Biotechnol. Bioeng. 2011;108: 404-412).*

(Continued)

*Primary Examiner* — Joanne Hama
*Assistant Examiner* — Fozia M Hamud
(74) *Attorney, Agent, or Firm* — Lathrop GPM LLP; James H. Velema, Esq.; Michael J. Spellberg, Esq.

(57) ABSTRACT

The present disclosure relates to multifunctional binding proteins comprising a first and a second antigen binding domains (ABDs) and all or part of an immunoglobulin Fc region or variant thereof, wherein the first ABD binds specifically to human CD123 and the second ABD binds specifically to human NKp46 and wherein all or part of the immunoglobulin Fc region or variant thereof to a human Fc-γ receptor.

The disclosure also relates to methods for making said binding proteins, compositions thereof, and their uses, including the treatment or prevention of proliferative disorders, including Acute Myeloid Leukemia (AML) and myelodysplastic syndromes (MDS).

22 Claims, 26 Drawing Sheets

Specification includes a Sequence Listing.

(56) References Cited

U.S. PATENT DOCUMENTS

| | | | |
|---|---|---|---|
| 10,611,814 B2 | 4/2020 | Bachmann et al. | |
| 10,709,775 B2 | 7/2020 | Dusseaux | |
| 11,001,629 B2 | 5/2021 | Gauthier et al. | |
| 11,208,480 B2 | 12/2021 | Gauthier et al. | |
| 11,267,897 B2 | 3/2022 | Gauthier et al. | |
| 2003/0045474 A1* | 3/2003 | Sailer | A61K 38/1875 514/8.8 |
| 2010/0209341 A1 | 8/2010 | Vairo et al. | |
| 2011/0052574 A1 | 3/2011 | Dick et al. | |
| 2012/0070448 A1 | 3/2012 | Tawara et al. | |
| 2013/0230510 A1 | 9/2013 | Dick et al. | |
| 2014/0086912 A1 | 3/2014 | Panousis | |
| 2014/0154743 A1* | 6/2014 | Levy | C07K 16/00 435/69.6 |
| 2014/0178364 A1 | 6/2014 | Vairo et al. | |
| 2015/0017180 A1 | 1/2015 | Vairo et al. | |
| 2015/0132315 A1 | 5/2015 | Jordan | |
| 2015/0152185 A1 | 6/2015 | Dick et al. | |
| 2015/0307615 A1 | 10/2015 | Panousis | |
| 2017/0029515 A1 | 2/2017 | Dick et al. | |
| 2018/0079818 A1 | 3/2018 | Dick et al. | |
| 2018/0244786 A1 | 8/2018 | Lopez et al. | |
| 2019/0055315 A1 | 2/2019 | Gauthier et al. | |
| 2019/0185573 A1 | 6/2019 | Wilson et al. | |
| 2020/0031942 A1 | 1/2020 | Jordan | |
| 2020/0048345 A1 | 2/2020 | Gauthier et al. | |
| 2020/0131268 A1 | 4/2020 | Gauthier et al. | |
| 2020/0207861 A1 | 7/2020 | Dick et al. | |
| 2021/0269523 A1 | 9/2021 | Gauthier et al. | |
| 2021/0388097 A1 | 12/2021 | Zhou et al. | |
| 2022/0135676 A1 | 5/2022 | Gauthier et al. | |

FOREIGN PATENT DOCUMENTS

| | | | |
|---|---|---|---|
| EP | | 1032660 B1 | 11/2009 |
| EP | | 1263463 B1 | 5/2011 |
| EP | | 2536468 A1 | 12/2012 |
| EP | | 2626069 A1 | 8/2013 |
| EP | | 2426148 B1 | 8/2015 |
| EP | | 2778175 B1 | 3/2016 |
| EP | | 2329847 B1 | 11/2016 |
| EP | | 2635604 B1 | 11/2016 |
| EP | | 2536430 B1 | 12/2016 |
| EP | | 2436397 B1 | 5/2017 |
| EP | | 2575444 B1 | 5/2017 |
| EP | | 3189081 A1 | 7/2017 |
| EP | | 1629013 B1 | 1/2018 |
| EP | | 3156421 B1 | 6/2018 |
| EP | | 2635605 B1 | 7/2018 |
| EP | | 3097121 B1 | 12/2018 |
| EP | | 3119807 B1 | 4/2019 |
| WO | WO 1997/024373 A1 | | 7/1997 |
| WO | WO 1999/025818 A1 | | 5/1999 |
| WO | WO 2000/047620 A1 | | 8/2000 |
| WO | WO 2001/066139 A1 | | 9/2001 |
| WO | WO 2004/106383 A1 | | 12/2004 |
| WO | WO 2006/064136 A1 | | 6/2006 |
| WO | WO 2009/070844 A1 | | 6/2009 |
| WO | WO 2010/094068 A1 | | 8/2010 |
| WO | WO 2010/126066 A1 | | 11/2010 |
| WO | WO 2010/137654 A1 | | 12/2010 |
| WO | WO 2011/100786 A1 | | 8/2011 |
| WO | WO 2012/021934 A1 | | 2/2012 |
| WO | WO 2012/059857 A2 | | 5/2012 |
| WO | WO 2012/059858 A1 | | 5/2012 |
| WO | WO 2012/089814 A1 | | 7/2012 |
| WO | WO 2014/138805 A1 | | 9/2014 |
| WO | WO 2014/138819 A1 | | 9/2014 |
| WO | WO 2015/112900 A1 | | 7/2015 |
| WO | WO 2015/184099 A1 | | 12/2015 |
| WO | WO 2015/193406 A1 | | 12/2015 |
| WO | WO 2015/197593 A1 | | 12/2015 |
| WO | WO 2015/197598 A2 | | 12/2015 |
| WO | WO 2016/030414 A1 | | 3/2016 |
| WO | WO 2016/036937 A1 | | 3/2016 |
| WO | WO 2016/077526 A1 | | 5/2016 |
| WO | WO 2016/116626 A1 | | 7/2016 |
| WO | WO 2016/120216 A1 | | 8/2016 |
| WO | WO 2016/179257 A2 | | 11/2016 |
| WO | WO 2016/201065 A1 | | 12/2016 |
| WO | WO 2016/207098 A1 | | 12/2016 |
| WO | WO 2016/207273 A2 | | 12/2016 |
| WO | WO 2016/207278 A1 | | 12/2016 |
| WO | WO 2017/083582 A1 | | 5/2017 |
| WO | WO 2017/096179 A1 | | 6/2017 |
| WO | WO 2017/096189 A1 | | 6/2017 |
| WO | WO 2017/096276 A1 | | 6/2017 |
| WO | WO 2017/096281 A1 | | 6/2017 |
| WO | WO 2017/114694 A1 | | 7/2017 |
| WO | WO 2017/160954 A1 | | 9/2017 |
| WO | WO 2017/214433 A1 | | 12/2017 |
| WO | WO 2019/101695 A1 | | 5/2019 |
| WO | WO 2022/200525 A1 | | 9/2022 |
| WO | WO 2022/258662 A1 | | 12/2022 |

OTHER PUBLICATIONS

Almagro et al., Humanization of Antibodies, Frontiers in Bioscience, Jan. 2008, 13(5): 1619-1633.

Dickopf et al., "Format and geometries matter: Structure-based design defines the functionality of bispecific antibodies", Computational and Structural Biotechnology Journal, May 14, 2020, 18: 1221-1227.

Dondelinger et al., "Understanding the Significance and Implications of Antibody Numbering and Antigen-Binding Surface/Residue Definition", Frontiers in Immunology, Oct. 16, 2018, 9(2278): 1-15.

Ernst et al., "Humanized anti-CD123 antibody facilitates NK cell antibody-dependent cell-mediated cytotoxicity (ADCC) of Hodgkin lymphoma targets via ARF6/PLD-1", Blood Cancer Journal, Jan. 15, 2019, 9(6): 1-11.

Extended European Search Report for European Patent Application No. 20306717.8, dated Jun. 7, 2021.

Gauthier et al., "852 Trifunctional NKp46/CD16a-NK cell engager targeting CD123 overcomes acute myeloid leukemia resistance to ADCC", Journal for ImmunoTherapy of Cancer, Nov. 2021, 9(Suppl. 2): A893.

Gauthier et al., "Multifunctional Natural Killer Cell Engagers Targeting NKp46 Trigger Protective Tumor Immunity", Cell, Jun. 13, 2019, 177(7): 1701-1713, e16, ePublished May 30, 2019.

International Search Report and Written Opinion for PCT International Patent Application No. PCT/IB2021/062494, dated Mar. 29, 2022.

Moraga et al., "Tuning cytokine receptor signaling by re-orienting dimer geometry with surrogate ligands", Cell, Mar. 12, 2015, 160(6): 1196-1208, ePublished Feb. 26, 2015.

Shi et al., "A biparatopic agonistic antibody that mimics fibroblast growth factor 21 ligand activity", Journal of Biological Chemistry, Apr. 20, 2018, 293(16): 5909-5919, Published online Feb. 26, 2018.

Stein et al., "Novel conjugates of single-chain Fv antibody fragments specific for stem cell antigen CD123 mediate potent death of acute myeloid leukaemia cells", British Journal of Haematology, Mar. 1, 2010, 148(6): 879-889.

Uchanska-Ziegler et al., "Human Single-Chain Fv Fragments Specific for Natural Killer Cell Receptors from Phage Display Libraries", Methods in Molecular Biology, Feb. 2000, 121: 219-237.

Bachiller et al., "Natural Killer Cells in Immunotherapy: Are We Nearly There?", Cancers, 2020, 12(3139): 1-27.

Blanchard et al., "Multi-Specific Antibody Technology Engaging NK Cells in Oncology", PEGS Europe, 2018.

DeMaria, "Harnessing NK Cells in Cancer Therapies by Antibody-Based NK Cell Engager Therapeutics (ANKET)", PEGS Boston, May 4, 2022.

DeMaria et al., "Natural killer cell engagers in cancer immunotherapy: Naxt generation of immuno-oncology treatments", Eur. J. Immunol., 2021, 51(8): 1934-1942.

DeMaria, "Antitumor immunity induced by antibody-based NK cell engager therapeutics armed with not-alpha IL-2 variant", Cell Reports Medicine, Oct. 18, 2022, 3: 100783.

(56) References Cited

OTHER PUBLICATIONS

Dilillo et al., "A BCMAxCD3 bispecific T cell-engaging antibody demonstrates robust antitumor efficacy similar to that of anti-BCMA CAR T cells", Bllod Advances, Mar. 9, 2021, 5(5): 1291-1304.

Ellwanger et al., "Redirected Optimized Cell Killing (ROCK®): A highly versatile multispecific fit-for-purpose antibody platform for engaging innate immunity", MABS, Jun. 7, 2019, 11(5): 899-918.

Extended European Search Report for European Patent Application No. 22305783.7, dated Nov. 7, 2022.

Extended European Search Report for European Patent Application No. 22305784.5, dated Nov. 7, 2022.

Fleming et al., "Trifunctional antibodies unleash NK cells", Nature Reviews—Immunology, Jul. 2019, 19: 411.

Gantke et al., "AFM26—Targeting B Cell Maturation Antigen (BCMA) for NK Cell-Mediated Immunotherapy of Multiple Myeloma", Blood, 2017, 130(Suppl. 1): 3082.

Gauthier et al., "#852 Trifunctional NKp46/CD16a-NK cell engager targeting CD123 overcomes acute myeloid leukemia resistance to ADCC", Poster, SITC, Nov. 10-14, 2021.

Gauthier et al., "Multifunctional Natural Killer Cell Engagers", PEGS Europe Summit, Engineering Biospecific Antibodies, Nov. 4, 2021.

Gauthier et al., "Poster #P776 Multifunctional Natural Killer Cell Engagers Targeting NKp46 Trigger Protective Tumor Immunity", SITC, 2019.

Hipp et al., "A novel BCMA/CD3 bispecific T-cell engager for the treatment of multiple lyeloma induces lysis in vitro and in vivo", Leukemia, Jan. 13, 2017, 31(8): 1743-1751, online preview Dec. 27, 2016.

Innate Pharma, "Innate's First NK Cell Engager Selected by Sanofi as Drug Candidate for Development", Press Release, Jan. 5, 2021.

Jacobsen et al., "Engineering an IgG Scaffold Lacking Effector Function with Optimized Developability", The Journal of Biological Chemistry, Feb. 3, 2017, 292(5): 1865-1875.

Mullard, "FDA approves second BCMA-targeted CAR-T cell therapy", Nature Reviews, Drug Discovery, Apr. 2022, 21(4): 249.

Panowski et al., "Preclinical Efficacy and Safety Comparison of CD3 Bispecific and ADC Modalities Targeting BCMA for the Treatrment of Multiple Myeloma", Molecular Cancer Therapeutics, Nov. 2019, 18(11): OF1-OF13, Epub. Aug. 21, 2019.

Sun et al., "Monoclonal Antibody 7G3 Recognizes the N-Terminal Domain of the Human Interleukin-3 (IL-3) Receptor α-Chain and Functions as a Specific IL-3 Receptor Antagonist", Blood, Jan. 1, 1996, 87(1): 83-92.

Vivier, "Natural Killer Cell Engagers", FOCIS—Federation of Clinical Immunology Societies, Jun. 6, 2021.

Vivier, "Targeting Innate Immunity in Cancer", AACR, 2019.

Wang et al., "BCMA-targeting Bispecific Antibody That Simultaneously Simulates MKG2D-enhanced Efficacy Against Multiple Myeloma", Journal of Immunotherapy, Jul./Aug. 2020, 43(6): 175-188.

Zhou et al., "The landscape of bispecific T cell engager in cancer treatment", Biomarker Research, 2021, 9(38): 1-23.

\* cited by examiner

THP1 GFP

NKp46-CD123_F25 100 ng/ml
NKp46-CD123_F25 10 ng/ml
NKp46-CD123_F25 ng/ml
NKp46-CD123_F250,1 ng/ml

MULTIFUNCTIONAL NATURAL KILLER (NK) CELL ENGAGERS BINDING TO NKP46 AND CD123

RELATED APPLICATIONS

This application claims priority to European Patent Application No. 20306717.8, filed Dec. 31, 2020, and U.S. Provisional Patent Application Ser. No. 63/256,950, filed Oct. 18, 2021, the entire disclosures of which are hereby incorporated herein by reference.

SEQUENCE LISTING

The instant application contains a Sequence Listing which has been submitted electronically in ASCII format and is hereby incorporated by reference in its entirety. Said ASCII copy, created on Feb. 16, 2022, is named 723198_SA9-309_ST25.txt and is 130.8 KB in size.

TECHNICAL FIELD

The disclosure relates to multifunctional binding proteins comprising a first and a second antigen binding domains (ABDs) and all or part of an immunoglobulin Fc region or variant thereof, wherein the first ABD binds specifically to human CD123 and the second ABD binds specifically to human NKp46 and wherein all or part of the immunoglobulin Fc region or variant thereof to a human Fc-γ receptor.

The disclosure also relates to methods for making said binding proteins, compositions thereof, and their uses including the treatment or prevention of proliferative disorders, including Acute Myeloid Leukemia (AML) and myelodysplastic syndromes (MDS).

BACKGROUND

Acute myeloid leukemia (AML) and myelodysplastic syndromes (MDS) are heterogeneous clonal neoplastic diseases, which are thought to arise from subpopulations of leukemic stem cells, which tend to be resistant to conventional chemotherapy, and which may be further responsible for disease relapse.

Natural killer (NK) cells are a subpopulation of lymphocytes that are involved in non-conventional immunity. NK cells provide an efficient immunosurveillance mechanism by which undesired cells such as tumor- or virally-infected cells can be eliminated. Characteristics and biological properties of NK cells include the expression of surface antigens including CD16, CD56 and/or CD57, the absence of the α/β or γ/δ TCR complex on the cell surface, the ability to bind to and kill cells in a MHC-unrestrictive manner and in particular cells that fail to express "self" MHC/HLA antigens by the activation of specific cytolytic enzymes, the ability to kill tumor cells or other diseased cells that express a ligand for NK activating receptors, and the ability to release protein molecules called cytokines that stimulate the immune response.

Interest has also focused on natural killer (NK) cells due to their potential anti-tumor properties.

Still, there is an urgent need for active agents for treating or preventing proliferative disorders such as Acute myeloid leukemia (AML) and myelodysplastic syndromes (MDS).

There is also a need for novel NK engagers with a therapeutic effect.

There is also a need for novel compounds which are easier to manufacture and/or administer, with no or decreased side-effects. In particular, there is a need for novel compounds with no or decreased risk of cytokine release syndrome in patients (e.g. no or decreased IL-6 associated cytokine release).

SUMMARY

In one embodiment, the disclosure relates to a binding protein comprising a first and a second antigen binding domain (ABD) and all or part of an immunoglobulin Fc region or variant thereof, wherein each of said ABD comprises an immunoglobulin heavy chain variable domain ($V_H$) and an immunoglobulin light chain variable domain ($V_L$), wherein each $V_H$ and $V_L$ comprises three complementary determining regions (CDR-1 to CDR-3); and wherein:

(i) the first ABD binds specifically to human CD123 and comprises:

a $V_{H1}$ comprising a CDR-H1, H2 and H3 corresponding to the amino acid sequences of SEQ ID NO:1 to 3 respectively or corresponding to the amino acid sequences of SEQ ID NO: 4 to 6 respectively, and a $V_{L1}$ comprising a CDR-L1, L2 and L3 corresponding to the amino acid sequences of SEQ ID NO: 7 to 9 respectively or corresponding to the amino acid sequences of SEQ ID NO: 10 to 12 respectively;

(ii) the second ABD binds specifically to human NKp46 and comprises:

a $V_{H2}$ comprising a CDR-H1, 2 and 3 corresponding to:
the amino acid sequences of SEQ ID NO:13 to 15 respectively;
the amino acid sequences of SEQ ID NO:16 to 18 respectively;
the amino acid sequences of SEQ ID NO:19 to 21 respectively;
the amino acid sequences of SEQ ID NO:22 to 24 respectively; or
the amino acid sequences of SEQ ID NO:16, 25 and 26 respectively; and a $V_{L2}$ comprising a CDR-L1, 2 and 3 corresponding to:
the amino acid sequences of SEQ ID NO:27 to 29 respectively;
the amino acid sequences of SEQ ID NO:30 to 32 respectively;
the amino acid sequences of SEQ ID NO:33 to 35 respectively;
the amino acid sequences of SEQ ID NO:36 to 38 respectively; or
the amino acid sequences of SEQ ID NO:39, 31 and 40 respectively;

and wherein all or part of the immunoglobulin Fc region or variant thereof binds to a human Fc-γ receptor.

In certain embodiments, the binding protein comprises three polypeptide chains (I), (II) and (III) that form two ABDs, as defined below:

$$V_{1A}\text{-}C_{1A}\text{-Hinge}_1\text{-}(C_H2\text{-}C_H3)_A \quad \text{(I)}$$

$$V_{1B}\text{-}C_{1B}\text{-Hinge}_2\text{-}(C_H2\text{-}C_H3)B\text{-}L_1\text{-}V_{2A}\text{-}C_{2A}\text{-Hinge}_3 \quad \text{(II)}$$

$$V_{2B}\text{-}C_{2B} \quad \text{(III)}$$

wherein:
$V_{1A}$ and $V_{1B}$ form a binding pair $V_1$ ($V_{H1}/V_{L1}$);
$V_{2A}$ and $V_{2B}$ form a binding pair $V_2$ ($V_{H2}/V_{L2}$);
$C_{1A}$ and $C_{1B}$ form a pair $C_1$ ($C_H1/C_L$) and $C_{2A}$ and $C_{2B}$ form a pair $C_2$ ($C_H1/C_L$) wherein $C_H1$ is an immunoglobulin heavy chain constant domain 1 and $C_L$ is an immunoglobulin light chain constant domain;

Hinge$_1$, Hinge$_2$ and Hinge$_3$ are identical or different and correspond to all or part of an immunoglobulin hinge region;

(C$_H$2-C$_H$3)$_A$ and (C$_H$2-C$_H$3)$_B$ are identical or different, and comprise an immunoglobulin heavy chain constant domain 2 (C$_H$2) and an immunoglobulin heavy chain constant domain 3 (C$_H$3);

L$_1$ is an amino acid linker.

In certain embodiments, C$_{1B}$ is an immunoglobulin heavy chain constant domain 1 (C$_H$1); C$_{2A}$ is an immunoglobulin heavy chain constant domain 1 (C$_H$1); C$_L$ corresponds to an immunoglobulin kappa light chain constant domain (C$_\kappa$); (C$_H$2-C$_H$3)$_A$ corresponds to the amino acid sequence of SEQ ID NO: 69; (C$_H$2-C$_H$3)$_B$ corresponds to the amino acid sequence of SEQ ID NO: 70; Hinge$_1$ corresponds to the amino acid sequence of SEQ ID NO:74; Hinge$_2$ corresponds to the amino acid sequence of SEQ ID NO:75; Hinge$_3$ corresponds to the amino acid sequence of SEQ ID NO: 77; L$_1$ corresponds to the amino acid sequence of SEQ ID NO: 76.

In certain embodiments, the residue N297 of the Fc region or variant thereof according to EU numbering comprises a N-linked glycosylation.

In certain embodiments, the all or part of the Fc region or variant thereof binds to a human CD16A (FcγRIII) polypeptide.

In certain embodiments, the binding protein comprises at least two polypeptide chains linked by at least one disulfide bridge.

In certain embodiments, the polypeptide chains (I) and (II) are linked by at least one disulfide bridge between C$_{1A}$ and Hinge$_2$ and/or wherein the polypeptide chains (II) and (III) are linked by at least one disulfide bridge between Hinge$_3$ and C$_{2B}$.

In certain embodiments, V$_{1A}$ is V$_{L1}$ and V$_{1B}$ is V$_{H1}$. In certain embodiments, V$_{2A}$ is V$_{H2}$ and V$_{2B}$ is V$_{L2}$.

In certain embodiments, (a) V$_{H1}$ comprises a CDR-H1 comprising the amino acid sequence of SEQ ID NO: 1; a CDR-H2 comprising the amino acid sequence of SEQ ID NO: 2; a CDR-H3 comprising the amino acid sequence of SEQ ID NO: 3; V$_{L1}$ comprises a CDR-L1 comprising the amino acid sequence of SEQ ID NO: 7; a CDR-L2 comprising the amino acid sequence of SEQ ID NO: 8; a CDR-L3 comprising the amino acid sequence of SEQ ID NO: 9; V$_{H2}$ comprises a CDR-H1 comprising the amino acid sequence of SEQ ID NO: 13; a CDR-H2 comprising the amino acid sequence of SEQ ID NO: 14; a CDR-H3 comprising the amino acid sequence of SEQ ID NO: 15; V$_{L2}$ comprises a CDR-L1 comprising the amino acid sequence of SEQ ID NO: 27; a CDR-L2 comprising the amino acid sequence of SEQ ID NO: 28; a CDR-L3 comprising the amino acid sequence of SEQ ID NO: 29; (b) V$_{H1}$ comprises a CDR-H1 comprising the amino acid sequence of SEQ ID NO: 1; a CDR-H2 comprising the amino acid sequence of SEQ ID NO: 2; a CDR-H3 comprising the amino acid sequence of SEQ ID NO: 3; V$_{L1}$ comprises a CDR-L1 comprising the amino acid sequence of SEQ ID NO: 7; a CDR-L2 comprising the amino acid sequence of SEQ ID NO: 8; a CDR-L3 comprising the amino acid sequence of SEQ ID NO: 9; V$_{H2}$ comprises a CDR-H1 comprising the amino acid sequence of SEQ ID NO: 16; a CDR-H2 comprising the amino acid sequence of SEQ ID NO: 17; a CDR-H3 comprising the amino acid sequence of SEQ ID NO: 18; V$_{L2}$ comprises a CDR-L1 comprising the amino acid sequence of SEQ ID NO: 30; a CDR-L2 comprising the amino acid sequence of SEQ ID NO: 31; a CDR-L3 comprising the amino acid sequence of SEQ ID NO: 32; (c) V$_{H1}$ comprises a CDR-H1 comprising the amino acid sequence of SEQ ID NO: 1; a CDR-H2 comprising the amino acid sequence of SEQ ID NO: 2; a CDR-H3 comprising the amino acid sequence of SEQ ID NO: 3; V$_{L1}$ comprises a CDR-L1 comprising the amino acid sequence of SEQ ID NO: 7; a CDR-L2 comprising the amino acid sequence of SEQ ID NO: 8; a CDR-L3 comprising the amino acid sequence of SEQ ID NO: 9; V$_{H2}$ comprises a CDR-H1 comprising the amino acid sequence of SEQ ID NO: 19; a CDR-H2 comprising the amino acid sequence of SEQ ID NO: 20; a CDR-H3 comprising the amino acid sequence of SEQ ID NO: 21; V$_{L2}$ comprises a CDR-L1 comprising the amino acid sequence of SEQ ID NO: 33; a CDR-L2 comprising the amino acid sequence of SEQ ID NO: 34; a CDR-L3 comprising the amino acid sequence of SEQ ID NO: 35; (d) V$_{H1}$ comprises a CDR-H1 comprising the amino acid sequence of SEQ ID NO: 1; a CDR-H2 comprising the amino acid sequence of SEQ ID NO: 2; a CDR-H3 comprising the amino acid sequence of SEQ ID NO: 3; V$_{L1}$ comprises a CDR-L1 comprising the amino acid sequence of SEQ ID NO: 7; a CDR-L2 comprising the amino acid sequence of SEQ ID NO: 8; a CDR-L3 comprising the amino acid sequence of SEQ ID NO: 9; V$_{H2}$ comprises a CDR-H1 comprising the amino acid sequence of SEQ ID NO: 22; a CDR-H2 comprising the amino acid sequence of SEQ ID NO: 23; a CDR-H3 comprising the amino acid sequence of SEQ ID NO: 24; V$_{L2}$ comprises a CDR-L1 comprising the amino acid sequence of SEQ ID NO: 36; a CDR-L2 comprising the amino acid sequence of SEQ ID NO: 37; a CDR-L3 comprising the amino acid sequence of SEQ ID NO: 38; (e) V$_{H1}$ comprises a CDR-H1 comprising the amino acid sequence of SEQ ID NO: 1; a CDR-H2 comprising the amino acid sequence of SEQ ID NO: 2; a CDR-H3 comprising the amino acid sequence of SEQ ID NO: 3; V$_{L1}$ comprises a CDR-L1 comprising the amino acid sequence of SEQ ID NO: 7; a CDR-L2 comprising the amino acid sequence of SEQ ID NO: 8; a CDR-L3 comprising the amino acid sequence of SEQ ID NO: 9; V$_{H2}$ comprises a CDR-H1 comprising the amino acid sequence of SEQ ID NO: 16; a CDR-H2 comprising the amino acid sequence of SEQ ID NO: 25; a CDR-H3 comprising the amino acid sequence of SEQ ID NO: 26; V$_{L2}$ comprises a CDR-L1 comprising the amino acid sequence of SEQ ID NO: 39; a CDR-L2 comprising the amino acid sequence of SEQ ID NO: 31; a CDR-L3 comprising the amino acid sequence of SEQ ID NO: 40; (0 V$_{H1}$ comprises a CDR-H1 comprising the amino acid sequence of SEQ ID NO: 4; a CDR-H2 comprising the amino acid sequence of SEQ ID NO: 5; a CDR-H3 comprising the amino acid sequence of SEQ ID NO: 6; V$_{L1}$ comprises a CDR-L1 comprising the amino acid sequence of SEQ ID NO: 10; a CDR-L2 comprising the amino acid sequence of SEQ ID NO: 11; a CDR-L3 comprising the amino acid sequence of SEQ ID NO: 12; V$_{H2}$ comprises a CDR-H1 comprising the amino acid sequence of SEQ ID NO: 13; a CDR-H2 comprising the amino acid sequence of SEQ ID NO: 14; a CDR-H3 comprising the amino acid sequence of SEQ ID NO: 15; V$_{L2}$ comprises a CDR-L1 comprising the amino acid sequence of SEQ ID NO: 27; a CDR-L2 comprising the amino acid sequence of SEQ ID NO: 28; a CDR-L3 comprising the amino acid sequence of SEQ ID NO: 29; (g) V$_{H1}$ comprises a CDR-H1 comprising the amino acid sequence of SEQ ID NO: 4; a CDR-H2 comprising the amino acid sequence of SEQ ID NO: 5; a CDR-H3 comprising the amino acid sequence of SEQ ID NO: 6; V$_{L1}$ comprises a CDR-L1 comprising the amino acid sequence of SEQ ID NO: 10; a CDR-L2 comprising the amino acid sequence of SEQ ID NO: 11; a CDR-L3 comprising the amino acid sequence of SEQ ID NO: 12; $V_{H2}$ comprises a CDR-H1 comprising the amino acid sequence of SEQ ID NO: 16; a CDR-H2 comprising the amino acid sequence of SEQ ID NO: 17; a CDR-H3 comprising the amino acid sequence of SEQ ID NO: 18; $V_{L2}$ comprises a CDR-L1 comprising the amino acid sequence of SEQ ID NO: 30; a CDR-L2 comprising the amino acid sequence of SEQ ID NO: 31; a CDR-L3 comprising the amino acid sequence of SEQ ID NO: 32; (h) $V_{H1}$ comprises a CDR-H1 comprising the amino acid sequence of SEQ ID NO: 4; a CDR-H2 comprising the amino acid sequence of SEQ ID NO: 5; a CDR-H3 comprising the amino acid sequence of SEQ ID NO: 6; $V_{L1}$ comprises a CDR-L1 comprising the amino acid sequence of SEQ ID NO: 10; a CDR-L2 comprising the amino acid sequence of SEQ ID NO: 11; a CDR-L3 comprising the amino acid sequence of SEQ ID NO: 12; $V_{H2}$ comprises a CDR-H1 comprising the amino acid sequence of SEQ ID NO: 19; a CDR-H2 comprising the amino acid sequence of SEQ ID NO: 20; a CDR-H3 comprising the amino acid sequence of SEQ ID NO: 21; $V_{L2}$ comprises a CDR-L1 comprising the amino acid sequence of SEQ ID NO: 33; a CDR-L2 comprising the amino acid sequence of SEQ ID NO: 34; a CDR-L3 comprising the amino acid sequence of SEQ ID NO: 35; (i) VHA comprises a CDR-H1 comprising the amino acid sequence of SEQ ID NO: 4; a CDR-H2 comprising the amino acid sequence of SEQ ID NO: 5; a CDR-H3 comprising the amino acid sequence of SEQ ID NO: 6; $V_{L1}$ comprises a CDR-L1 comprising the amino acid sequence of SEQ ID NO: 10; a CDR-L2 comprising the amino acid sequence of SEQ ID NO: 11; a CDR-L3 comprising the amino acid sequence of SEQ ID NO: 12; $V_{H2}$ comprises a CDR-H1 comprising the amino acid sequence of SEQ ID NO: 22; a CDR-H2 comprising the amino acid sequence of SEQ ID NO: 23; a CDR-H3 comprising the amino acid sequence of SEQ ID NO: 24; $V_{L2}$ comprises a CDR-L1 comprising the amino acid sequence of SEQ ID NO: 36; a CDR-L2 comprising the amino acid sequence of SEQ ID NO: 37; a CDR-L3 comprising the amino acid sequence of SEQ ID NO: 38; or (j) VHA comprises a CDR-H1 comprising the amino acid sequence of SEQ ID NO: 4; a CDR-H2 comprising the amino acid sequence of SEQ ID NO: 5; a CDR-H3 comprising the amino acid sequence of SEQ ID NO: 6; $V_{L1}$ comprises a CDR-L1 comprising the amino acid sequence of SEQ ID NO: 10; a CDR-L2 comprising the amino acid sequence of SEQ ID NO: 11; a CDR-L3 comprising the amino acid sequence of SEQ ID NO: 12; $V_{H2}$ comprises a CDR-H1 comprising the amino acid sequence of SEQ ID NO: 16; a CDR-H2 comprising the amino acid sequence of SEQ ID NO: 25; a CDR-H3 comprising the amino acid sequence of SEQ ID NO: 26; $V_{L2}$ comprises a CDR-L1 comprising the amino acid sequence of SEQ ID NO: 39; a CDR-L2 comprising the amino acid sequence of SEQ ID NO: 31; a CDR-L3 comprising the amino acid sequence of SEQ ID NO: 40.

In certain embodiments, (a) $V_{H1}$ and $V_{L1}$ corresponds to the amino acid sequences of SEQ ID NO: 41 and 43 respectively or corresponds to the amino acid sequences of SEQ ID NO: 42 and 44 respectively; and/or (b) $V_{H2}$ and $V_{L2}$ corresponds to the amino acid sequences of SEQ ID NO: 45 and 53 respectively; the amino acid sequences of SEQ ID NO: 46 and 54 respectively; the amino acid sequences of SEQ ID NO: 47 and 55 respectively; the amino acid sequences of SEQ ID NO: 48 and 56 respectively; the amino acid sequences of SEQ ID NO: 49 and 57 respectively; the amino acid sequences of SEQ ID NO: 50 and 58 respectively; the amino acid sequences of SEQ ID NO: 51 and 59 respectively; or the amino acid sequences of SEQ ID NO: 52 and 60 respectively.

In certain embodiments, (a) $V_{H1}$ comprises the amino acid sequence of SEQ ID NO: 41; $V_{L1}$ comprises the amino acid sequence of SEQ ID NO: 43; $V_{H2}$ comprises the amino acid sequence of SEQ ID NO: 45; $V_{L2}$ comprises the amino acid sequence of SEQ ID NO: 53;

(b) $V_{H1}$ comprises the amino acid sequence of SEQ ID NO: 41; $V_{L1}$ comprises the amino acid sequence of SEQ ID NO: 43; $V_{H2}$ comprises the amino acid sequence of SEQ ID NO: 46; $V_{L2}$ comprises the amino acid sequence of SEQ ID NO: 54;

(c) $V_{H1}$ comprises the amino acid sequence of SEQ ID NO: 41; $V_{L1}$ comprises the amino acid sequence of SEQ ID NO: 43; $V_{H2}$ comprises the amino acid sequence of SEQ ID NO: 47; $V_{L2}$ comprises the amino acid sequence of SEQ ID NO: 55;

(d) $V_{H1}$ comprises the amino acid sequence of SEQ ID NO: 41; $V_{L1}$ comprises the amino acid sequence of SEQ ID NO: 43; $V_{H2}$ comprises the amino acid sequence of SEQ ID NO: 48; $V_{L2}$ comprises the amino acid sequence of SEQ ID NO: 56;

(e) $V_{H1}$ comprises the amino acid sequence of SEQ ID NO: 41; $V_{L1}$ comprises the amino acid sequence of SEQ ID NO: 43; $V_{H2}$ comprises the amino acid sequence of SEQ ID NO: 49; $V_{L2}$ comprises the amino acid sequence of SEQ ID NO: 57;

(f) VHA comprises the amino acid sequence of SEQ ID NO: 41; $V_{L1}$ comprises the amino acid sequence of SEQ ID NO: 43; $V_{H2}$ comprises the amino acid sequence of SEQ ID NO: 50; $V_{L2}$ comprises the amino acid sequence of SEQ ID NO: 58;

(g) $V_{H1}$ comprises the amino acid sequence of SEQ ID NO: 41; $V_{L1}$ comprises the amino acid sequence of SEQ ID NO: 43; $V_{H2}$ comprises the amino acid sequence of SEQ ID NO: 51; $V_{L2}$ comprises the amino acid sequence of SEQ ID NO: 59;

(h) $V_{H1}$ comprises the amino acid sequence of SEQ ID NO: 41; $V_{L1}$ comprises the amino acid sequence of SEQ ID NO: 43; $V_{H2}$ comprises the amino acid sequence of SEQ ID NO: 52; $V_{L2}$ comprises the amino acid sequence of SEQ ID NO: 60;

(i) $V_{H1}$ comprises the amino acid sequence of SEQ ID NO: 42; $V_{L1}$ comprises the amino acid sequence of SEQ ID NO: 44; $V_{H2}$ comprises the amino acid sequence of SEQ ID NO: 45; $V_{L2}$ comprises the amino acid sequence of SEQ ID NO: 53;

(j) $V_{H1}$ comprises the amino acid sequence of SEQ ID NO: 42; $V_{L1}$ comprises the amino acid sequence of SEQ ID NO: 44; $V_{H2}$ comprises the amino acid sequence of SEQ ID NO: 46; $V_{L2}$ comprises the amino acid sequence of SEQ ID NO: 54;

(k) $V_{H1}$ comprises the amino acid sequence of SEQ ID NO: 42; $V_{L1}$ comprises the amino acid sequence of SEQ ID NO: 44; $V_{H2}$ comprises the amino acid sequence of SEQ ID NO: 47; $V_{L2}$ comprises the amino acid sequence of SEQ ID NO: 55;

(l) $V_{H1}$ comprises the amino acid sequence of SEQ ID NO: 42; $V_{L1}$ comprises the amino acid sequence of SEQ ID NO: 44; $V_{H2}$ comprises the amino acid sequence of SEQ ID NO: 48; $V_{L2}$ comprises the amino acid sequence of SEQ ID NO: 56;

(m) $V_{H1}$ comprises the amino acid sequence of SEQ ID NO: 42; $V_{L1}$ comprises the amino acid sequence of SEQ ID NO: 44; $V_{H2}$ comprises the amino acid sequence of SEQ ID NO: 49; $V_{L2}$ comprises the amino acid sequence of SEQ ID NO: 57;

(n) $V_{H1}$ comprises the amino acid sequence of SEQ ID NO: 42; $V_{L1}$ comprises the amino acid sequence of SEQ ID NO: 44; $V_{H2}$ comprises the amino acid sequence of SEQ ID NO: 50; $V_{L2}$ comprises the amino acid sequence of SEQ ID NO: 58.

(o) $V_{H1}$ comprises the amino acid sequence of SEQ ID NO: 42; $V_{L1}$ comprises the amino acid sequence of SEQ ID NO: 44; $V_{H2}$ comprises the amino acid sequence of SEQ ID NO: 51; $V_{L2}$ comprises the amino acid sequence of SEQ ID NO: 59;

(p) $V_{H1}$ comprises the amino acid sequence of SEQ ID NO: 42; $V_{L1}$ comprises the amino acid sequence of SEQ ID NO: 44; $V_{H2}$ comprises the amino acid sequence of SEQ ID NO: 52; $V_{L2}$ comprises the amino acid sequence of SEQ ID NO: 60.

In certain embodiments, polypeptide (I) comprises an amino acid sequence of SEQ ID NO: 64; polypeptide (II) comprises an amino acid sequence of SEQ ID NO: 65; and polypeptide (III) comprises an amino acid sequence of SEQ ID NO: 66.

In certain embodiments, polypeptide (I) consists of an amino acid sequence of SEQ ID NO: 64; polypeptide (II) consists of an amino acid sequence of SEQ ID NO: 65; and polypeptide (III) consists of an amino acid sequence of SEQ ID NO: 66.

In one embodiment, the disclosure relates to a pharmaceutical composition comprising the binding protein defined above, and a pharmaceutically acceptable carrier.

In one embodiment, the disclosure relates to an isolated nucleic acid molecule comprising a nucleotide sequence that encodes the binding protein defined above.

In one embodiment, the disclosure relates to an expression vector comprising the nucleic acid molecule defined above.

In one embodiment, the disclosure relates to an isolated cell comprising the nucleic acid molecule defined above.

In one embodiment, the disclosure relates to an isolated cell comprising the expression vector defined above. In certain embodiments, the host cell is a mammalian cell.

In one embodiment, the disclosure relates to a method for making the binding protein defined above, comprising the steps of: (a) introducing the expression vector defined above into a host cell; (b) culturing the host cell under conditions suitable for expressing the binding protein; and (c) optionally recovering the expressed binding protein.

In one embodiment, the disclosure relates to an isolated nucleic acid molecule comprising a nucleotide sequence that encodes a binding protein as defined above, and characterized in that it comprises a first and a second antigen binding domain (ABD) and all or part of an immunoglobulin Fc region or variant thereof, wherein each of said ABD comprises an immunoglobulin heavy chain variable domain ($V_H$) and an immunoglobulin light chain variable domain ($V_L$), wherein each $V_H$ and $V_L$ comprises three complementary determining regions (CDR-1 to CDR-3); wherein:

(i) the first ABD binds specifically to human CD123 and comprises:
a $V_{H1}$ comprising a CDR-H1, H2 and H3 corresponding to the amino acid sequences of SEQ ID NO:1 to 3 respectively or corresponding to the amino acid sequences of SEQ ID NO: 4 to 6 respectively, and a $V_{L1}$ comprising a CDR-L1, L2 and L3 corresponding to the amino acid sequences of SEQ ID NO: 7 to 9 respectively or corresponding to the amino acid sequences of SEQ ID NO: 10 to 12 respectively;

(ii) the second ABD binds specifically to human NKp46 and comprises:
a $V_{H2}$ comprising a CDR-H1, 2 and 3 corresponding to:
the amino acid sequences of SEQ ID NO:13 to 15 respectively;
the amino acid sequences of SEQ ID NO:16 to 18 respectively;
the amino acid sequences of SEQ ID NO:19 to 21 respectively;
the amino acid sequences of SEQ ID NO:22 to 24 respectively; or
the amino acid sequences of SEQ ID NO:16, 25 and 26 respectively; and
a $V_{L2}$ comprising a CDR-L1, 2 and 3 corresponding to:
the amino acid sequences of SEQ ID NO:27 to 29 respectively;
the amino acid sequences of SEQ ID NO:30 to 32 respectively;
the amino acid sequences of SEQ ID NO:33 to 35 respectively;
the amino acid sequences of SEQ ID NO:36 to 38 respectively; or
the amino acid sequences of SEQ ID NO:39, 31 and 40 respectively;
and wherein all or part of the immunoglobulin Fc region or variant thereof binds to a human Fc-γ receptor.

In one embodiment, the disclosure relates to an expression vector comprising a nucleic acid molecule comprising a nucleotide sequence that encodes of or more polypeptide chains of the binding protein, as defined above.

In one embodiment, the disclosure relates to an isolated cell comprising the nucleic acid molecule as defined above.

In one embodiment, the disclosure relates to an isolated cell comprising the expression vector as defined above.

In one embodiment, the disclosure relates to a method for making the binding protein, comprising a step of:
(a) culturing host cell(s) under conditions suitable for expressing a plurality of recombinant polypeptides, said plurality comprising (i) a polypeptide comprising an amino acid sequence of SEQ ID NO: 64, and (ii) a polypeptide comprising an amino acid sequence of SEQ ID NO: 65, and (iii) a polypeptide comprising an amino acid sequence of SEQ ID NO: 66;
(b) optionally recovering the expressed recombinant polypeptides.

In one embodiment, the disclosure relates to a method of treating or preventing a blood cancer, the method comprising administering to a subject in need of said treatment or prevention the pharmaceutical composition defined above.

In one embodiment, the disclosure relates to a method of treating or preventing a myelodysplastic syndrome (MDS) or a lymphoproliferative disorder, the method comprising administering to a subject in need of said treatment or prevention the pharmaceutical composition defined above.

In one embodiment, the disclosure relates to a method of treating or preventing an Acute Myeloid Leukemia (AML), the method comprising administering to a subject in need of said treatment or prevention the pharmaceutical composition defined above.

In one embodiment, the disclosure relates to a method of treating or preventing a CD64-positive and CD64-negative Acute Myeloid Leukemia (AML), the method comprising administering to a subject in need of said treatment or prevention the pharmaceutical composition defined above.

In one embodiment, the disclosure relates to a method of treating or preventing a CD64-positive Acute Myeloid Leukemia (AML), the method comprising administering to a subject in need of said treatment or prevention a binding protein comprising a first and a second antigen binding domain (ABD) and all or part of an immunoglobulin Fc region or variant thereof, wherein the first ABD binds specifically to human CD123, the second ABD binds specifically to human NKp46, and wherein all or part of the immunoglobulin Fc region or variant thereof binds to a human Fc-γ receptor.

BRIEF DESCRIPTION OF THE FIGURES

If not specified otherwise, the binding proteins of the present disclosure are oriented with the amino terminal direction ("N-terminal end" or "N-term") on the left-hand side and the carboxyl-terminal direction ("C-terminal end" or "C-term") on the right-hand side, in accordance with standard usage and convention.

FIG. 2A shows a two-dimensional schematic representation of the F25 format. This representation represents the claimed "NKp46-CD123_F25" binding protein.

FIG. 2B shows a two-dimensional schematic representation of the F5 format. When compared to F25, the F5 differs in that the $C_L$ and $C_H$ pair of the NKp46 binding domain are swapped, with the third polypeptide chain comprising a $C_H1$ domain and a $V_L$ domain.

FIG. 2C shows a two-dimensional schematic representation of the F26 format. This F26 differs from F25 of FIG. 2A in that it includes a Fc-silent N297S mutation on each $C_H2$ domain.

FIG. 2D shows a two-dimensional schematic representation of the F6 format. This F6 differs from F5 of FIG. 2B in that it includes a Fc-silent N297S mutation on each $C_H2$ domain.

FIG. 4A shows the in vitro cytotoxicity of the NKp46-CD123_F25 binding protein of the present disclosure and negative isotype control variant of format F25 binding NKp46 only (NKp46-IC_F25) against AML cell line (MOLM-13). FIG. 4B reproduces the same experiment with ex vivo patient samples where the cytotoxicity of NKp46-CD123_F25, NKp46-IC_F25, an anti-CD123 ADCC-enhanced antibody with no specificity for NKp46 (Reference-1) and a negative isotype control Fc-optimized antibody with increased ADCC activity and no specificity for NKp46 nor CD123 (IC-hIgG1-ADCC-enh) is assessed against primary AML blast cells.

FIGS. 6A and 6B lower panels reports the phenotype of the malignant AML cell lines and sub-clones and the expression of CD123, CD64, CD32a/b by flow cytometry analysis. Background staining of AML cells with mouse-IgG2a (IC mouse IgG2a) and mouse-IgG1 (IC mouse IgG1) isotype controls is also shown.

(orange) and M2 (purple) treated with 3 mg/kg as single 1-hour intravenous infusion, and monkeys M3 (red) and M4 (blue) treated with 3 µg/kg as single 1-hour intravenous infusion.

Figure 20A:
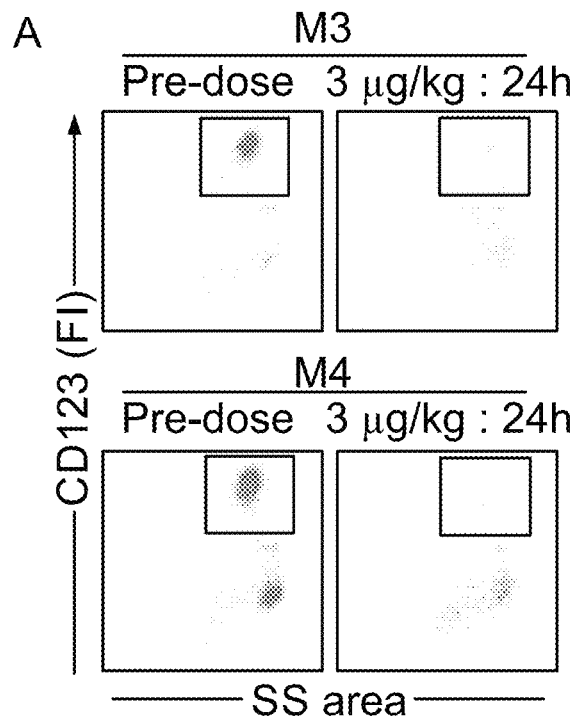
FIG. 20A depicts the depletion of CD123-positive basophils from the blood of monkeys M3 and M4 treated at the low dose of 3 µg/kg as single 1-hour intravenous infusion. Blood samples were collected before dosing (pre-dose) and 24 hours after the start of the infusion and analyzed by flow cytometry. CD123-positive basophils are shown in the gate.
Figure 20B:
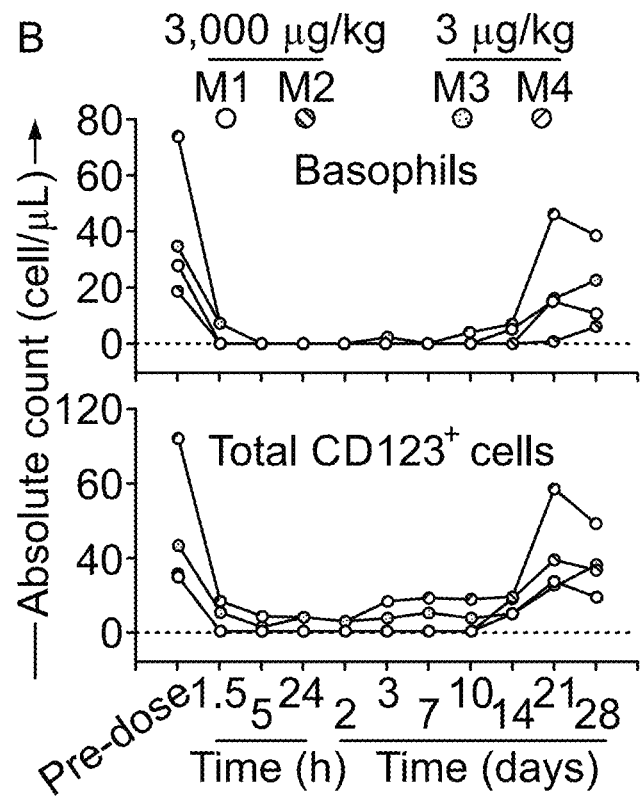
FIG. 20B displays the numbers of circulating CD123-positive basophils (open symbols) and total CD123-positive leukocytes (close symbols) at time of study in monkeys M1
Figure 20C:
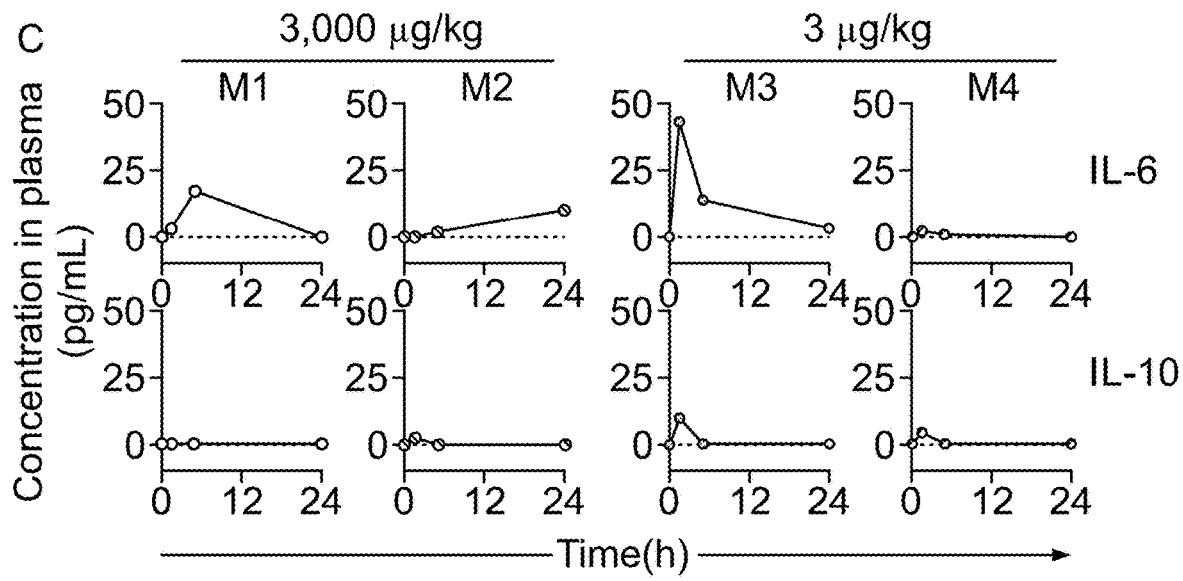

FIG. 20C reports cytokine production in cynomolgus monkeys treated with the high and low doses of 3 mg/kg and 3 µg/kg as single 1-hour intravenous infusion, respectively. Plasma IL-6 and IL-10 concentrations are shown before dosing (0), and 1.5, 5 and 24 hours after the start of the treatment.

Figure 20D:
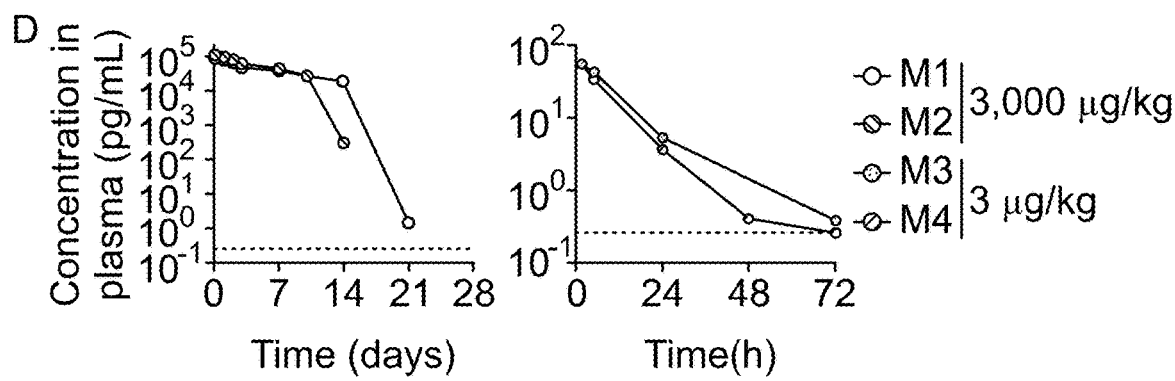

FIG. 20D reports the plasma NKp46-CD123_F25 (CD123-NKCE) concentration monitored 1.5, 5, 24, 48, 72, 168, 240, 336, 504 and 672 hours (i.e., 0.04, 0.06, 0.21, 1, 2, 3, 7, 10, 14, 21 and 28 days) after the start of the 1-hour infusion of cynomolgus monkeys treated with the high and low doses of 3 mg/kg and 3 µg/kg. The lower limit of quantification (LLOQ; 0.25 ng/mL) is indicated by the horizontal dotted line.

Figure 21A:
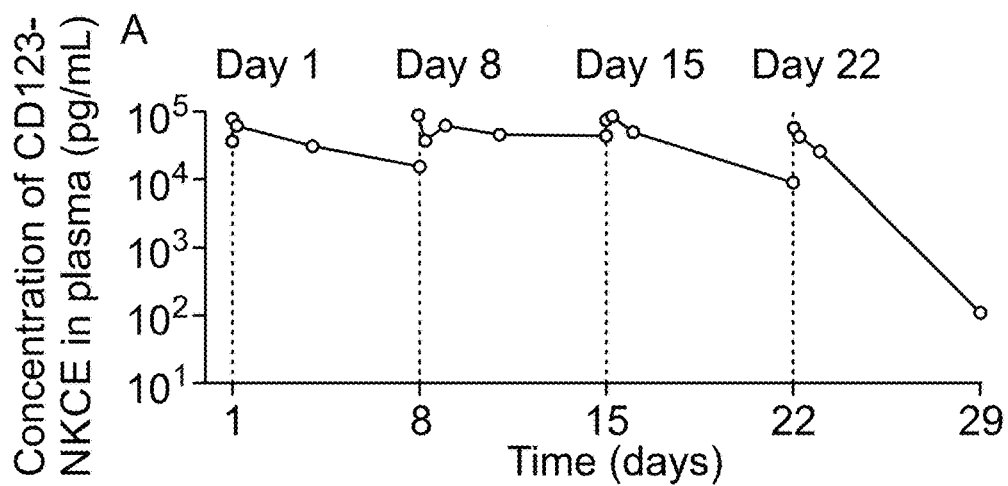

FIG. 21A shows the toxicokinetics (TK) of the NKp46-CD123_F25 (CD123-NKCE) molecule in male monkey M5 weekly treated at a dose of 3 mg/kg/administration for four weeks (on Days 1, 8, 15 and 22). Plasma CD123-NKCE concentrations were determined before dosing (predose) and 1, 1.5, 5, 24, and/or 72 hours after the start of the 1-hour infusion on days 1, 8, 15 and before dosing and, 1, 1.5, 5, 24, and 168 hours after the start of the last fourth 1-hour infusion on day 22. Values below the lower limit of quantification (LLOQ: 0.25 ng/mL) are not reported on the graphs. Infusion days are indicated by vertical dotted lines.

Figure 21B:
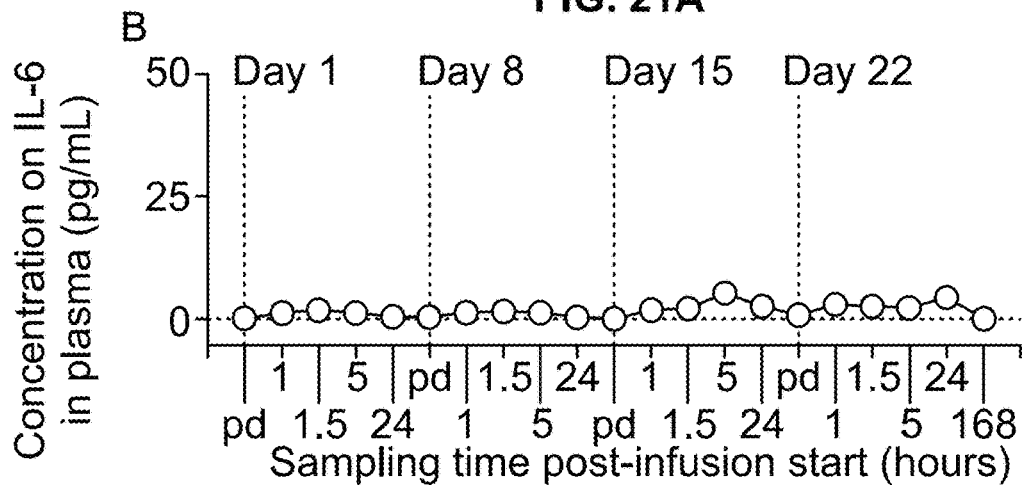

FIG. 21B is an analysis of the interleukin-6 production in monkey M5 weekly treated with the high dose of 3 mg/kg/administration for four weeks. Plasma IL-6 concentrations were monitored before dosing and 1, 1.5, 5 and 24 hours after the start of the one-hour infusion on days 1, 8, 15 and before dosing and 1, 1.5, 5, 24, and 168 hours after the start of the last fourth one-hour infusion on day 22.

Figure 21C:
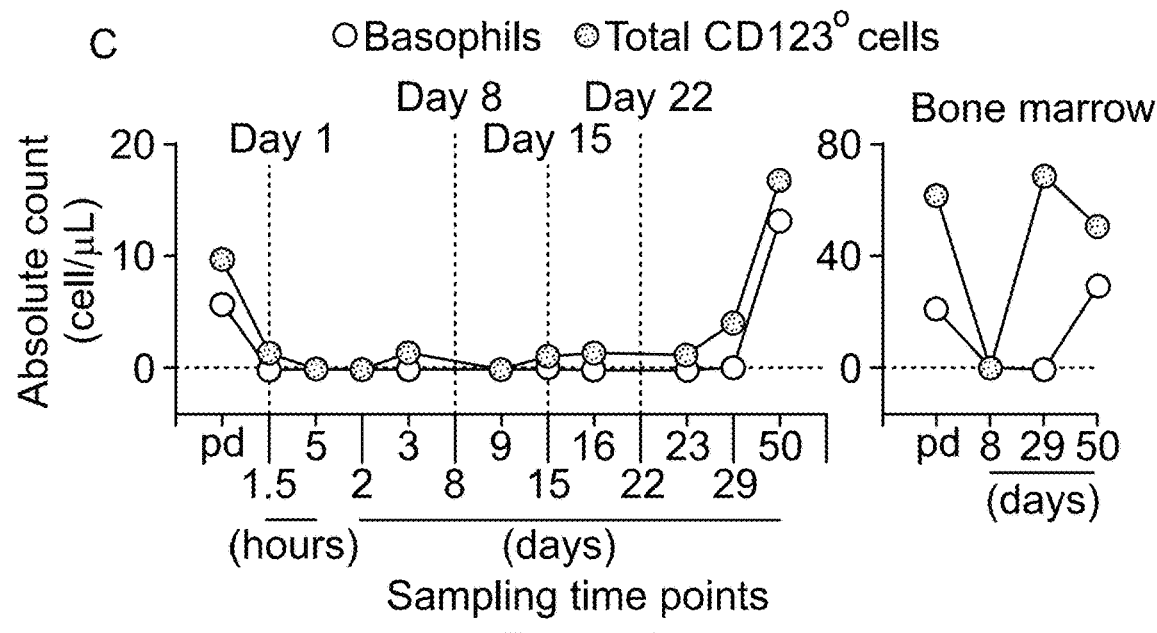

FIG. 21C quantifies the number of circulating CD123-positive basophils (open symbols) and total CD123-positive leukocytes (closed symbols) in blood (left panel) or bone marrow (right panel), by timepoint in the study, for monkey M5, treated at a dose of 3 mg/kg/week.

Figure 22:
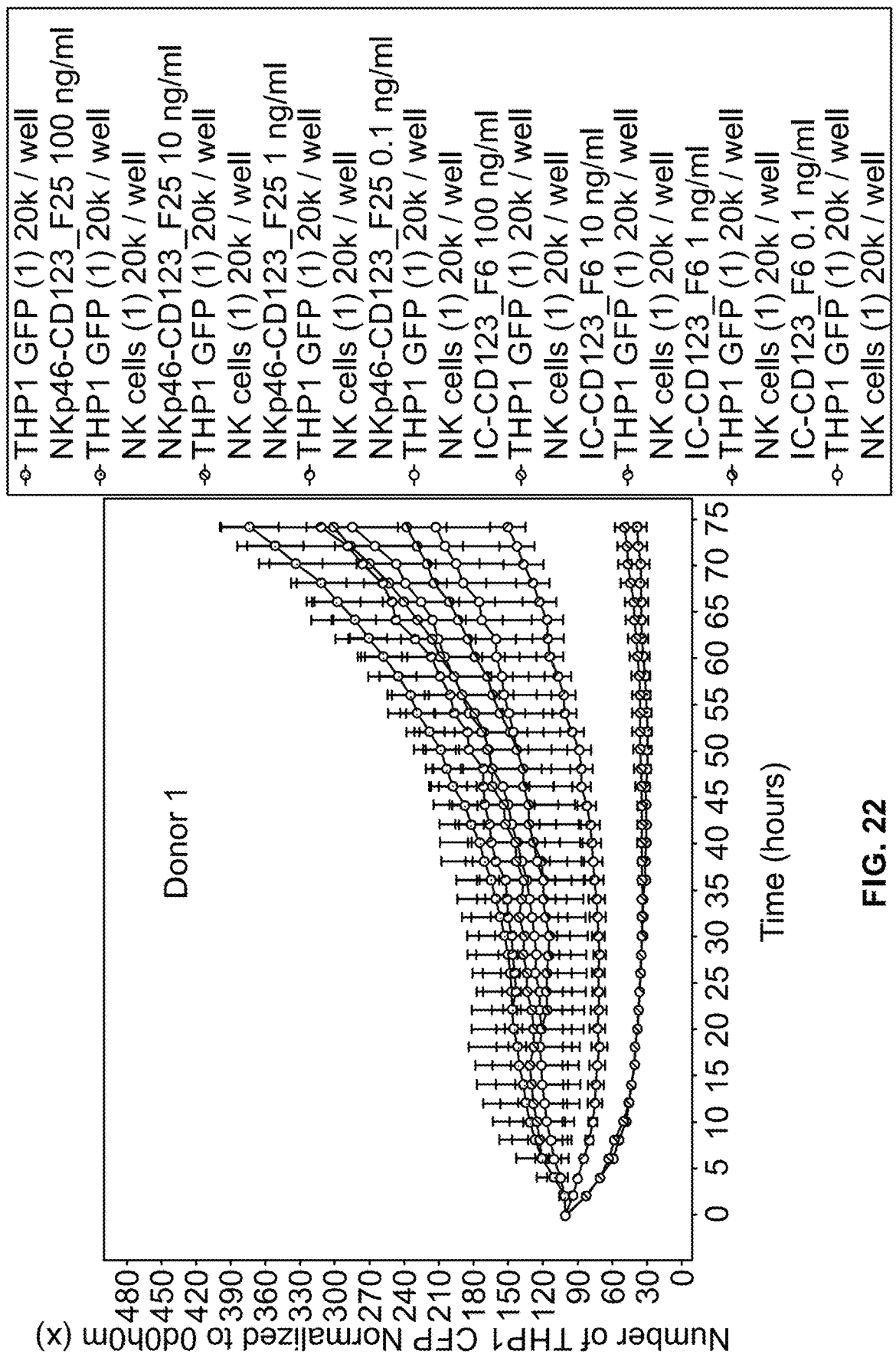
Figure 22:
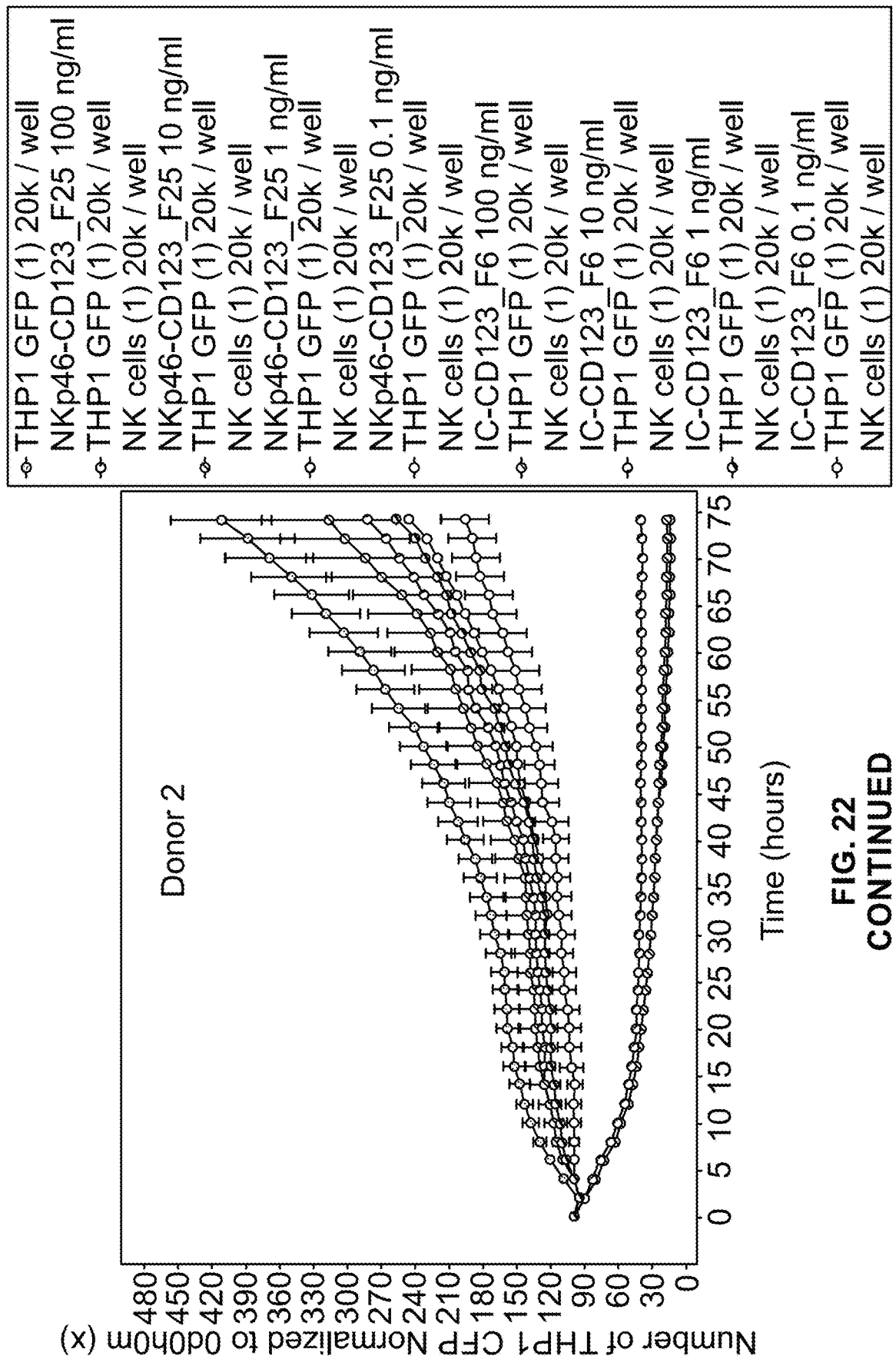

FIG. 22 graphically depicts THP1 cytotoxic activity in an assay with human peripheral blood mononuclear cells (PBMC) from 2 healthy donors (HD). NK cells and THP1 GFP target cells were incubated in presence of NKp46-CD123_F25 or its isotype control IC-CD123_F6 engaging CD123 and inducing reduced ADCC-activity with its Fc silent format (F6) at 0.1, 1, 10 and 100 ng/mL.

DETAILED DESCRIPTION

The disclosure provides multifunctional binding proteins that bind one surface biomarker on immune NK cells, i.e., NKp46 and one antigen of interest on tumoral target cells i.e., CD123 and is capable of redirecting NK cells to lyse a target cell that expresses the CD123 surface biomarker. The multifunctional binding proteins of the present disclosure further comprises all or part of a Fc region or variant thereof which binds a Fc-γ receptor (FcγR), in particular an activating Fc-γ receptor (FcγR), for example FcγRIIIa also called CD16a.

The exemplified multifunctional binding proteins of the present disclosure also possess a dimeric Fc domain that comprises N-linked glycosylation and bind an activating Fc-γ receptor (FcγR) such as receptor CD16a thereby providing advantageous immune enhancing activity.

The inventors provide experimental evidence that optimal NK cell modulation, in particular NK cell activation, can be achieved with a better safety profile, both in vitro on AML cell lines MOLM-13 and THP1 and ex vivo on primary samples from AML patients (e.g., peripheral blood lymphocytes from AML patients), by engaging NKp46, a FcγR such as CD16a, and the cell surface biomarker CD123.

Importantly, the in vitro cytotoxic activity of the NKp46-CD123 binding protein of the present disclosure, characterized by a format reported herein as the "F25" and comprising a central Fragment crystallizable (Fc) region retaining binding to a human CD16 polypeptide, was reproduced ex vivo.

Accordingly, the inventors provide experimental support of the therapeutic properties of a bispecific NKp46/CD16-CD123 binding protein in particular for use in treating and preventing AML and other proliferative disorders.

The inventors further provide experimental evidence that NKp46-CD123 binding protein activate NK cells in primary samples from AML patients irrespective of their CD64 expression status.

Hence, engagement of NK cells through the binding of cell surface markers NKp46/CD16 is validated as a robust and reproducible strategy for use as a medicament.

I. Definitions

As used herein, the "CD123" marker, or "Cluster of Differentiation 123" is also known as "Interleukin 3 receptor, alpha (IL3RA)" or "IL3R", "IL3RX", "IL3RY", "IL3RAY", "hIL-3Ra" and denotes an interleukin 3 specific subunit of a heterodimeric cytokine receptor. The functional interleukin 3 receptor is a heterodimer that comprises a specific alpha chain (IL-3A; CD123) and the IL-3 receptor beta chain (βθ; CD131) that is shared with the receptors for granulocyte macrophage colony stimulating factor (GM-CSF) and interleukin 5 (IL-5). CD123 is a type I integral transmembrane protein with a deduced Molecular Weight of about 43 kDa containing an extracellular domain involved in IL-3 binding, a transmembrane domain and a short cytoplasmic tail of about 50 amino acids. The extracellular domain is composed of two regions: a N-terminal region of about 100 amino acids, the sequence of which exhibits similarity to equivalent regions of the GM-CSF and IL-5 receptor alpha-chains; and a region proximal to the transmembrane domain that contains four conserved cysteine residues and a motif, common to other members of this cytokine receptor family. The IL-3 binding domain comprises about 200 amino acid residue cytokine receptor motifs (CRMs) made up of two Ig-like folding domains. The extracellular domain of CD123 is highly glycosylated, with N-glycosylation necessary for both ligand binding and receptor signaling. The protein family gathers three members: IL3RA (CD123A), CSF2RA and IL5RA. The overall structure is well conserved between the three members, but sequence homologies are very low. One 300 amino-acid long isoform of CD123 has been discovered so far, but only on the RNA level which is accessible on the Getentry database under the accession number ACM241 16.1. A reference sequence of full-length human CD123 protein, including signal peptide, is available from the NCBI database under the accession number NP_002174.1 and under the Uniprot accession number P26951. The extracellular domain of human CD123 (ECD) consists of the amino acid sequence of SEQ ID NO: 86. CD123 (the interleukin-3 receptor alpha chain IL-3Ra) is a tumor antigen overexpressed in a variety of hematological neoplasms. The majority of AML blasts express surface CD123 and this expression does not vary by subtype of AML. Higher expression of CD123 on AML at diagnosis has been reported to be associated with poorer prognosis. CD123 expression has been reported in other hematological malignancies including myelodysplasia, systemic mastocytosis, blastic plasmacytoid dendritic cell neoplasm (BPDCN), ALL and hairy cell leukemia.

As used herein, "Natural killer" or "NK cells" refers to a sub-population of lymphocytes that is involved in non-conventional immunity. NK cells can be identified by virtue of certain characteristics and biological properties, such as the expression of specific surface antigens including CD16, CD56 and/or CD57, NKp46 for human NK cells, the absence of the alpha/beta or gamma/delta TCR complex on the cell surface, the ability to bind to and kill cells that fail to express "self" MHC/HLA antigens by the activation of specific cytolytic machinery, the ability to kill tumor cells or other diseased cells that express a ligand for NK activating receptors, and the ability to release protein molecules called cytokines that stimulate or inhibit the immune response. Any of these characteristics and activities can be used to identify NK cells, using methods well known in the art. Any sub-population of NK cells will also be encompassed by the term NK cells. Within the context herein "active" NK cells designate biologically active NK cells, including NK cells having the capacity of lysing target cells or enhancing the immune function of other cells. NK cells can be obtained by various techniques known in the art, such as isolation from blood samples, cytapheresis, tissue or cell collections, etc. Useful protocols for assays involving NK cells can be found in Natural Killer Cells Protocols (edited by Campbell K S and Colonna M). Human Press. pp. 219-238 (2000).

As used herein, the "NKp46" marker, or "Natural cytotoxicity triggering receptor 1", also known as "CD335" or "NKP46" or "NK-p46" or "LY94" refers to a protein—or polypeptide—encoded by the Ncr1 gene. A reference sequence of full-length human NKp46 protein is available from the NCBI database under the accession number NP_004820. The human NKp46 extracellular domain (ECD) corresponds to the amino acid sequence of SEQ ID NO: 84. The human NKp46 mRNA sequence is described in NCBI accession number NM_004829.

As used herein, the term "Fc-γ receptor" or "FcγR" or "Fc-gamma receptor" may refer to both activating and inhibitory FcγRs. Fc-gamma receptors (FcγR) are cellular receptors for the Fc region of an Immunoglobulin G (IgG). Upon binding a complexed IgG, FcγRs can modulate cellular it effector functions, thereby linking the adaptive and innate immune systems, including ADCC-mediated immune responses. In humans, six classic FcγRs are currently reported: one high-affinity receptor (FcγRI) and five low-to-medium-affinity FcγRs (FcγRIIA, -B and -C, FcγRIIIA and -B). All FcγRs bind the same region on IgG Fc, yet with differing high (FcgRI) and low (FcgRII and FcgRIII) affinities. On a functional level, most of the FcγRs are activating receptors that can induce the cellular responses mentioned above, including ADCC-mediated immune response. Whereas FcγRI, FcγRIIa, FcγRIIc, and FcγRIIIa are activating receptors characterized by an intracellular immunoreceptor tyrosine-based activation motif (ITAM), FcγRIIb has an inhibition motif (ITIM) and is therefore inhibitory. Unless specified otherwise, the term FcγRs encompasses activating receptors, including FcγRI (CD64), FcγRIIA (CD32a), FcγRIIIa (CD16a) and FcγRIIIb (CD16b), and preferably FcγRIIIa (CD16a).

As used herein, the term "FcγRIIIa (CD16a)" or "FcγRIIIa" or "CD16a" or "CD16" or "Cluster of Differentiation 16" may refer to a 50-65 kDa cell surface molecule expressed on mast cells, macrophages, and natural killer cells as a transmembrane receptor. FcγRIIIa is an activating receptor containing immunoreceptor tyrosine activating motifs (ITAMs) in the associated FcR γ-chain, ITAMs being necessary for receptor expression, surface assembly and signaling. CD16a is a low affinity receptor for IgG and is an important receptor mediating. ADCC (antibody dependent cell mediated cytotoxicity) by NK cells. The high affinity receptor CD16a is preferentially found on NK cells and monocytes and induces antibody-dependent cellular cytotoxicity (ADCC) upon IgG binding.

As used herein, the term "FcγRII CD32", "FcγRII", "FCGR2" or "CD32a" or "CD32A" or "CD32" or "cluster of differentiation 32" is a surface receptor glycoprotein belonging to the Ig gene superfamily. CD32A is expressed on all myeloid cells but not on lymphocytes. CD32 has a low-affinity for the Fc region of IgG antibodies in monomeric form, but high affinity for IgG immune complexes. CD32 has two major functions: cellular response regulation, and the uptake of immune complexes. Cellular responses regulated by CD32 include phagocytosis, cytokine stimulation, and endocytic transport. Dysregulated CD32 is associated with different forms of autoimmunity, including systemic lupus erythematosus. In humans, there are three major CD32 subtypes: CD32A, CD32B, and CD32C. While CD32A and CD32C are involved in activating cellular responses, CD32B is inhibitory and balances the activating properties of CD32A. CD32A is an activating subtype of CD32 that can be found on a variety of immune cells. Notably, CD32A (FcγRIIA) mediates effector functions of granulocytes, monocytes, B cells, platelets, and dendritic cells upon low affinity binding of aggregated IgG. When bound to an IgG immune complex, the cytosolic ITAM can promote phagocytic activity and cytokine secretion in neutrophils and macrophages.

As used herein, the term "hFcγRICD64", "hFcγRI", or "CD64" or "Cluster of Differentiation 64" is a surface receptor expressed constitutively only on monocytes and macrophages, but is upregulated on granulocytes upon cytokine stimulation.

As used herein, the terms "Format 5" or "F5", "Format 25" or "F25", "Format F6" or "F6" and "Format 26" or "F26" refer to specific binding protein configurations of bispecific or multispecific antibodies specifically designed to engineer multiple antigen binding domains into a single antibody molecule. The multifunctional binding proteins of the present disclosure which comprise a NKp46-binding domain and a CD123-binding domain, are made based on the F25 format, as exemplified in FIG. 1 and FIG. 2. F25 and format F26 respectively differ from format F5 and F6 in that one $C_H1/C_L$ pair between the second and third polypeptide chain are swapped to form a $C_L/C_H1$ pair. The F5 and F6 format have been previously described in the international patent application WO2017114694, incorporated herein by reference.

As used herein, the term "bispecific binding protein" refers to a binding protein that specifically binds to two different antigen targets (e.g. human NKp46 and human CD123) through two distinct antigen-binding domains (ABDs).

As used herein, the term "specifically binds to" or "binds specifically to" refers to the ability of an antigen-binding domain (ABD) to bind to an antigen (e.g. human NKp46 and/or human CD123) containing an epitope with an Kd of at least about $1 \times 10^{-6}$ M, $1 \times 10^{-7}$ M, $1 \times 10^{-8}$ M, $1 \times 10^{-9}$ M, $1 \times 10^{-10}$ M, $1 \times 10^{-11}$ M, $1 \times 10^{-12}$ M, or more, and/or to bind to an epitope with an affinity that is at least twofold greater than its affinity for a nonspecific antigen.

As used herein, the term "specifically binds to human NK46 polypeptide" may refer to a specific binding toward a polypeptide comprising an amino acid sequence of SEQ ID NO: 84.

As used herein, the term "specifically to a human CD123 polypeptide" may refer to a specific binding toward a polypeptide comprising an amino acid sequence of SEQ ID NO: 86.

As used herein, the term "binds to a human Fc-γ receptor polypeptide" may refer to a binding toward a polypeptide comprising an amino acid sequence of SEQ ID NO: 87 or SEQ ID NO: 88.

Competitive binding assays and other methods for determining specific binding are further described below and are well known in the art. Expressions such as "specifically binds to", or "with specificity for" are used interchangeably. Those terms are not construed to refer exclusively to those antibodies, polypeptides and/or multichain polypeptides which actually bind to the recited target/binding partner, but also to those which, although provided in a non-bound form, retain the specificity to the recited target. Binding specificity can be quantitatively determined by an affinity constant KA (or $K_A$) and a dissociation constant KD (or $K_D$).

As used herein, the term "affinity", concentration (EC50) or the equilibrium dissociation constant (KD) means the strength of the binding of an antibody or polypeptide to an epitope. The affinity of an antibody is given by a specific type of equilibrium constant, which is the dissociation constant KD, defined as [Ab]×[Ag]/[Ab–Ag], where [Ab–Ag] is the molar concentration of the antibody-antigen complex, [Ab] is the molar concentration of the unbound antibody and [Ag] is the molar concentration of the unbound antigen. The affinity constant KA is defined by 1/KD. Preferred methods for determining the affinity of mAbs can be found in Harlow, et al., Antibodies: A Laboratory Manual, Cold Spring Harbor Laboratory Press, Cold Spring Harbor, N.Y., 1988), Coligan et al., eds., Current Protocols in Immunology, Greene Publishing Assoc. and Wiley Interscience, N.Y., (1992, 1993), and Muller, Meth. Enzymol. 92:589-601 (1983), which references are entirely incorporated herein by reference. One preferred and standard method well known in the art for determining the affinity of mAbs is the use of surface plasmon resonance (SPR) screening (such as by analysis with a BIAcore™ SPR analytical device). In a non-limitative manner, a $K_D$ of less than 50 nM as determined by SPR, and under physiological conditions (e.g. at a pH ranging from 6 to 8 under normal buffer conditions), may generally be considered as indicative of specificity of binding for antigen-antigen binding domain (ABD) interactions. As an illustration, and according to some particular and exemplified embodiments, binding proteins reported herein comprise:

an antigen binding domain which binds specifically to human CD123 with a $K_D$ of less than 10 nM, in particular with a $K_D$ of less than 0.5 nM, as determined by SPR, under physiological conditions;

an antigen binding domain which binds specifically to human NKp46 with a $K_D$ of less than 50 nM, in particular with a $K_D$ of less than 20 nM, as determined by SPR, under physiological conditions.

As used herein, the term "and/or" is a grammatical conjunction that is to be interpreted as encompassing that one or more of the cases it connects may occur. For example, the wording "such native sequence proteins can be made using standard recombinant and/or synthetic methods" indicates that native sequence proteins can be made using standard recombinant and synthetic methods or native sequence proteins can be made using standard recombinant methods or native sequence proteins can be made using synthetic methods.

As used herein, "treating" refers to a therapeutic use (i.e., on a subject having a given disease) and means reversing, alleviating, inhibiting the progress of one or more symptoms of such disorder or condition. Therefore, treatment does not only refer to a treatment that leads to a complete cure of the disease, but also to treatments that slow down the progression of the disease and/or prolong the survival of the subject.

As used herein, "preventing" means a prophylactic use (i.e., on a subject susceptible of developing a given disease and encompasses the treatment of relapsed AML patient.

As used herein, the terms "therapeutically effective amount" of the multifunctional binding protein or pharmaceutical composition thereof is meant a sufficient amount of the antibody-like multifunctional binding protein to treat said cancer disease, at a reasonable benefit/risk ratio applicable to any medical treatment. It will be understood, however, that the total daily usage of the polypeptides and compositions of the present disclosure will be decided by the attending physician within the scope of sound medical judgment. The specific therapeutically effective dose level for any particular patient will depend upon a variety of factors including the disorder being treated and the severity of the disorder; activity of the specific polypeptide employed; the specific composition employed, the age, body weight, general health, sex and diet of the patient; the time of administration, route of administration, and rate of excretion of the specific polypeptide employed; the duration of the treatment; drugs used in combination or coincidental with the specific polypeptide employed; and like factors well known in the medical arts. For example, it is well known within the skill of the art to start doses of the compound at levels lower than those required to achieve the desired therapeutic effect and to gradually increase the dosage until the desired effect is achieved.

As used herein, the term "subject" or "individual" or "patient" are used interchangeably and may encompass a human or a non-human mammal, rodent or non-rodent. The term includes, but is not limited to, mammals, e.g., humans including man, woman and child, other primates (monkey), pigs, rodents such as mice and rats, rabbits, guinea pigs, hamsters, cows, horses, cats, dogs, sheep and goats.

As used herein, the singular form "a", "an" and "the" include plural references unless the context clearly dictates otherwise. For example, the term "a pharmaceutically acceptable carrier" encompasses a plurality of pharmaceutically acceptable carriers, including mixtures thereof.

As used herein, "a plurality of" may thus include «two» or «two or more».

As used herein, "antibody" or "immunoglobulin" may refer to a natural or conventional antibody in which two heavy chains are linked to each other by disulfide bonds and each heavy chain is linked to a light chain by a disulfide bond. There are two types of light chain, lambda (λ) and kappa (κ). There are five main heavy chain classes (or isotypes) which determine the functional activity of an antibody molecule: IgM, IgD, IgG, IgA and IgE. Each chain contains distinct sequence domains. The light chain includes two domains or regions, a variable domain ($V_L$) and a constant domain ($C_L$). The heavy chain generally includes four domains, a variable domain ($V_H$) and three constant domains ($C_H1$, $C_H2$ and $C_H3$, collectively referred to as $C_H$). In particular, classes IgG, IgA, and IgD have three heavy chain constant region domains, which are designated $C_H1$ $C_H2$, and $C_H3$; and the IgM and IgE classes have four heavy chain constant region domains, $C_H1$, $C_H2$, $C_H3$, and $C_H4$. The variable regions of both light ($V_L$) and heavy ($V_H$) chains determine binding recognition and specificity to the antigen. The constant region domains of the light (CL) and heavy (CH) chains confer important biological properties such as antibody chain association, secretion, trans-placental mobility, complement binding, and binding to Fc receptors (FcR). The Fv fragment is the N-terminal part of the antigen-binding fragment (Fab) of an immunoglobulin and consists of the variable portions of one light chain and one heavy chain.

As used herein, when referring to "IgG" or "Immunoglobulin G" in general, IgG1, IgG2, IgG3 and IgG4 are included, unless defined otherwise. In particular, IgG is IgG1.

As used herein, the term "antibody-like" or "immunoglobulin-like" polypeptide may also refer to non-conventional or synthetic antigen-binding polypeptides or binding protein, including single domain antibodies and fragments thereof, in particular variable heavy chain of single domain antibodies, and chimeric, humanized, bispecific or multimeric antibodies.

As used herein, the term "multifunctional binding protein" encompass a multi-chain protein, including but not limited to antibody-like polypeptide or protein formats, which comprises at least one first variable region (e.g. a first immunoglobulin heavy chain variable domain ($V_H$) and/or an immunoglobulin light chain variable domain ($V_L$)) binding specifically to a human CD123 polypeptide, and at least one second variable region (e.g, a second immunoglobulin heavy chain variable domain ($V_H$) and/or immunoglobulin light chain variable domain ($V_L$)) binding specifically to a human NKp46 polypeptide. Although not limited specifically to a particular type of construct, one general embodiment is particularly considered throughout the specification: the polypeptide constructs reported in WO2015197593 and WO2017114694, each of which is incorporated herein by reference. In particular, the multifunctional binding protein such as those reported in WO2015197593 and WO2017114694, may encompass any construct comprising one or more polypeptide chains.

As used herein, the term "humanized", as in "humanized antibody" refers to a polypeptide (i.e., an antibody or an antibody-like polypeptide) which is wholly or partially of non-human origin and which has been modified to replace certain amino acids, in particular in the framework regions of the heavy and light chains, in order to avoid or minimize an immune response in humans. The constant domains of a humanized antibody are most of the time human $C_H$ and $C_L$ domains. Numerous methods for humanization of an antibody sequence are known in the art; see e.g., the review by Almagro & Fransson (2008) Front Biosci. 13: 1619-1633. One commonly used method is CDR grafting, or antibody reshaping, which involves grafting of the CDR sequences of a donor antibody, generally a mouse antibody, into the framework scaffold of a human antibody of different specificity.

For chimeric antibodies, humanization typically involves modification of the framework regions of the variable region sequences. Amino acid residues that are part of a CDR will typically not be altered in connection with humanization, although in certain cases it may be desirable to alter individual CDR amino acid residues, for example to remove a glycosylation site, a deamidation site or an undesired cysteine residue. N-linked glycosylation occurs by attachment of an oligosaccharide chain to an asparagine residue in the tripeptide sequence Asn-X-Ser or Asn-X-Thr, where X may be any amino acid except Pro. Removal of an N-glycosylation site may be achieved by mutating either the Asn or the Ser/Thr residue to a different residue, in particular by way of conservative substitution. Deamidation asparagine and glutamine residues can occur depending on factors such as pH and surface exposure. Asparagine residues are particularly susceptible to deamidation, primarily when present in the sequence Asn-Gly, and to a lesser extent in other dipeptide sequences such as Asn-Ala. When such a deamidation site, in particular Asn-Gly, is present in a CDR sequence, it may therefore be desirable to remove the site, typically by conservative substitution to remove one of the implicated residues. Substitution in a CDR sequence to remove one of the implicated residues is also intended to be encompassed by the claimed multifunctional binding protein.

As used herein, the term "conservative amino acid substitution" refers to substitutions in which an amino acid residue is replaced with an amino acid residue having a side chain with similar physicochemical properties. Families of amino acid residues having similar side chains are known in the art, and include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, leucine, isoleucine, proline, phenylalanine, methionine), and aromatic side chains (e.g., tyrosine, phenylalanine, tryptophan). When an amino acid belongs to two different classes (i.e., tyrosine & phenylalanine), both can be accepted. As a reference, the following classification will be followed throughout the specification, unless stated otherwise.

| Conservative Substitution | Type of Amino acid |
| --- | --- |
| Ala, Val, Leu, Ile, Met, Pro, Phe, Trp | Amino acids with non-polar side chains |
| Ser, Thr, Tyr, Asn, Gln, Cys, Gly | Amino acids with uncharged polar side chains |
| Asp, Glu | Amino acids with acidic side chains |
| Lys, Arg, His | Amino acids with basic side chains |
| Tyr, Phe, Trp, | Aromatic amino acids |

As used herein, the term "domain" may be any region of a protein, generally defined on the basis of sequence homologies or identities, which is related to a specific structural or functional entity. Accordingly, the term "region", as used in the context of the present disclosure, is broader in that it may comprise additional regions beyond the corresponding domain.

As used herein, the terms "linker region", "linker peptide" or "linker polypeptide" or "amino acid linker" or "linker" refer to any amino acid sequence suitable for covalently linking two polypeptide domains, such as two antigen-binding domains together and/or a Fc region to one or more variable regions, such as one or more antigen-binding domains. Although the term is not limited to a particular size or polypeptide length, such amino acid linkers are generally less than 50 amino acids in length, preferably less than 30 amino acids in length, for instance 20 or less than 20 amino acids in length, for instance 15 or less than 15 amino acids in length. Such amino acid linkers may optionally comprise all or part of an immunoglobulin polypeptide chain, such as all or part of a hinge region of an immunoglobulin. Alternatively, the amino acid linker may comprise a polypeptide sequence that is not derived from a hinge region of an immunoglobulin, or even that is not derived from an immunoglobulin heavy or light polypeptide chain.

As used herein, an immunoglobulin hinge region, or a fragment thereof, may thus be considered as a particular type of linker, which is derived from an immunoglobulin polypeptide chain.

As used herein, the term "hinge region" or "hinge" refers to a generally flexible region and born by the corresponding heavy chain polypeptides, and which separates the Fc and Fab portions of certain isotypes of immunoglobulins, more particularly of the IgG, IgA or IgD isotypes. Such hinge regions are known in the Art to depend upon the isotype of immunoglobulin which is considered. For native IgG, IgA and IgD isotypes, the hinge region thus separates the $C_H1$ domain and the $C_H2$ domain and is generally cleaved upon papain digestion. On the other hand, the region corresponding to the hinge in IgM and IgE heavy chains is generally formed by an additional constant domain with lower flexibility. Additionally, the hinge region may comprise one or more cysteines involved in interchain disulfide bonds. The hinge region may also comprise one or more binding sites to a Fcγ receptor, in addition to FcγR binding sites born by the $C_H2$ domain, when applicable. Additionally, the hinge region may comprise one or more post-translational modification, such as one or more glycosylated residues depending on the isotype which is considered. Thus, it will be readily understood that the reference to the term "hinge" throughout the specification is not limited to a particular set of hinge sequences or to a specific location on the structure. Unless instructed otherwise, the hinge regions which are still particularly considered comprise all or part of a hinge from an immunoglobulin belonging to one isotype selected from: the IgG isotype, the IgA isotype and the IgD isotype; in particular the IgG isotype.

As used herein, the terms "CH domain", or "$C_H$ domain", or "constant domain", can be used interchangeably and refer to any one or more heavy chain immunoglobulin constant domain(s). Such $C_H$ domains are natively folded as immunoglobulin-like domains, although they may be partly disordered in an isolated form (e.g., $C_H1$ domains when not associated with the constant domain of a light chain ($C_L$)). Unless instructed otherwise, the term may thus refer to a $C_H1$ domain, a $C_H2$ domain, a $C_H3$ domain; or any combinations thereof.

As used herein, the terms "$C_H1$ domain", or "$C_H1$ domain", or "constant domain 1", can be used interchangeably and refer to the corresponding heavy chain immunoglobulin constant domain 1.

As used herein, the term "$C_H2$ domain", or "$C_H2$ domain", or "constant domain 2" can be used interchangeably and refer to the corresponding heavy chain immunoglobulin constant domain 2.

As used herein, the term "$C_H3$ domain", or "$C_H3$ domain", or "constant domain 3" can be used interchangeably and refer to the corresponding heavy chain immunoglobulin constant domain 3.

As used herein, the term "$C_H2$-$C_H3$", as in $(C_H2\text{-}C_H3)_A$ and $(C_H2\text{-}C_H3)_B$, thus refers to a polypeptide sequence comprising an immunoglobulin heavy chain constant domain 2 ($C_H2$) and an immunoglobulin heavy chain constant domain 3 ($C_H3$).

As used herein, the term "CL domain", or "$C_L$ domain" can be used interchangeably and refer to the corresponding light chain immunoglobulin constant domain. Unless instructed otherwise, this term may thus encompass a $C_L$ domain of the kappa (κ or к) or lambda (λ) class of immunoglobulin light chains, including all known subtypes (e.g. $λ_1$, $λ_2$, $λ_3$, and $λ_7$). In particular, when the $C_L$ domain is of the kappa class, it may also be referred herein as a Cκ or $C_K$ or $C_k$ domain.

As used herein, the terms "pair C ($C_H1/C_L$)", or "paired C ($C_H1/C_L$)" "refers to one constant heavy chain domain 1 and one constant light chain domain (e.g., a kappa (κ or к) or lambda (λ) class of immunoglobulin light chains) bound to one another by covalent or non-covalent bonds, preferably non-covalent bonds; thus forming a heterodimer. Unless specified otherwise, when the constant chain domains forming the pair are not present on a same polypeptide chain, this term may thus encompass all possible combinations. Preferably, the corresponding $C_H1$ and $C_L$ domains will thus be selected as complementary to each other, such that they form a stable pair C ($C_H1/C_L$).

Advantageously, when the binding protein comprises a plurality of paired C domains, such as one "pair $C_1$ ($C_H1/C_L$)" and one "pair $C_2$ ($C_H1/C_L$)", each $C_H1$ and $C_L$ domain forming the pairs will be selected so that they are formed between complementary $C_H1$ and $C_L$ domains. Examples of complementary $C_H1$ and $C_L$ domains have been previously described in the international patent applications WO2006064136 or WO2012089814 or WO2015197593A1.

Unless instructed otherwise, the terms "pair $C_1$ ($C_H1/C_L$)" or "pair $C_2$ ($C_H1/C_L$)" may refer to distinct constant pair domains ($C_1$ and $C_2$) formed by identical or distinct constant heavy 1 domains ($C_H1$) and identical or distinct constant light chain domains ($C_L$). Preferably, the terms "pair $C_1$ ($C_H1/C_L$)" or "pair C2 ($C_H1/C_L$)" may refer to distinct constant pair domains ($C_1$ and $C_2$) formed by identical constant heavy 1 domains ($C_H1$) and identical constant light chain domains ($C_L$).

As used herein, the term "Fc region" or "fragment crystallizable region", or alternatively "Fc portion", encompasses all or parts of the "Fc domain", which may thus include all or parts of an immunoglobulin hinge region (which natively bears a first binding site to FcγRs), a $C_H2$ domain (which natively bears a second binding site to FcγRs), and a $C_H3$ domain of an immunoglobulin (e.g. of an IgG, IgA or IgD immunoglobulin), and/or when applicable of a $C_H4$ domain of an immunoglobulin (e.g. for IgM and IgE). Preferably, the Fc region includes all or parts of, at least, a $C_H2$ domain and a $C_H3$ domain, and optionally all or parts of an immunoglobulin hinge region. The term may thus refer to a molecule comprising the sequence of a non-antigen-binding fragment resulting from digestion of an antibody or produced by other means, whether in monomeric or multimeric form, and can contain the hinge region. The original immunoglobulin source of the native Fc is, in particular, of human origin and can be any of the immunoglobulins, although IgG1 are preferred. Native Fc molecules are made up of monomeric polypeptides that can be linked into dimeric or multimeric forms by covalent (i.e., disulfide bonds) and non-covalent association. The number of intermolecular disulfide bonds between monomeric subunits of native Fc molecules ranges from 1 to 13 depending on class (e.g., IgG, IgA, and IgE) or subclass (e.g., IgG1, IgG2, IgG3, IgGA1, and IgGA2). One example of a native Fc is a disulfide-bonded dimer resulting from papain digestion of an IgG. The term "native Fc" as used herein is generic to the monomeric, dimeric, and multimeric forms. Under that terminology, a "Fc region" may thus comprise or consist of $C_H2$-$C_H3$ (e.g., $(C_H2\text{-}C_H3)_A$ or $(C_H2\text{-}C_H3)_B$ or a binding pair thereof, and optionally all or part of an immunoglobulin hinge region, comprising a binding site to a human FcγR.

Unless specified otherwise, the term "Fc region" may refer to either a native or variant Fc region.

The term "Fc variant" as used herein refers to a molecule or sequence that is modified from a native Fc but still comprises a binding site for the receptor, FcRn (neonatal Fc receptor). Exemplary Fc variants, and their interaction with the receptor, are known in the art. Thus, the term "Fc variant" can comprise a molecule or sequence that is humanized from a non-human native Fc. Furthermore, a native Fc comprises regions that can be removed because they provide structural features or biological activity that are not required for the antibody-like binding proteins of the invention. Thus, the term "Fc variant" comprises a molecule or sequence that lacks one or more native Fc sites or residues, or in which one or more Fc sites or residues has be modified, that affect or are involved in: (1) disulfide bond formation, (2) incompatibility with a selected host cell, (3) N-terminal heterogeneity upon expression in a selected host cell, (4) glycosylation, (5) interaction with complement, (6) binding to an Fc receptor other than a salvage receptor, or (7) antibody-dependent cellular cytotoxicity (ADCC).

The fragment crystallizable (Fc) regions (e.g., native or variant) according to the present disclosure retain a capacity to bind to a human Fc-γ receptor polypeptide (Fcγ) which generally occurs on native Fc regions through binding of the antibody Fc-hinge region. As a reference, overall structures of IgG1, IgG2, and IgG4 are similar with more than 90% sequence homology, the major differences residing in the hinge region and $C_H2$ domain, which form primary binding sites to FcγRs. The hinge region also functions as a flexible linker between the Fab and Fc portion.

Fc regions having one or more amino acid modifications substitutions, deletions, insertions) in one or more portions, which modifications increase the affinity and avidity of the variant Fc region for an FcγR (including activating and inhibitory FcγRs) are further considered as Fc regions. In some embodiments, said one or more amino acid modifications increase the affinity of the Fc region for FcγRIIIA and/or FcγRIIA. In another embodiment, the variant Fc region further specifically binds FcγRIIB with a lower affinity than does the Fc region of the reference parent antibody (e.g., an antibody having the same amino acid sequence as the antibody except for the one or more amino acid modifications in the Fc region). Hence, native and variant Fc regions considered herein generally comprise a domain (i.e., a $C_H2$ domain) capable of binding to human CD16, e.g., a human Fc domain comprising N-linked glycosylation at amino acid residue N297 (according to EU numbering).

As used herein, the term "Fc-competent" thus refers to a binding protein that is capable of binding specifically to a FcγR, in particular of an activating FcγR, in particular to one selected from FcγRI (CD64a), FcγRIIa (CD32a), and FcγRIIIa (CD16a), and more particularly to FcγRIIIa (CD16a).

Alternatively, several modifications are reported to directly affect the binding to FcγRs, including mutation on residues 297 (according to EU numbering), or alternatively on residues 234 and 235 in the lower hinge region (according to the EU numbering system).

As used herein, the term "Fc-silent" refers to a binding protein with a Fc region, wherein the Fc region lacks a binding site to a FcγR (e.g., a Fc region lacking a $C_H2$ domain with said binding site and hinge region with said binding site); in particular FcγRI, FcγRIIa, and FcγRIIIa, and more particularly to FcγRIIIa (CD16a).

As used herein, the term "variable", as in "variable domain", refers to certain portions of the relevant binding protein which differ extensively in sequence between and among antibodies and are used in the specific recognition and binding of a particular antibody for its particular target. However, the variability is not evenly distributed throughout the entire variable domains of antibodies. The variability is concentrated in three segments called complementarity determining regions (CDRs; i.e., CDR1, CDR2, and CDR3) also known as hypervariable regions, both in the light chain and the heavy chain variable domains. The more highly conserved portions of variable domains are called the framework (FR) regions or sequences.

As used herein, the term "VH domain", or "$V_H$ domain" can be used interchangeably and refer to the corresponding heavy chain immunoglobulin variable domain.

As used herein, the term "VL domain", or "$V_L$ domain" can be used interchangeably and refer to the corresponding light chain immunoglobulin variable domain.

When the VH or VL domains are associated to a first antigen-binding domain (ABD) or to a second antigen-binding domain, they may also be respectively referred herein as "$V_H1$" and "$V_L1$", or "$V_H2$" and "$V_L2$".

The terms "binding pair V (VH/VL)", "$V_H/V_L$ pair" "($V_H/V_L$) pair" or "$V_L/V_H$ pair" or "($V_L/V_H$) pair" can be used interchangeably. Heavy chain and light chain variable domain can pair in parallel to form the antigen binding domains (ABDs). Each binding pair includes both a $V_H$ and a $V_L$ region. Unless instructed otherwise, these terms do not specify which immunoglobulin variable regions are $V_H$ or $V_L$ regions and which ABD will bind specifically the protein expressed on the surface of an immune effector cell or a target cell (e.g., NKp46 and CD123).

As used herein, the term "hypervariable region" when used herein refers to the amino acid residues of an antibody that are responsible for antigen binding. This term may be substituted by the terms "Complementarity Determining Regions" or "CDRs".

Thus, as used herein "Complementarity Determining Regions" or "CDRs" refer to amino acid sequences that together define the binding affinity and specificity of the natural Fv region of a native immunoglobulin binding site. The light and heavy chains of an immunoglobulin each have three CDRs, designated CDR-L1, CDR-L2, CDR-L3 and CDR-H1, CDR-H2, CDR-H3, respectively. A conventional antibody antigen-binding domain, therefore, includes six CDRs, comprising the CDR set from each of a heavy and a light chain variable region. Also, as used herein, "Framework Regions" (FRs) refer to amino acid sequences interposed between CDRs, i.e., to those portions of immunoglobulin light and heavy chain variable regions that are relatively conserved among different immunoglobulins in a single species. The light and heavy chains of an immunoglobulin each have four FRs, designated FR-L1, FR-L2, FR-L3, FR-L4, and FR-H1, FR-H2, FR-H3, FR-H4, respectively. Accordingly, the light chain variable domain may thus be designated as (FR-L1)-(CDR-L1)-(FR-L2)-(CDR-L2)-(FR-L3)-(CDR-L3)-(FR-L4) and the heavy chain variable domain may thus be designated as (FR-H1)-(CDR-H1)-(FR-H2)-(CDR-H2)-(FR-H3)-(CDR-H)-(FR4-H3).

The hypervariable region generally comprises amino acid residues from a "complementarity-determining region" or "CDR" (e.g. residues 24-34 (L1), 50-56 (L2) and 89-97 (L3) in the light-chain variable domain and 31-35 (H1), 50-65 (H2) and 95-102 (H3) in the heavy-chain variable domain; Kabat et al. 1991) and/or those residues from a "hypervariable loop" (e.g. residues 26-32 (L1), 50-52 (L2) and 91-96

(L3) in the light-chain variable domain and 26-32 (H1), 53-55 (H2) and 96-101 (H3) in the heavy-chain variable domain; Chothia and Lesk, J. Mol. Biol 1987; 196:901-917). The numbering of amino acid residues in this region is performed by the method described in Kabat et al., supra. Accordingly, phrases such as "Kabat position", "variable domain residue numbering as in Kabat" and "according to Kabat" herein refer to this numbering system for heavy chain variable domains or light chain variable domains. Using the Kabat numbering system, the actual linear amino acid sequence of a peptide may contain fewer or additional amino acids corresponding to a shortening of, or insertion into, a FR or CDR of the variable domain. For example, a heavy chain variable domain may include a single amino acid insert (residue 52a according to Kabat) after residue 52 of CDR H2 and inserted residues (e.g., residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

Optionally, CDRs are as defined by EU, Kabat, Chotia or IMGT numbering. Correspondences between those classifications are known in the Art, by reference to the IMGT®, or international ImMunoGeneTics information system® (CNRS and Montpellier University), and as further detailed in Lefranc (Biomolecules; 2014; 4, 1102-1139) and Dondelinger (Frontiers in Immunology; 2018; 9, 2278).

Unless instructed otherwise, the numbering of residues will be considered herein by reference to the EU, Kabat, Chotia or IMGT numbering convention. In case of conflict regarding the exact position of hypervariable regions within a reference sequence, the Kabat numbering convention will prevail. In case of conflict regarding the exact position of constant regions within a reference sequence, the EU numbering convention will prevail.

As used herein, the term "cytotoxicity" refers to the quality of a compound, such as the multifunctional binding protein according to the present disclosure, to be toxic to tumoral cells. Cytotoxicity may be induced by different mechanisms of action and can thus be divided into cell-mediated cytotoxicity, apoptosis, antibody-dependent cell-mediated cytotoxicity (ADCC), antibody-dependent cellular phagocytosis (ADCP) or complement-dependent cytotoxicity (CDC).

As used herein, the term "antibody-dependent cell-mediated cytotoxicity" or "ADCC" refers to a mechanism of cell-mediated immune defence whereby an effector cell of the immune system actively lyses a target cell, whose membrane-surface antigens have been bound by specific antibodies or the multifunctional binding protein of the present disclosure.

As used herein, the terms "proliferative disorders", "hyper proliferative disorders" and/or "cancer" not only refer to solid tumors, such as cancers of the breast, respiratory tract, brain, reproductive organs, digestive tract, urinary tract, eye, liver, skin, head and neck, thyroid, parathyroid and their distant metastases, but also include blood cancers, including tumors of the hematopoietic and lymphoid tissues, such as lymphomas, myelomas, and leukemias. Leukemias include, but are not limited to acute myeloid leukemia, acute lymphoblastic leukemia, chronic lymphocytic leukemia, chronic myelogenous leukemia, and hairy cell leukemia.

As used herein, "Acute myelogenous leukemia (AML)" is a clonal disorder clinically presenting as increased proliferation of heterogeneous and undifferentiated myeloid blasts. Without wishing to be bound by the theory, the leukemic hierarchy is maintained by a small population of LSCs (Leukemic Stem Cells) (AML-LSCs), which have the distinct ability for self-renewal, and are able to differentiate into leukemic progenitors. These progenitors generate the large numbers of leukemic blasts readily detectable in patients at diagnosis and relapse, leading ultimately to mortality. AML-LSC have been commonly reported as quiescent cells, in contrast to rapidly dividing clonogenic progenitors.

Within the context of AML, the term "relapse" may in particular be defined as the reoccurrence of AML after complete remission. In that sense "complete remission" or "CR" may be defined as follows: normal values for neutrophil ($>1.0*10^9$/L), haemoglobin level of 10 g/dl and platelet count ($>100*10^9$/L) and independence from red cell transfusion; blast cells less than 5%, no clusters or collections of blasts, and absence of Auer rods on bone marrow examination; and normal maturation of blood cells (morphology; myelogramme) and absence of extramedullary leukemia.

As used herein, "myelodysplastic syndromes" ("MDS"), formerly known as preleukemia, are a collection of hematological conditions that involve ineffective production (or dysplasia) of the myeloid class of blood cells. They represent a spectrum of clonal hematopoietic stem cell disorders characterized by progressive bone marrow failure and increased risk of progression to acute myeloid leukemia ("AML", also known as "acute myelogenous leukemia"). The International Prognostic Scoring System ("IPSS") is widely used to identify patients with high-risk features based on the severity of their cytopenias, bone marrow myeloblast percentage, and cytogenetic abnormalities.

As used herein, a "pharmaceutically acceptable carrier" is intended to include any and all carrier (such as any solvents, dispersion media, coatings, antibacterial and antifungal agents, isotonic and absorption delaying agents, and the like) which is compatible with pharmaceutical administration, in particular parenteral administration. The use of such media and agents for pharmaceutically active substances are known. Except insofar as any conventional media or agent is incompatible with the active compound, such media can be used in the compositions of the present disclosure. For example, preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. In a non-exhaustive manner, pharmaceutically acceptable carriers include, but are not limited to, 0.01-0.1M (e.g., 0.05M) phosphate buffer or 0.8% saline. Other common parenteral vehicles include sodium phosphate solutions, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present such as for example, antimicrobials, antioxidants, chelating agents, and inert gases and the like. More particularly, pharmaceutical compositions suitable for injectable use include sterile aqueous solutions (where water soluble) or dispersions and sterile powders for the extemporaneous preparation of sterile injectable solutions or dispersions. In such cases, the composition must be sterile and should be fluid to the extent that easy syringeability exists. It should be stable under the conditions of manufacture and storage and will in an embodiment be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal and the like. In certain embodiments, isotonic agents are included, for example, sugars, polyalcohols, such as mannitol, sorbitol, or sodium chloride in the composition. Prolonged absorption of the injectable compositions can be brought about by including in the composition an agent which delays absorption, for example, aluminum monostearate and gelatin.

As used herein, and unless instructed otherwise, the term "at least one" may encompass "one or more", or even "two or more" (or "a plurality"). For instance, it may encompass 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or more than 100.

As used herein, and unless instructed otherwise, the term "less than . . . " may encompass all values from 0 to the corresponding threshold, For instance, it may encompass less than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or less than 100, when applicable.

As used herein, the term "cell" may encompass any prokaryotic cell or eukaryotic cell. Cell types which are particularly considered are those suitable for the production and/or engineering of recombinant antibodies, or fragments, or polypeptide chains thereof. In a non-exhaustive manner, such cells may be selected from the group consisting of: bacterial cells, yeast cells, mammalian cells, non-mammalian cells, insect cells, and plant cells.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell but may contain mutations. Mutant progeny that have the same function or biological activity as screened or selected for in the originally transformed cell are included herein. A host cell is any type of cellular system that can be used to generate binding proteins of the present disclosure. Host cells may thus include cultured cells, e.g., mammalian cultured cells, such as CHO cells, HEK cells, BHK cells, NSO cells, SP2/0 cells, YO myeloma cells, P3X63 mouse myeloma cells, PER cells, PER.C6 cells or hybridoma cells, bacterial cells, yeast cells, insect cells, and plant cells, to name only a few.

By "isolated" nucleic acid molecule or polynucleotide is intended a nucleic acid molecule, DNA or RNA, which has been removed from its native environment. For example, a recombinant polynucleotide encoding a polypeptide contained in a vector is considered isolated for the purposes of the present disclosure. Further examples of an isolated polynucleotide include recombinant polynucleotides maintained in heterologous host cells or purified (partially or substantially) polynucleotides in solution. An isolated polynucleotide includes a polynucleotide molecule contained in cells that ordinarily contain the polynucleotide molecule, but the polynucleotide molecule is present extrachromosomally or at a chromosomal location that is different from its natural chromosomal location. Isolated RNA molecules include in vivo or in vitro RNA transcripts of the present disclosure, as well as positive and negative strand forms, and double-stranded forms. Isolated polynucleotides or nucleic acids according to the present disclosure further include such molecules produced synthetically. In addition, a polynucleotide or a nucleic acid may be or may include a regulatory element such as a promoter, ribosome binding site, or a transcription terminator.

The term "vector' or "expression vector" is intended to mean the vehicle by which a nucleic acid, in particular a DNA or RNA sequence (e.g., a foreign gene), can be introduced into a host cell, so as to transform the host and promote expression (e.g., transcription and translation) of the introduced sequence.

II. Binding Protein

In one embodiment, the disclosure relates to a binding protein characterized in that it comprises:

(i) a first antigen-binding domain (ABD) comprising a variable region which binds specifically to a human CD123 polypeptide, (ii) a second antigen-binding domain (ABD) comprising a variable region which binds specifically to a human NKp46 polypeptide, and (iii) all or part of an immunoglobulin Fc region or variant thereof which binds to a human Fc-γ receptor.

In some embodiments, the binding protein is characterized in that it comprises:

(i) a first antigen-binding domain (ABD) comprising a variable region which binds specifically to a human CD123 polypeptide and comprising at least one CDR selected from SEQ ID NO: 1 to SEQ ID NO: 12, or a variant thereof with one or more conservative substitution(s);

(ii) a second antigen-binding domain (ABD) comprising a variable region which binds specifically to a human NKp46 polypeptide, and (iii) all or part of an immunoglobulin Fc region or variant thereof which binds to a human Fc-γ receptor polypeptide.

In some embodiments, the disclosure relates to a binding protein characterized in that it comprises:

(i) a first antigen-binding domain (ABD) comprising a variable region which binds specifically to a human CD123 polypeptide, (ii) a second antigen-binding domain (ABD) comprising a variable region which binds specifically to a human NKp46 polypeptide and comprising at least one CDR selected from SEQ ID NO: 13 to SEQ ID NO: 40, or a variant thereof with one or more conservative substitution(s);

and (iii) all or part of an immunoglobulin Fc region or variant thereof which binds to a human Fc-γ receptor polypeptide.

In some embodiments, the binding protein is characterized in that it comprises:

(i) a first antigen-binding domain (ABD) comprising a variable region which binds specifically to a human CD123 polypeptide and comprising at least one CDR selected from SEQ ID NO: 1 to SEQ ID NO: 12, or a variant thereof with one or more conservative substitution(s); and (ii) a second antigen-binding domain (ABD) comprising a variable region which binds specifically to a human NKp46 polypeptide and comprising at least one CDR selected from SEQ ID NO: 13 to SEQ ID NO: 40, or a variant thereof with one or more conservative substitution(s);

and (iii) all or part of an immunoglobulin Fc region or variant thereof which binds to a human Fc-γ receptor polypeptide.

In some embodiments, the binding protein is characterized in that it comprises:

(i) a first antigen-binding domain (ABD) comprising a variable region which binds specifically to a human CD123 polypeptide and comprising three CDRs selected from SEQ ID NO: 1 to SEQ ID NO: 12, or a variant thereof with one or more conservative substitution(s), and (ii) a second antigen-binding domain (ABD) comprising a variable region which binds specifically to a human NKp46 polypeptide and comprising three CDRs selected from SEQ ID NO: 13 to SEQ ID NO: 40, or a variant thereof with one or more conservative substitution(s), and (iii) all or part of an immunoglobulin Fc region or variant thereof which binds to a human Fc-γ receptor polypeptide.

In some embodiments, the binding protein is characterized in that it comprises:

(i) a first antigen-binding domain (ABD) comprising a variable region which binds specifically to a human CD123 polypeptide, and comprising an immunoglobulin heavy chain variable region ($V_H$) and an immunoglobulin light chain variable region ($V_L$), wherein each $V_H$ and $V_L$ comprises three complementary determining regions (CDR-1 to CDR-3 respectively), and (ii) a second antigen-binding domain (ABD) comprising a variable region which binds specifically to a human NKp46 polypeptide, and comprising an immunoglobulin light chain variable region ($V_L$), wherein each $V_H$ and $V_L$ comprises three complementary determining regions (CDR-1 to CDR-3 respectively), and (iii) all or part of an immunoglobulin Fc region or variant thereof which binds to a human Fc-γ receptor polypeptide.

In some embodiments, the binding protein is characterized in that it comprises:

(i) a first antigen-binding domain (ABD) comprising a variable region which binds specifically to a human CD123 polypeptide, and comprising an immunoglobulin heavy chain variable region ($V_H$) with three complementary determining regions, at least one being selected from SEQ ID NO: 1 to SEQ ID NO: 6, and an immunoglobulin light chain variable region ($V_L$) with three complementary determining regions, at least one being selected from SEQ ID NO: 7 to SEQ ID NO: 12;

(ii) a second antigen-binding domain (ABD) comprising a variable region which binds specifically to a human NKp46 polypeptide, and comprising an immunoglobulin heavy chain variable region ($V_H$) with three complementary determining regions at least one being selected from SEQ ID NO: 13 to SEQ ID NO: 26, and an immunoglobulin light chain variable region ($V_L$) with three complementary determining regions at least one being selected from SEQ ID NO: 27 to SEQ ID NO: 40; and (iii) all or part of an immunoglobulin Fc region or variant thereof which binds to a human Fc-γ receptor polypeptide.

In some embodiments, the binding protein is characterized in that it comprises:

(i) a first antigen-binding domain (ABD) comprising a variable region which binds specifically to a human CD123 polypeptide, and comprising an immunoglobulin heavy chain variable region ($V_H$) with three complementary determining regions, at least two being selected from SEQ ID NO: 1 to SEQ ID NO: 6, and an immunoglobulin light chain variable region ($V_L$) with three complementary determining regions at least two being selected from SEQ ID NO: 7 to SEQ ID NO: 12;

(ii) a second antigen-binding domain (ABD) comprising a variable region which binds specifically to a human NKp46 polypeptide, and comprising an immunoglobulin heavy chain variable region ($V_H$) with three complementary determining regions at least two being selected from SEQ ID NO: 13 to SEQ ID NO: 26, and an immunoglobulin light chain variable region ($V_L$) with three complementary determining regions at least two being selected from SEQ ID NO: 27 to SEQ ID NO: 40; and (iii) all or part of an immunoglobulin Fc region or variant thereof which binds to a human Fc-γ receptor polypeptide.

In some embodiments, the binding protein is characterized in that it comprises:

(i) a first antigen-binding domain (ABD) comprising a variable region which binds specifically to a human CD123 polypeptide, and comprising an immunoglobulin heavy chain variable region ($V_H$) with three complementary determining regions, selected from SEQ ID NO: 1 to SEQ ID NO: 6, and an immunoglobulin light chain variable region ($V_L$) with three complementary determining regions selected from SEQ ID NO: 7 to SEQ ID NO: 12;

(ii) a second antigen-binding domain (ABD) comprising a variable region which binds specifically to a human NKp46 polypeptide, and comprising an immunoglobulin heavy chain variable region ($V_H$) with three complementary determining regions selected from SEQ ID NO: 13 to SEQ ID NO: 26, and an immunoglobulin light chain variable region ($V_L$) with three complementary determining regions selected from SEQ ID NO: 27 to SEQ ID NO: 40; and (iii) all or part of an immunoglobulin Fc region or variant thereof which binds to a human Fc-γ receptor polypeptide.

In some embodiments, the binding protein is characterized in that the first ABD binds specifically to human CD123 and comprises an immunoglobulin heavy chain variable domain ($V_H$) comprising a CDR-H1, H2 and H3 corresponding to the amino acid sequences of SEQ ID NO: 1 to SEQ ID NO: 3 respectively or corresponding to the amino acid sequences of SEQ ID NO: 4 to SEQ ID NO: 6 respectively.

According to some particular embodiments of this first general object, the binding protein is characterized in that the first ABD binds specifically to human CD123 and comprises an immunoglobulin light chain variable domain ($V_L$) comprising a CDR-L1, L2 and L3 corresponding to the amino acid sequences of SEQ ID NO: 7 to SEQ ID NO: 9 respectively or corresponding to the amino acid sequences of SEQ ID NO: 10 to SEQ ID NO: 12 respectively.

According to some particular embodiments of this first general object, the binding protein is characterized in that the second ABD binds specifically to human NKp46 and comprises an immunoglobulin heavy chain variable domain ($V_H$) comprising a CDR-H1, H2 and H3 corresponding to the amino acid sequences of SEQ ID NO: 13 to SEQ ID NO: 15 respectively.

According to some particular embodiments of this first general object, the binding protein is characterized in that the second ABD binds specifically to human NKp46 and comprises an immunoglobulin heavy chain variable domain ($V_H$) comprising a CDR-H1, H2 and H3 corresponding to the amino acid sequences of SEQ ID NO: 16 to SEQ ID NO: 18 respectively.

According to some particular embodiments of this first general object, the binding protein is characterized in that the second ABD binds specifically to human NKp46 and comprises an immunoglobulin heavy chain variable domain ($V_H$) comprising a CDR-H1, H2 and H3 corresponding to the amino acid sequences of SEQ ID NO: 19 to SEQ ID NO: 21 respectively.

According to some particular embodiments of this first general object, the binding protein is characterized in that the second ABD binds specifically to human NKp46 and comprises an immunoglobulin heavy chain variable domain ($V_H$) comprising a CDR-H1, H2 and H3 corresponding to the amino acid sequences of SEQ ID NO: 22 to SEQ ID NO: 24 respectively.

According to some particular embodiments of this first general object, the binding protein is characterized in that the second ABD binds specifically to human NKp46 and comprises an immunoglobulin heavy chain variable domain ($V_H$) comprising a CDR-H1, H2 and H3 corresponding to the amino acid sequences of SEQ ID NO: 16, SEQ ID NO: 25 and SEQ ID NO: 26 respectively.

According to some particular embodiments of this first general object, the binding protein is characterized in that the second ABD binds specifically to human NKp46 and comprises an immunoglobulin light chain variable domain ($V_L$) comprising a CDR-L1, L2 and L3 corresponding to the amino acid sequences of SEQ ID NO: 27 to SEQ ID NO: 29 respectively.

According to some particular embodiments of this first general object, the binding protein is characterized in that the second ABD binds specifically to human NKp46 and comprises an immunoglobulin light chain variable domain ($V_L$) comprising a CDR-L1, L2 and L3 corresponding to the amino acid sequences of SEQ ID NO: 30 to SEQ ID NO: 32 respectively.

According to some particular embodiments of this first general object, the binding protein is characterized in that the second ABD binds specifically to human NKp46 and comprises an immunoglobulin light chain variable domain ($V_L$) comprising a CDR-L1, L2 and L3 corresponding to the amino acid sequences of SEQ ID NO: 33 to SEQ ID NO: 35 respectively.

According to some particular embodiments of this first general object, the binding protein is characterized in that the second ABD binds specifically to human NKp46 and comprises an immunoglobulin light chain variable domain ($V_L$) comprising a CDR-L1, L2 and L3 corresponding to the amino acid sequences of SEQ ID NO: 36 to SEQ ID NO: 38 respectively.

According to some particular embodiments of this first general object, the binding protein is characterized in that the second ABD binds specifically to human NKp46 and comprises an immunoglobulin light chain variable domain ($V_L$) comprising a CDR-L1, L2 and L3 corresponding to the amino acid sequences of SEQ ID NO: 39, SEQ ID NO: 31 and SEQ ID NO: 40 respectively.

According to one embodiment, the disclosure relates to a binding protein comprising a first and a second antigen binding domains (ABDs) and all or part of an immunoglobulin Fc region or variant thereof, wherein each of said ABDs comprises an immunoglobulin heavy chain variable domain ($V_H$) and an immunoglobulin light chain variable domain ($V_L$), wherein each $V_H$ and $V_L$ comprises three complementary determining regions (CDR-1 to CDR-3); and wherein:

(i) the first ABD binds specifically to human CD123 and comprises:

a $V_{H1}$ comprising a CDR-H1, H2 and H3 corresponding to the amino acid sequences of SEQ ID NO: 1 to SEQ ID NO: 3 respectively or corresponding to the amino acid sequences of SEQ ID NO: 4 to SEQ ID NO: 6 respectively, and a $V_{L1}$ comprising a CDR-L1, L2 and L3 corresponding to the amino acid sequences of SEQ ID NO: 7 to SEQ ID NO: 9 respectively or corresponding to the amino acid sequences of SEQ ID NO: 10 to SEQ ID NO: 12 respectively;

(ii) the second ABD binds specifically to human NKp46 and comprises:

a $V_{H2}$ comprising a CDR-H1, 2 and 3 corresponding to:
the amino acid sequences of SEQ ID NO: 13 to SEQ ID NO: 15 respectively;
the amino acid sequences of SEQ ID NO: 16 to SEQ ID NO: 18 respectively;
the amino acid sequences of SEQ ID NO: 19 to SEQ ID NO: 21 respectively;
the amino acid sequences of SEQ ID NO: 22 to SEQ ID NO: 24 respectively; or
the amino acid sequences of SEQ ID NO: 16, SEQ ID NO: 25 and SEQ ID NO: 26 respectively;
and
a $V_{L2}$ comprising a CDR-L1, 2 and 3 corresponding to:
the amino acid sequences of SEQ ID NO: 27 to SEQ ID NO: 29 respectively;
the amino acid sequences of SEQ ID NO: 30 to SEQ ID NO: 32 respectively;
the amino acid sequences of SEQ ID NO: 33 to SEQ ID NO: 35 respectively;
the amino acid sequences of SEQ ID NO: 36 to SEQ ID NO: 38 respectively; or
the amino acid sequences SEQ ID NO: 39, SEQ ID NO: 31 and SEQ ID NO: 40 respectively;
and wherein all or part of the immunoglobulin Fc region or variant thereof binds to a human Fc-γ receptor.

It will be readily understood by the skilled in the Art that the above described binding protein may consist of one single polypeptide chain, or be a multimeric binding protein, and hence comprise a plurality (two or more) polypeptide chains.

According to some particular embodiments, the binding protein is a multimeric binding protein, and the two antigen-binding domains may be born at least in part by distinct polypeptide chains.

Optionally, when the binding protein comprises a plurality of polypeptide chains, (e.g., two or three polypeptide chains), some of those polypeptide chains may be linked covalently. When two polypeptide chains are linked covalently, the covalent linker(s) may advantageously be selected from disulfide bridges, or any other covalent linker, including peptide bond(s) bridging one polypeptide chain with another, and/or linker peptide(s) bridging one polypeptide chain with another.

According to some particular embodiments, the binding protein is characterized in that it comprises three polypeptide chains (I), (II) and (III) that form two ABDs:

  (I)

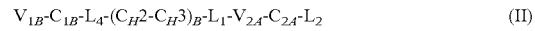  (II)

  (III)

wherein:
$V_{1A}$ and $V_{1B}$ form a binding pair $V_1$ ($V_{H1}/V_{L1}$);
$V_{2A}$ and $V_{2B}$ form a binding pair $V_2$ ($V_{H2}/V_{L2}$);
$C_{1A}$ and $C_{1B}$ form a pair $C_1$ ($C_H1/C_L$) and $C_{2A}$ and $C_{2B}$ form a pair $C_2$ ($C_H1/C_L$) wherein $C_H1$ is an immunoglobulin heavy chain constant domain 1 and $C_L$ is an immunoglobulin light chain constant domain;
$(C_H2\text{-}C_H3)_A$ and $(C_H2\text{-}C_H3)_B$ are identical or different, and comprise an immunoglobulin heavy chain constant domain 2 ($C_H2$) and an immunoglobulin heavy chain constant domain 3 ($C_H3$);
$L_1$, $L_2$, $L_3$, $L_4$ are optional independent amino acid linkers, which may be identical or different.

In some embodiments, the $(C_H2\text{-}C_H3)_A$ and $(C_H2\text{-}C_H3)_B$ comprise each at least one identical $C_H2$ domain, such as a $C_H2$ domain corresponding to the amino acid sequence of SEQ ID NO: 71.

In some embodiments, the $(C_H2\text{-}C_H3)_A$ and $(C_H2\text{-}C_H3)_B$ are identical or different and may comprise a polypeptide sequence selected from amino acid sequences of SEQ ID NO: 69 or SEQ ID NO: 70.

In some embodiments, some of $L_1$, $L_2$, $L_3$ and $L_4$ may be identical or different, and may comprise all or part of an amino acid sequence selected from SEQ ID NO: 74 to SEQ ID NO: 79; for example, one or more than four consecutive amino acids of an amino acid sequence selected from SEQ ID NO: 74 to SEQ ID NO: 79.

According to some particular embodiments, some of $L_1$, $L_2$, $L_3$ and $L_4$ may be identical or different, and may comprise all or part of an immunoglobulin hinge region, such as one selected from amino acid sequences SEQ ID NO: 74, SEQ ID NO: 75, SEQ ID NO: 77, SEQ ID NO: 78 and/or SEQ ID NO: 79; for example four or more than four consecutive amino acids of an immunoglobulin hinge region, such as one selected from amino acid sequences SEQ ID NO: 74, SEQ ID NO: 75, SEQ ID NO: 77, SEQ ID NO: 78 and/or SEQ ID NO: 79.

According to some more particular embodiments, $L_2$, $L_3$ and $L_4$ may be identical or different, and may comprise all or part of an immunoglobulin hinge region, such as one selected from sequences SEQ ID NO: 74, SEQ ID NO: 75, SEQ ID NO: 77, SEQ ID NO: 78 and/or SEQ ID NO: 79; for example, four or more than four consecutive amino acids of an immunoglobulin hinge region, such as one selected from sequences SEQ ID NO: 74, SEQ ID NO: 75, SEQ ID NO: 77, SEQ ID NO: 78 and/or SEQ ID NO: 79.

According to some more particular embodiments, $L_2$, $L_3$ and $L_4$ may be identical or different, and may comprise all or part of an immunoglobulin hinge region, such as one selected from sequences SEQ ID NO: 74, SEQ ID NO: 75, SEQ ID NO: 77, SEQ ID NO: 78 and/or SEQ ID NO: 79 (for example four or more than four consecutive amino acids of an immunoglobulin hinge region, such as one selected from sequences SEQ ID NO: 74, SEQ ID NO: 75, SEQ ID NO: 77, SEQ ID NO: 78 and/or SEQ ID NO: 79), and $L_1$ may comprise all or part of the linker which corresponds to the amino acid sequence of SEQ ID NO: 76.

According to some particular embodiments, the binding protein is characterized in that it comprises three polypeptide chains (I), (II) and (III) that form two ABDs, as defined below:

$$V_{1A}\text{-}C_{1A}\text{-}L_3\text{-}(C_H2\text{-}C_H3)_A \quad (I)$$

$$V_{1B}\text{-}C_{1B}\text{-}L_4\text{-}(C_H2\text{-}C_H3)_B\text{-}L_1\text{-}V_{2A}\text{-}C_{2A}\text{-}L_2 \quad (II)$$

$$V_{2B}\text{-}C_{2B} \quad (III)$$

wherein:
$V_{1A}$ and $V_{1B}$ form a binding pair $V_1$ ($V_{H1}/V_{L1}$), which binds specifically to a human CD123 polypeptide;
$V_{2A}$ and $V_{2B}$ form a binding pair $V_2$ ($V_{H2}/V_{L2}$), which binds specifically to a human NKp46 polypeptide;
$C_{1A}$ and $C_{1B}$ form a pair $C_1$ ($C_H1/C_L$) and $C_{2A}$ and $C_{2B}$ form a pair $C_2$ ($C_H1/C_L$) wherein $C_H1$ is an immunoglobulin heavy chain constant domain 1 and $C_L$ is an immunoglobulin light chain constant domain;
$(C_H2\text{-}C_H3)_A$ and $(C_H2\text{-}C_H3)_B$ are identical or different, and comprise an immunoglobulin heavy chain constant domain 2 ($C_H2$) and an immunoglobulin heavy chain constant domain 3 ($C_H3$);
$L_1$, $L_2$, $L_3$, $L_4$ are optional independent amino acid linkers, which may be identical or different.

In one embodiment, the binding protein is characterized in that it comprises three polypeptide chains (I), (II) and (III) that form two ABDs, as defined below:

$$V_{1A}\text{-}C_{1A}\text{-}Hinge_1\text{-}(C_H2\text{-}C_H3)_A \quad (I)$$

$$V_{1B}\text{-}C_{1B}\text{-}Hinge_2\text{-}(C_H2\text{-}C_H3)_B\text{-}L_1\text{-}V_{2A}\text{-}C_{2A}\text{-}Hinge_3 \quad (II)$$

$$V_{2B}\text{-}C_{2B} \quad (III)$$

wherein:
$V_{1A}$ and $V_{1B}$ form a binding pair $V_1$ ($V_{H1}/V_{L1}$);
$V_{2A}$ and $V_{2B}$ form a binding pair $V_2$ ($V_{H2}/V_{L2}$);
$C_{1A}$ and $C_{1B}$ form a pair $C_1$ ($C_H1/C_L$) and $C_{2A}$ and $C_{2B}$ form a pair $C_2$ ($C_H1/C_L$) wherein $C_H1$ is an immunoglobulin heavy chain constant domain 1 and $C_L$ is an immunoglobulin light chain constant domain;
Hinge$_1$, Hinge$_2$ and Hinge$_3$ are identical or different and correspond to all or part of an immunoglobulin hinge region;
$(C_H2\text{-}C_H3)_A$ and $(C_H2\text{-}C_H3)_B$ are identical or different, and comprise an immunoglobulin heavy chain constant domain 2 ($C_H2$) and an immunoglobulin heavy chain constant domain 3 ($C_H3$);
$L_1$ is an amino acid linker.

In one embodiment, the binding protein is characterized in that it comprises three polypeptide chains (I), (II) and (III) that form two ABDs, as defined below:

$$V_{1A}\text{-}C_{1A}\text{-}Hinge_1\text{-}(C_H2\text{-}C_H3)_A \quad (I)$$

$$V_{1B}\text{-}C_{1B}\text{-}Hinge_2\text{-}(C_H2\text{-}C_H3)_B\text{-}L_1\text{-}V_{2A}\text{-}C_{2A}\text{-}Hinge_3 \quad (II)$$

$$V_{2B}\text{-}C_{2B} \quad (III)$$

wherein:
$V_{1A}$ and $V_{1B}$ form a binding pair $V_1$ ($V_{H1}/V_{L1}$) which binds specifically to a human CD123 polypeptide;
$V_{2A}$ and $V_{2B}$ form a binding pair $V_2$ ($V_{H2}/V_{L2}$) which binds specifically to a human NKp46 polypeptide;
$C_{1A}$ and $C_{1B}$ form a pair $C_1$ ($C_H1/C_L$) and $C_{2A}$ and $C_{2B}$ form a pair $C_2$ ($C_H1/C_L$) wherein $C_H1$ is an immunoglobulin heavy chain constant domain 1 and $C_L$ is an immunoglobulin light chain constant domain;
Hinge$_1$, Hinge$_2$ and Hinge$_3$ are identical or different and correspond to all or part of an immunoglobulin hinge region;
$(C_H2\text{-}C_H3)_A$ and $(C_H2\text{-}C_H3)_B$ are identical or different, and comprise an immunoglobulin heavy chain constant domain 2 ($C_H2$) and an immunoglobulin heavy chain constant domain 3 ($C_H3$);
$L_1$ is an amino acid linker.

In some embodiments of the binding protein, the polypeptide chains (I), (II) and (III) are characterized in that:
$C_{1A}$ comprises a $C_L$ domain;
$C_{1B}$ comprises a $C_H1$ domain;
$C_{2A}$ comprises a $C_H1$ domain;

$C_{2B}$ comprises a $C_L$ domain.

In some embodiments of the binding protein, the polypeptide chains (I), (II) and (III) are characterized in that:
- $C_{1A}$ comprises a $C_H1$ domain;
- $C_{1B}$ comprises a $C_L$ domain;
- $C_{2A}$ comprises a $C_L$ domain;
- $C_{2B}$ comprises a $C_H1$ domain.

According to some of those particular embodiments of the binding protein, the polypeptide chains (I), (II) and (III) are characterized in that:
- $C_{1A}$ comprises a $C_H1$ domain;
- $C_{1B}$ comprises a $C_L$ domain;
- $C_{2A}$ comprises a $C_H1$ domain;
- $C_{2B}$ comprises a $C_L$ domain.

According to some of those particular embodiments of the binding protein, the polypeptide chains (I), (II) and (III) are characterized in that:
- $C_{1A}$ comprises a $C_L$ domain;
- $C_{1B}$ comprises a $C_H1$ domain;
- $C_{2A}$ comprises a $C_L$ domain;
- $C_{2B}$ comprises a $C_H1$ domain.

In some embodiments, $C_L$ and $C_H1$ domains which form $C_{1A}$, $C_{1B}$, $C_{2A}$, and $C_{2B}$ may be identical or different. Hence in some embodiments of the binding protein, the polypeptide chains (I), (II) and (III) are characterized in that:
- $C_{1A}$ and $C_{2A}$ are identical and comprise a $C_L$ domain; or
- $C_{1A}$ and $C_{2B}$ are identical and comprise a $C_L$ domain; or
- $C_{1B}$ and $C_{2A}$ are identical and comprise a $C_L$ domain; or
- $C_{1B}$ and $C_{2B}$ are identical and comprise a $C_L$ domain.

In some embodiments of the binding protein, the polypeptide chains (I), (II) and (III) are characterized in that:
- $C_{1A}$ and $C_{2A}$ are identical and comprise a $C_H1$ domain; or
- $C_{1A}$ and $C_{2B}$ are identical and comprise a $C_H1$ domain; or
- $C_{1B}$ and $C_{2A}$ are identical and comprise a $C_H1$ domain; or
- $C_{1B}$ and $C_{2B}$ are identical and comprise a $C_H1$ domain.

In some embodiments of polypeptide chains (I), (II) and (III): $V_{1A}$ is a $V_H$ and $V_{1B}$ is a $V_L$.

In some embodiments of polypeptide chains (I), (II) and (III): $V_{1A}$ is a $V_L$ and $V_{1B}$ is a $V_H$.

In some embodiments of polypeptide chains (I), (II) and (III): $V_{2A}$ is a $V_H$ and $V_{2B}$ is a $V_L$.

In some embodiments of polypeptide chains (I), (II) and (III): $V_{2A}$ is a $V_L$ and $V_{2B}$ is a $V_H$.

In some embodiments of polypeptide chains (I), (II) and (III): $V_{1A}$ is a $V_H$ and $V_{1B}$ is a $V_L$; and $V_{2A}$ is a $V_H$ and $V_{2B}$ is a $V_L$.

In some embodiments of polypeptide chains (I), (II) and (III): $V_{1A}$ is a $V_L$ and $V_{1B}$ is a $V_H$; and $V_{2A}$ is a $V_H$ and $V_{2B}$ is a $V_L$.

In some embodiments of polypeptide chains (I), (II) and (III): $V_{1A}$ is a $V_H$ and $V_{1B}$ is a $V_L$; and $V_{2A}$ is a $V_L$ and $V_{2B}$ is a $V_H$.

In some embodiments of polypeptide chains (I), (II) and (III): $V_{1A}$ is a $V_L$ and $V_{1B}$ is a $V_H$; and $V_{2A}$ is a $V_L$ and $V_{2B}$ is a $V_H$.

In some embodiment of the binding protein, $V_{1A}$ is $V_{L1}$ and $V_{1B}$ is $V_{H1}$; and $V_{2A}$ is $V_{H2}$ and $V_{2B}$ is $V_{L2}$.

In some embodiment of the binding protein, $V_{1A}$ is $V_{L1}$ and $V_{1B}$ is $V_{H1}$.

In some embodiment of the binding protein, $V_{2A}$ is $V_{H2}$ and $V_{2B}$ is $V_{L2}$.

In some embodiment of the binding protein, the polypeptide chains (I), (II) and (III) are characterized in that:
- $C_{1B}$ is an immunoglobulin heavy chain constant domain 1 ($C_H1$);
- $C_{2A}$ is an immunoglobulin heavy chain constant domain 1 ($C_H1$);
- $C_L$ corresponds to an immunoglobulin kappa light chain constant domain ($C_\kappa$);
- $(C_H2-C_H3)_A$ corresponds to the amino acid sequence of SEQ ID NO: 69;
- $(C_H2-C_H3)_B$ corresponds to the amino acid sequence of SEQ ID NO: 70;
- $L_2$ or $Hinge_1$ corresponds to the amino acid sequence of SEQ ID NO:74;
- $L_3$ or $Hinge_2$ corresponds to the amino acid sequence of SEQ ID NO:75;
- $L_4$ or $Hinge_3$ corresponds to the amino acid sequence of SEQ ID NO: 77.
- $L_1$ corresponds to the amino acid sequence of SEQ ID NO: 76.

In some embodiment of the binding protein, the polypeptide chains (I), (II) and (III) are characterized in that:
- $C_{1B}$ is an immunoglobulin heavy chain constant domain 1 ($C_H1$);
- $C_{2A}$ is an immunoglobulin heavy chain constant domain 1 ($C_H1$);
- $C_L$ corresponds to an immunoglobulin kappa light chain constant domain ($C_\kappa$);
- $(C_H2-C_H3)_A$ corresponds to the amino acid sequence of SEQ ID NO: 69;
- $(C_H2-C_H3)_B$ corresponds to the amino acid sequence of SEQ ID NO: 70;
- $Hinge_1$ corresponds to the amino acid sequence of SEQ ID NO:74;
- $Hinge_2$ corresponds to the amino acid sequence of SEQ ID NO:75;
- $Hinge_3$ corresponds to the amino acid sequence of SEQ ID NO: 77;
- $L_1$ corresponds to the amino acid sequence of SEQ ID NO: 76.

In some embodiment of the binding protein:

(a) $V_{H1}$ comprises a CDR-H1 comprising the amino acid sequence of SEQ ID NO: 1; a CDR-H2 comprising the amino acid sequence of SEQ ID NO: 2; a CDR-H3 comprising the amino acid sequence of SEQ ID NO: 3; $V_{L1}$ comprises a CDR-L1 comprising the amino acid sequence of SEQ ID NO: 7; a CDR-L2 comprising the amino acid sequence of SEQ ID NO: 8; a CDR-L3 comprising the amino acid sequence of SEQ ID NO:9; $V_{H2}$ comprises a CDR-H1 comprising the amino acid sequence of SEQ ID NO: 13; a CDR-H2 comprising the amino acid sequence of SEQ ID NO: 14; a CDR-H3 comprising the amino acid sequence of SEQ ID NO: 15; $V_{L2}$ comprises a CDR-L1 comprising the amino acid sequence of SEQ ID NO: 27; a CDR-L2 comprising the amino acid sequence of SEQ ID NO: 28; a CDR-L3 comprising the amino acid sequence of SEQ ID NO: 29;

(b) $V_{H1}$ comprises a CDR-H1 comprising the amino acid sequence of SEQ ID NO: 1; a CDR-H2 comprising the amino acid sequence of SEQ ID NO: 2; a CDR-H3 comprising the amino acid sequence of SEQ ID NO: 3; $V_{L1}$ comprises a CDR-L1 comprising the amino acid sequence of SEQ ID NO: 7; a CDR-L2 comprising the amino acid sequence of SEQ ID NO: 8; a CDR-L3 comprising the amino acid sequence of SEQ ID NO: 9; $V_{H2}$ comprises a CDR-H1 comprising the amino acid sequence of SEQ ID NO: 16; a CDR-H2 comprising the amino acid sequence of SEQ ID NO: 17; a CDR-H3 comprising the amino acid sequence of SEQ ID NO: 18; $V_{L2}$ comprises a CDR-L1 comprising the amino acid sequence of SEQ ID NO: 30; a CDR-L2 comprising the amino acid sequence of SEQ ID NO: 31; a CDR-L3 comprising the amino acid sequence of SEQ ID NO: 32;

(c) $V_{H1}$ comprises a CDR-H1 comprising the amino acid sequence of SEQ ID NO: 1; a CDR-H2 comprising the amino acid sequence of SEQ ID NO: 2; a CDR-H3 comprising the amino acid sequence of SEQ ID NO: 3; $V_{L1}$ comprises a CDR-L1 comprising the amino acid sequence of SEQ ID NO: 7; a CDR-L2 comprising the amino acid sequence of SEQ ID NO: 8; a CDR-L3 comprising the amino acid sequence of SEQ ID NO: 9; $V_{H2}$ comprises a CDR-H1 comprising the amino acid sequence of SEQ ID NO: 19; a CDR-H2 comprising the amino acid sequence of SEQ ID NO: 20; a CDR-H3 comprising the amino acid sequence of SEQ ID NO: 21; $V_{L2}$ comprises a CDR-L1 comprising the amino acid sequence of SEQ ID NO: 33; a CDR-L2 comprising the amino acid sequence of SEQ ID NO: 34; a CDR-L3 comprising the amino acid sequence of SEQ ID NO: 35;

(d) $V_{H1}$ comprises a CDR-H1 comprising the amino acid sequence of SEQ ID NO: 1; a CDR-H2 comprising the amino acid sequence of SEQ ID NO: 2; a CDR-H3 comprising the amino acid sequence of SEQ ID NO: 3; $V_{L1}$ comprises a CDR-L1 comprising the amino acid sequence of SEQ ID NO: 7; a CDR-L2 comprising the amino acid sequence of SEQ ID NO: 8; a CDR-L3 comprising the amino acid sequence of SEQ ID NO: 9; $V_{H2}$ comprises a CDR-H1 comprising the amino acid sequence of SEQ ID NO: 22; a CDR-H2 comprising the amino acid sequence of SEQ ID NO: 23; a CDR-H3 comprising the amino acid sequence of SEQ ID NO: 24; $V_{L2}$ comprises a CDR-L1 comprising the amino acid sequence of SEQ ID NO: 36; a CDR-L2 comprising the amino acid sequence of SEQ ID NO: 37; a CDR-L3 comprising the amino acid sequence of SEQ ID NO: 38;

(e) $V_{H1}$ comprises a CDR-H1 comprising the amino acid sequence of SEQ ID NO: 1; a CDR-H2 comprising the amino acid sequence of SEQ ID NO: 2; a CDR-H3 comprising the amino acid sequence of SEQ ID NO: 3; $V_{L1}$ comprises a CDR-L1 comprising the amino acid sequence of SEQ ID NO: 7; a CDR-L2 comprising the amino acid sequence of SEQ ID NO: 8; a CDR-L3 comprising the amino acid sequence of SEQ ID NO: 9; $V_{H2}$ comprises a CDR-H1 comprising the amino acid sequence of SEQ ID NO: 16; a CDR-H2 comprising the amino acid sequence of SEQ ID NO: 25; a CDR-H3 comprising the amino acid sequence of SEQ ID NO: 26; $V_{L2}$ comprises a CDR-L1 comprising the amino acid sequence of SEQ ID NO: 39; a CDR-L2 comprising the amino acid sequence of SEQ ID NO: 31; a CDR-L3 comprising the amino acid sequence of SEQ ID NO: 40;

(f) $V_{H1}$ comprises a CDR-H1 comprising the amino acid sequence of SEQ ID NO: 4; a CDR-H2 comprising the amino acid sequence of SEQ ID NO: 5; a CDR-H3 comprising the amino acid sequence of SEQ ID NO: 6; $V_{L1}$ comprises a CDR-L1 comprising the amino acid sequence of SEQ ID NO: 10; a CDR-L2 comprising the amino acid sequence of SEQ ID NO: 11; a CDR-L3 comprising the amino acid sequence of SEQ ID NO: 12; $V_{H2}$ comprises a CDR-H1 comprising the amino acid sequence of SEQ ID NO: 13; a CDR-H2 comprising the amino acid sequence of SEQ ID NO: 14; a CDR-H3 comprising the amino acid sequence of SEQ ID NO: 15; $V_{L2}$ comprises a CDR-L1 comprising the amino acid sequence of SEQ ID NO: 27; a CDR-L2 comprising the amino acid sequence of SEQ ID NO: 28; a CDR-L3 comprising the amino acid sequence of SEQ ID NO: 29;

(g) $V_{H1}$ comprises a CDR-H1 comprising the amino acid sequence of SEQ ID NO: 4; a CDR-H2 comprising the amino acid sequence of SEQ ID NO: 5; a CDR-H3 comprising the amino acid sequence of SEQ ID NO: 6; $V_{L1}$ comprises a CDR-L1 comprising the amino acid sequence of SEQ ID NO: 10; a CDR-L2 comprising the amino acid sequence of SEQ ID NO: 11; a CDR-L3 comprising the amino acid sequence of SEQ ID NO: 12; $V_{H2}$ comprises a CDR-H1 comprising the amino acid sequence of SEQ ID NO: 16; a CDR-H2 comprising the amino acid sequence of SEQ ID NO: 17; a CDR-H3 comprising the amino acid sequence of SEQ ID NO: 18; $V_{L2}$ comprises a CDR-L1 comprising the amino acid sequence of SEQ ID NO: 30; a CDR-L2 comprising the amino acid sequence of SEQ ID NO: 31; a CDR-L3 comprising the amino acid sequence of SEQ ID NO: 32;

(h) $V_{H1}$ comprises a CDR-H1 comprising the amino acid sequence of SEQ ID NO: 4; a CDR-H2 comprising the amino acid sequence of SEQ ID NO: 5; a CDR-H3 comprising the amino acid sequence of SEQ ID NO: 6; $V_{L1}$ comprises a CDR-L1 comprising the amino acid sequence of SEQ ID NO: 10; a CDR-L2 comprising the amino acid sequence of SEQ ID NO: 11; a CDR-L3 comprising the amino acid sequence of SEQ ID NO: 12; $V_{H2}$ comprises a CDR-H1 comprising the amino acid sequence of SEQ ID NO: 19; a CDR-H2 comprising the amino acid sequence of SEQ ID NO: 20; a CDR-H3 comprising the amino acid sequence of SEQ ID NO: 21; $V_{L2}$ comprises a CDR-L1 comprising the amino acid sequence of SEQ ID NO: 33; a CDR-L2 comprising the amino acid sequence of SEQ ID NO: 34; a CDR-L3 comprising the amino acid sequence of SEQ ID NO: 35;

(i) $V_{H1}$ comprises a CDR-H1 comprising the amino acid sequence of SEQ ID NO: 4; a CDR-H2 comprising the amino acid sequence of SEQ ID NO: 5; a CDR-H3 comprising the amino acid sequence of SEQ ID NO: 6; $V_{L1}$ comprises a CDR-L1 comprising the amino acid sequence of SEQ ID NO: 10; a CDR-L2 comprising the amino acid sequence of SEQ ID NO: 11; a CDR-L3 comprising the amino acid sequence of SEQ ID NO: 12; $V_{H2}$ comprises a CDR-H1 comprising the amino acid sequence of SEQ ID NO: 22; a CDR-H2 comprising the amino acid sequence of SEQ ID NO: 23; a CDR-H3 comprising the amino acid sequence of SEQ ID NO: 24; $V_{L2}$ comprises a CDR-L1 comprising the amino acid sequence of SEQ ID NO: 36; a CDR-L2 comprising the amino acid sequence of SEQ ID NO: 37; a CDR-L3 comprising the amino acid sequence of SEQ ID NO: 38;

(j) $V_{H1}$ comprises a CDR-H1 comprising the amino acid sequence of SEQ ID NO: 4; a CDR-H2 comprising the amino acid sequence of SEQ ID NO: 5; a CDR-H3 comprising the amino acid sequence of SEQ ID NO: 6; $V_{L1}$ comprises a CDR-L1 comprising the amino acid sequence of SEQ ID NO: 10; a CDR-L2 comprising the amino acid sequence of SEQ ID NO: 11; a CDR-L3 comprising the amino acid sequence of SEQ ID NO: 12; $V_{H2}$ comprises a CDR-H1 comprising the amino acid sequence of SEQ ID NO: 16; a CDR-H2 comprising the amino acid sequence of SEQ ID NO: 25; a CDR-H3 comprising the amino acid sequence of SEQ ID NO: 26; $V_{L2}$ comprises a CDR-L1 comprising the amino acid sequence of SEQ ID NO: 39; a CDR-L2 comprising the amino acid sequence of SEQ ID NO: 31; a CDR-L3 comprising the amino acid sequence of SEQ ID NO: 40.

In some embodiments of the binding protein:

(a) $V_{H1}$ and $V_{L1}$ corresponds to the amino acid sequences of SEQ ID NO: 41 and 43 respectively or corresponds to the amino acid sequences of SEQ ID NO: 42 and 44 respectively; and/or (b) $V_{H2}$ and $V_{L2}$ corresponds to the amino acid sequences of SEQ ID NO: 45 and 53 respectively;

the amino acid sequences of SEQ ID NO: 46 and 54 respectively;

the amino acid sequences of SEQ ID NO: 47 and 55 respectively;

the amino acid sequences of SEQ ID NO: 48 and 56 respectively;

the amino acid sequences of SEQ ID NO: 49 and 57 respectively;

the amino acid sequences of SEQ ID NO: 50 and 58 respectively;

the amino acid sequences of SEQ ID NO: 51 and 59 respectively; or the amino acid sequences of SEQ ID NO: 52 and 60 respectively.

In some embodiments of the binding protein:

(a) $V_{H1}$ comprises the amino acid sequence of SEQ ID NO: 41; $V_{L1}$ comprises the amino acid sequence of SEQ ID NO: 43; $V_{H2}$ comprises the amino acid sequence of SEQ ID NO: 45; $V_{L2}$ comprises the amino acid sequence of SEQ ID NO: 53;

(b) $V_{H1}$ comprises the amino acid sequence of SEQ ID NO: 41; $V_{L1}$ comprises the amino acid sequence of SEQ ID NO: 43; $V_{H2}$ comprises the amino acid sequence of SEQ ID NO: 46; $V_{L2}$ comprises the amino acid sequence of SEQ ID NO: 54;

(c) $V_{H1}$ comprises the amino acid sequence of SEQ ID NO: 41; $V_{L1}$ comprises the amino acid sequence of SEQ ID NO: 43; $V_{H2}$ comprises the amino acid sequence of SEQ ID NO: 47; $V_{L2}$ comprises the amino acid sequence of SEQ ID NO: 55;

(d) $V_{H1}$ comprises the amino acid sequence of SEQ ID NO: 41; $V_{L1}$ comprises the amino acid sequence of SEQ ID NO: 43; $V_{H2}$ comprises the amino acid sequence of SEQ ID NO: 48; $V_{L2}$ comprises the amino acid sequence of SEQ ID NO: 56;

(e) $V_{H1}$ comprises the amino acid sequence of SEQ ID NO: 41; $V_{L1}$ comprises the amino acid sequence of SEQ ID NO: 43; $V_{H2}$ comprises the amino acid sequence of SEQ ID NO: 49; $V_{L2}$ comprises the amino acid sequence of SEQ ID NO: 57;

(f) $V_{H1}$ comprises the amino acid sequence of SEQ ID NO: 41; $V_{L1}$ comprises the amino acid sequence of SEQ ID NO: 43; $V_{H2}$ comprises the amino acid sequence of SEQ ID NO: 50; $V_{L2}$ comprises the amino acid sequence of SEQ ID NO: 58;

(g) $V_{H1}$ comprises the amino acid sequence of SEQ ID NO: 41; $V_{L1}$ comprises the amino acid sequence of SEQ ID NO: 43; $V_{H2}$ comprises the amino acid sequence of SEQ ID NO: 51; $V_{L2}$ comprises the amino acid sequence of SEQ ID NO: 59;

(h) $V_{H1}$ comprises the amino acid sequence of SEQ ID NO: 41; $V_{L1}$ comprises the amino acid sequence of SEQ ID NO: 43; $V_{H2}$ comprises the amino acid sequence of SEQ ID NO: 52; $V_{L2}$ comprises the amino acid sequence of SEQ ID NO: 60;

(i) $V_{H1}$ comprises the amino acid sequence of SEQ ID NO: 42; $V_{L1}$ comprises the amino acid sequence of SEQ ID NO: 44; $V_{H2}$ comprises the amino acid sequence of SEQ ID NO: 45; $V_{L2}$ comprises the amino acid sequence of SEQ ID NO: 53;

(j) $V_{H1}$ comprises the amino acid sequence of SEQ ID NO: 42; $V_{L1}$ comprises the amino acid sequence of SEQ ID NO: 44; $V_{H2}$ comprises the amino acid sequence of SEQ ID NO: 46; $V_{L2}$ comprises the amino acid sequence of SEQ ID NO: 54;

(k) $V_{H1}$ comprises the amino acid sequence of SEQ ID NO: 42; $V_{L1}$ comprises the amino acid sequence of SEQ ID NO: 44; $V_{H2}$ comprises the amino acid sequence of SEQ ID NO: 47; $V_{L2}$ comprises the amino acid sequence of SEQ ID NO: 55;

(l) $V_{H1}$ comprises the amino acid sequence of SEQ ID NO: 42; $V_{L1}$ comprises the amino acid sequence of SEQ ID NO: 44; $V_{H2}$ comprises the amino acid sequence of SEQ ID NO: 48; $V_{L2}$ comprises the amino acid sequence of SEQ ID NO: 56;

(m) $V_{H1}$ comprises the amino acid sequence of SEQ ID NO: 42; $V_{L1}$ comprises the amino acid sequence of SEQ ID NO: 44; $V_{H2}$ comprises the amino acid sequence of SEQ ID NO: 49; $V_{L2}$ comprises the amino acid sequence of SEQ ID NO: 57;

(n) $V_{H1}$ comprises the amino acid sequence of SEQ ID NO: 42; $V_{L1}$ comprises the amino acid sequence of SEQ ID NO: 44; $V_{H2}$ comprises the amino acid sequence of SEQ ID NO: 50; $V_{L2}$ comprises the amino acid sequence of SEQ ID NO: 58;

(o) $V_{H1}$ comprises the amino acid sequence of SEQ ID NO: 42; $V_{L1}$ comprises the amino acid sequence of SEQ ID NO: 44; $V_{H2}$ comprises the amino acid sequence of SEQ ID NO: 51; $V_{L2}$ comprises the amino acid sequence of SEQ ID NO: 59;

(p) $V_{H1}$ comprises the amino acid sequence of SEQ ID NO: 42; $V_{L1}$ comprises the amino acid sequence of SEQ ID NO: 44; $V_{H2}$ comprises the amino acid sequence of SEQ ID NO: 52; $V_{L2}$ comprises the amino acid sequence of SEQ ID NO: 60.

In some embodiments, the binding protein comprises at least two polypeptide chains linked by at least one disulfide bridge.

In some embodiments of the binding protein, the polypeptide chains (I), (II) and (III) are characterized in that: polypeptide chain (I) is covalently linked to polypeptide chain (II), in particular covalently liked to polypeptide (II) by one or more disulfide bonds.

According to some of those particular embodiments of the binding protein, the polypeptide chains (I), (II) and (III) are characterized in that: polypeptide chain (II) is covalently linked to polypeptide chain (III), by one or more disulfide bonds.

In some embodiments, the polypeptide chains (I) and (II) are linked by at least one disulfide bridge between $C_{1A}$ and $Hinge_2$ and/or wherein the polypeptide chains (II) and (III) are linked by at least one disulfide bridge between $Hinge_3$ and $C_{2B}$.

In some embodiments, the binding protein is characterized in that the Fc region or variant thereof (e.g. $(C_H2\text{-}C_H3)_A$ or $(C_H2\text{-}C_H3)_B$ or $Hinge_1\text{-}(C_H2\text{-}C_H3)_A$ or $Hinge_2\text{-}(C_H2\text{-}C_H3)_B$) which binds to a human Fc-γ receptor polypeptide, comprises a $C_H2$ heavy chain constant domain with a N-linked glycosylation at residue N297 according to EU numbering.

In some embodiments, the binding protein is characterized in that the residue N297 of the Fc region or variant thereof according to EU numbering comprises a N-linked glycosylation.

In some embodiments, the binding protein is characterized in that all or part of the Fc region or variant thereof binds to a human Fc-γ receptor polypeptide. In some embodiments, the binding protein is characterized in that all or part of the Fc region or variant thereof binds to a human CD16A (FcγRIII) polypeptide.

In one embodiment, the binding protein comprises:

a polypeptide comprising an amino acid sequence of SEQ ID NO: 61, a polypeptide comprising an amino acid sequence of SEQ ID NO: 62 and a polypeptide comprising an amino acid sequence of SEQ ID NO: 63, or a variant thereof with at least 80% of sequence identity; or a polypeptide comprising an amino acid sequence of SEQ ID NO: 64, a polypeptide comprising an amino acid sequence of SEQ ID NO: 65 and a polypeptide comprising an amino acid sequence of SEQ ID NO: 66 or a variant thereof with at least 80% of sequence identity; and/or a polypeptide comprising an amino acid sequence of SEQ ID NO: 61 or 64, a polypeptide comprising an amino acid sequence of SEQ ID NO: 62 or 65 and a polypeptide comprising an amino acid sequence of SEQ ID NO: 63 or 66, or a variant thereof with at least 80% of sequence identity.

In some embodiments, the binding protein comprises:

a polypeptide comprising an amino acid sequence SEQ ID NO: 61, a polypeptide comprising an amino acid sequence SEQ ID NO: 62 and a polypeptide comprising an amino acid sequence SEQ ID NO: 63 or a variant thereof with at least 80% of sequence identity; or a polypeptide comprising an amino acid sequence of SEQ ID NO: 64, a polypeptide comprising an amino acid sequence of SEQ ID NO: 65 and a polypeptide comprising an amino acid sequence of SEQ ID NO: 66 or a variant thereof with at least 80% of sequence identity.

In some embodiments, the binding protein comprises: a polypeptide comprising an amino acid sequence of SEQ ID NO: 61, a polypeptide comprising a sequence SEQ ID NO: 62 and a polypeptide comprising an amino acid sequence of SEQ ID NO: 63 or a variant thereof with at least 80% of sequence identity.

In some embodiments, the binding protein comprises: a polypeptide comprising an amino acid sequence of SEQ ID NO: 64, a polypeptide comprising an amino acid sequence of SEQ ID NO: 65 and a polypeptide comprising an amino acid sequence of SEQ ID NO: 66 or a variant thereof with at least 80% of sequence identity.

In some embodiments, the binding protein comprises: a polypeptide comprising an amino acid sequence of SEQ ID NO: 61, a polypeptide comprising an amino acid sequence of SEQ ID NO: 62 and a polypeptide comprising an amino acid sequence of SEQ ID NO: 63 or a variant thereof with at least 90% of sequence identity.

In some embodiments, the binding protein comprises: a polypeptide comprising an amino acid sequence of SEQ ID NO: 64, a polypeptide comprising a amino acid sequence of SEQ ID NO: 65 and a polypeptide comprising an amino acid sequence of SEQ ID NO: 66 or a variant thereof with at least 90% of sequence identity.

In some embodiments, the binding protein comprises: a polypeptide comprising an amino acid sequence of SEQ ID NO: 61, a polypeptide comprising an amino acid sequence of SEQ ID NO: 62 and a polypeptide comprising an amino acid sequence of SEQ ID NO: 63 or a variant thereof with at least 95% of sequence identity.

In some embodiments, the binding protein comprises: a polypeptide comprising an amino acid sequence of SEQ ID NO: 64, a polypeptide comprising a amino acid sequence of SEQ ID NO: 65 and a polypeptide comprising an amino acid sequence of SEQ ID NO: 66 or a variant thereof with at least 95% of sequence identity.

In some embodiments, the binding protein comprises: a polypeptide (I) comprising an amino acid sequence of SEQ ID NO: 61, a polypeptide (II) comprising an amino acid sequence of SEQ ID NO: 62 and a polypeptide (III) comprising an amino acid sequence of SEQ ID NO: 63.

In some embodiments, the binding protein comprises:
polypeptide (I) consisting of an amino acid sequence of SEQ ID NO: 61;
polypeptide (II) consisting of an amino acid sequence of SEQ ID NO: 62; and
polypeptide (III) consisting of an amino acid sequence of SEQ ID NO: 63.

In some embodiments, the binding protein comprises: a polypeptide (I) comprising an amino acid sequence of SEQ ID NO: 64, a polypeptide (II) comprising an amino acid sequence of SEQ ID NO: 65 and a polypeptide (III) comprising an amino acid sequence of SEQ ID NO: 66.

In some embodiments, the binding protein comprises:
polypeptide (I) consisting of an amino acid sequence of SEQ ID NO: 64;
polypeptide (II) consisting of an amino acid sequence of SEQ ID NO: 65; and
polypeptide (III) consisting of an amino acid sequence of SEQ ID NO: 66.

In some variants of those embodiments, the binding protein comprises polypeptide sequences derived from immunoglobulins chains (in particular immunoglobulins of the IgG type), and/or amino acid sequences selected from any one of SEQ ID NO: 1 to SEQ ID NO: 79, which may thus include any variant sequence with conservative substitutions, and/or any variant with a degree of percent sequence identity with a reference sequence; especially a reference sequence derived from an immunoglobulin chain.

In some embodiments, the binding protein comprises polypeptide sequences derived from immunoglobulins chains of the IgG type, in particular of the IgG1, IgG2, IgG3 or IgG4 type, preferably of the IgG1 type.

When variants of Fc and constant regions and non-CDRs polypeptide sequences from a variable region are considered herein, they may consist of Fc and constant regions and non-CDRs polypeptide sequences having at least 80% of sequence identity with a reference polypeptide sequence; more particularly having at least 90% of sequence identity with a reference polypeptide sequence; and preferably having at least 95% of sequence identity with a reference polypeptide sequence.

Alternatively, when variants of polypeptide sequences include CDR polypeptide sequences (e.g., CDR1, CDR2, and CDR3 from either one of a VH or $V_L$ domain), it will be understood herein that those variants do not have modifications on their CDR polypeptide sequences.

In some embodiments, the binding protein comprises an amino acid sequence having at least 80% of sequence identity with an amino acid sequence selected from SEQ ID NO: 67 to 73.

In some embodiments, the binding protein comprises a amino acid sequence having at least 90% of sequence identity with an amino acid sequence selected from SEQ ID NO: 67 to 73.

In some embodiments, the binding protein comprises an amino acid sequence having at least 95% of sequence identity with an amino acid sequence selected from SEQ ID NO: 67 to 73.

In some embodiments, the binding protein comprises a Fc region or variant thereof having at least 80% of sequence identity with an amino acid sequence selected from SEQ ID NO: 69 to 73.

In some embodiments, the binding protein comprises a Fc region or variant thereof having at least 90% of sequence identity with an amino acid sequence selected from SEQ ID NO: 69 to 73.

In some embodiments, the binding protein comprises a Fc region or variant thereof having at least 95% of sequence identity with an amino acid s sequence selected from SEQ ID NO: 69 to 73.

In some embodiments, the binding protein comprises a Fc region or variant thereof with a $C_H2$-$C_H3$ domain having at least 80% of sequence identity with an amino acid sequence selected from SEQ ID NO: 69 or 70; or alternatively comprises a Fc region or variant thereof with a $C_H2$ domain having at least 80% of sequence identity with an amino acid sequence of SEQ ID NO: 71; or alternatively comprises a Fc region or variant thereof with a $C_H3$ domain having at least 80% of sequence identity with an amino acid sequence of SEQ ID NO: 72 or 73.

In some embodiments, the binding protein comprises a Fc region or variant thereof with a $C_H2$-$C_H3$ domain having at least 90% of sequence identity with an amino acid sequence selected from SEQ ID NO: 69 or 70; or alternatively comprises a Fc region or variant thereof with a $C_H2$ domain having at least 90% of sequence identity with an amino acid sequence SEQ ID NO: 71; or alternatively comprises a Fc region or variant thereof with a $C_H3$ domain having at least 90% of sequence identity with an amino acid sequence of SEQ ID NO: 72 or 73.

In some embodiments, the binding protein comprises a Fc region or variant thereof with a $C_H2$-$C_H3$ domain having at least 95% of sequence identity with an amino acid sequence selected from SEQ ID NO: 69 or 70; or alternatively comprises a Fc region or variant thereof with a $C_H2$ domain having at least 95% of sequence identity with an amino acid sequence of SEQ ID NO: 71; or alternatively comprises a Fc region or variant thereof with a $C_H3$ domain having at least 95% of sequence identity with an amino acid sequence of SEQ ID NO: 72 or 73.

Preferably, the multispecific binding proteins of the present disclosure are bispecific binding proteins.

The disclosure further relates to a pharmaceutical composition comprising a binding protein as defined above, and a pharmaceutically acceptable carrier.

Hence, in one embodiment, the disclosure relates to a pharmaceutical composition comprising a binding protein, and a pharmaceutically acceptable carrier, said binding protein comprising:

(i) a first antigen-binding domain (ABD) comprising a variable region which binds specifically to a human CD123 polypeptide, (ii) a second antigen-binding domain (ABD) comprising a variable region which binds specifically to a human NKp46 polypeptide, and (iii) all or part of an immunoglobulin fragment crystallizable (Fc) region or variant thereof which binds to a human Fc-γ receptor polypeptide.

Hence, in one embodiment, the disclosure relates to a pharmaceutical composition comprising the binding protein defined above, and a pharmaceutically acceptable carrier, said binding protein comprising a first and a second antigen binding domains (ABDs) and all or part of an immunoglobulin Fc region or variant thereof, wherein each of said ABDs comprises an immunoglobulin heavy chain variable domain ($V_H$) and an immunoglobulin light chain variable domain ($V_L$), wherein each $V_H$ and $V_L$ comprises three complementary determining regions (CDR-1 to CDR-3); and wherein:

(i) the first ABD binds specifically to human CD123 and comprises:

a $V_{H1}$ comprising a CDR-H1, H2 and H3 corresponding to the amino acid sequences of SEQ ID NO:1 to 3 respectively or corresponding to the amino acid sequences of SEQ ID NO: 4 to 6 respectively, and a $V_{L1}$ comprising a CDR-L1, L2 and L3 corresponding to the amino acid sequences of SEQ ID NO: 7 to 9 respectively or corresponding to the amino acid sequences of SEQ ID NO: 10 to 12 respectively;

(ii) the second ABD binds specifically to human NKp46 and comprises:

a $V_{H2}$ comprising a CDR-H1, 2 and 3 corresponding to:
the amino acid sequences of SEQ ID NO:13 to 15 respectively;
the amino acid sequences of SEQ ID NO:16 to 18 respectively;
the amino acid sequences of SEQ ID NO:19 to 21 respectively;
the amino acid sequences of SEQ ID NO:22 to 24 respectively; or
the amino acid sequences of SEQ ID NO:16, 25 and 26 respectively; and a $V_{L2}$ comprising a CDR-L1, 2 and 3 corresponding to:
the amino acid sequences of SEQ ID NO:27 to 29 respectively;
the amino acid sequences of SEQ ID NO:30 to 32 respectively;
the amino acid sequences of SEQ ID NO:33 to 35 respectively;
the amino acid sequences of SEQ ID NO:36 to 38 respectively; or
the amino acid sequences of SEQ ID NO:39, 31 and 40 respectively;

and wherein all or part of the immunoglobulin Fc region or variant thereof to a human Fc-γ receptor Preferably, the binding protein according to the disclosure, and pharmaceutical compositions thereof, are sterile and suitable for parenteral use.

III. Medical Applications

The disclosed binding protein, and compositions thereof, are particularly suitable for use as a medicament. Methods and uses for the preparation of such medicament are further disclosed herein.

Hence, in one embodiment, the disclosure relates to a binding protein comprising:

(i) a first antigen-binding domain (ABD) comprising a variable region which binds specifically to a human CD123 polypeptide, (ii) a second antigen-binding domain (ABD) comprising a variable region which binds specifically to a human NKp46 polypeptide, and (iii) all or part of an immunoglobulin fragment crystallizable (Fc) region which binds to a human Fc-γ receptor polypeptide; for use as a medicament.

According to some particular embodiments of this third general object, the disclosure relates to a binding protein comprising:

(i) a first antigen-binding domain (ABD) comprising a variable region which binds specifically to a human CD123 polypeptide, (ii) a second antigen-binding domain (ABD) comprising a variable region which binds specifically to a human NKp46 polypeptide, and (iii) all or part of an immunoglobulin fragment crystallizable (Fc) region which binds to a human Fc-γ receptor polypeptide; for use in a method for the treatment or prevention of cancer.

According to some particular embodiments of this third general object, the disclosure relates to a binding protein comprising:
(i) a first antigen-binding domain (ABD) comprising a variable region which binds specifically to a human CD123 polypeptide, (ii) a second antigen-binding domain (ABD) comprising a variable region which binds specifically to a human NKp46 polypeptide, and (iii) all or part of an immunoglobulin fragment crystallizable (Fc) region which binds to a human Fc-γ receptor polypeptide; for use in a method for the treatment or prevention of blood cancer.

According to some particular embodiments of this third general object, the disclosure relates to a binding protein comprising:
(i) a first antigen-binding domain (ABD) comprising a variable region which binds specifically to a human CD123 polypeptide, (ii) a second antigen-binding domain (ABD) comprising a variable region which binds specifically to a human NKp46 polypeptide, and (iii) all or part of an immunoglobulin fragment crystallizable (Fc) region which binds to a human Fc-γ receptor polypeptide; for use in a method for the treatment or prevention of a myelodysplastic syndrome (MDS) or of a lymphoproliferative disorder.

According to some particular embodiments of this third general object, the disclosure relates to a binding protein comprising:
(i) a first antigen-binding domain (ABD) comprising a variable region which binds specifically to a human CD123 polypeptide, (ii) a second antigen-binding domain (ABD) comprising a variable region which binds specifically to a human NKp46 polypeptide, and (iii) all or part of an immunoglobulin fragment crystallizable (Fc) region which binds to a human Fc-γ receptor polypeptide; for use in a method for the treatment or prevention of Acute Myeloid Leukemia (AML).

According to some particular embodiments of this third general object, the disclosure relates to a binding protein comprising:
(i) a first antigen-binding domain (ABD) comprising a variable region which binds specifically to a human CD123 polypeptide, (ii) a second antigen-binding domain (ABD) comprising a variable region which binds specifically to a human NKp46 polypeptide, and (iii) all or part of an immunoglobulin fragment crystallizable (Fc) region which binds to a human Fc-γ receptor polypeptide; for use in a method for the treatment or prevention of CD64-positive and CD64-negative Acute Myeloid Leukemia (AML).

In some embodiment, the disclosure relates to a binding protein comprising a first and a second antigen binding domains (ABDs) and all or part of an immunoglobulin Fc region or variant thereof, wherein each of said ABDs comprises an immunoglobulin heavy chain variable domain ($V_H$) and an immunoglobulin light chain variable domain ($V_L$), wherein each $V_H$ and $V_L$ comprises three complementary determining regions (CDR-1 to CDR-3); and wherein:
(i) the first ABD binds specifically to human CD123 and comprises:
a $V_{H1}$ comprising a CDR-H1, H2 and H3 corresponding to the amino acid sequences of SEQ ID NO:1 to 3 respectively or corresponding to the amino acid sequences of SEQ ID NO: 4 to 6 respectively, and
a $V_{L1}$ comprising a CDR-L1, L2 and L3 corresponding to the amino acid sequences of SEQ ID NO: 7 to 9 respectively or corresponding to the amino acid sequences of SEQ ID NO: 10 to 12 respectively;
(ii) the second ABD binds specifically to human NKp46 and comprises:
a $V_{H2}$ comprising a CDR-H1, 2 and 3 corresponding to:
the amino acid sequences of SEQ ID NO:13 to 15 respectively;
the amino acid sequences of SEQ ID NO:16 to 18 respectively;
the amino acid sequences of SEQ ID NO:19 to 21 respectively;
the amino acid sequences of SEQ ID NO:22 to 24 respectively; or
the amino acid sequences of SEQ ID NO:16, 25 and 26 respectively; and
a $V_{L2}$ comprising a CDR-L1, 2 and 3 corresponding to:
the amino acid sequences of SEQ ID NO:27 to 29 respectively;
the amino acid sequences of SEQ ID NO:30 to 32 respectively;
the amino acid sequences of SEQ ID NO:33 to 35 respectively;
the amino acid sequences of SEQ ID NO:36 to 38 respectively; or
the amino acid sequences of SEQ ID NO:39, 31 and 40 respectively;
and wherein all or part of the immunoglobulin Fc region or variant thereof binds to a human Fc-γ receptor; for use as a medicament.

In some embodiment, the disclosure relates to a binding protein comprising a first and a second antigen binding domains (ABDs) and all or part of an immunoglobulin Fc region or variant thereof, wherein each of said ABDs comprises an immunoglobulin heavy chain variable domain ($V_H$) and an immunoglobulin light chain variable domain ($V_L$), wherein each $V_H$ and $V_L$ comprises three complementary determining regions (CDR-1 to CDR-3); and wherein:
(i) the first ABD binds specifically to human CD123 and comprises:
a $V_{H1}$ comprising a CDR-H1, H2 and H3 corresponding to the amino acid sequences of SEQ ID NO:1 to 3 respectively or corresponding to the amino acid sequences of SEQ ID NO: 4 to 6 respectively, and
a $V_{L1}$ comprising a CDR-L1, L2 and L3 corresponding to the amino acid sequences of SEQ ID NO: 7 to 9 respectively or corresponding to the amino acid sequences of SEQ ID NO: 10 to 12 respectively;
(ii) the second ABD binds specifically to human NKp46 and comprises:
a $V_{H2}$ comprising a CDR-H1, 2 and 3 corresponding to:
the amino acid sequences of SEQ ID NO:13 to 15 respectively;
the amino acid sequences of SEQ ID NO:16 to 18 respectively;
the amino acid sequences of SEQ ID NO:19 to 21 respectively;
the amino acid sequences of SEQ ID NO:22 to 24 respectively; or
the amino acid sequences of SEQ ID NO:16, 25 and 26 respectively; and
a $V_{L2}$ comprising a CDR-L1, 2 and 3 corresponding to:
the amino acid sequences of SEQ ID NO:27 to 29 respectively;
the amino acid sequences of SEQ ID NO:30 to 32 respectively;
the amino acid sequences of SEQ ID NO:33 to 35 respectively;
the amino acid sequences of SEQ ID NO:36 to 38 respectively; or
the amino acid sequences of SEQ ID NO:39, 31 and 40 respectively;

and wherein all or part of the immunoglobulin Fc region or variant thereof binds to a human Fc-γ receptor; for use in a method for the treatment or prevention of cancer.

According to some particular embodiments of this third main object, the disclosure relates to a binding protein comprising a first and a second antigen binding domains (ABDs) and all or part of an immunoglobulin Fc region or variant thereof, wherein each of said ABDs comprises an immunoglobulin heavy chain variable domain ($V_H$) and an immunoglobulin light chain variable domain ($V_L$), wherein each $V_H$ and $V_L$ comprises three complementary determining regions (CDR-1 to CDR-3); and wherein:

(i) the first ABD binds specifically to human CD123 and comprises:

a $V_{H1}$ comprising a CDR-H1, H2 and H3 corresponding to the amino acid sequences SEQ ID NO:1 to 3 respectively or corresponding to the amino acid sequences of SEQ ID NO: 4 to 6 respectively, and a $V_{L1}$ comprising a CDR-L1, L2 and L3 corresponding to the amino acid sequences of SEQ ID NO: 7 to 9 respectively or corresponding to the amino acid sequences of SEQ ID NO: 10 to 12 respectively;

(ii) the second ABD binds specifically to human NKp46 and comprises:

a $V_{H2}$ comprising a CDR-H1, 2 and 3 corresponding to:
the amino acid sequences of SEQ ID NO:13 to 15 respectively;
the amino acid sequences of SEQ ID NO:16 to 18 respectively;
the amino acid sequences of SEQ ID NO:19 to 21 respectively;
the amino acid sequences of SEQ ID NO:22 to 24 respectively; or
the amino acid sequences of SEQ ID NO:16, 25 and 26 respectively; and a $V_{L1}$ comprising a CDR-L1, 2 and 3 corresponding to:
the amino acid sequences of SEQ ID NO:27 to 29 respectively;
the amino acid sequences of SEQ ID NO:30 to 32 respectively;
the amino acid sequences of SEQ ID NO:33 to 35 respectively;
the amino acid sequences of SEQ ID NO:36 to 38 respectively; or
the amino acid sequences of SEQ ID NO:39, 31 and 40 respectively;

and wherein all or part of the immunoglobulin Fc region or variant thereof binds to a human Fc-γ receptor; for use in a method for the treatment or prevention of blood cancer.

According to some particular embodiments of this third main object, the disclosure relates to a binding protein comprising a first and a second antigen binding domains (ABDs) and all or part of an immunoglobulin Fc region or variant thereof, wherein each of said ABDs comprises an immunoglobulin heavy chain variable domain ($V_H$) and an immunoglobulin light chain variable domain ($V_L$), wherein each $V_H$ and $V_L$ comprises three complementary determining regions (CDR-1 to CDR-3); and wherein:

(i) the first ABD binds specifically to human CD123 and comprises:

a $V_{H1}$ comprising a CDR-H1, H2 and H3 corresponding to the amino acid sequences of SEQ ID NO:1 to 3 respectively or corresponding to the amino acid sequences of SEQ ID NO: 4 to 6 respectively, and a $V_{L1}$ comprising a CDR-L1, L2 and L3 corresponding to the amino acid sequences of SEQ ID NO: 7 to 9 respectively or corresponding to the amino acid sequences of SEQ ID NO: 10 to 12 respectively;

(ii) the second ABD binds specifically to human NKp46 and comprises:

a $V_{H2}$ comprising a CDR-H1, 2 and 3 corresponding to:
the amino acid sequences of SEQ ID NO:13 to 15 respectively;
the amino acid sequences of SEQ ID NO:16 to 18 respectively;
the amino acid sequences of SEQ ID NO:19 to 21 respectively;
the amino acid sequences of SEQ ID NO:22 to 24 respectively; or
the amino acid sequences of SEQ ID NO:16, 25 and 26 respectively; and a $V_{L2}$ comprising a CDR-L1, 2 and 3 corresponding to:
the amino acid sequences of SEQ ID NO:27 to 29 respectively;
the amino acid sequences of SEQ ID NO:30 to 32 respectively;
the amino acid sequences of SEQ ID NO:33 to 35 respectively;
the amino acid sequences of SEQ ID NO:36 to 38 respectively; or
the amino acid sequences of SEQ ID NO:39, 31 and 40 respectively;

and wherein all or part of the immunoglobulin Fc region or variant thereof binds to a human Fc-γ receptor; for use in a method for the treatment or prevention of a myelodysplastic syndrome (MDS) or of a lymphoproliferative disorder.

According to some particular embodiments of this third main object, the disclosure relates to a binding protein comprising a first and a second antigen binding domains (ABDs) and all or part of an immunoglobulin Fc region or variant thereof, wherein each of said ABDs comprises an immunoglobulin heavy chain variable domain ($V_H$) and an immunoglobulin light chain variable domain ($V_L$), wherein each $V_H$ and $V_L$ comprises three complementary determining regions (CDR-1 to CDR-3); and wherein:

(i) the first ABD binds specifically to human CD123 and comprises:

a $V_{H1}$ comprising a CDR-H1, H2 and H3 corresponding to the amino acid sequences of SEQ ID NO:1 to 3 respectively or corresponding to the amino acid sequences of SEQ ID NO: 4 to 6 respectively, and a $V_{L1}$ comprising a CDR-L1, L2 and L3 corresponding to the amino acid sequences SEQ ID NO: 7 to 9 respectively or corresponding to the amino acid sequences SEQ ID NO: 10 to 12 respectively;

(ii) the second ABD binds specifically to human NKp46 and comprises:

a $V_{H2}$ comprising a CDR-H1, 2 and 3 corresponding to:
the amino acid sequences of SEQ ID NO:13 to 15 respectively;
the amino acid sequences of SEQ ID NO:16 to 18 respectively;
the amino acid sequences of SEQ ID NO:19 to 21 respectively;
the amino acid sequences of SEQ ID NO:22 to 24 respectively; or
the amino acid sequences of SEQ ID NO:16, 25 and 26 respectively; and a V$_{L2}$ comprising a CDR-L1, 2 and 3 corresponding to:
the amino acid sequences of SEQ ID NO:27 to 29 respectively;
the amino acid sequences of SEQ ID NO:30 to 32 respectively;
the amino acid sequences of SEQ ID NO:33 to 35 respectively;
the amino acid sequences of SEQ ID NO:36 to 38 respectively; or
the amino acid sequences of SEQ ID NO:39, 31 and 40 respectively;
and wherein all or part of the immunoglobulin Fc region or variant thereof binds to a human Fc-γ receptor; for use in a method for the treatment or prevention of Acute Myeloid Leukemia (AML).

According to some particular embodiments of this third main object, the disclosure relates to a binding protein comprising a first and a second antigen binding domains (ABDs) and all or part of an immunoglobulin Fc region or variant thereof, wherein each of said ABDs comprises an immunoglobulin heavy chain variable domain (V$_H$) and an immunoglobulin light chain variable domain (V$_L$), wherein each V$_H$ and V$_L$ comprises three complementary determining regions (CDR-1 to CDR-3); and wherein:

(i) the first ABD binds specifically to human CD123 and comprises:
a V$_{H1}$ comprising a CDR-H1, H2 and H3 corresponding to the amino acid sequences of SEQ ID NO:1 to 3 respectively or corresponding to the amino acid sequences of SEQ ID NO: 4 to 6 respectively, and
a V$_{L1}$ comprising a CDR-L1, L2 and L3 corresponding to the amino acid sequences of SEQ ID NO: 7 to 9 respectively or corresponding to the amino acid sequences of SEQ ID NO: 10 to 12 respectively;

(ii) the second ABD binds specifically to human NKp46 and comprises:
a V$_{H2}$ comprising a CDR-H1, 2 and 3 corresponding to:
the amino acid sequences of SEQ ID NO:13 to 15 respectively;
the amino acid sequences of SEQ ID NO:16 to 18 respectively;
the amino acid sequences of SEQ ID NO:19 to 21 respectively;
the amino acid sequences of SEQ ID NO:22 to 24 respectively; or
the amino acid sequences of SEQ ID NO:16, 25 and 26 respectively; and
a V$_{L2}$ comprising a CDR-L1, 2 and 3 corresponding to:
the amino acid sequences of SEQ ID NO:27 to 29 respectively;
the amino acid sequences of SEQ ID NO:30 to 32 respectively;
the amino acid sequences of SEQ ID NO:33 to 35 respectively;
the amino acid sequences of SEQ ID NO:36 to 38 respectively; or
the amino acid sequences of SEQ ID NO:39, 31 and 40 respectively;
and wherein all or part of the immunoglobulin Fc region or variant thereof binds to a human Fc-γ receptor; for use in a method for the treatment or prevention of CD64-positive and CD64-negative Acute Myeloid Leukemia (AML).

The disclosure further relates to a use of the above-mentioned binding proteins for the preparation of a medicament.

The disclosure further relates to a use of the above-mentioned binding proteins as a medicament.

The disclosure further relates to a use of the above-mentioned binding proteins for the preparation of a medicament for the treatment or prevention of cancer.

The disclosure further relates to a use of the above-mentioned binding proteins for the preparation of a medicament for the treatment or prevention of cancer characterized by tumor cells that express CD123 at their surface.

The disclosure further relates to a use of the above-mentioned binding proteins for the preparation of a medicament for the treatment or prevention of cancer characterized by tumor cells that express CD123 and CD64 at their surface.

The disclosure further relates to a use of the above-mentioned binding proteins for the preparation of a medicament for the treatment or prevention of blood cancer.

The disclosure further relates to a use of the above-mentioned binding proteins for the preparation of a medicament for the treatment or prevention of blood cancer characterized by tumor cells that express CD123 at their surface.

The disclosure further relates to a use of the above-mentioned binding proteins for the preparation of a medicament for the treatment or prevention of blood cancer characterized by tumor cells that express CD123 and CD64 at their surface.

The disclosure further relates to a use of the above-mentioned binding proteins for the preparation of a medicament for the treatment or prevention of a myelodysplastic syndrome (MDS) or of a lymphoproliferative disorder.

The disclosure further relates to a use of the above-mentioned binding proteins for the preparation of a medicament for the treatment or prevention of Acute Myeloid Leukemia (AML).

The disclosure further relates to a use of the above-mentioned binding proteins for the preparation of a medicament for the treatment or prevention of CD64-positive and CD64-negative Acute Myeloid Leukemia (AML).

In one aspect, provided is a method for treating a cancer characterized by tumor cells that express CD123 and CD64 at their surface, the method comprising administering to and individual having such cancer a binding protein comprising: (i) a first antigen-binding domain (ABD) comprising a variable region which binds specifically to a human CD123 polypeptide, (ii) a second antigen-binding domain (ABD) comprising a variable region which binds specifically to a human NKp46 polypeptide, and (iii) all or part of an immunoglobulin Fc region or variant thereof which binds to a human Fc-γ receptor polypeptide.

In one aspect, provided is method for treating a CD123-expressing tumor (e.g. a hematological malignancy, AML) in an individual who is susceptible to having tumor cells that express CD64 at their surface, the method comprising administering to the individual a binding protein comprising: (i) a first antigen-binding domain (ABD) comprising a variable region which binds specifically to a human CD123 polypeptide, (ii) a second antigen-binding domain (ABD) comprising a variable region which binds specifically to a human NKp46 polypeptide, and (iii) all or part of an immunoglobulin Fc region or variant thereof which binds to a human Fc-γ receptor polypeptide.

In one aspect, provided is method for treating a hematological malignancy (e.g. AML) in an individual, the method comprising administering to the individual a binding protein comprising: (i) a first antigen-binding domain (ABD) comprising a variable region which binds specifically to a human CD123 polypeptide, (ii) a second antigen-binding domain (ABD) comprising a variable region which binds specifically to a human NKp46 polypeptide, and (iii) all or part of an immunoglobulin Fc region or variant thereof which binds to a human Fc-γ receptor polypeptide.

In another aspect, provided is a method of treating a hematological malignancy (e.g., AML) in an individual, the method comprising: (a) assessing or determining whether malignant cells (e.g. AML cells) from the individual express CD64 at their surface; and (b) if the individual is determined to have malignant cells (e.g., AML cells) expressing CD64 at their surface (e.g., at a predetermined level), administering to the individual a binding protein comprising: (i) a first antigen-binding domain (ABD) comprising a variable region which binds specifically to a human CD123 polypeptide, (ii) a second antigen-binding domain (ABD) comprising a variable region which binds specifically to a human NKp46 polypeptide, and (iii) all or part of an immunoglobulin Fc region or variant thereof which binds to a human Fc-γ receptor polypeptide.

In another aspect, provided is a method for depleting malignant cells in an individual, and/or directing NK cell-mediated cytotoxicity toward CD64-expressing malignant cells (e.g., an individual having AML), the method comprising administering, to an individual having malignant cells (e.g. AML cells) expressing CD64 at their surface, a binding protein comprising: (i) a first antigen-binding domain (ABD) comprising a variable region which binds specifically to a human CD123 polypeptide, (ii) a second antigen-binding domain (ABD) comprising a variable region which binds specifically to a human NKp46 polypeptide, and (iii) all or part of an immunoglobulin Fc region or variant thereof which binds to a human Fc-γ receptor polypeptide.

In another aspect, provided is a method of causing NK cells to eliminate malignant cells that express both CD123 and CD64, the method comprising bringing the malignant cells (e.g. AML cells) into contact, in the presence of NK cells, with a binding protein comprising: (i) a first antigen-binding domain (ABD) comprising a variable region which binds to a human CD123 polypeptide, (ii) a second antigen-binding domain (ABD) comprising a variable region which binds to a human NKp46 polypeptide, and (iii) all or part of an Fc region or variant thereof which binds to a human Fc-γ receptor polypeptide.

Assessing the expression of CD64 by malignant cells (e.g., AML cells), e.g. at their surface, can be carried out by any suitable method. Generally, a biological sample from an individual, for example from a blood sample or suitable biopsy, can be obtained and assessed and expression of CD64 in tumor cells can be determined using assays such as immunohistochemistry (IHC) assays, fluorescence activated cell sorting (FACS) assays, for example quantitative FACS, ELISA, immunoblotting (e.g., western blotting, dot blotting, or in-cell western blotting), and other immunoassays. Anti-CD64 antibodies for use in such assays are available in the art.

IV. Means for Making the Binding Protein

Means for making the binding protein of the present disclosure in vitro are further disclosed herein. As used herein, a "binding protein of present disclosure" refers to multifunctional binding proteins comprising a first and a second antigen binding domains (ABDs) and all or part of an immunoglobulin Fc region or variant thereof, wherein the first ABD binds specifically to human CD123 and the second ABD binds specifically to human NKp46 and wherein all or part of the immunoglobulin Fc region or variant thereof to a human Fc-γ receptor. It also refers to all particular embodiments of the binding protein which are described throughout the disclosure.

More particularly, the provided means may refer to the making of a binding protein comprising a first and a second antigen binding domains (ABDs) and all or part of an immunoglobulin Fc region or variant thereof, wherein each of said ABDs comprises an immunoglobulin heavy chain variable domain (VH) and an immunoglobulin light chain variable domain (VL), wherein each VH and VL comprises three complementary determining regions (CDR-1 to CDR-3); and wherein:

(i) the first ABD binds specifically to human CD123 and comprises:
a VH1 comprising a CDR-H1, H2 and H3 corresponding to the amino acid sequences of SEQ ID NO:1 to 3 respectively or corresponding to the amino acid sequences of SEQ ID NO: 4 to 6 respectively, and
a VL1 comprising a CDR-L1, L2 and L3 corresponding to the amino acid sequences of SEQ ID NO: 7 to 9 respectively or corresponding to the amino acid sequences of SEQ ID NO: 10 to 12 respectively;

(ii) the second ABD binds specifically to human NKp46 and comprises:
a VH2 comprising a CDR-H1, 2 and 3 corresponding to:
the amino acid sequences of SEQ ID NO:13 to 15 respectively;
the amino acid sequences of SEQ ID NO:16 to 18 respectively;
the amino acid sequences of SEQ ID NO:19 to 21 respectively;
the amino acid sequences of SEQ ID NO:22 to 24 respectively; or
the amino acid sequences of SEQ ID NO:16, 25 and 26 respectively; and
a VL2 comprising a CDR-L1, 2 and 3 corresponding to:
the amino acid sequences of SEQ ID NO:27 to 29 respectively;
the amino acid sequences of SEQ ID NO:30 to 32 respectively;
the amino acid sequences of SEQ ID NO:33 to 35 respectively;
the amino acid sequences of SEQ ID NO:36 to 38 respectively; or
the amino acid sequences SEQ ID NO:39, 31 and 40 respectively;
and wherein all or part of the immunoglobulin Fc region or variant thereof binds to a human Fc-γ receptor.

Hence, in one embodiment, the disclosure relates to an isolated nucleic acid molecule comprising a nucleotide sequence that encodes a binding protein of the present disclosure.

Hence, in one embodiment, the disclosure relates to an expression vector comprising a nucleic acid molecule comprising a nucleotide sequence that encodes the binding protein of the present disclosure.

Hence, in one embodiment, the disclosure relates to an isolated cell comprising the nucleic acid molecules of the present disclosure.

Hence, in one embodiment, the disclosure relates to an isolated cell comprising the expression vector of the present disclosure.

According to a particular embodiment, the cell is an eukaryotic cell, in particular an insect cell or a mammalian cell. In one embodiment, the cell is a mammalian cell and the expression vector is a mammalian expression vector.

Hence, in one embodiment, the disclosure relates to a method for making the binding protein of the present disclosure, comprising a step of making a binding protein comprising (i) a first antigen-binding domain (ABD) comprising a variable region which binds specifically to a human CD123 polypeptide, (ii) a second antigen-binding domain (ABD) comprising a variable region which binds specifically to a human NKp46 polypeptide, and (iii) all or part of an immunoglobulin Fc region or variant thereof which binds to a human Fc-γ receptor polypeptide.

According to some particular embodiments, the disclosure relates to a method for making the binding protein, comprising a step of:

(a) culturing host cell(s) under conditions suitable for expressing one or more recombinant polypeptide(s) comprising (i) a first antigen-binding domain (ABD) comprising a variable region which binds specifically to a human CD123 polypeptide, and/or (ii) a second antigen-binding domain (ABD) comprising a variable region which binds specifically to a human NKp46 polypeptide, and/or (iii) all or part of an immunoglobulin Fc region or variant thereof which binds to a human Fc-γ receptor polypeptide;

(b) optionally recovering the expressed recombinant polypeptide(s).

According to some particular embodiments, the disclosure relates to a method for making the binding protein, comprising a step of:

(a) culturing host cell(s) under conditions suitable for expressing one or more recombinant polypeptide(s) comprising (i) a first antigen-binding domain (ABD) comprising a variable region which binds specifically to a human CD123 polypeptide, and (ii) a second antigen-binding domain (ABD) comprising a variable region which binds specifically to a human NKp46 polypeptide, and (iii) all or part of an immunoglobulin Fc region or variant thereof which binds to a human Fc-γ receptor polypeptide;

(b) optionally recovering the expressed recombinant polypeptide(s).

According to some particular embodiments, the disclosure relates to a method for making the binding protein, comprising a step of:

(a) culturing host cell(s) under conditions suitable for expressing a plurality of recombinant polypeptides, said plurality comprising (i) a first antigen-binding domain (ABD) comprising a variable region which binds specifically to a human CD123 polypeptide, and (ii) a second antigen-binding domain (ABD) comprising a variable region which binds specifically to a human NKp46 polypeptide, and (iii) all or part of an immunoglobulin Fc region or variant thereof which binds to a human Fc-γ receptor polypeptide;

(b) optionally recovering the expressed recombinant polypeptides.

According to some particular embodiments, the disclosure relates to a method for making the binding protein, comprising a step of:

(a) culturing host cell(s) under conditions suitable for expressing a plurality of recombinant polypeptides, said plurality comprising (i) a polypeptide comprising an amino acid sequence of SEQ ID NO: 61 or 64, and (ii) a polypeptide comprising an amino acid sequence of SEQ ID NO: 62 or 65, and (iii) a polypeptide comprising an amino acid sequence of SEQ ID NO: 63 or 66;

(b) optionally recovering the expressed recombinant polypeptides.

According to some particular embodiments, the disclosure relates to a method for making the binding protein, comprising a step of:

(a) culturing host cell(s) under conditions suitable for expressing a plurality of recombinant polypeptides, said plurality comprising (i) a polypeptide comprising an amino acid sequence of SEQ ID NO: 64, and (ii) a polypeptide comprising an amino acid sequence of SEQ ID NO: 65, and (iii) a polypeptide comprising an amino acid sequence of SEQ ID NO: 66;

(b) optionally recovering the expressed recombinant polypeptides.

According to some particular embodiments, the disclosure relates to a method for making the binding protein, comprising a step of:

(a) culturing host cell(s) under conditions suitable for co-expressing a plurality of recombinant polypeptides, said plurality comprising (i) a polypeptide comprising an amino acid sequence of SEQ ID NO: 61 or 64, and (ii) a polypeptide comprising an amino acid sequence of SEQ ID NO: 62 or 65, and (iii) a polypeptide comprising an amino acid sequence of SEQ ID NO: 63 or 66;

(b) optionally recovering the co-expressed recombinant polypeptides.

According to some particular embodiments, the disclosure relates to a method for making the binding protein, comprising a step of:

(a) culturing host cell(s) under conditions suitable for co-expressing a plurality of recombinant polypeptides, said plurality comprising (i) a polypeptide comprising an amino acid sequence of SEQ ID NO: 64, and (ii) a polypeptide comprising an amino acid sequence of SEQ ID NO: 65, and (iii) a polypeptide comprising an amino acid sequence of SEQ ID NO: 66;

(b) optionally recovering the expressed recombinant polypeptides.

According to some particular embodiments, the disclosure relates to a method for making the binding protein, comprising a step of:

(a) culturing host cell(s) under conditions suitable for expressing a plurality of recombinant polypeptides, said plurality comprising (i) a first polypeptide chain (I), (ii) a second polypeptide chain (II), and (iii) a third polypeptide (III), that form two antigen-binding domains (ABD), one ABD which binds specifically to a human CD123 polypeptide and the one other ABD which binds specifically to a human NKp46 polypeptide; characterized in that it the three polypeptide chains (I), (II) and (III) consist of:

  (I)

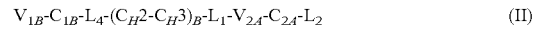  (II)

  (III)

wherein:
$V_{1A}$ and $V_{1B}$ form a binding pair $V_1$ ($V_{H1}/V_{L1}$);
$V_{2A}$ and $V_{2B}$ form a binding pair $V_2$ ($V_{H2}/V_{L2}$);
$C_{1A}$ and $C_{1B}$ form a pair $C_1$ ($C_H1/C_L$) and $C_{2A}$ and $C_{2B}$ form a pair $C_2$ ($C_H1/C_L$) wherein $C_H1$ is an immunoglobulin heavy chain constant domain 1 and $C_L$ is an immunoglobulin light chain constant domain;
$(C_H2-C_H3)_A$ and $(C_H2-C_H3)_B$ are identical or different, and comprise an immunoglobulin heavy chain constant domain 2 ($C_H2$) and an immunoglobulin heavy chain constant domain 3 ($C_H3$);

$L_1$, $L_2$, $L_3$, $L_4$ are optional independent amino acid linkers, which may be identical or different;

(b) optionally recovering the expressed polypeptide chains (I), (II) and (III).

According to some particular embodiments, the disclosure relates to a method for making the binding protein, comprising a step of:

(a) culturing host cell(s) under conditions suitable for co-expressing a plurality of recombinant polypeptides, said plurality comprising (i) a first polypeptide chain (I), (ii) a second polypeptide chain (II), and (iii) a third polypeptide (III), that form two antigen-binding domains (ABD), one ABD which binds specifically to a human CD123 polypeptide and the one other ABD which binds specifically to a human NKp46 polypeptide; characterized in that it the three polypeptide chains (I), (II) and (III) consist of:

$$V_{1A}\text{-}C_{1A}\text{-}L_3\text{-}(C_H2\text{-}C_H3)_A \quad (I)$$

$$V_{1B}\text{-}C_{1B}\text{-}L_4\text{-}(C_H2\text{-}C_H3)_B\text{-}L_1\text{-}V_{2A}\text{-}C_{2A}\text{-}L_2 \quad (II)$$

$$V_{2B}\text{-}C_{2B} \quad (III)$$

wherein:
$V_{1A}$ and $V_{1B}$ form a binding pair $V_1$ ($V_{H1}/V_{L1}$);
$V_{2A}$ and $V_{2B}$ form a binding pair $V_2$ ($V_{H2}/V_{L2}$);
$C_{1A}$ and $C_{1B}$ form a pair $C_1$ ($C_H1/C_L$) and $C_{2A}$ and $C_{2B}$ form a pair $C_2$ ($C_H1/C_L$) wherein $C_H1$ is an immunoglobulin heavy chain constant domain 1 and $C_L$ is an immunoglobulin light chain constant domain;
$(C_H2\text{-}C_H3)_A$ and $(C_H2\text{-}C_H3)_B$ are identical or different, and comprise an immunoglobulin heavy chain constant domain 2 ($C_H2$) and an immunoglobulin heavy chain constant domain 3 ($C_H3$);
$L_1$, $L_2$, $L_3$, $L_4$ are optional independent amino acid linkers, which may be identical or different;

(b) optionally recovering the co-expressed polypeptide chains (I), (II) and (III).

Hence, according to some particular embodiment, the disclosure relates to a method for making the binding protein, comprising a step of:

(a) culturing host cell(s) under conditions suitable for expressing a plurality of recombinant polypeptides, said plurality comprising (i) a first polypeptide chain (I) comprising an amino acid sequence of SEQ ID NO: 61 or 64, (ii) a second polypeptide chain (II) comprising an amino acid sequence of SEQ ID NO: 62 or 65, and (iii) a third polypeptide (III) comprising an amino acid sequence of SEQ ID NO: 63 or 66;

(b) optionally recovering the expressed polypeptide chains (I), (II) and (III).

Hence, according to some particular embodiments, the disclosure relates to a method for making the binding protein, comprising a step of:

(a) culturing host cell(s) under conditions suitable for co-expressing a plurality of recombinant polypeptides, said plurality comprising (i) a first polypeptide chain (I) comprising an amino acid sequence of SEQ ID NO: 61 or 64, (ii) a second polypeptide chain (II) comprising an amino acid sequence of SEQ ID NO: 62 or 65, and (iii) a third polypeptide (III) comprising an amino acid sequence of SEQ ID NO: 63 or 66;

(b) optionally recovering the co-expressed polypeptide chains (I), (II) and (III).

Methods for making the binding protein of the disclosure, such as those defined above, may further include a prior step of providing host cell(s) with a nucleic acid, in particular an isolated nucleic acid (i.e., a recombinant nucleic acid), encoding all or part(s) of the said binding protein. In particular, such step may comprise or consist of transfecting said host cell(s) with a nucleic acid, in particular an isolated nucleic acid, encoding all or part(s) of the said binding protein.

Hence, according to some particular embodiments, the disclosure relates to a method for making the binding protein, comprising a step of:

(a) providing host cell(s) with a nucleic acid encoding all or part(s) of the said binding protein;

(b) culturing said host cell(s) under conditions suitable for expressing one or more recombinant polypeptide(s) comprising (i) a first antigen-binding domain (ABD) comprising a variable region which binds specifically to a human CD123 polypeptide, and/or (ii) a second antigen-binding domain (ABD) comprising a variable region which binds specifically to a human NKp46 polypeptide, and/or (iii) all or part of an immunoglobulin Fc region or variant thereof which binds to a human Fc-γ receptor polypeptide;

(c) optionally recovering the expressed recombinant polypeptide(s).

In one embodiment, the method for making the binding protein of the present disclosure comprises a step of (a) providing one or more nucleic acid(s) encoding a first polypeptide chain (I), a second polypeptide chain (II), and a third polypeptide chain (III);

(b) transfecting host cell(s) with the one or more nucleic acid(s);

(c) culturing the host cell(s) under conditions suitable to express (or co-express) the said polypeptide chain(s); and (d) optionally recovering the expressed (or co-expressed) polypeptide chain(s) (I), (II) and (III).

In one embodiment, the method for making the binding protein of the present disclosure comprises a step of (a) providing one or more nucleic acid(s) encoding a first polypeptide chain (I) comprising an amino acid sequence of SEQ ID NO: 61 or 64, a second polypeptide chain (II) comprising an amino acid sequence of SEQ ID NO: 62 or 65, and a third polypeptide chain (III) comprising an amino acid sequence of SEQ ID NO: 63 or 66;

(b) transfecting host cell(s) with the one or more nucleic acid(s);

(c) culturing the host cell(s) under conditions suitable to express (or co-express) the said polypeptide chain(s); and (d) optionally recovering the expressed (or co-expressed) polypeptide chain(s) (I), (II) and (III).

In some particular embodiments, a method of making the binding protein of the present disclosure comprises:

(a) providing a first nucleic acid encoding a first polypeptide chain according to any of amino acid sequences of SEQ ID NO: 61 or 64, a second nucleic acid encoding a second polypeptide according to any of amino acid sequences of SEQ ID NO: 62 or 65, and a third nucleic acid encoding a third polypeptide chain according to any of amino acid sequences of SEQ ID NO: 63 or 66; and (b) expressing said first, second and third nucleic acids in the one or more host cell(s) to produce a binding protein comprising said first, second and third polypeptide chains, respectively;

(c) optionally loading the protein produced onto an affinity purification support, optionally a Protein-A support, and recovering the binding protein.

It will thus be readily understood by the skilled in the Art that such method of making the binding protein of the disclosure may encompass the production and assembly of some or all of the above-mentioned polypeptides, polypeptide chains and/or regions (e.g. variable regions and Fc region or variants thereof) within one or more host cell(s), as part of an in vitro method of production.

Alternatively, the method may encompass the production of some or all of the above-mentioned polypeptides, polypeptide chains and/or regions within one or more host cell(s), and their assembly outside of the host cell(s). The step of bringing into contact said polypeptides, polypeptide chains and/or regions can thus be achieved simultaneously or sequentially.

According to some embodiments, one or more of said regions may be present in distinct polypeptide chain(s) or fragments thereof.

As a reference, the "F25" format of binding proteins which is described herein in the examples section possesses four predicted interchain disulfide bridges:

one disulfide bridge connecting a cysteine within the $C_L$ domain of polypeptide (I) to the first cysteine within the Hinge region of polypeptide chain (II);

two disulfide bridges connecting two cysteines within the Hinge regions of polypeptide chain (I) and (II);

one disulfide bridge connecting a C-terminal cysteine at the $C_L$ domain of polypeptide chain (III) to a C-terminal cysteine on polypeptide chain (II).

In some embodiment, the disclosure relates to a method for making the binding protein of the present disclosure, comprising a step of bringing into contact (i) a first antigen-binding domain (ABD) comprising a variable region which binds specifically to a human CD123 polypeptide, said variable region comprising at least one complementary determining region (CDR) selected from the group of amino acid sequences consisting of SEQ ID NO: 1 to 12, (ii) a second antigen-binding domain (ABD) comprising a variable region which binds specifically to a human NKp46 polypeptide, said variable region comprising at least one complementary determining region (CDR) selected from the group of amino acid sequences consisting of SEQ ID NO: 13 to 40 and (iii) all or part of a Fc region or variant thereof which binds to a human Fc-γ receptor polypeptide, especially which binds to a human CD16a Fc-γ receptor polypeptide.

In some embodiment, the disclosure relates to a method for making the binding protein of the present disclosure, comprising a step of bringing into contact (i) a first antigen-binding domain (ABD) comprising a variable region which binds specifically to a human CD123 polypeptide, said variable region comprising at least one complementary determining region (CDR) selected from the group of amino acid sequences consisting of SEQ ID NO: 1 to 6 and at least one complementary determining region (CDR) selected from the group of amino acid sequences consisting of SEQ ID NO: 7 to 12, (ii) a second antigen-binding domain (ABD) comprising a variable region suitable which binds specifically to a human NKp46 polypeptide, said variable region comprising at least one complementary determining region (CDR) selected from the group of amino acid sequences consisting of SEQ ID NO: 13 to 26 and at least one complementary determining region (CDR) selected from the group of amino acid sequences consisting of SEQ ID NO: 27 to 40, and (iii) all or part of an immunoglobulin Fc region or variant thereof which binds to a human Fc-γ receptor polypeptide, especially which binds to a human CD16a Fc-γ receptor polypeptide.

In some embodiments, the disclosure relates to a method for making the binding protein of the present disclosure, comprising a step of bringing into contact (i) a first antigen-binding domain (ABD) comprising a variable region which binds specifically to a human CD123 polypeptide, said variable region comprising at least two complementary determining region (CDR) selected from the group of amino acid sequences consisting of SEQ ID NO: 1 to 6 and at least two complementary determining region (CDR) selected from the group of amino acid sequences consisting of SEQ ID NO: 7 to 12, (ii) a second antigen-binding domain (ABD) comprising a variable region which binds specifically to a human NKp46 polypeptide, said variable region comprising at least two complementary determining region (CDR) selected from the group of amino acid sequences consisting of SEQ ID NO: 13 to 26 and at least two complementary determining region (CDR) selected from the group of amino acid sequences consisting of SEQ ID NO: 27 to 40, and (iii) all or part of an immunoglobulin Fc region or variant thereof which binds to a human Fc-γ receptor polypeptide, especially which binds to a human CD16 Fc-γ receptor polypeptide.

In some embodiments, the disclosure relates to a method for making the binding protein related to the present disclosure, comprising a step of bringing into contact (i) a first antigen-binding domain (ABD) comprising a variable region which binds specifically to a human CD123 polypeptide, said variable region comprising three complementary determining region (CDR) selected from the group of amino acid sequences consisting of SEQ ID NO: 1 to 6 and three complementary determining region (CDR) selected from the group of amino acid sequences consisting of SEQ ID NO: 7 to 12, (ii) a second antigen-binding domain (ABD) comprising variable region which binds specifically to a human NKp46 polypeptide, said variable region comprising three complementary determining region (CDR) selected from the group of amino acid sequences consisting of SEQ ID NO: 13 to 26 and three complementary determining region (CDR) selected from the group of amino acid sequences consisting of SEQ ID NO: 27 to 40, and (iii) all or part of an immunoglobulin Fc region or variant thereof which binds to a human Fc-γ receptor polypeptide, especially which binds to a human CD16 Fc-γ receptor polypeptide.

In some embodiments, the disclosure relates to a method for making the binding protein related to the present disclosure, comprising a step of bringing into contact (i) a first antigen-binding domain (ABD) comprising a variable region which binds specifically to a human CD123 polypeptide, (ii) a second antigen-binding domain (ABD) comprising a variable region suitable which binds specifically to a human NKp46 polypeptide, and (iii) all or part of an immunoglobulin Fc region or variant thereof which binds to a human Fc-γ receptor polypeptide, especially which binds to a human CD16 Fc-γ receptor polypeptide; characterized in that the step of bringing into contact said regions comprises bringing into contact a plurality of polypeptide chains selected from of amino acid sequences SEQ ID NO: 61 to 66.

All or parts of the above-mentioned antigen-binding domain(s) and immunoglobulin Fc region or variant thereof may be expressed in vitro, through recombinant means, in an isolated cell or population of cells, in particular in a eukaryotic cell, and preferably in a mammalian or insect cell. Most preferably, the expression system relates to a mammalian cell.

According to alternative embodiments, parts of the above-mentioned antigen-binding domain(s) and Fc region or variant thereof may be expressed in a first population of isolated cells, whereas other parts of the above-mentioned antigen-binding domain(s) and Fc region or variant thereof may be expressed in a second population of isolated cells.

According to alternative embodiments, all the parts of the above-mentioned antigen-binding domain(s) and immunoglobulin Fc region or variant thereof may be expressed in a same population of isolated cells, and then recovered, thereby brought into contact during or at the end of the recovery step.

Hence, the method for making the binding protein may comprise the steps of:

(a) expressing at least one of said first antigen-binding domain and/or said second antigen-binding domain and/or said all or part of immunoglobulin Fc region or variant thereof in an isolated cell or population of cells, most preferably in a mammalian cell;

(b) recovering said first antigen-binding domain and/or said second antigen-binding domain and/or said all or part of Fc region or variant thereof.

According to one of said preferred embodiment, the disclosure relates to a method for making the binding protein related to the present disclosure, which comprises the steps of:

(a) expressing at least one of said first antigen-binding domain and/or said second antigen-binding domain and/or said all or part of Fc region or variant thereof in an isolated cell or population of cells, most preferably in a mammalian cell;

(b) recovering said first antigen-binding domain and/or said second antigen-binding domain and/or said all or part of Fc region or variant thereof;

(c) bringing into contact the said first antigen-binding domain and/or said second antigen-binding domain and/or said all or part of Fc region or variant thereof, steps (b) and (c) being achieved simultaneously or sequentially.

Preferably, the method for making the binding protein comprises the steps of:

(a) expressing said first antigen-binding domain and said second antigen-binding domain and said all or part of immunoglobulin Fc region or variant thereof in an isolated cell;

(b) recovering said first antigen-binding domain and said second antigen-binding domain and said all or part of immunoglobulin Fc region or variant thereof;

(c) bringing into contact the said first antigen-binding domain and said second antigen-binding domain and said all or part of immunoglobulin Fc region or variant thereof, steps (b) and (c) being achieved simultaneously or sequentially.

Advantageously, when the said first antigen-binding domain and said second antigen-binding domain and said all or part of immunoglobulin Fc region or variant thereof are expressed in the same isolated cell or population of cells and/or the same cell culture thereof, they may be brought into contact during the recovery step, thereby making the binding protein.

Alternatively, when the said first antigen-binding domain and/or said second antigen-binding domain and/or said all or part of immunoglobulin Fc region or variant thereof are expressed in different isolated cells or population of cells, they may be brought into contact after the recovery step.

The recovery step may consist of any method known in the Art. In a non-exhaustive manner, the recovery of the expressed polypeptides bearing all or part of the antigen-binding domain(s) and Fc region or variant thereof (e.g. the expressed one or more polypeptide chain(s)) may comprise the following steps:

(b1) recovering the isolated cell or cell culture thereof, (b2) optionally centrifugating, depth filtering, membrane filtering, ultrafiltering and/or diafiltering the isolated cell or cell culture thereof.

SEQUENCE LISTING

In the protein sequences notation used herein, the left-hand direction is the amino terminal direction (the "N terminus" or "N-term") and the right-hand direction is the carboxyl-terminal direction (the "C terminus" or "C-term"), in accordance with standard usage and convention.

| SEQ ID NO: | Name | Sequence |
|---|---|---|
| 1 | $V_{H1}$ CDR-H1 Anti-CD123 CD123-1 | GYSFTDYYMK |
| 2 | $V_{H1}$ CDR-H2 Anti-CD123 CD123-1 | DIIPSSGATF |
| 3 | $V_{H1}$ CDR-H3 Anti-CD123 CD123-1 | SHLLRASWFAY |
| 4 | Anti-CD123 CD123-2 | GFTFSHYN |
| 5 | $V_{H1}$ CDR-H2 Anti-CD123 CD123-2 | ITYDDHST |
| 6 | $V_{H1}$ CDR-H3 Anti-CD123 CD123-2 | ARLVNYAFAY |
| 7 | $V_{L1}$ CDR-L1 Anti-CD123 CD123-1 | ESSQSLLSSGNQKNYLT |
| 8 | $V_{L1}$ CDR-L2 Anti-CD123 CD123-1 | WASTRES |

-continued

| SEQ ID NO: | Name | Sequence |
|---|---|---|
| 9 | V<sub>L1</sub> CDR-L3 Anti-CD123 CD123-1 | QNDYSYPYT |
| 10 | V<sub>L1</sub> CDR-L1 Anti-CD123 CD123-2 | QTVGNN |
| 11 | V<sub>L1</sub> CDR-L2 Anti-CD123 CD123-2 | YAS |
| 12 | V<sub>L1</sub> CDR-L3 Anti-CD123 CD123-2 | QRMYNSPT |
| 13 | V<sub>H2</sub> CDR-H1 Anti-NKp46 NKp46-1 | DYVIN |
| 14 | V<sub>H2</sub> CDR-H2 Anti-NKp46 3D9 and NKp46-1 | EIYPGSGTNYYNEKFKA |
| 15 | V<sub>H2</sub> CDR-H3 Anti-NKp46 3D9 and NKp46-1 | RGRYGLYAMDY |
| 16 | V<sub>H2</sub> CDR-H1 Anti-NKp46 NKp46-2 13G4 | SDYAWN |
| 17 | V<sub>H2</sub> CDR-H2 Anti-NKp46 NKp46-2 | YITYSGSTSYNPSLES |
| 18 | V<sub>H2</sub> CDR-H3 Anti-NKp46 NKp46-2 | GGYYGSSWGVFAY |
| 19 | V<sub>H2</sub> CDR-H1 Anti-NKp46 NKp46-3 | EYTMH |
| 20 | V<sub>H2</sub> CDR-H2 Anti-NKp46 NKp46-3 | GISPNIGGTSYNQKFKG |
| 21 | V<sub>H2</sub> CDR-H3 Anti-NKp46 NKp46-3 | RGGSFDY |
| 22 | V<sub>H2</sub> CDR-H1 Anti-NKp46 NKp46-4 | SFTMH |
| 23 | V<sub>H2</sub> CDR-H2 Anti-NKp46 NKp46-4 | YINPSSGYTEYNQKFKD |
| 24 | V<sub>H2</sub> CDR-H3 Anti-NKp46 NKp46-4 | GSSRGFDY |
| 25 | V<sub>H2</sub> CDR-H2 Anti-NKp46 13G4 | YITYSGSTNYNPSLKS |
| 26 | V<sub>H2</sub> CDR-H3 Anti-NKp46 13G4 | CWDYALYAMDC |

| SEQ ID NO: | Name | Sequence |
|---|---|---|
| 27 | V$_{L2}$ CDR-H1 Anti-NKp46 3D9 and NKp46-1 | RASQDISNYLN |
| 28 | V$_{L2}$ CDR-H2 Anti-NKp46 3D9 and NKp46-1 | YTSRLHS |
| 29 | V$_{L2}$ CDR-H3 Anti-NKp46 3D9 and NKp46-1 | QQGNTRPWT |
| 30 | V$_{L2}$ CDR-H1 Anti-NKp46 NKp46-2 | RVSENIYSYLA |
| 31 | V$_{L2}$ CDR-H2 Anti-NKp46 NKp46-2 13G4 | NAKTLAE |
| 32 | V$_{L2}$ CDR-H3 Anti-NKp46 NKp46-2 | QHHYGTPWT |
| 33 | V$_{L2}$ CDR-H1 Anti-NKp46 NKp46-3 | RASQSISDYLH |
| 34 | V$_{L2}$ CDR-H2 Anti-NKp46 NKp46-3 | YASQSIS |
| 35 | V$_{L2}$ CDR-H3 Anti-NKp46 NKp46-3 | QNGHSFPLT |
| 36 | V$_{L2}$ CDR-H1 Anti-NKp46 NKp46-4 | RASENIYSNLA |
| 37 | V$_{L2}$ CDR-H2 Anti-NKp46 NKp46-4 | AATNLAD |
| 38 | V$_{L2}$ CDR-H3 Anti-NKp46 NKp46-4 | QHFWGTPRT |
| 39 | V$_{L2}$ CDR-H2 Anti-NKp46 13G4 | RTSENIYSYLA |
| 40 | V$_{L2}$ CDR-H3 Anti-NKp46 13G4 | QHHYDTPLT |
| 41 | VH-full length-anti-CD123 | EVQLVQSGAEVKKPGESLKISCKGSGYSFTDYYMKWARQMPGKG LEWMG*DIIPSSGATF*YNQKFKGQVTISADKSISTTYLQWSSLKASDT AMYYCARSHLLRASWFAYWGQGTMVTVSS |
| 42 | VH-full length-anti-CD123 | EVQLVESGGGLVQPGRSLKLSCAASGFTFSHYNMAWVRQAPK KGLEWVATITYDDHSTYYRDSVKGRFTISRDTAKSTLYLQMDS LRSEDTATYYCARLVNYAFAYWGQGTLVTVSS |
| 43 | VL-full length-anti-CD123 | DIVMTQSPDSLAVSLGERATINCESSQSLLSSGNQKNYLTWYQQKP GQPPKPLIY*WASTRESG*VPDRFSGSGSGTDFTLTISSLQAEDVAVYY CQNDYSYPYTFGQGTKLEIK |
| 44 | VL-full length-anti-CD123 | NIVMTQSPKSMSISVGDRVTMNCKASQTVGNNIAWYQQKPGLSPQ LLIDYASNRYTGVPNRFTGGGYGTDFILTINSVQAEDAAFYYCQR MYNSPTFGGGTKLELK |

| SEQ ID NO: | Name | Sequence |
|---|---|---|
| 45 | VH-full length-anti-NKp46 | QVQLVQSGAEVKKPGSSVKVSCKASGYTFSDYVINWVRQAPGQG LEWMG*EIYPGSGTN*YYNEKFKAKATITADKSTSTAYMELSSLRSED TAVYYCARR*GRYGLYAMDY*WGQGTTVTVSS |
| 46 | VH-full length-anti-NKp46-1 | QVQLQQSGPELVKPGASVKMSCKASGYTFTDYVINWGKQRSGQG LEWIGETYPGSGTNYYNEKFKAKATLTADKSSNIAYMQLSSLTSED SAVYFCARRGRYGLYAMDYWGQGTSVTVSS |
| 47 | VH-full length-anti-NKp46-2 | EVQLQESGPGLVKPSQSLSLTCTVTGYSITSDYAWNWIRQFPGNKL EWMGYITYSGSTSYNPSLESRISITRDTSTNQFFLQLNSVTTEDTAT YYCARGGYYGSSWGVFAYWGQGTLVTVSA |
| 48 | VH-full length-anti-NKp46-3 | EVQLQQSGPELVKPGASVKISCKTSGYTFTEYTMHWVKQSHGKSL EWIGGISPNIGGTSYNQKFKGKATLTVDKSSSTAYMELRSLTSEDS AVYYCARRGGSFDYWGQGTTLTVSS |
| 49 | VH-full length-anti-NKp46-4 | QVQLQQSAVELARPGASVKMSCKASGYTFTSFTMHWVKQRPGQG LEWIGYINPSSGYTEYNQKFKDKTTLTADKSSSTAYMQLDSLTSDD SAVYYCVRGSSRGFDYWGQGTLVTVSA |
| 50 | VH-full length-anti-NKp46 10B8 | QVQLQESGPGLVKPSQTLSLTCTVSGYSISSDYAWNWIRQPPGKGL EWIGYITYSGSTSYNPSLESRVTISRDTSKNQFSLKLSSVTAADTAV YYCARGGYYGSSWGVFAYWGQGTLVTVSS |
| 51 | VH-full length-anti-NKp46 12E12 | QVQLVQSGAEVKKPGASVKVSCKASGYTFTSFTMHWVRQAPGQG LEWIGYINPSSGYTEYNQKFKDRVTITADKSTSTAYMELSSLRSED TAVYYCVRGSSRGFDYWGQGTLVTVSS |
| 52 | VH-full length-anti-NKp46 13G4 | QVQLQESGPGLVKPSQTLSLTCTVSGYSISSDYAWNWIRQPPGKGL EWIGYITYSGSTNYNPSLKSRVTISRDTSKNQFSLKLSSVTAADTAV YYCARCWDYALYAMDCWGQGTTVTVSS |
| 53 | VL-full length-anti-NKp46 3D9 | DIQMTQSPSSLSASVGDRVTITCRASQDISNYLNWYQQKPGKAPKL LIYYTSRLHSGVPSRFSGSGSGTDFTFTISSLQPEDIATYFC*QQGNTRP WT*FGGGTKVEIK |
| 54 | VL-full length-anti-NKp46-1 | DIQMTQTTSSLSASLGDRVTISCRASQDISNYLNWYQQKPDGTVKL LIYYTSRLHSGVPSRFSGSGSGTDYSLTINNLEQEDIATYFCQQGNT RPWTFGGGTKLEIK |
| 55 | VL-full length-anti-NKp46-2 | DIQMTQSPASLSASVGETVTITCRVSENIYSYLAWYQQKQGKSPQL LVYNAKTLAEGVPSRFSGSGSGTQFSLKINSLQPEDFGSYYCQHHY GTPWTFGGGTKLEIK |
| 56 | VL-full length-anti-NKp46-3 | DIVMTQSPATLSVTPGDRVSLSCRASQSISDYLHWYQQKSHESPRL LIKYASQSISGIPSRFSGSGSGSDFTLSINSVEPEDVGVYYCQNGHSF PLTFGAGTKLELK |
| 57 | VL_full length-anti-NKp46-4 | DIQMIQSPASLSVSVGETVTITCRASENIYSNLAWFQQKQGKSPQLL VYAATNLADGVPSRFSGSGSGTQYSLKINSLQSEDFGIYYCQHFWG TPRTFGGGTKLEIK |
| 58 | VL-full length-anti-NKp46 10B8 | DIQMTQSPSSLSASVGDRVTITCRVSENIYSYLAWYQQKPGKAPKL LVYNAKTLAEGVPSRFSGSGSGTDFTLTISSLQPEDFATYYCQHHY GTPWTFGGGTKVEIK |
| 59 | VL-full length-anti-NKp46 12E12 | DIQMTQSPSSLSASVGDRVTITCRASENIYSNLAWFQQKPGKAPKL LVYAATNLADGVPSRFSGSGSGTDYTLTISSLQPEDFATYYCQHFW GTPRTFGGGTKVEIK |
| 60 | VL-full length-anti-NKp46 13G4 | DIQMTQSPSSLSASVGDRVTITCRTSENIYSYLAWCQQKPGKAPKL LIYNAKTLAEGVPSRFSGSGSGTDFTLTISSLQPEDFATYYCQHHYD TPLTFGQGTKLEIK |
| 61 | Polypeptide chain (I) | MSVPTQVLGLLLLWLTDARCDIVMTQSPDSLAVSLGERATINCESS QSLLSSGNQKNYLTWYQQKPGQPPKPLIYWASTRESGVPDRFSGS GSGTDFTLTISSLQAEDVAVYYCQNDYSYPYTFGQGTKLEIKRTVA APSVFIFPPSDEQLKSGTASVVCLLNNFYPREAKVQWKVDNALQS GNSQESVTEQDSKDSTYSLSSTLTLSKADYEKHKVYACEVTHQGL SSPVTKSFNRGECDKTHTCPPCPAPELLGGPSVFLFPPKPKDTLMIS RTPEVTCVVVDVSHEDPEVKFNWYVDGVEVHNAKTKPREEQYNS TYRVVSVLTVLHQDWLNGKEYKCKVSNKALPAPIEKTISKAKGQP |

| SEQ ID NO: | Name | Sequence |
|---|---|---|
| | | REPQVYTLPPSREEMTKNQVSLTCLVKGFYPSDIAVEWESNGQPEN NYKTTPPVLDSDGSFFLYSKLTVDKSRWQQGNVFSCSVMHEALHN HYTQKSLSLSPGK |
| 62 | Polypeptide chain (II) | MEWSWVFLFFLSVTTGVHSEVQLVQSGAEVKKPGESLKISCKGSG YSFTDYYMKWARQMPGKGLEWMGDIIPSSGATFYNQKFKGQVTI SADKSISTTYLQWSSLKASDTAMYYCARSHLLRASWFAYWGQGT MVTVSSASTKGPSVFPLAPSSKSTSGGTAALGCLVKDYFPEPVTVS WNSGALTSGVHTFPAVLQSSGLYSLSSVVTVPSSSLGTQTYICNVN HKPSNTKVDKRVEPKSCDKTHTCPPCPAPELLGGPSVFLFPPKPKD TLMISRTPEVTCVVVDVSHEDPEVKFNWYVDGVEVHNAKTKPRE EQYNSTYRVVSVLTVLHQDWLNGKEYKCKVSNKALPAPIEKTISK AKGQPREPQVYTLPPSREEMTKNQVSLTCLVKGFYPSDIAVEWES NGQPENNYKTTPPVLDSDGSFFLYSKLTVDKSRWQQGNVFSCSVM HEALHNHYTQKSLSLSPGSTGSQVQLVQSGAEVKKPGSSVKVSCK ASGYTFSDYVINWVRQAPGQGLEWMGEIYPGSGTNYYNEKFKAK ATITADKSTSTAYMELSSLRSEDTAVYYCARRGRYGLYAMDYWG QGTTVTVSSASTKGPSVFPLAPSSKSTSGGTAALGCLVKDYFPEPV TVSWNSGALTSGVHTFPAVLQSSGLYSLSSVVTVPSSSLGTQTYIC NVNHKPSNTKVDKRVEPKSCDKTHS |
| 63 | Polypeptide chain (III) | MSVPTQVLGLLLLWLTDARCDIQMTQSPSSLSASVGDRVTITCRAS QDISNYLNWYQQKPGKAPKLLIYYTSRLHSGVPSRFSGSGSGTDFT FTISSLQPEDIATYFCQQGNTRPWTFGGGTKVEIKRTVAAPSVFIFPP SDEQLKSGTASVVCLLNNFYPREAKVQWKVDNALQSGNSQESVT EQDSKDSTYSLSSTLTLSKADYEKHKVYACEVTHQGLSSPVTKSFN RGEC |
| 64 | F25 polypeptide chain (I) Cleaved (without leader peptide) | DIVMTQSPDSLAVSLGERATINCESSQSLLSSGNQKNYLTWYQQKP GQPPKPLIYWASTRESGVPDRFSGSGSGTDFTLTISSLQAEDVAVY YCQNDYSYPYTFGQGTKLEIKRTVAAPSVFIFPPSDEQLKSGTASV VCLLNNFYPREAKVQWKVDNALQSGNSQESVTEQDSKDSTYSLSS TLTLSKADYEKHKVYACEVTHQGLSSPVTKSFNRGECDKTHTCPP CPAPELLGGPSVFLFPPKPKDTLMISRTPEVTCVVVDVSHEDPEVKF NWYVDGVEVHNAKTKPREEQYNSTYRVVSVLTVLHQDWLNGKE YKCKVSNKALPAPIEKTISKAKGQPREPQVYTLPPSREEMTKNQVS LTCLVKGFYPSDIAVEWESNGQPENNYKTTPPVLDSDGSFFLYSKL TVDKSRWQQGNVFSCSVMHEALHNHYTQKSLSLSPGK |
| 65 | F25 polypeptide chain (II) Cleaved (without leader peptide) | EVQLVQSGAEVKKPGESLKISCKGSGYSFTDYYMKWARQMPGKG LEWMGDIIPSSGATFYNQKFKGQVTISADKSISTTYLQWSSLKASD TAMYYCARSHLLRASWFAYWGQGTMVTVSSASTKGPSVFPLAPS SKSTSGGTAALGCLVKDYFPEPVTVSWNSGALTSGVHTFPAVLQS SGLYSLSSVVTVPSSSLGTQTYICNVNHKPSNTKVDKRVEPKSCDK THTCPPCPAPELLGGPSVFLFPPKPKDTLMISRTPEVTCVVVDVSHE DPEVKFNWYVDGVEVHNAKTKPREEQYNSTYRVVSVLTVLHQD WLNGKEYKCKVSNKALPAPIEKTISKAKGQPREPQVYTLPPSREEM TKNQVSLTCLVKGFYPSDIAVEWESNGQPENNYKTTPPVLDSDGSF FLYSKLTVDKSRWQQGNVFSCSVMHEALHNHYTQKSLSLSPGSTG SQVQLVQSGAEVKKPGSSVKVSCKASGYTFSDYVINWVRQAPGQ GLEWMGEIYPGSGTNYYNEKFKAKATITADKSTSTAYMELSSLRS EDTAVYYCARRGRYGLYAMDYWGQGTTVTVSSASTKGPSVFPLA PSSKSTSGGTAALGCLVKDYFPEPVTVSWNSGALTSGVHTFPAVL QSSGLYSLSSVVTVPSSSLGTQTYICNVNHKPSNTKVDKRVEPKSC DKTHS |
| 66 | F25 polypeptide chain (III) Cleaved (without leader peptide) | DIQMTQSPSSLSASVGDRVTITCRASQDISNYLNWYQQKPGKAPKL LIYYTSRLHSGVPSRFSGSGSGTDFTFTISSLQPEDIATYFCQQGNTR PWTFGGGTKVEIKRTVAAPSVFIFPPSDEQLKSGTASVVCLLNNFY PREAKVQWKVDNALQSGNSQESVTEQDSKDSTYSLSSTLTLSKAD YEKHKVYACEVTHQGLSSPVTKSFNRGEC |
| 67 | CK | RTVAAPSVFIFPPSDEQLKSGTASVVCLLNNFYPREAKVQWKVDN ALQSGNSQESVTEQDSKDSTYSLSSTLTLSKADYEKHKVYACEVT HQGLSSPVTKSFNRGEC |
| 68 | $C_H 1$ | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNTK VDKRV |
| 69 | $(C_H 2-C_H 3)_A$ | APELLGGPSVFLFPPKPKDTLMISRTPEVTCVVVDVSHEDPEVKFN WYVDGVEVHNAKTKPREEQYNSTYRVVSVLTVLHQDWLNGKEY KCKVSNKALPAPIEKTISKAKGQPREPQVYTLPPSREEMTKNQVSL TCLVKGFYPSDIAVEWESNGQPENNYKTTPPVLDSDGSFFLYSKLT VDKSRWQQGNVFSCSVMHEALHNHYTQKSLSLSPGK |

| SEQ ID NO: | Name | Sequence |
|---|---|---|
| 70 | $(C_H2-C_H3)_B$ | APELLGGPSVFLFPPKPKDTLMISRTPEVTCVVVDVSHEDPEVKFN WYVDGVEVHNAKTKPREEQYNSTYRVVSVLTVLHQDWLNGKEY KCKVSNKALPAPIEKTISKAKGQPREPQVYTLPPSREEMTKNQVSL TCLVKGFYPSDIAVEWESNGQPENNYKTTPPVLDSDGSFFLYSKLT VDKSRWQQGNVFSCSVMHEALHNHYTQKSLSLSPG |
| 71 | $C_H2$ | APELLGGPSVFLFPPKPKDTLMISRTPEVTCVVVDVSHEDPEVKFN WYVDGVEVHNAKTKPREEQYNSTYRVVSVLTVLHQDWLNGKEY KCKVSNKALPAPIEKTISKAK GQPREPQVYTLPPSREEMTKNQVSLTCLVKGFYPSDIAVEWESNG |
| 72 | $C_H3$ of $(C_H2-C_H3)_A$ | QPENNYKTTPPVLDSDGSFFLYSKLTVDKSRWQQGNVFSCSVMHE ALHNHYTQKSLSLSPGK |
| 73 | C-term truncated $C_H3$ of $(C_H2-C_H3)_B$ | GQPREPQVYTLPPSREEMTKNQVSLTCLVKGFYPSDIAVEWESNG QPENNYKTTPPVLDSDGSFFLYSKLTVDKSRWQQGNVFSCSVMHE ALHNHYTQKSLSLSPG |
| 74 | $Hinge_1$ | DKTHTCPPCP |
| 75 | $Hinge_2$ | EPKSCDKTHTCPPCP |
| 76 | $Linker_1$ | STGS |
| 77 | $Hinge_3$ | EPKSCDKTHS |
| 78 | $Hinge_{ALT1}$ | EPKSCDKTH |
| 79 | $Hinge_{ALT2}$ | EPKSCDKTHT |
| 80 | Single guide RNA | CUUGAGGUGUCAUGCGUGGA |
| 81 | Single guide RNA | AAGCAUCGCUACACAUCAGC |
| 82 | DNA primer 1 | TACGACTCACAAGCTTGCCGCCACCATGTCTTCCACACTCCCTG C |
| 83 | DNA primer 2 | CCGCCCCGACTCTAGATCAATGGTGATGGTGGTGATGATTCTGG GCAGTGTGATCCC |
| 84 | Human NKp46 extracellular domain (ECD) | MSSTLPALLCVGLCLSQRISAQQQTLPKPFIWAEPHFMVPKEKQVT ICCQGNYGAVEYQLHFEGSLFAVDRPKPPERINKVKFYIPDMNSRM AGQYSCIYRVGELWSEPSNLLDLVVTEMYDTPTLSVHPGPEVISGE KVTFYCRLDTATSMFLLLKEGRSSHVQRGYGKVQAEFPLGPVTTA HRGTYRCFGSYNNHAWSFPSEPVKLLVTGDIENTSLAPEDPTFPAD TWGTYLLTTETGLQKDHALWDHTAQN |
| 85 | Cynomolgus NK46-FlagM2 extracellular domain (ECD) | MSSTLRALLCLGLCLSQRISAPKQTLPKPIIRAESTYMVPKEKQATL CCQGSYGAVEYQLHFEGSLFAVERPKPPERINGVKFHIPDMNSRKA GRYSCIYRVGELWSERSDLLDLVVTEMYDTPTLSVHPGPEVTSGE KVTFYCRLDTATSMFLLLKEGRSRDVQRSYGKVQAEFPMGPVTTA HRGSYRCFGSYNNYAWSFPSEPVKLLVTGDIENTSLAPTDPTFPDS WDTCLLTRETGLQKDLALWDHTAQNDYKDDDDK |
| 86 | Human CD123 extracellular domain (ECD) | TKEDPNPPITNLRMKAKAQQLTWDLNRNVTDIECVKDADYSMPA VNNSYCQFGAISLCEVTNYTVRVANPPFSTWILFPENSGKPWAGAE NLTCWIHDVDFLSCSWAVGPGAPADVQYDLYLNVANRRQQYECL HYKTDAQGTRIGCRFDDISRLSSGSQSSHILVRGRSAAFGIPCTDKF VVFSQIEILTPPNMTAKCNKTHSFMHWKMRSHFNRKFRYELQIQK RMQPVITEQVRDRTSFQLLNPGTYTVQIRARERVYEFLSAWSTPQR FECDQEEGANTRAWR |
| 87 | Human Fc-gamma-receptor 3A (CD16A). | MWQLLLLPTALLLLVSAGMRTEDLPKAVVFLEPQWYRVLEKDSVT LKCQGAYSPEDNSTQWFHNESLISSQASSYFIDAATVDDSGEYRCQ TNLSTLSDPVQLEVHIGWLLLQAPRWVFKEEDPIHLRCHSWKNTA LHKVTYLQNGKGRKYFHHNSDFYIPKATLKDSGSYFCRGLVGSKN VSSETVNITITQGLAVSTISSFFPPGYQVSFCLVMVLLFAVDTGLYFS VKTNIRSSTRDWKDHKFKWRKDPQDK |

| SEQ ID NO: | Name | Sequence |
|---|---|---|
| 88 | Human Fc-gamma-receptor 3A (CD16A) (V176F polymorphic variant) | MWQLLLPTALLLLVSAGMRTEDLPKAVVFLEPQWYRVLEKDSVT LKCQGAYSPEDNSTQWFHNESLISSQASSYFIDAATVDDSGEYRCQ TNLSTLSDPVQLEVHIGWLLLQAPRWVFKEEDPIHLRCHSWKNTA LHKVTYLQNGKGRKYFHHNSDFYIPKATLKDSGSYFCRGLFGSKN VSSETVNITITQGLAVSTISSFFPPGYQVSFCLVMVLLFAVDTGLYFS VKTNIRSSTRDWKDHKFKWRKDPQDK |
| 89 | DNA primer 3 | TACGACTCACAAGCTTGCCGCCACCATGTCTTCCACACTCCGTG C |
| 90 | DNA primer 4 | CCGCCCCGACTCTAGATCACTTGTCATCGTCATCTTTGTAATCAT TCTGGGCAGTGTGGTCC |
| 91 | NKp46-IC_F25 Fragment 1 | EIVLTQSPATLSLSPGERATLSCRASQSVRSYLAWYQQKPGQAPRL LFSDASNRATGIPARFSGSGSGTDFTLTISSLEPEDFAVYYCQQYRY SPRTFGQGTKVEIKRTVAAPSVFIFPPSDEQLKSGTASVVCLLNNFY PREAKVQWKVDNALQSGNSQESVTEQDSKDSTYSLSSTLTLSKAD YEKHKVYACEVTHQGLSSPVTKSFNRGECDKTHTCPPCPAPELLG GPSVFLFPPKPKDTLMISRTPEVTCVVVDVSHEDPEVKFNWYVDG VEVHNAKTKPREEQYNSTYRVVSVLTVLHQDWLNGKEYKCKVSN KALPAPIEKTISKAKGQPREPQVYTLPPSREEMTKNQVSLTCLVKG FYPSDIAVEWESNGQPENNYKTTPPVLDSDGSFFLYSKLTVDKSRW QQGNVFSCSVMHEALHNHYTQKSLSLSPGK |
| 92 | NKp46-IC_F25 Fragment 2 | EVQLVESGGGLVQPGRSLRLSCAASGFTFDNYAMHWVRQAPGKG LEWVSGISRSSGDIDYADSVKGRFTISRDNAKNSLYLQMNSLRAED TALYYCARGGVGSFDTWGQGTMVTVSSASTKGPSVFPLAPSSKST SGGTAALGCLVKDYFPEPVTVSWNSGALTSGVHTFPAVLQSSGLY SLSSVVTVPSSSLGTQTYICNVNHKPSNTKVDKRVEPKSCDKTHTC PPCPAPELLGGPSVFLFPPKPKDTLMISRTPEVTCVVVDVSHEDPEV KFNWYVDGVEVHNAKTKPREEQYNSTYRVVSVLTVLHQDWLNG KEYKCKVSNKALPAPIEKTISKAKGQPREPQVYTLPPSREEMTKNQ VSLTCLVKGFYPSDIAVEWESNGQPENNYKTTPPVLDSDGSFFLYS KLTVDKSRWQQGNVFSCSVMHEALHNHYTQKSLSLSPGSTGSQV QLVQSGAEVKKPGSSVKVSCKASGYTFSDYVINWVRQAPGQGLE WMGEIYPGSGTNYYNEKFKAKATITADKSTSTAYMELSSLRSEDT AVYYCARRGRYGLYAMDYWGQGTTVTVSSASTKGPSVFPLAPSS KSTSGGTAALGCLVKDYFPEPVTVSWNSGALTSGVHTFPAVLQSS GLYSLSSVVTVPSSSLGTQTYICNVNHKPSNTKVDKRVEPKSCDKT HS |
| 93 | NKp46-IC_F25 Fragment 3 | DIQMTQSPSSLSASVGDRVTITCRASQDISNYLNWYQQKPGKAPKL LIYYTSRLHSGVPSRFSGSGSGTDFTFTISSLQPEDIATYFCQQGNTR PWTFGGGTKVEIKRTVAAPSVFIFPPSDEQLKSGTASVVCLLNNFY PREAKVQWKVDNALQSGNSQESVTEQDSKDSTYSLSSTLTLSKAD YEKHKVYACEVTHQGLSSPVTKSFNRGEC |
| 94 | moNKp46-huCD123_F25 Fragment 1 | DIVMTQSPDSLAVSLGERATINCESSQSLLSSGNQKNYLTWYQQKP GQPPKPLIYWASTRESGVPDRFSGSGSGTDFTLTISSLQAEDVAVY YCQNDYSYPYTFGQGTKLEIKRTVAAPSVFIFPPSDEQLKSGTASV VCLLNNFYPREAKVQWKVDNALQSGNSQESVTEQDSKDSTYSLSS TLTLSKADYEKHKVYACEVTHQGLSSPVTKSFNRGECDKTHTCPP CPAPELLGGPSVFLFPPKPKDTLMISRTPEVTCVVVDVSHEDPEVKF NWYVDGVEVHNAKTKPREEQYNSTYRVVSVLTVLHQDWLNGKE YKCKVSNKALPAPIEKTISKAKGQPREPQVYTLPPSREEMTKNQVS LTCLVKGFYPSDIAVEWESNGQPENNYKTTPPVLDSDGSFFLYSKL TVDKSRWQQGNVFSCSVMHEALHNHYTQKSLSLSPGK |
| 95 | moNKp46-huCD123_F25 Fragment 2 | EVQLVQSGAEVKKPGESLKISCKGSGYSFTDYYMKWARQMPGKG LEWMGDIIPSSGATFYNQKFKGQVTISADKSISTTYLQWSSLKASD TAMYYCARSHLLRASWFAYWGQGTMVTVSSASTKGPSVFPLAPS SKSTSGGTAALGCLVKDYFPEPVTVSWNSGALTSGVHTFPAVLQS SGLYSLSSVVTVPSSSLGTQTYICNVNHKPSNTKVDKRVEPKSCDK THTCPPCPAPELLGGPSVFLFPPKPKDTLMISRTPEVTCVVVDVSHE DPEVKFNWYVDGVEVHNAKTKPREEQYNSTYRVVSVLTVLHQD WLNGKEYKCKVSNKALPAPIEKTISKAKGQPREPQVYTLPPSREEM TKNQVSLTCLVKGFYPSDIAVEWESNGQPENNYKTTPPVLDSDGSF FLYSKLTVDKSRWQQGNVFSCSVMHEALHNHYTQKSLSLSPGSTG SEVQLVESGGGLVKPGGSLKSCAASGFTFSDYGMHWVRQAPEK GLEWVAYISSGSSTIYYADTVKGRFTISRDNAKNTLFLQMTSLRSE DTAMYYCARGTTIFNYFEYWGQGTSVTVSSASTKGPSVFPLAPSSK STSGGTAALGCLVKDYFPEPVTVSWNSGALTSGVHTFPAVLQSSG LYSLSSVVTVPSSSLGTQTYICNVNHKPSNTKVDKRVEPKSCDKTH S |

| SEQ ID NO: | Name | Sequence |
|---|---|---|
| 96 | moNKp46-huCD123_F25 Fragment 3 | DIVMSQSPSSLAVSVGEKVTMSCKSSQSLLYSSNQKNYLAWYQQK PGQSPKLLIYWASTRESGVPDRFTGSGSGTDFTLTISSVKAEDLAVY YCQQYYEIPPTFGAGTKLELKRTVAAPSVFIFPPSDEQLKSGTASVV CLLNNFYPREAKVQWKVDNALQSGNSQESVTEQDSKDSTYSLSST LTLSKADYEKHKVYACEVTHQGLSSPVTKSFNRGEC |
| 97 | NKp46-CD123_F5 Fragment 1 | DIVMTQSPDSLAVSLGERATINCESSQSLLSSGNQKNYLTWYQQKP GQPPKPLIYWASTRESGVPDRFSGSGSGTDFTLTISSLQAEDVAVY YCQNDYSYPYTFGQGTKLEIKRTVAAPSVFIFPPSDEQLKSGTASV VCLLNNFYPREAKVQWKVDNALQSGNSQESVTEQDSKDSTYSLSS TLTLSKADYEKHKVYACEVTHQGLSSPVTKSFNRGECDKTHTCPP CPAPELLGGPSVFLFPPKPKDTLMISRTPEVTCVVVDVSHEDPEVKF NWYVDGVEVHNAKTKPREEQYNSTYRVVSVLTVLHQDWLNGKE YKCKVSNKALPAPIEKTISKAKGQPREPQVYTLPPSREEMTKNQVS LTCLVKGFYPSDIAVEWESNGQPENNYKTTPPVLDSDGSFFLYSKL TVDKSRWQQGNVFSCSVMHEALHNHYTQKSLSLSPGK |
| 98 | NKp46-CD123_F5 Fragment 2 | EVQLVQSGAEVKKPGESLKISCKGSGYSFTDYYMKWARQMPGKG LEWMGDIIPSSGATFYNQKFKGQVTISADKSISTTYLQWSSLKASD TAMYYCARSHLLRASWFAYWGQGTMVTVSSASTKGPSVFPLAPS SKSTSGGTAALGCLVKDYFPEPVTVSWNSGALTSGVHTFPAVLQS SGLYSLSSVVTVPSSSLGTQTYICNVNHKPSNTKVDKRVEPKSCDK THTCPPCPAPELLGGPSVFLFPPKPKDTLMISRTPEVTCVVVDVSHE DPEVKFNWYVDGVEVHNAKTKPREEQYNSTYRVVSVLTVLHQD WLNGKEYKCKVSNKALPAPIEKTISKAKGQPREPQVYTLPPSREEM TKNQVSLTCLVKGFYPSDIAVEWESNGQPENNYKTTPPVLDSDGSF FLYSKLTVDKSRWQQGNVFSCSVMHEALHNHYTQKSLSLSPGSTG SQVQLVQSGAEVKKPGSSVKVSCKASGYTFSDYVINWVRQAPGQ GLEWMGEIYPGSGTNYYNEKFKAKATITADKSTSTAYMELSSLRS EDTAVYYCARRGRYGLYAMDYWGQGTTVTVSSRTVAAPSVFIFP PSDEQLKSGTASVVCLLNNFYPREAKVQWKVDNALQSGNSQESV TEQDSKDSTYSLSSTLTLSKADYEKHKVYACEVTHQGLSSPVTKSF NRGEC |
| 99 | NKp46-CD123_F5 Fragment 3 | DIQMTQSPSSLSASVGDRVTITCRASQDISNYLNWYQQKPGKAPKL LIYYTSRLHSGVPSRFSGSGSGTDFTFTISSLQPEDIATYFCQQGNTR PWTFGGGTKVEIKASTKGPSVFPLAPSSKSTSGGTAALGCLVKDYF PEPVTVSWNSGALTSGVHTFPAVLQSSGLYSLSSVVTVPSSSLGTQ TYICNVNHKPSNTKVDKRVEPKSCDKTHS |
| 100 | IC-CD123_F5 Fragment 1 | DIVMTQSPDSLAVSLGERATINCESSQSLLSSGNQKNYLTWYQQKP GQPPKPLIYWASTRESGVPDRFSGSGSGTDFTLTISSLQAEDVAVY YCQNDYSYPYTFGQGTKLEIKRTVAAPSVFIFPPSDEQLKSGTASV VCLLNNFYPREAKVQWKVDNALQSGNSQESVTEQDSKDSTYSLSS TLTLSKADYEKHKVYACEVTHQGLSSPVTKSFNRGECDKTHTCPP CPAPELLGGPSVFLFPPKPKDTLMISRTPEVTCVVVDVSHEDPEVKF NWYVDGVEVHNAKTKPREEQYNSTYRVVSVLTVLHQDWLNGKE YKCKVSNKALPAPIEKTISKAKGQPREPQVYTLPPSREEMTKNQVS LTCLVKGFYPSDIAVEWESNGQPENNYKTTPPVLDSDGSFFLYSKL TVDKSRWQQGNVFSCSVMHEALHNHYTQKSLSLSPGK |
| 101 | IC-CD123_F5 Fragment 2 | EVQLVQSGAEVKKPGESLKISCKGSGYSFTDYYMKWARQMPGKG LEWMGDIIPSSGATFYNQKFKGQVTISADKSISTTYLQWSSLKASD TAMYYCARSHLLRASWFAYWGQGTMVTVSSASTKGPSVFPLAPS SKSTSGGTAALGCLVKDYFPEPVTVSWNSGALTSGVHTFPAVLQS SGLYSLSSVVTVPSSSLGTQTYICNVNHKPSNTKVDKRVEPKSCDK THTCPPCPAPELLGGPSVFLFPPKPKDTLMISRTPEVTCVVVDVSHE DPEVKFNWYVGVEVHNAKTKPREEQYNSTYRVVSVLTVLHQD WLNGKEYKCKVSNKALPAPIEKTISKAKGQPREPQVYTLPPSREEM TKNQVSLTCLVKGFYPSDIAVEWESNGQPENNYKTTPPVLDSDGSF FLYSKLTVDKSRWQQGNVFSCSVMHEALHNHYTQKSLSLSPGSTG SEVQLVQSGAEVKKSGESLKISCKGSGYSFTSYWIGWVRQMPGKG LEWMGIFYPGDSSTRYSPSFQGQVTISNVNTAYLQWSSLKASD TAMYYCARRRNWGNAFDIWGQGTMVTVSSRTVAAPSVFIFPPSDE QLKSGTASVVCLLNNFYPREAKVQWKVDNALQSGNSQESVTEQD SKDSTYSLSSTLTLSKADYEKHKVYACEVTHQGLSSPVTKSFNRGE C |
| 102 | IC-CD123_F5 Fragment 3 | EIVLTQSPGTLSLSPGERATLSCRASQSVSSSYLAWYQQKPGQAPR LLIYGASSRATGIPDRFSGSGSGTDFTLTISRLEPEDFAVYYCQQYG SSTWTFGQGTKVEIKASTKGPSVFPLAPSSKSTSGGTAALGCLVKD YFPEPVTVSWNSGALTSGVHTFPAVLQSSGLYSLSSVVTVPSSSLG TQTYICNVNHKPSNTKVDKRVEPKSCDKTHS |

| SEQ ID NO: | Name | Sequence |
|---|---|---|
| 103 | IC-hIGg1-ADCC-enh Light Chain | EIVLTQSPATLSLSPGERATLSCRASQSVRSYLAWYQQKPGQAPRL LFSDASNRATGIPARFSGSGSGTDFTLTISSLEPEDFAVYYCQQYRY SPRTFGQGTKVEIKRTVAAPSVFIFPPSDEQLKSGTASVVCLLNNFY PREAKVQWKVDNALQSGNSQESVTEQDSKDSTYSLSSTLTLSKAD YEKHKVYACEVTHQGLSSPVTKSFNRGEC |
| 104 | IC-hIGg1-ADCC-enh Heavy Chain | EVQLVESGGGLVQPGRSLRLSCAASGFTFDNYAMHWVRQAPGKG LEWVSGISRSSGDIDYADSVKGRFTISRDNAKNSLYLQMNSLRAED TALYYCARGGVGSFDTWGQGTMVTVSSASTKGPSVFPLAPSSKST SGGTAALGCLVKDYFPEPVTVSWNSGALTSGVHTFPAVLQSSGLY SLSSVVTVPSSSLGTQTYICNVNHKPSNTKVDKRVEPKSCDKTHTC PPCPAPELLGGPDVFLFPPKPKDTLMISRTPEVTCVVVDVSHEDPEV KFNWYVDGVEVHNAKTKPREEQYNSTYRVVSVLTVLHQDWLNG KEYKCKVSNKALPAPEEKTISKAKGQPREPQVYTLPPSREEMTKN QVSLTCLVKGFYPSDIAVEWESNGQPENNYKTTPPVLDSDGSFFLY SKLTVDKSRWQQGNVFSCSVMHEALHNHYTQKSLSLSPGK |

EXAMPLES

Materials & Methods

A.1. NKp46-CD123 NKCE Expression by Transient Transfection of EXPI-293F™ Cells.

The sequences encoding each polypeptide chain of NKp46-CD123_F25 binding proteins of the present disclosure were inserted into the pTT-5 vector between the HindIII and BamHI restriction sites. The three vectors (made as endotoxin-free midipreps) were used to cotransfect EXPI-293F cells (Life Technologies) in the presence of PEI (37° C., 5% CO2, 150 rpm). The cells were used to seed culture flasks at a density of 1×106 cells per ml (EXPI293 medium, Gibco). As a reference, for the NKp46-CD123_F25 binding protein, we used a DNA ratio of 0.1 µg/ml (polypeptide chain I), 0.4 µg/ml (polypeptide chain II), or 0.8 µg/ml (polypeptide chain III). Valproic Acid (final concentration 0.5 mM), glucose (4 g/L) and tryptone N1 (0.5%) were added. The supernatant was harvested after six days after and passed through a Stericup filter with 0.22 µm pores.

A.2. Purification of NKCEs.

The NKp46-CD123_F25 binding proteins of the present disclosure were purified from the supernatant following harvesting using rProtein A Sepharose Fast Flow (GE Healthcare, reference 17-1279-03). A Cation Ion Exchange Chromatography (CIEX) purification was then performed after dialysis of the sample in a $Na_2HPO_4/KH_2PO_4$ 50 mM pH 6.2 phosphate buffer. Prior to injection to the two «in series» column HiTrap SP-HP 1 mL from GE Healthcare (ref 17-1151-01), the sample was filtered on a 0.22 µm device. The starting and the elution buffers were respectively $Na_2HPO_4/KH_2PO_4$ 50 mM pH 6.2 and $Na_2HPO_4/KH_2PO_4$ 25 mM pH 6.2; 1M NaCl. The elution was performed using a linear gradient from 0% to 50% (elution buffer) on 100 CV. The peak of interest is finally dialyzed against PBS1x, overnight at 4° C. under agitation.

A.3. Biological Samples

Healthy Human buffy coats were provided by the Etablissement Français du Sang (EFS, Marseille; AC-2019-3428). Peripheral mononuclear cells (PBMC) were isolated from buffy coats by using Ficoll density gradient centrifugation. Human NK cells were purified from PBMC by using beads-based negative selection kit from StemCell or Miltenyi.

Acute myeloid leukemia (AML) samples from patients were provided by Institut Paoli-Calmettes (Marseille, SA-IPH-MImAbs Contract).

A.4. Cell Lines

CD123 expressing Acute myeloid leukemia (AML) cell line: MOLM-13 and THP-1 were purchased at ATCC. Cells were cultured in complete RPMI medium (RPMI-1640 containing 10% FBS, 2 mM L-Glutamine, 1 mM Sodium pyruvate and non-essential amino-acids 1×). 25 mM HEPES were added in the culture medium for THP-1 cells.

THP-1 CD64KO and THP-1 CD32KO cells were generated with CRISPR/Cas endonucleases. THP-1 cells were cultured in RPMI-1640, 10% SVF, 2 mM L-Glu, 1 mM sodium pyruvate, 0.1 mM non-essential amino acid. To generate CD64 deficient THP-1 cells, 2,5.106 cells were nucleofected (Neon Transfection System, 100 ul tip, 1700V, 20 ms, 1 pulse) with two sgRNAs (CD64.1: CUUGAGGU-GUCAUGCGUGGA (SEQ ID NO: 80); CD64.2: AAGCAUCGCUACACAUCAGC (SEQ ID NO: 81; Synthego) at a CAS9:sgRNA ratio of 1:9 (Alt-R™ S.p. Cas9 Nuclease 3NLS, Integrated DNA Technology). Lack of CD64 expression was monitored by flow cytometry and cells were either sorted or sub-cloned.

To generate CD32-knockout (KO) THP-1 cells, $2.5.10^6$ cells were nucleofected (Neon Transfection System, 100 µL tip, 1700 V, 20 ms, 1 pulse) with a couple of sgRNAs (CD32A: AUGUAUGUCCCAGAAACCUG (SEQ ID NO: 105); CD32B: AAGCAUAUGACCCCAAGGCU (SEQ ID NO: 106) (Integrated DNA Technologies)) at a CAS9: sgRNA ratio of 1:9 (Alt-R™ S.p. Cas9 Nuclease 3NLS, Integrated DNA Technology). The THP-1 CD32KO cells were cell sorted only. Following cell sorting, absence of CD32 expression was monitored by flow cytometry.

A.5. NK Cell-Based Cytotoxic Assay

Target cells were loaded with $^{51}Cr$ (for MOLM-13, THP-1 or THP-1 CD64KO, THP-1 CD32KO cells) or with CalceinAM (Life technologies, ref: C3100MP or equivalent) for AML blasts from patient samples. Tested antibodies, labelled target cells and fresh or overnight-rested human NK cells from healthy donors were successively added in each well of round bottom 96-well plates to obtain a 10:1 (E:T) ratio. After 4 h of co-incubation, the supernatant was transferred into a Lumaplate (for $^{51}Cr$) or into a flat bottom culture plate (for CalceinAM).

For $^{51}Cr$-based cytotoxic assay, the $^{51}Cr$ released from dead target cells was dosed using a TopCount NXT™ (Microplate Scintillation and Luminescence Counter; Perkin Elmer). Radioactivity was measured by counting γ-emission during 60 s for each well and these results was expressed in cpm=count per minute.

For Calcein-based cytotoxic assay, the CalceinAM released from dead target cells was dosed by measuring relative fluorescence units (RFU) with a Luminoter (EnSpire®Multimode Plate Reader (Perkinelmer): fluorescence emission at λ=516 nm after an excitation at λ=495 nm).

For the analysis, the percent specific lysis was calculated using the following formula:

$$\text{Specific lysis (\%)} = \frac{ER \ (cpm \ or \ RFU) - SR \ (cpm \ or \ RFU)}{MR \ (cpm \ or \ RFU) - SR \ (cpm \ or \ RFU)} \times 100$$

with ER=experimental release, SR=spontaneous release and MR=maximal release $EC_{50}$ of each antibody are determined with drawing appropriate non-linear regression curve (choice of "log(agonist) vs. response—Variable slope (four parameters)" model) by using Graphpad Prism Software.

Phenotyping AML Cells

Figure 6A:
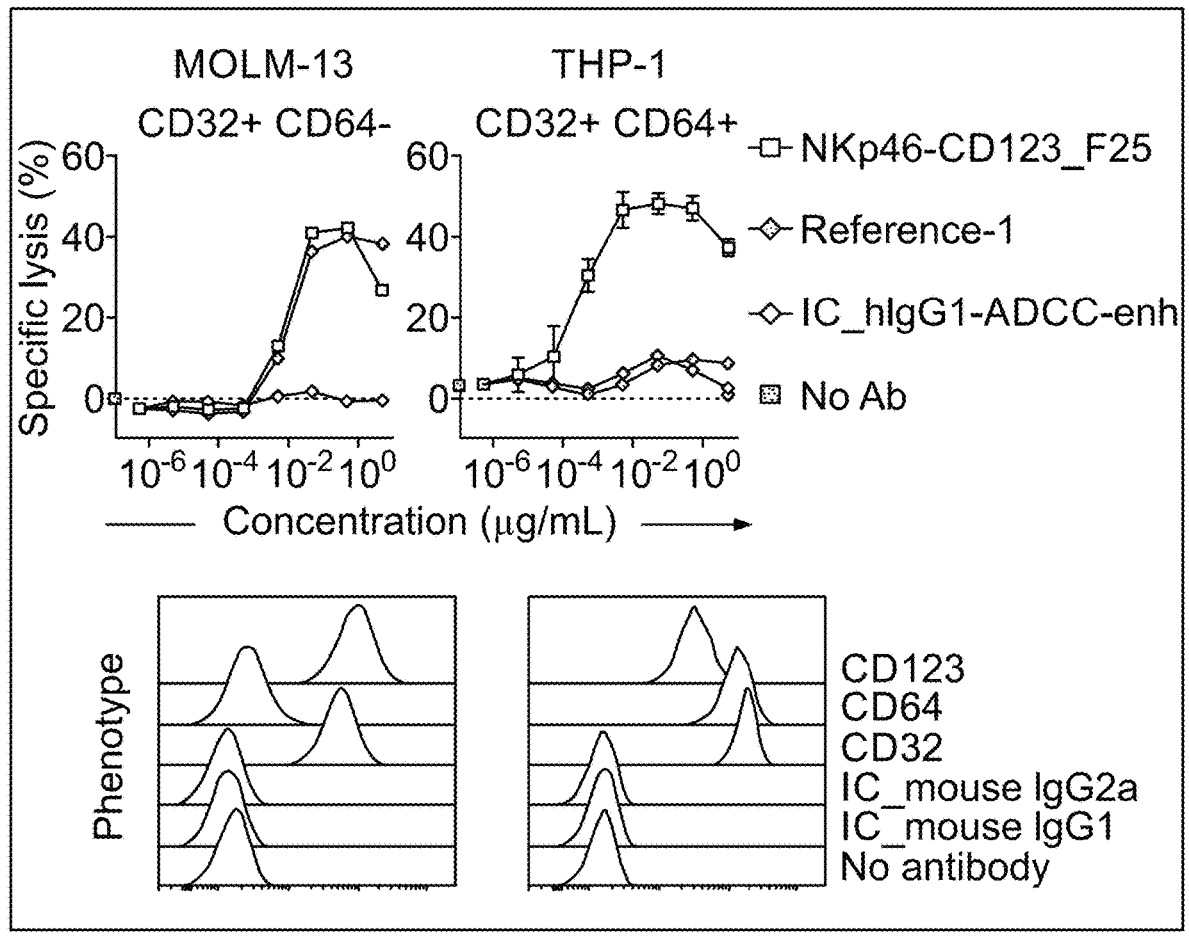
FIG. 6A-FIG. 6B upper panels report the in vitro cytotoxicity of the NKp46-CD123_F25 binding protein of the present disclosure, an anti-CD123 ADCC-enhanced antibody with no binding for NKp46 (Reference-1) and a negative isotype control Fc-optimized antibody with increased ADCC activity with no specificity for NKp46 nor CD123 (IC_hIgG1-ADCC-enh) against different AML cell lines. The AML cell lines tested are: THP-1, a cell line expressing CD64(+) and CD32(+) (FIG. 6A); MOLM-13, a cell line not expressing CD64(−) but expressing CD32(+) (FIG. 6A), THP-1 CD64KO, a cell line knockout for CD64 (−) expressing CD32(+) (FIG. 6B); and THP-1 CD32KO, a cell line expressing CD64(+) and knockout for CD32(−) (FIG. 6B).
Figure 6B:
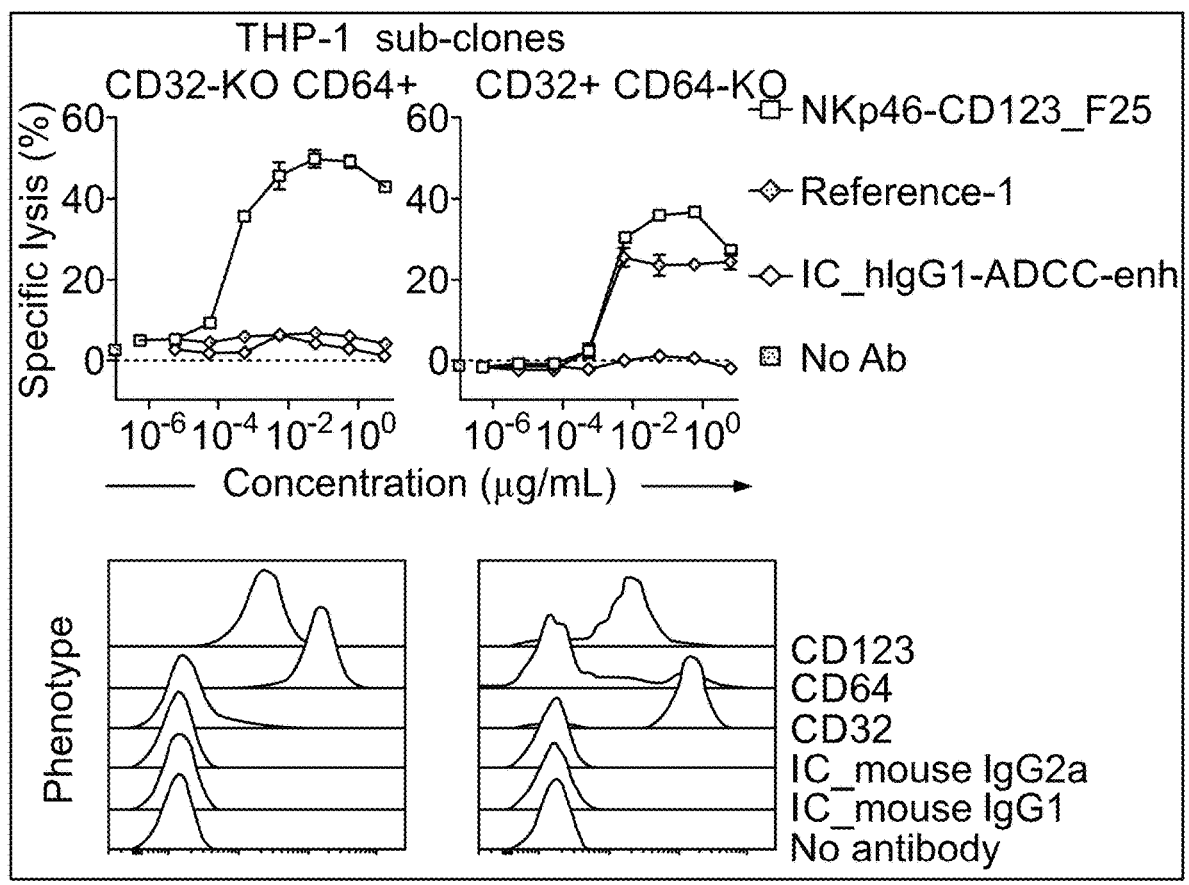

The expression of CD32, CD64 and CD123 on AML samples derived from patient blood and on AML cell lines was controlled by flow cytometry using Anti-human CD33-BB515 (BD Biosciences 564588 Clone WM53), Anti-human CD45-Viogreen (Miltenyi 130-096-906 Clone 5B1), Anti-human CD123-AF647 (BD Biosciences 563599 Clone 9F5), Anti-human CD32-PE (Beckman Coulter IM1935 Clone 2E1), Anti-human CD64-PE (Beckman Coulter IM3601U Clone 22), Anti-human CD123-PE (Biolegend 306006 Clone 6H6), and cognate isotype control antibodies mIgG1-PE (IC-1; BD Biosciences 555749 Clone MOPC-21), and mIgG2a-PE (IC-2a; Beckman Coulter A09142 Clone 7T4-1F5). Target cells were saturated with normal mouse serum diluted at 1/10e in staining buffer (SB) and then mix with antibodies coupled to dyes. Cells were fixed in BD Cellfix diluted at 1/10e in $H_2O$ during 30 min after staining and analyzed by flow cytometry with a FACS Canto II. FSC-A, FSC-H, SSC-A, SSC-H, FL2-A, FL4-A and FL7-A or FSC-A, FSC-H, SSC-A, SSC-H, FL1-A, FL2-A, FL3-A, FL5-A and FL8-A (for AML samples derived from patient blood) parameters were recorded and the analyses were done with FlowJo software. The phenotyping results are shown in FIG. 6A, FIG. 6B, and FIG. 14B.

A.6. NK Cell Degranulation Assay with AML Samples

Figure 7A:
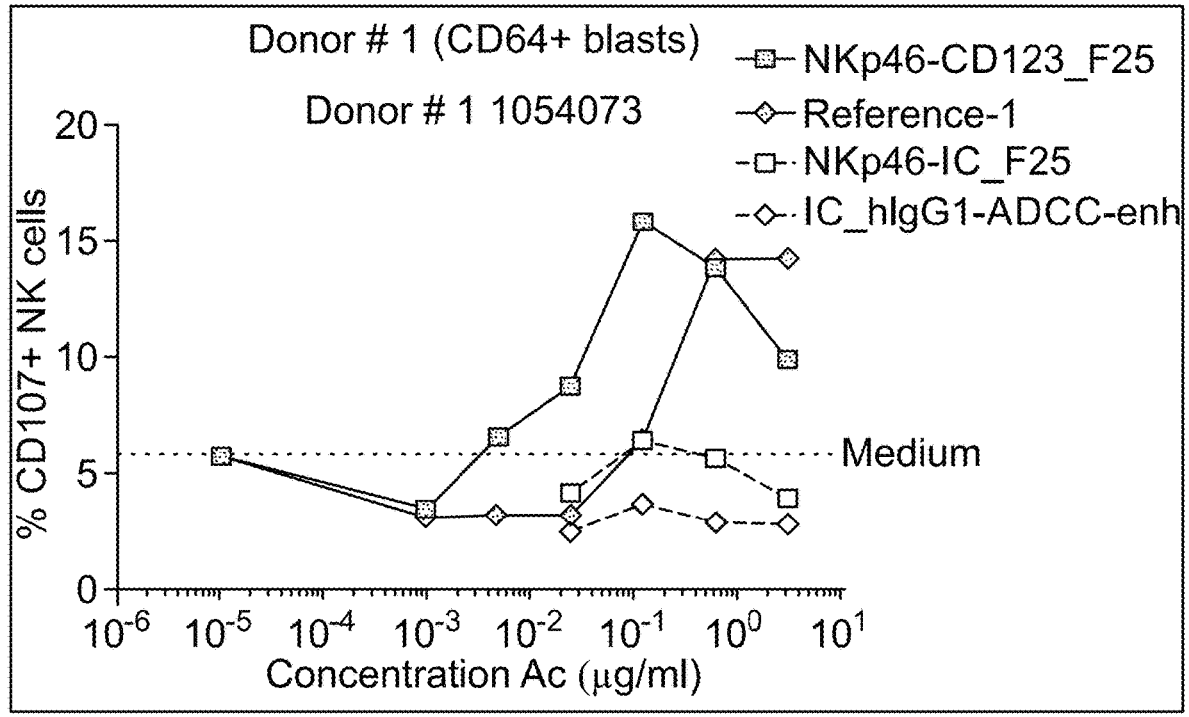
FIG. 7A-FIG. 7B report the ex vivo induction of NK degranulation measured through the percentage of CD107a-positive NK cells against primary AML blasts from two different donors. Primary AML blasts from donor #1 are CD64(+) (FIG. 7A) and primary AML blasts from donor #2 are CD64(−) (FIG. 7B). The tested binding proteins are the NKp46-CD123_F25 binding protein of the present disclosure, an anti-CD123 ADCC-enhanced antibody with no specificity for NKp46 (Reference-1), a negative isotype control variant of format F25 not binding CD123 but binding NKp46 and CD16a (NKp46-IC_F25) and a negative isotype control Fc-optimized antibody with increased ADCC activity with no specificity for NKp46 nor CD123 (IC_hIgG1-ADCC-enh).
Figure 7B:
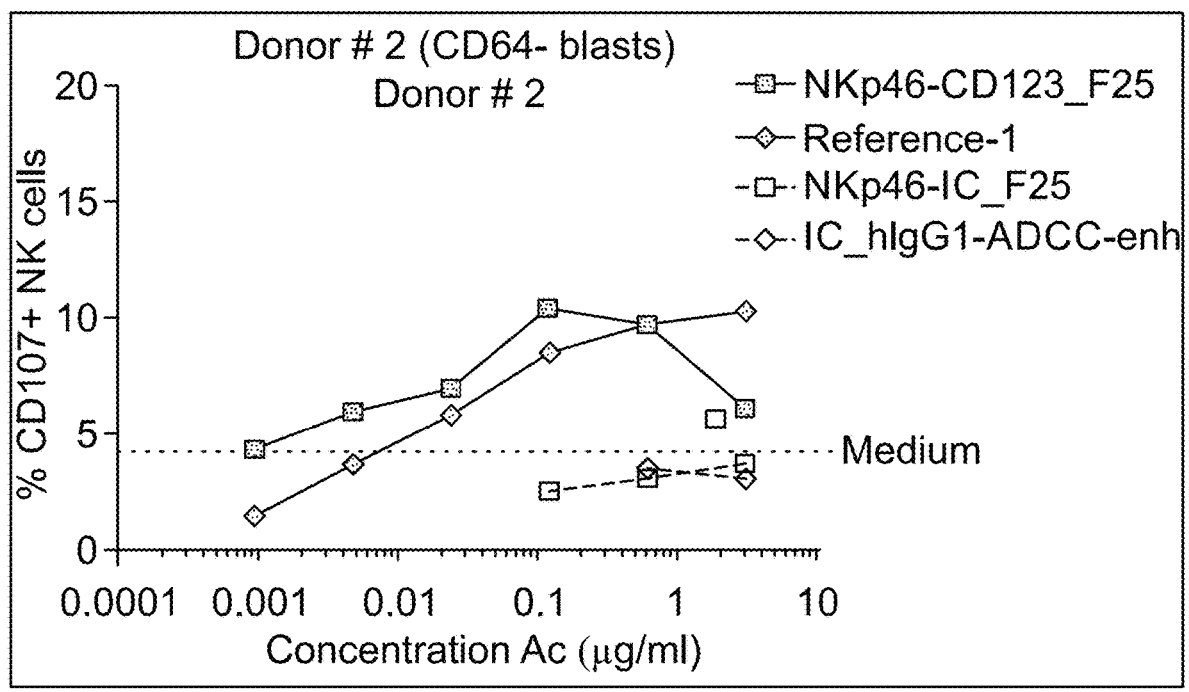

In order to test NK cell activation as in FIG. 7, tested antibodies, AML blast and autologous NK cells derived from AML patients were successively added in each well of round bottom 96-well plates. After overnight co-incubation with the NKp46-CD123_F25 binding proteins of the present disclosure, anti-human CD107a and CD107b antibodies were added in each well for 4 hours. Cells were then washed and stained with the following mix: markers of viability, APC-coupled anti-human CD45, BB515-coupled anti-human CD33, PeCy7-coupled anti-human CD56, BV510-coupled anti-human CD3 antibodies. Cells were then washed, fixed and analyzed by flow cytometry. Obtained data were analyzed by using Flowjo Software to analyze NK cell degranulation through the expression of CD107 on NK cells identified as alive $CD45^+CD33^-CD56^+CD3^-$ cells.

Figure 17:
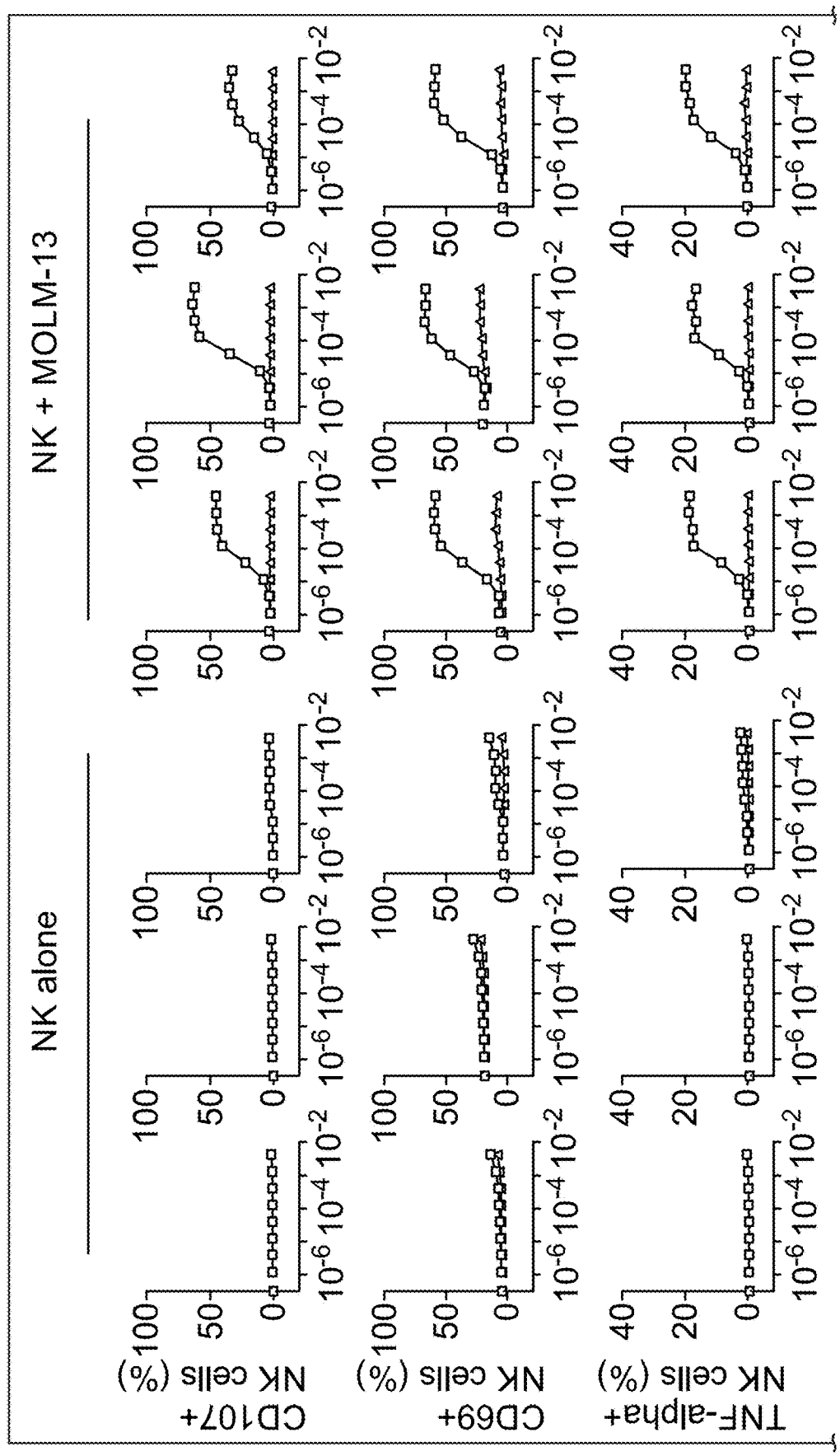
FIG. 17 shows percent of marker expression (CD107, CD69, TNF-α, IFN-γ, and MIP-1β) expression by NK cells treated with increasing concentrations of NKp46-CD123_F25 in comparison to controls, including one engaging NKp46 and CD16 only (NKp46-IC_F25) in an experimental setting using NK cells co-cultured or not with MOLM-13 cells (NK+MOLM-13 versus NK alone). Results for three NK cell donors are shown.
Figure 17:
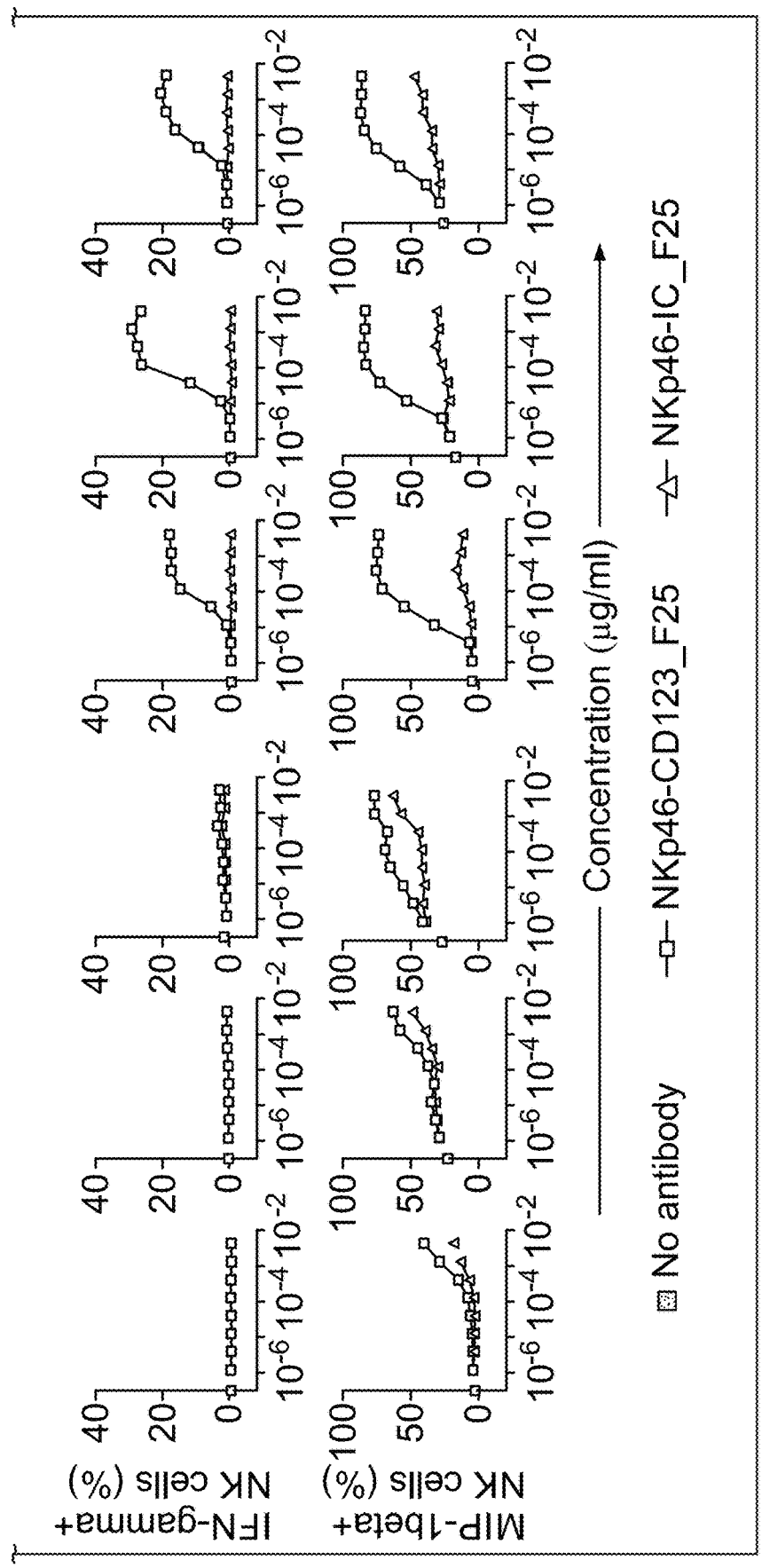

In order to test NK cell activation and cytokine/chemokine production towards MOLM-13 cells via NKp46-CD123_F25 binding proteins as in FIG. 17, flow cytometric analysis was performed using the following antibody markers: CD69, CD107a/b, IFNα, TNFα, MIP1β.

First, purified primary human NK cells from three separate donors were co-incubated with or without MOLM-13 cells at a 1:1 ratio (seeded at 50,000 cells/well; U bottom 96-well plate) for 4 h at 37° C., in the presence of increasing concentrations of NKp46-CD123_F25 or controls (NKp46-IC_F25 and no antibody). Concomitantly, BD GolgiSTOP™ was added to both experimental and control samples at a final dilution of 1/6000 in each well. A positive control of NK cell activation was performed by using 125 ng/mL final of PMA and 1 µg/mL final of IONO added on 50,000 resting NK cells by well (data not shown).

After the 4 hr incubation, cells were washed in staining buffer (PBS with 0.2% BSA, 2 mM EDTA, and 0.02% sodium azide and stained with the following extracellular antibody mixture: anti-human CD3-Pacific Blue, anti-human CD56-Pe-Vio770, anti-human CD69-FITC, anti-human CD107a (LAMP-1)-APC, anti-human CD107b-APC according to manufacturer's recommended incubation and dilution ratios. After a fixation and permeabilization step, intracellular staining was performed using the following intracellular antibody mixture: anti-human IFNγ-BV605, anti-human TNFα-BUV395, and anti-human MIP1β-PE. To eliminate aggregates, antibody mixtures were centrifuged at 16,000 g for 10 min at 4° C., washed, and resuspended in sample buffer.

Flow cytometry was performed on a LSR Fortessa™ X-20, equipped with BD FACSDiva acquisition software measuring FSC-A, FSC-H, SSC-A, SSC-H, FL-1, FL-3, FL-6, FL-7, FL-9, FL-13 and FL-16 parameters. All data were analyzed with FlowJo software.

Marker percent of NK cell sample was done using GraphPad prism. Top of activation values corresponded to the observed maximum activation. Half maximal effective concentration ($EC_{50}$) values were calculated using 4 parameter logistics non-linear regression model corresponding to the following equation:

$$NK \text{ cell activation (\%)} = \text{calculated bottom} + \frac{\text{calculated top} - \text{calculated bottom}}{1 + 10^{(log(EC50) - log(concentration))^{slope}}}$$

Calculated bottom of activation, calculated top of activation, slope and 95% confidence interval (CI) values were calculated using the same model as $EC_{50}$.

These parameters were calculated for each activation marker (CD69, CD107a/b), cytokine (IFNα, TNFα) and chemokine (MIP1β).

A.7. Human Recombinant Protein, Cloning, Production and Purification (SPR)

The sequence encoding the Extracellular Domain (ECD) of human NKp46 (Gln22-Asn255, NCBI Reference: NM_004829.5) was inserted into the SLX192 vector (Selexis) between the HindIII and XbaI restriction sites. A C-terminal 6× His tag (SEQ ID NO: 107) was added for purification. The following primers were used for PCR on human PBMCs: 5' TACGACTCACAAGCTTGCCGC-CACCATGTCTTCCACACTCCCTGC 3' (SEQ ID NO: 82) and 5' CCGCCCCGACTCTAGATCAATGGT-GATGGTGGTGATGATTCTGGGCAGTGTGA TCCC 3' (SEQ ID NO: 83). The sequence of the amplicon was checked. The vector was then used to transfect a CHO cell line and a clone producing the protein was selected. The protein was purified from the culture supernatant with Ni-NTA beads (Qiagen, #1018244) and S200 size exclusion chromatography was performed to ensure the elimination of aggregates prior to characterization of binding kinetics with surface plasmon resonance (SPR). The recombinant human NKp46-derived polypeptide sequence is reported herein as SEQ ID NO: 84; which includes part of the extracellular domain of NKp46.

The sequence encoding the ECD of Cynomolgus NKp46 (Gln17-Asn254, NP_001271509.1) was cloned into the SLX192 vector between the HindIII and XbaI restriction sites. A C-terminal Flag-M2 tag was added for purification. The primers used to amplify the expected sequence from cynomolgus PBMC were: 5' TACGACTCACAAGCTTGCCGCCACCATGTCTTCCACACTCCGTGC 3' (SEQ ID NO: 89) and 5' CCGCCCCGACTCTAGATCACTTGTCATCGTCATCTTTGTAATCATTCTGGGCAG TGTGGTCC 3' (SEQ ID NO: 90). After sequence validation, the vector was used to transfect the CHO-K1SV cell line and a producing cell clone was selected. The recombinant Cynomolgus NKp46-FlagM2 protein sequence is reported herein as SEQ ID NO: 85; which includes part of the extracellular domain of NKp46 (GenBank number: CAC41080.1). The first three batches (150602CCe batch 1, 150618CCe batch 2 and 150715CCe batch 3) were purified by M2 affinity chromatography. The beads were incubated with the supernatant containing the recombinant protein overnight. The beads were then washed with PBS1× and the elution is performed with elution peptide at 150 ng/µl in PBS1×. The proteins are then dialyzed against PBS1×. The next batches (161003CDe batch 1 and 161116CDe batch 2) were purified by affinity chromatography by coupling the anti-NKp46 antibody HUX1-M-H46-17E1 to the AminoLink Coupling Resin according to the manufacturer's instructions (GE Healthcare, #20381, batch QB213815). The beads were then incubated with the supernatant containing the recombinant protein overnight. The beads were then washed with PBS1× and the elution is performed using Glycine 0.1M pH2.5. The proteins are then dialyzed against TBS buffer pH7.5 and concentrated to perform a preparative size exclusion chromatography on a Superdex 200 Increase 10/300 GL column.

A recombinant human CD123 from ACRO Biosystems (catalog no. ILA-H52H6), recombinant Human Fc gamma RIIIA/CD16a (V176) (Biotechne, catalog no. 4325-FC), and recombinant Human Fc gamma RIIIA/CD16a (V176F) (Biotechne, catalog no. 8894-FC) were further used.

A.8. Analytical Procedure for Determination of the Antigen Binding Properties of Multispecific Binding Proteins by Surface Plasmon Resonance.

A Biacore T200 instrument (Cytiva, Uppsala, Catalog No. 28975001) was used with a Series S CMS sensor chip (Cytiva, Uppsala, Catalog No. 29149603).

For binding kinetics measurements with NKp46 and CD123, HBS-EP+ buffer (Cytiva, Uppsala, Catalog No. BR1006-69) was prepared by mixing 100 mL 10× HBS-EP+ buffer with 900 mL of purified water. Affinity capture of the bispecific Ab sample was achieved using the human antibody capture kit (Cytiva, Uppsala, Catalog No. BR1008-39). The anti-Fc capture antibody was diluted in running buffer 1:20 and coupled to the CMS chip (Cytiva, Uppsala, Catalog No. 29149603) using standard amine coupling to yield approximately 8000 response units (RU) using the amine coupling kit (Cytiva, Uppsala, Catalog No. BR-100-50). Seven serial 1:1 dilutions of either human NKp46 (Innate Pharma) or human CD123 (ACRO Biosystems) in HBS-EP+ assay buffer were prepared to concentrations of 1.56 nmol/L, 3.13 nmol/L, 6.25 nmol/L, 12.5 nmol/L, 25 nmol/L, 50 nmol/L and 100 nmol/L. The bispecific antibody was diluted with HBS-EP+ buffer to a concentration of 0.06 µg/mL and used at this concentration in the experiments. The antibody was captured at a flow rate of 10 µL/min for 90 sec to yield maximal response (Rmax) values of approximately 30 RU. Measurements were performed in multicycle kinetics experiments for both antigens. In each multicycle experiment the antibody was captured via an anti-human Fc antibody immobilized on a series S CMS sensor chip (human antibody capture kit, Cytiva, Uppsala, Catalog No. BR1008-39). Human and cynomolgus NKp46 (Innate Pharma) or human CD123 (ACRO Biosystems), diluted into HBS-EP+ buffer, were injected in a 1:1 dilution series from 1.56 nmol/L to 100 nmol/L for 240 sec at a flow rate of 30 µL/min followed by a dissociation phase of 1200 sec. All analyte concentrations were run in duplicate together with multiple buffer blanks for double referencing. Regeneration of the capture surface was performed with regeneration solution (3 mol/L $MgCl_2$) for 60 sec at 30 µL/min. Binding kinetics data were evaluated with the Biacore T200 Evaluation Software version 3.0 (Cytiva, Uppsala) for all other antibodies using a 1:1 binding model with mass transport limitation.

For binding affinity measurements with CD16a, HBS-EP+ buffer (Cytiva, Uppsala, Catalog No. BR1006-69) was prepared by mixing 100 mL 10× HBS-EP+ buffer with 900 mL of purified water. Affinity capture of the human CD16a proteins was achieved using the His capture kit (Cytiva, Uppsala, Catalog No. 28995056). The anti-His capture antibody was diluted in running buffer 1:20 and coupled to the CMS chip (Cytiva, Uppsala, Catalog No. 29149603) using standard amine coupling to yield approximately 8000 response units (RU) using the amine coupling kit (Cytiva, Uppsala, Catalog No. BR-100-50). Ten serial 1:1 dilutions of the bispecific antibody in HBS-EP+ assay buffer were prepared to concentrations of 5.8 nmol/L, 11.7 nmol/L, 23.4 nmol/L, 46.8 nmol/L, 93.75 nmol/L, 187.5 nmol/L, 375 nmol/L, 750 nmol/L, 1500 nmol/L and 3000 nmol/L. The CD16a (V/F) proteins were diluted with HBS-EP+ buffer to a concentration of 0.1 ng/mL and used at this concentration in the experiments. CD16a (V176) and CD16a (V176F) were captured at a flow rate of 10 µL/min for 30 sec on flow cells 2 and 4, respectively to yield maximal response (Rmax) values of approximately 30 RU. Measurements were performed in multicycle kinetics experiments. In each multicycle experiment CD16a was captured via an anti-His antibody immobilized on a series S CMS sensor chip (human antibody capture kit, Cytiva, Uppsala, Catalog No. BR1008-39). The bispecific antibody diluted into HBS-EP+ buffer, was injected in a 1:1 dilution series from 5.8 nmol/L to 3000 nmol/L for 120 sec at a flow rate of 30 µL/min followed by a dissociation phase of 120 sec. All analyte concentrations were run in duplicate together with multiple buffer blanks for double referencing. Regeneration of the capture surface was performed with two consecutive injects of regeneration solution (10 mmol/L Glycine pH 1.5) for 30 sec at 30 µL/min. Binding affinities (KD values) of the bispecific antibody to human CD16a were evaluated with the Biacore T200 Evaluation Software version 3.0 (Cytiva, Uppsala) using a steady state fit of the SPR response for the measured antibody concentrations.

A.9. Anti-Tumor Activity Against MOLM-13 Human AML Injected in SCID Mice.

The efficacy of muNKp46-huCD123_F25 a murine surrogate version of the NKp46-CD123_F25 was evaluated in severe-combined-immunodeficient (SCID) mice engrafted with disseminated human MOLM-13 cells. This surrogate is different from NKp46-CD123_F25 for the arm targeting the NKp46 protein (as it targets the murine protein instead of the human one) and is similar to NKp46-CD123_F25 for the other arms (human CD123 binding arm and human IgG1competent Fc domain able to bind to all activating murine FcγRs, to recruit murine effector cells and to induce ADCC with murine NK cells).

The muNKp46-huCD123_F25 activity was compared to an anti-CD123 ADCC-enhanced antibody (Reference-1) able to bind murine FcγRs and to recruit murine effector cells. The muNKp46-huCD123_F25 activity was also compared to an isotype control binding of muNKp46 and murine FcγRs but not to bind to huCD123 (muNKp46-IC).

Mice were intravenously inoculated with tumor cells ($5 \times 10^6$) on day 0. Treatments were administered by intraperitoneal route on day 1 post tumor implantation.

In the first experiment (FIG. 8), mice were randomized in 4 groups (n=10 mice in treated groups and 20 mice in control group) on day 1 post tumor implantation. muNKp46-huCD123_F25 was administered at 0.5, 0.25 and 0.05 mg/kg following intra-parenteral administrations on day 1.

In the second experiment (FIG. 18), muNKp46-IC was administered at 0.5 mg/kg. muNKp46-huCD123_F25 and Reference-1 were administered at 5, 0.5, 0.25 and 0.05 mg/kg. The control group was left untreated.

In the third experiment (FIG. 19), mice were randomized into the 4 groups (untreated control group; untreated control group+anti-asialoGM1; NKCE control; or NKCE+anti-asialoGM1). A day before tumor implantation (day −1) as well as at day 5 post-tumor implantation the experimental groups received NK cell depletion antibody, anti-asialo GM1. Treatments (Vehicle or NKCE) were administered intraperitoneally on day 1 post tumor implantation at a single dose of 0.5 mg/kg. NKCE included Nkp46-CD123_F25, muNKp46-IC, an isotype control antibody binding huCD123 and murine FcγRs but not murine NKp46 (IC-huCD123).

Mice were checked and adverse clinical reactions noted. Individual mice were weighed daily until the end of the experiment (day 70). Mice were euthanized when turning moribund according to predefined criteria in order to avoid animal suffering. Clinical signs related to the pathology, considered as critical are limb paralysis, ascites, palpable internal tumor mass, morbidity or weight loss superior or equal to 20%.

The primary efficacy endpoints were the Median Survival Time (MST) in day, the percent Increased Lifespan (% ILS), and the long-term survivor rate.

Individual days of death (if any) of each mouse was reported. MST was determined for each group and the ratio ILS was calculated and expressed as percentage:

$$ILS=100 \times (T-C)/C$$

Where T=MST of treated group and C=MST of control group.

For the purpose of this example, a dose was considered as therapeutically active when % ILS is superior to 25% and highly active when % ILS is superior to 50% (Johnson J I, Decker S, Zaharevitz D, Rubinstein L V, Venditti J M, Schepartz S, Kalyandrug S, et al. Relationships between drug activity in NCI preclinical in vitro and in vivo models and early clinical trials. Br. J. Cancer. 2001 May; 84(10): 1424-31).

Long term survivor rate is defined as the number of mice with survival duration superior or equal to 2 times the MST of control group on the total number of mice in the group expressed in percentage.

A.10. Anti-Tumor Activity in Non-Human Primate (NHP)

A qualified flow cytometry panel used for evaluating in monkey cynomolgus blood samples, the phenotyping and count of Basophils and total CD123 immune cells. The panel was composed by the antibodies against the antigen CD45 (Clone D058-1283), CD14 (clone REA599), CD203c (clone NP4D6), CD193 (clone 5E8), IgE (clone REA1049), CD123 (clone CD123), CD33 (clone AC104.3E3) and the viability marker Zombie Nir (Biolegend 423106). 100 µL of whole blood sample collected into a 3K-EDTA anticoagulated air-vacuum sampling were incubated with a lysis solution (Biocytex CP025) during 10 min following by a centrifugation step at 300 g at room temperature during 5 min with DPBS (Sigma D8537). The resuspended cells were stained during 10 min at room temperature with the antibodies and viability marker. A third step of centrifugation were done in order to eliminate non-fixed antibodies. Cells were resuspended into 250 µL of fixative solution (Biocytex CP026) and were incubated during one hour at room temperature. 100 µL of Flow count beads (Beckman A91346) were added into cells tube and were acquired on a Gallios Beckman coulter instrument equipped by 3 lasers and 10 colors.

A.11. In Vitro Effect on CD123+ Normal Blood Cells and Associated Cytokine Release in Human Peripheral Blood Mononuclear Cell (PBMC)

PBMCs from human healthy donors (N=10) were seeded in 96-well U-bottom plates (Ultra low binding Costar ref #CLS7007) in 190 µL complete culture medium (500,000 cells per well). and incubated at 37° C. in the presence of 5% CO2 for 20 hours with serial dilutions of CD123-NKCE, IC-NKCE control and CD123-TCE molecules. The basophil population, defined as TCRαβ negative, CD14 negative and IgE receptor positive viable cells, was analyzed by flow cytometry and cytokine absolute concentrations released in the supernatant were analyzed by meso scale discovery (MSD) assay.

Flow Cytometry—Assay

Cell pellets were suspended in cold 50 µL Stain Buffer (AutoMACS Running Buffer Miltenyi Ref #130-091-221) completed with 1 µL FcR Blocking reagent, human (Miltenyi Ref #130-059-901). A mix of PBMC subsets specific labelling antibodies and the viability reagent were added into the PBMC suspension following supplier recommendations. As Fluorescence Minus One (FMO) control, further points were performed by labelling PBMC with the same mix in which each labelling antibody was replaced by its corresponding isotype control Cells with mixed antibodies were incubated 1 hour at 4° C. in the dark. Then, cell suspensions were centrifuged twice at 300 g during 5 minutes at 4° C., with the supernatant discarded and 200 µL of Stain buffer added between each centrifugation. Cells were analyzed using the MACSQuant® Analyser, Miltenyi flow cytometer. Analysis of raw data (fcs-files) exported from the flow cytometer was performed using the VenturiOne® software (AppliedCytometry inc.). The populations were gated from forward scatter/sideward scatter dotplot, single cells and further viable cells were gated on Iodure Propidium viable negative gate. Gates were set according to FMO controls.

Cytokine MSD Assay

Cell supernatant was collected and diluted in MSD buffer following purchaser recommendations. Diluted samples or pre-diluted multi-analyte calibrators samples are added in pre-coated plate supplied in the kit. After adding a solution of detection antibodies conjugated with electrochemiluminescent labels (MSD SULFO-TAG), the plates were incubated at room temperature for 2 hours. Then, MSD buffer creating the appropriate chemical environment for elctrochemiluminescence (ECL)was added and the plates loaded into an MSD instrument where a voltage applied to the plate electrodes causes the captured labels to emit light. The instrument measures the intensity of emitted light and provide a quantitative measure of each analyte in the samples.

Analysis of raw data exported from the MSD instrument was performed using Excel software. Concentrations of IL-6, IL-1b, IFNγ and TNFα are determined from ECL signals by back-fitting to a calibration curve established with a 4-parameter logistic model with 1/Y2 weighting.

A.12. Cytokine Release Determination in Non-Human Primate (NHP) Plasma

An ECLIA (Electrochemoluminescence Assay) method using Mesoscale (MSD) Proinflammatory Panel1 (NHP) kit (ref. K15056D) was developed and validated to quantify IL-2, IFN-γ, IL-6, and IL-10 in monkey K3-EDTA plasma. It is a quantitative sandwich enzyme immunoassay using anti-human IL-2, IL-6, IL10 and IFN-γ antibodies immobilized on the working electrode surface and a Ruthenium anti-human IL-2, IL-6, IL-10 and IFN-γ antibodies. 50.0 μL of diluted samples were dispensed into the 96 microplate wells coated with the human anti-human IL-2, IL-6, IL-10 and IFN-γ antibodies. After an overnight period of incubation at room temperature and 3 steps of washing, 25.0 μL of sulfotag conjugated anti-human IL-2, IL-6, IL-10 and IFN-γ antibodies were added. After 3 steps of washing, 150 μL of read buffer (2×) were added that creates the appropriate chemical environment for the electrochemiluminescence. The instrument measures the intensity of emitted light to provide a quantitative measure of analytes in the sample. Analyses were performed in duplicate.

Pharmacokinetic and Pharmacodynamics Study in Non-Human Primate

CD123-NKCE solutions for administration were prepared extemporaneously by dilution of the stock solution in the vehicle and were kept at room temperature before and during administration. To avoid adsorption, PolyPropylene, PolyCarbonate or PETG containers were used for dilutions and these containers were coated with a solution of NaCl 0.9% containing 100 ppm of PS80 before use. Tubing used for each intravenous dosing (syringe/winged needle) were coated by successive flushes with a solution of NaCl 0.9% containing 100 ppm of PS80.

Animals were identified as M1 and M2 for males dosed at 0.1 mg/kg/administration, F3 and F4 for females dosed at 0.1 mg/kg/administration, M5 and M6 for males dosed at 3 mg/kg/administration, and F7 and F8 for females dosed at 0.1 mg/kg/administration, respectively. Dosing was performed on Days 1, 8, 15 and 22. The potential delayed onset toxicity and/or the reversibility of potential toxicity was assessed one week (Day 29) and up to 4 weeks (Day 50) after the last (4th) administration. M2, F4, M6 and F8 were euthanized and necropsied on Day 29.

Parameters were Evaluated for Each Treated Animal:
in blood
on pretest (predose)
Day 1 at 1.5, 5, 24, 72 hours after the start of infusion
Day 8 at 24 hours after the start of infusion
Day 15 at 1.5 and 24 hours after the start of infusion
Day 22 at 24 hours after the start of infusion
Day 29 (1 week after the last administration; all animals)
Day 50 (4 weeks after the last administration; recovery animals).
in bone marrow
Pretest (predose)
Day 9
Day 29 (1 week after the last administration; all animals)
Day 50 (4 weeks after the last administration; recovery animals)

Blood samples (serial sampling) were withdrawn from brachial or saphenous vein into K3-EDTA polypropylene tubes. Blood samples were placed on wet ice and centrifuged. Plasma samples obtained were frozen at −80° C. pending their analyses. CD123-NKCE concentrations were determined in plasma using a dedicated immunoassay method where CD123-NKCE were captured by biotin-coupled CD123 recombinant proteins and revealed by a monkey absorbed alexa-goat anti-human IgG, with a Lower Limit of Quantification (LLOQ) value of 0.250 ng/mL.

Results

B.1. NKp46-CD123_F25 Binding Protein

Figure 1:
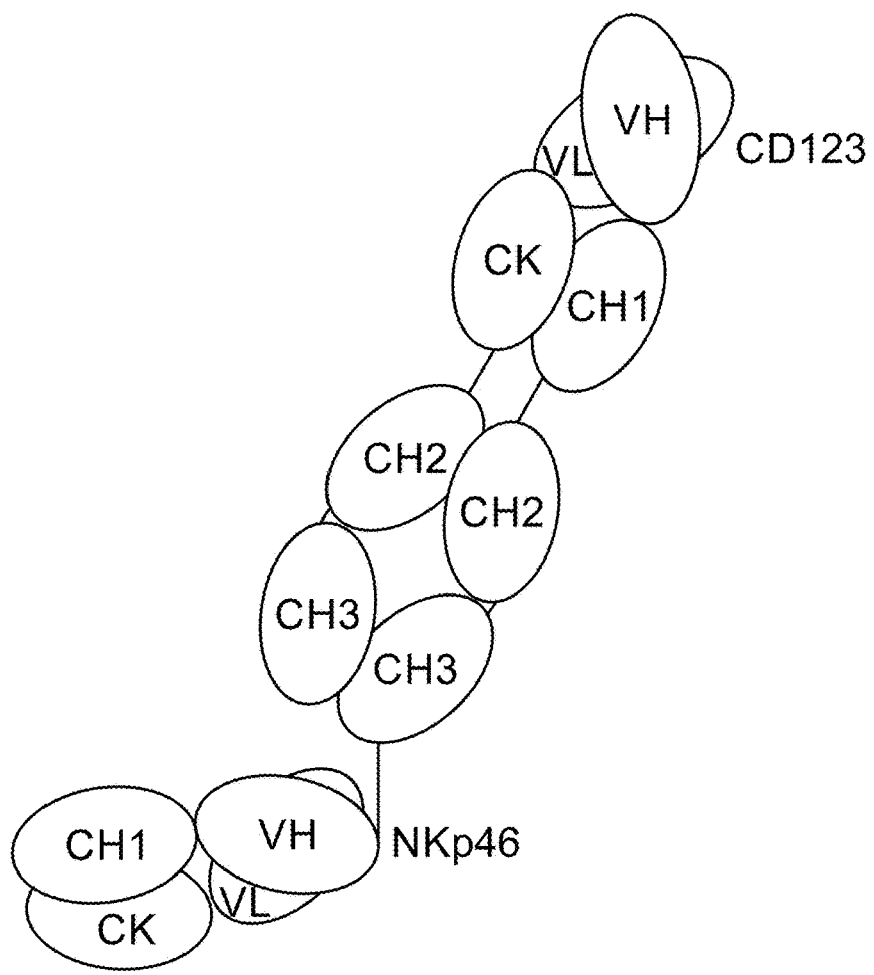
FIG. 1. Tri-dimensional schematic representation of the F25 format which is a variant of the bispecific F5 format, including one human NKp46 binding site and one human CD123 binding site. On FIG. 1, the C-term of the polypeptide is on the left-hand side and the N-term is on the right-hand side.
Figure 2A:
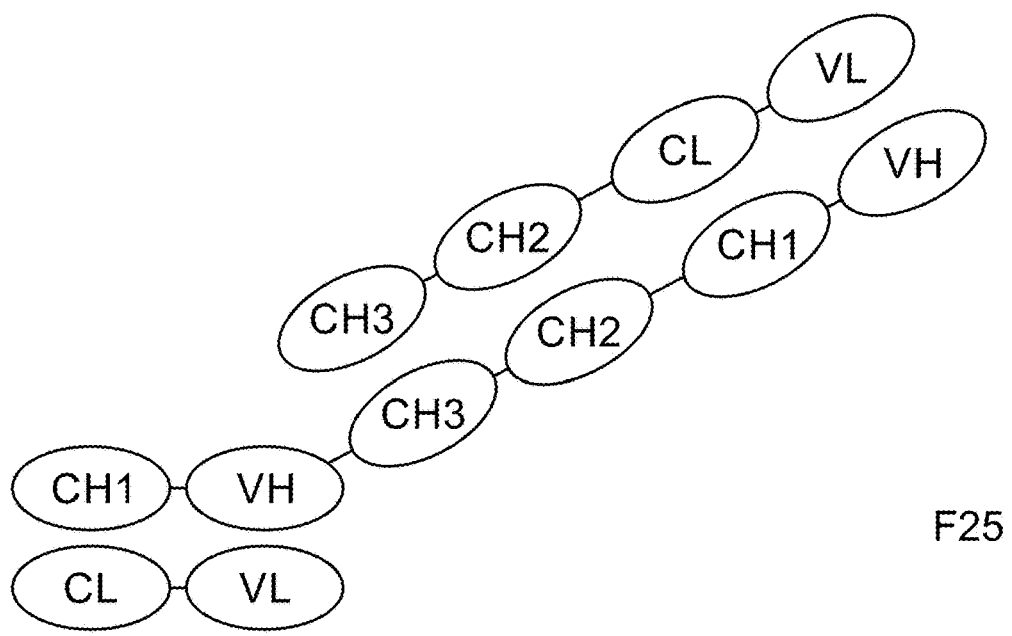
FIG. 2A-FIG. 2D show two-dimensional schematic representations of the F25, F5, F26 and F6 formats respectively including the relevant domains for each polypeptide chain. In the FIGS. 2A to 2D, the C-term of the polypeptide is on the left-hand side and the N-term is on the right-hand side. The human NKp46 binding domain is formed by the VH/VL pair on the left side. The human CD123 binding domain is formed by the VH/VL pair on the right side.
Figure 2B:
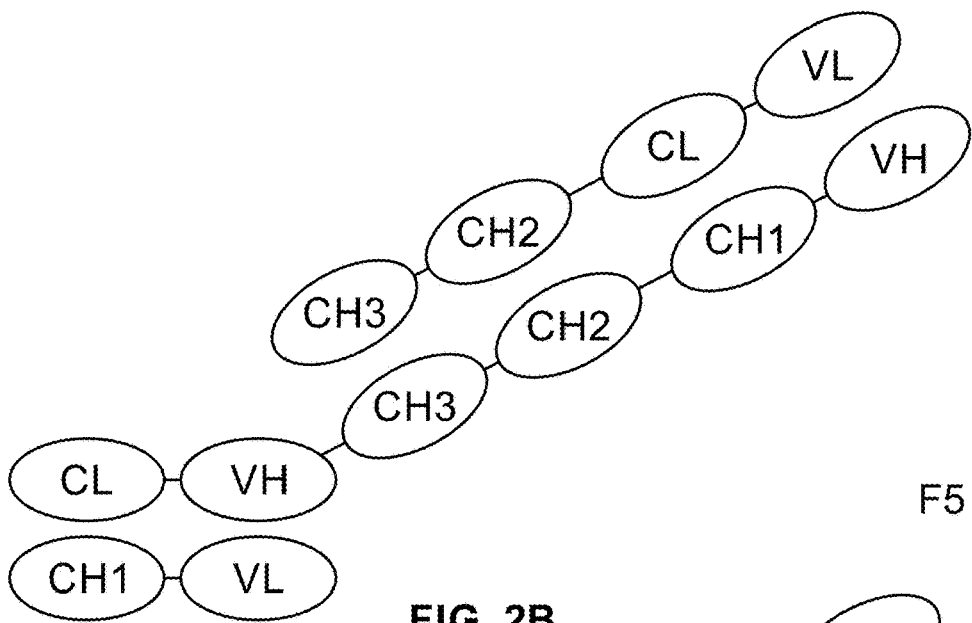
Figure 2C:
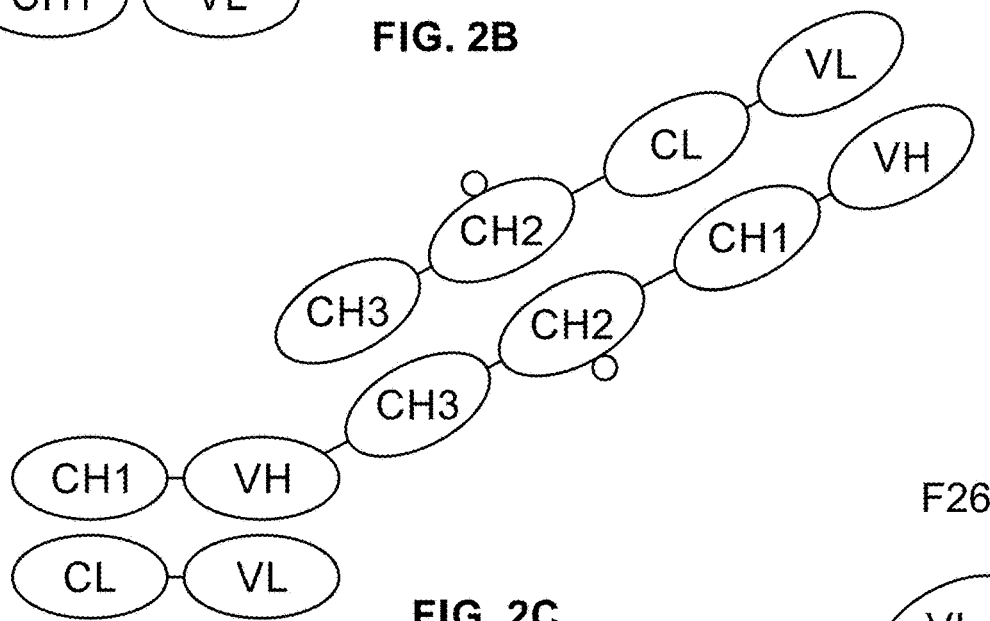
Figure 2D:
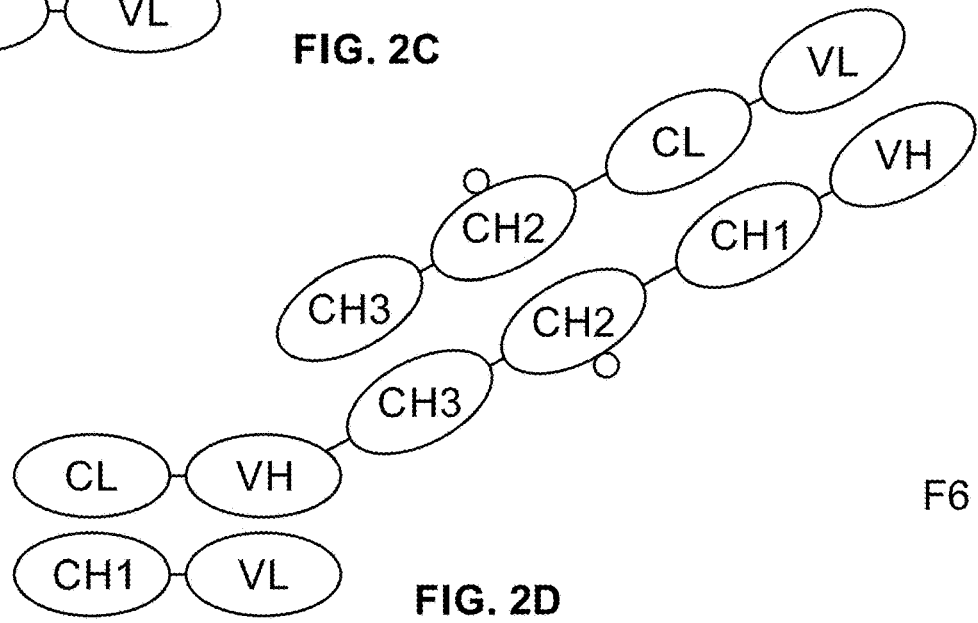
Figure 2E:
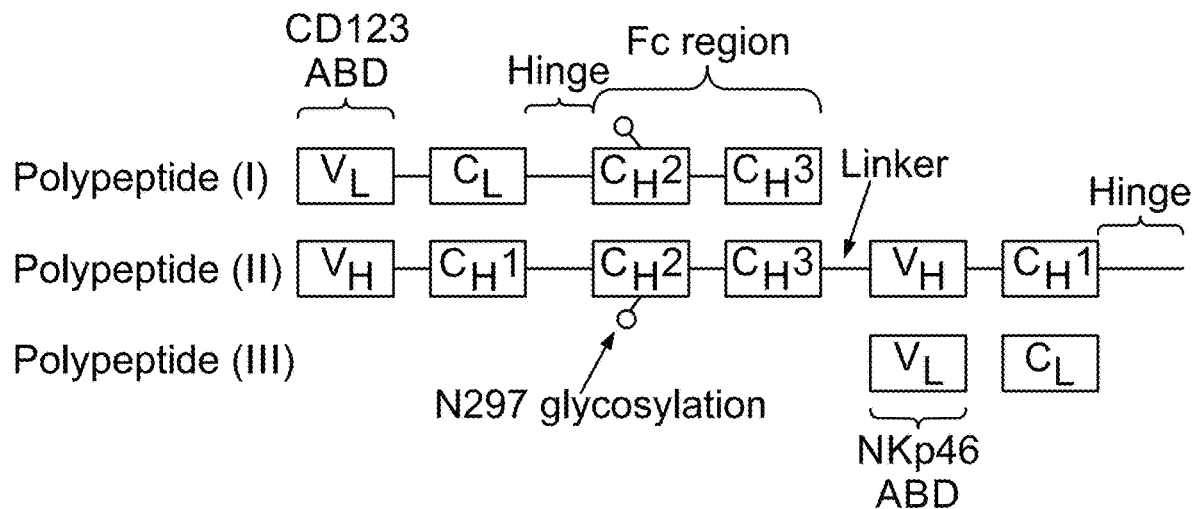
FIG. 2E shows a two-dimensional detailed representation of a variant of the F25 format. This F25 format representation corresponds to the one in FIG. 2A.
Figure 3:
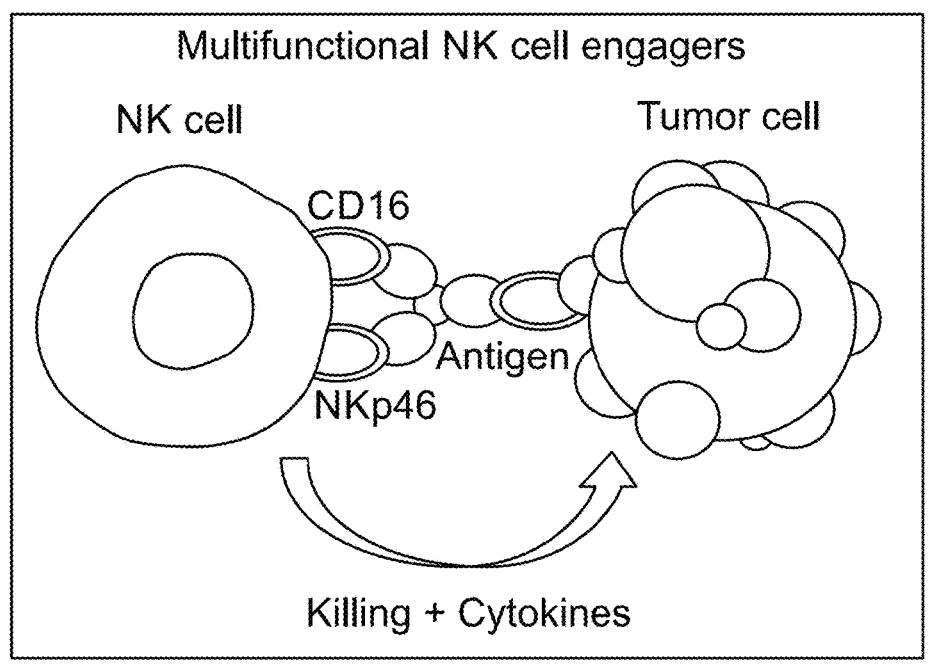
FIG. 3 shows a proposed mechanism of action of a NK Cell Engager (NKCE) for killing, following joint binding of a tumor cell (i.e. an AML cell line; i.e. MOLM-13) expressing CD123 and a NK cell expressing NKp46 and a Fcγ receptor (CD16a). Reproduced and adapted from Gauthier, L. et al. ("Multifunctional natural killer cell engagers targeting NKp46 trigger protective tumor immunity". Cell 177, 1701-1713 (2019)).

The F25 format, or its variants, is illustrated in FIGS. 1 and 2, and comprises three polypeptide chains. The NKp46-CD123_F25 binding protein comprises three polypeptide chains including a human CD123 binding domain and a human NKp46 binding domain, respectively including hypervariable regions comprising polypeptide sequences SEQ ID NO: 1, 2, 3, 7, 8, 9 and SEQ ID NO: 13, 14, 15, 27, 28, 29.

Each polypeptide chain (I, II, and III) is expressed with a signal (or "leader") sequence that is cleaved intracellularly before assembly.

The first polypeptide chain (or "polypeptide chain (I)" or "Fragment I" or "Fragment 1") comprises from N-term to C-term, the $V_L$ (CD123-binding) domain corresponding to the amino sequence of SEQ ID NO:43, a native $C_K$ (or $C_\kappa$) domain derived from human IgG1, a modified human IgG1 hinge region ("DKTHTCPPCP (SEQ ID NO: 74)") wherein residue D (position according to EU numbering) is connected to the C-terminal cysteine of the human $C_K$ domain. The Fc region or variant thereof is further derived from a native human IgG1 antibody comprising a $C_H2$-$C_H3$ domain. Disulfide bridges are potentially formed extracellularly with the second polypeptide chain ("chain II") with native cysteines.

The second polypeptide chain ("polypeptide chain (II)" or "Fragment II" or "Fragment 2") comprises, from N-term to C-term, the $V_H$ (CD123-binding) domain corresponding to the amino sequence of SEQ ID NO:41, a native $C_H1$ domain derived from human IgG1, an unmodified human IgG1 hinge region ("EPKSCDKTHTCPPCP (SEQ ID NO: 75)"), and a Fc region or variant thereof derived from a human IgG1 including a $C_H2$-$C_H3$ domain wherein the last residue of the $C_H3$ domain is removed and replaced by a small four amino-acid "STGS (SEQ ID NO: 76)" linker, a $V_H$ (NKp46-binding) domain corresponding to the amino sequence of SEQ ID NO:45, a second native $C_H1$ domain which is identical to the $C_H1$ domain of the first polypeptide chain, and a C-terminal hinge sequence from human IgG1.

The third polypeptide chain ("polypeptide chain (III)" or "Fragment III" or "Fragment 3") comprises a $V_L$ (NKp46-binding) domain corresponding to the amino sequence of SEQ ID NO: 53 and a $C_K$ domain terminated with a Cysteine.

The $C_H2$ domains of the Fc part of the NKp46-CD123_F25 binding protein of the present disclosure are glycosylated at position N297 to ensure binding to CD16 (FcγR).

Overall, the NKp46-CD123_F25 binding protein comprises four predicted interchain disulfide bridges:
(i) one disulfide bridge connecting the C-term $C_K$ cysteine of the first polypeptide chain to the first hinge cysteine of the second polypeptide chain;

(ii) two disulfide bridges formed with two cysteines of the hinge region of the first and second polypeptide chains;

(iii) one disulfide bridge connecting the last C-term cysteine of the second polypeptide chain to the C-terminal $C_H1$ domain of the second polypeptide chain.

The results related to binding, in-vitro, ex-vivo and in-vivo activity and safety profile showed in section B3 to B11 were obtained with NKp46-CD123_F25 binding protein of the present disclosure comprising polypeptide (I), (II) and (III); wherein the polypeptide (I) consists of an amino acid sequence of SEQ ID NO: 64, the polypeptide (II) consists of an amino acid sequence of SEQ ID NO: 65, and the polypeptide (III) consists of an amino acid sequence of SEQ ID NO: 66.

B.3. Characterization of the NKp46-CD123_F25 Binding Protein Construct Binding to Human Fc-γ Receptors by SPR The NKp46-CD123_F25 binding protein (NKp46-CD123_F25) was tested by SPR in order to confirm its affinity toward a set of human Fcγ receptors, including CD64 and two variants of the CD16a receptor.

| Kd (nM) | hFcγR1 hCD64* | hFcγR3a-V hCD16a-V | hFcγR3a-F hCD16a-F |
|---|---|---|---|
| NKp46-CD123_F25 | 6.9 | 462 | 2606 |

The human CD16a-V receptor, or CD16a$^V$, refers to a polypeptide construct comprising a fragment of the CD16 human receptor binding to a Fc region of a natural antibody, mediating antibody-dependent cellular cytotoxicity and bearing a Valine (V) on position 158, which is also reported in the literature as allotype CD16a V158.

The human CD16a-F receptor, or CD16a$^F$, refers to a polypeptide construct comprising a fragment of the CD16 human receptor binding to a Fc region of a natural antibody, mediating antibody-dependent cellular cytotoxicity and bearing a Phenylalanine (F) on position 158, which is also reported in the literature as allotype CD16a F158.

The conclusion of this experiment is that the constant regions which compose NKp46-CD123_F25 retains their affinity toward a plurality of human Fc-γ receptors, including human CD16 and human CD64.

B.4. Characterization of the NKp46-CD123_F25 Binding Protein Binding to NKp46 and CD123 by SPR The same experiment was performed with human and monkey versions of NKp46. The results are summarized in the two tables hereafter (Table 1 and Table 2).

The conclusion of this experiment is that the NKp46-CD123_F25 binding protein related to the present disclosure (NKp46-CD123_F25) retains affinity for NKp46 and CD123 targets, which applies both to human and monkey isoforms.

B.5. NKp46-CD123_F25 Binding Protein Induces AML Cell Cytotoxicity

Figure 4A:
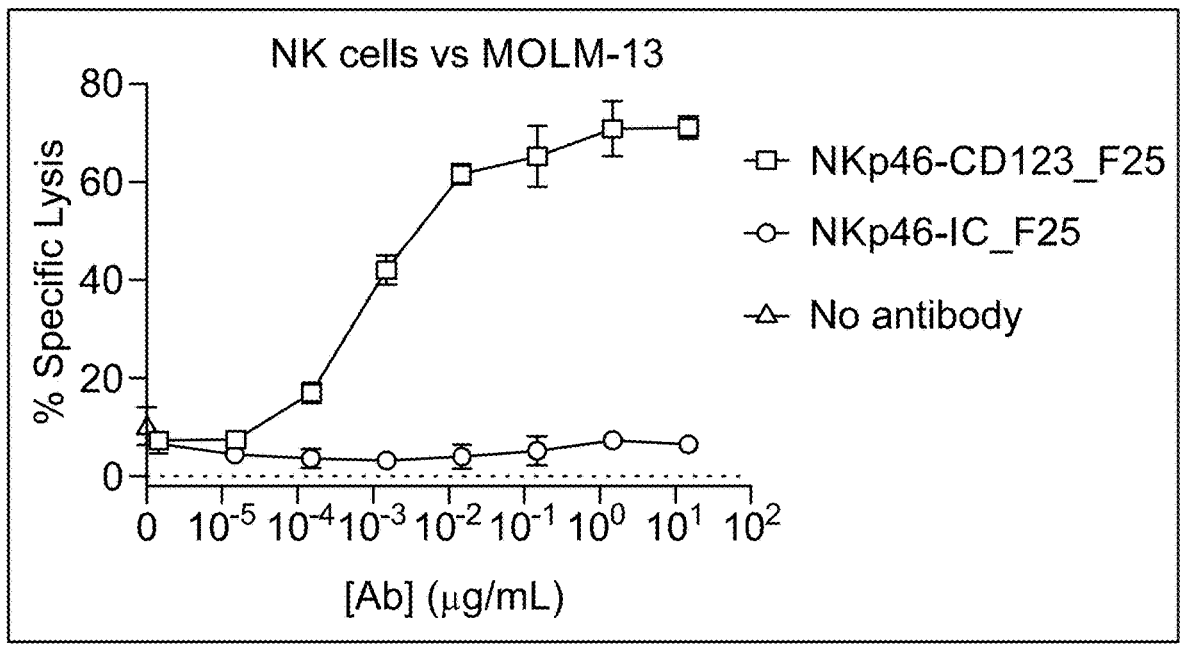
FIG. 4A-FIG. 4B report the in vitro cytotoxicity of the NKp46-CD123_F25 binding protein of the present disclosure against AML cell line (MOLM-13) or primary AML blast cells respectively.
Figure 4B:
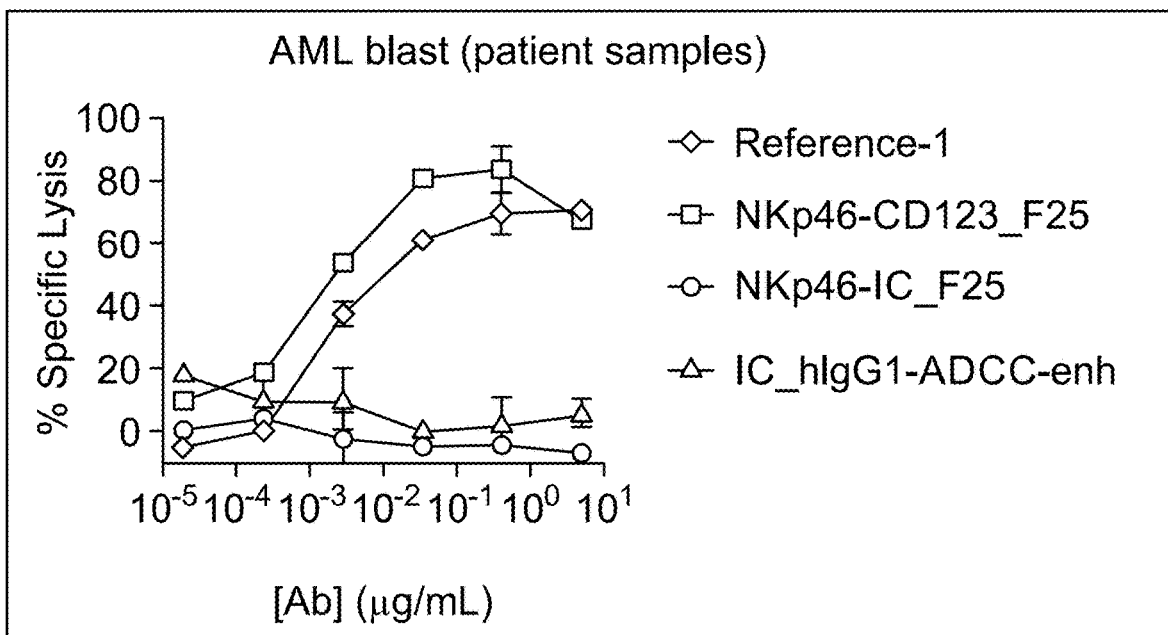

FIG. 4 reports in vitro cytotoxicity against MOLM-13 AML cells (FIG. 4A). The same experiment is reproduced against ex vivo patient blast samples as target cells (FIG. 4B). Cytotoxicity is assessed as a function of the tested NKp46-CD123_F25 binding protein (NKp46-CD123_F25) concentration in the experiment.

Overall, the experiments show that NKp46-CD123_F25 is responsible for dose-dependent cytotoxicity in both in vitro and ex vivo tested samples. For a similar concentration, the observed cytotoxicity is also higher than the one observed with an anti-CD123 antibody ADCC-enhanced with no specificity for NKp46 (Reference-1). Conversely, a negative control variant of format F25 binding NKp46 only (NKp46-IC_F25) shows little cytotoxicity under the tested conditions. Hence, the experiments support a synergistic effect of the dual binding toward both CD123 and NKp46 in a Fc-competent construct (F25) to lead to cytotoxicity against CD123-positive tumor cells.

Figure 5:
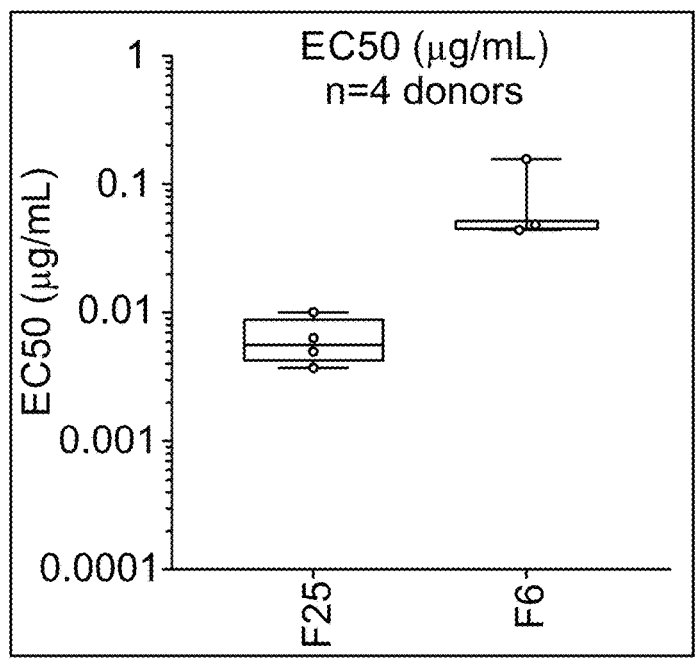
FIG. 5 provides in-vitro cytotoxicity data using fresh healthy donor NK cells against MOLM-13 AML cell line ($EC_{50}$ data) of the NKp46-CD123_F25 binding protein of the present disclosure which is capable of activating human NK cells by engaging both NKp46 and CD16a, inducing ADCC activity with its Fc competent format (F25), and a NKp46-CD123_F6 binding protein activating human NK cells by engaging NKp46 only and not CD16a, inducing reduced ADCC-activity with its Fc silent format (F6).

FIG. 5 provides data based on $EC_{50}$ on a MOLM-13 cell line. Improvement of in vitro cytotoxicity (which translates into a decreased $EC_{50}$) is observed with the NKp46-CD123_F25 binding protein (NKp46-CD123_F25). In contrast, the F6 control (NKp46-CD123_F6), which lacks N-glycosylation on residue 297, provides a decreased cytotoxicity since it activates NK cells by engaging NKp46 only and not CD16a. Hence, this second experiment provides evidence of the synergistic effect observed through binding and activation of NKp46 and CD16a NK cell markers.

Accordingly, specific lysis was illustrated with NKp46-CD123_F25, and with an anti-CD123 antibody ADCC-enhanced with no specificity for NKp46 (Reference-1) in the presence of human NK cells against CD123-positive MOLM-13 AML cells. The $EC_{50}$ value is established based on the variation of cell lysis over the concentration of binders. The results are shown hereafter.

TABLE 1

| | HUMAN (hNKp46) | | | MONKEY (CynoNKp46) | | |
|---|---|---|---|---|---|---|
| NKp46 | $k_a$ (1/Ms) | $k_d$ (1/S) | $K_D$ (nM) | $k_a$ (1/Ms) | $k_d$ (1/S) | $K_D$ (nM) |
| NKp46-CD123_F25 | 5.38E+04 | 9.43E−04 | 17.5 | 3.64E+04 | 2.47E−03 | 67.9 |

TABLE 2

| | HUMAN (hCD123) | | | MONKEY (CynoCD123) | | |
|---|---|---|---|---|---|---|
| CD123 | $k_a$ (1/Ms) | $k_d$ (1/S) | $K_D$ (nM) | $k_a$ (1/Ms) | $k_d$ (1/S) | $K_D$ (nM) |
| NKp46-CD123_F25 | 1.19E+05 | 2.85E−05 | 0.24 | 1.83E+05 | 5.29E−05 | 0.29 |

| Molecules | EC$_{50}$ (pm) Mean +/− sem (4 donors) |
|---|---|
| NKp46-CD123_F25 | 80.3 ± 44.9 |
| Reference-1 | 85.3 ± 41.3 |

Hence, it is shown that the NKp46-CD123_F25 binding protein (NKp46-CD123_F25) exhibits a cytotoxic activity which is at least equal or superior to the anti-CD123 ADCC-enhanced antibody (Reference-1).

Reference-1 is a fully-humanized monoclonal antibody indicated for the treatment of AML, which targets the alpha chain of the interleukin 3 receptor (IL3Rα; also known as CD123) and is optimized for enhanced activation of antibody-dependent cell-mediated cytotoxicity (ADCC) via natural killer cells.

B.6. CD64 Expression on AML Does Not Impact NKCE Cytotoxic Activity While it Negatively Impacts REFERENCE-1 Activity To further document and compare the activity of NKp46-CD123_F25 and Reference-1 antibody, cytotoxicity experiments were performed using different AML cell lines expressing CD123 as targets. Surprisingly, even though THP-1 and MOLM-13 cells express comparable level of CD123 at the cell surface, Reference-1 antibody efficiently killed MOLM-13 cells but was not active against THP-1 cells (FIG. 6A-upper panels). Contrary to Reference-1 antibody, NKp46-CD123_F25 demonstrated comparable killing activity on both AML cell lines (FIG. 6A—upper panels). FIG. 6A-lower panels show that MOLM-13 and THP-1 cells differ for the expression of CD32a/b and CD64 FcγRs at the cell surface as analyzed by flow cytometry. MOLM-13 cells had much lower CD64 levels, and also lower levels of CD32a/b, than THP-1 cells (FIG. 6A—lower panels). CD64 (FcγRI) is a high affinity receptor for human IgG expressed on healthy monocytes and macrophages and found expressed on AML blasts in about one third of patients which may be considered as CD64-positive Acute Myeloid Leukemia. To investigate the role of CD64 expression on cytotoxicity for the NK Cell engager (NKCE), compared to the humanized monoclonal antibody Reference-1, the expression of CD32a/b and CD64 was selectively knocked down in THP-1 cells.

Killing experiments performed on THP-1 sub-clones expressing CD32a/b but not CD64 or expressing CD64 but not CD32a/b (FIG. 6B) demonstrated that CD64 expression on THP-1 was responsible for the inhibition of Reference-1 ADCC activity as killing of this antibody was restored only on sub-clones inactivated for CD64 expression. Accordingly, these results indicate that cis capture of antibody FC by FcγR, CD64, at the surface of AML cells interfere with ADCC probably by competing with the binding of CD16a to NK cells.

Interestingly, NKp46-CD123_F25 demonstrated consistent killing activity on all AML cell lines and all THP-1 sub-clones emphasizing that the NKp46-CD123_F25 binding proteins related to the present disclosure are more efficient for inducing NK cell-mediated cytotoxicity of AML blasts, as compared to Reference-1, whatever the CD64 expression status.

Figure 14A:
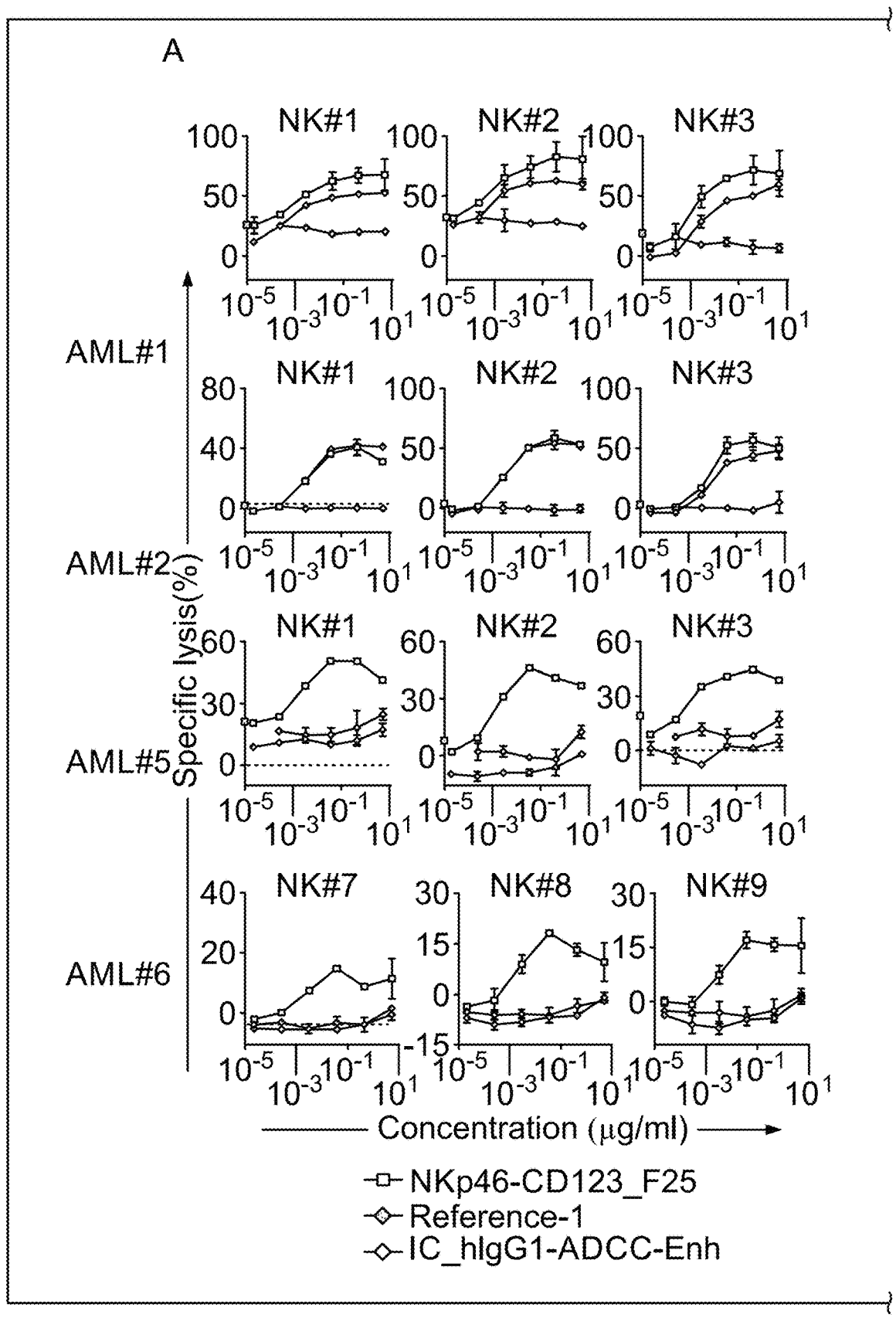
FIG. 14A displays the cytotoxicity of NKp46-CD123_F25 binding protein of the present disclosure as compared to an anti-CD123 ADCC-enhanced antibody with no specificity for NKp46 (Reference-1) and a negative isotype control Fc-optimized antibody with increased ADCC activity and no specificity for NKp46 nor CD123 (IC-hIgG1-ADCC-enh) against AML blasts from patients expressing (#AML5, #AML6) or not (#AML1, #AML2) CD64. Malignant cells from AML patients were used as targets and purified healthy donor NK cells were used as effectors. Results are shown for all healthy donor NK cells tested.
Figure 14B:
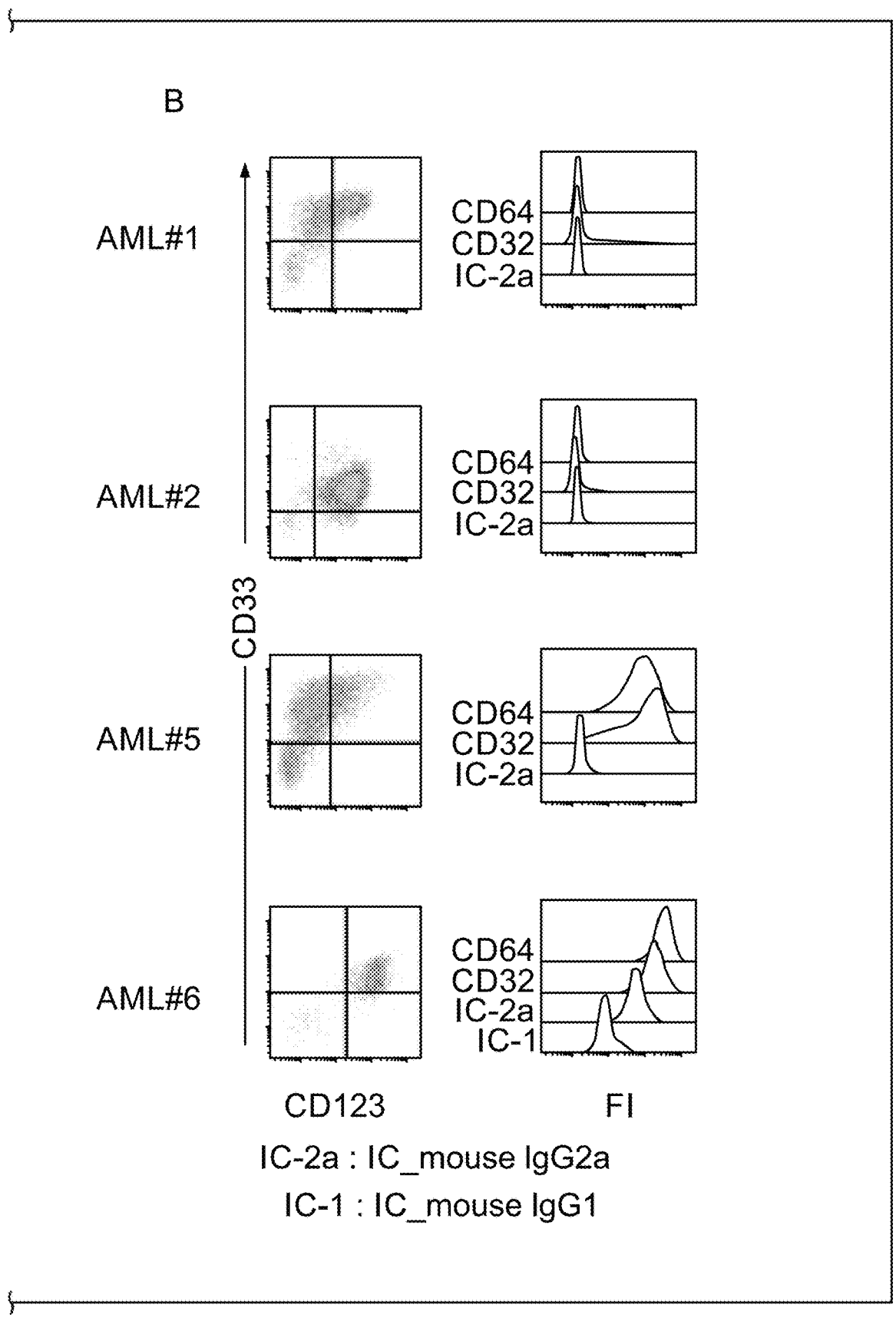
FIG. 14B reports the phenotype of the malignant AML cells from patients used in FIG. 14A showing the expression of CD33, CD123, CD32a/b, and CD64 by flow cytometry analysis.

FIG. 14A-B confirm that Reference-1 activity is negatively impacted by expression of CD64 on AML cells.

FIG. 14A reports the NKp46-CD123_F25 and Reference-1-mediated cytotoxicity of primary malignant AML blasts from four representative patients (AML #1, #2, #5 and #6; N=8) which were evaluated ex vivo using healthy donor NK cells as effectors. As observed with MOLM-13 and THP-1 cell lines, Reference-1 antibody mediated the killing of CD64-negative patient samples (AML #1 and #2; FIG. 14A) but was barely active against blasts from CD64-positive AML patient samples (AML #5 and #6; FIG. 14A). Accordingly, AML #5-AML #6, (Reference-1-non-responders) have higher staining levels of CD32 and CD64 than AML #1 and AML #2 (Reference-1 responders) (FIG. 14B, right panels, compare peak shifts in CD64 and CD32 from controls in both groups).

In contrast, trifunctional NKp46-NKCEs targeting CD123 had strong anti-tumor effects on both CD64-positive and CD64-negative AML patient samples (FIG. 14). FIGS. 6 and 14 demonstrate that CD123-NKp46_F25 was equally potent against the parental THP-1 cell line, THP-1 subclones, and MOLM-13 cells, regardless of FcγR expression status, and, more specifically, CD64 expression on target cells. Moreover, trifunctional NKCE molecules also display killing activity against all primary malignant AML cells, promoting significant antitumor activity in CD64-positive AML patient samples (AML #5 and 6) against which Reference-1 was completely inactive (FIG. 14A).

Figure 15A:
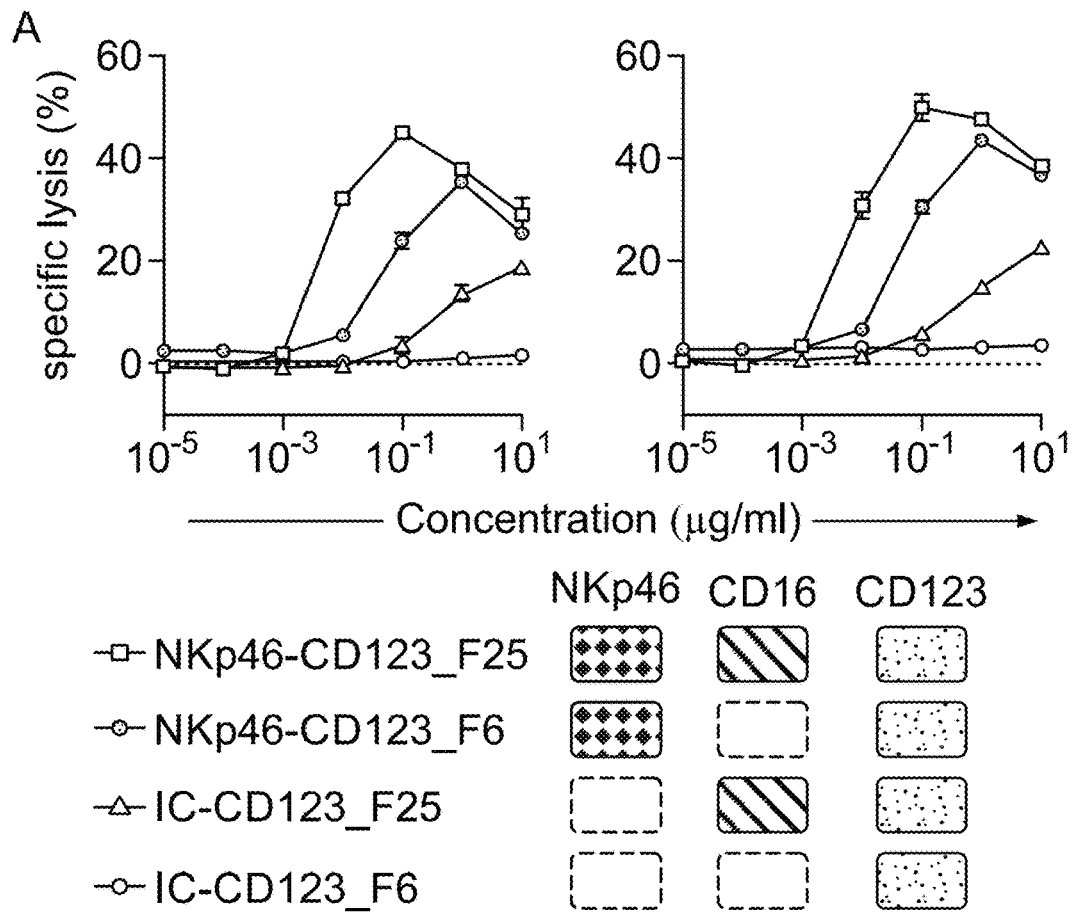
FIG. 15A is a comparison of the cytotoxicities of NKCEs targeting CD123 on tumor cells and not engaging NK cells (IC-CD123_F6) or engaging NK cells by CD16a only (IC-CD123_F25) or NKp46 only (NKp46-CD123_F6) or co-engaging NKp46+CD16 (NKp46-CD123_F25). MOLM-13 cells were used as the target cells and purified resting healthy donor NK cells as effectors. Two NK donors are shown.
Figure 15B:
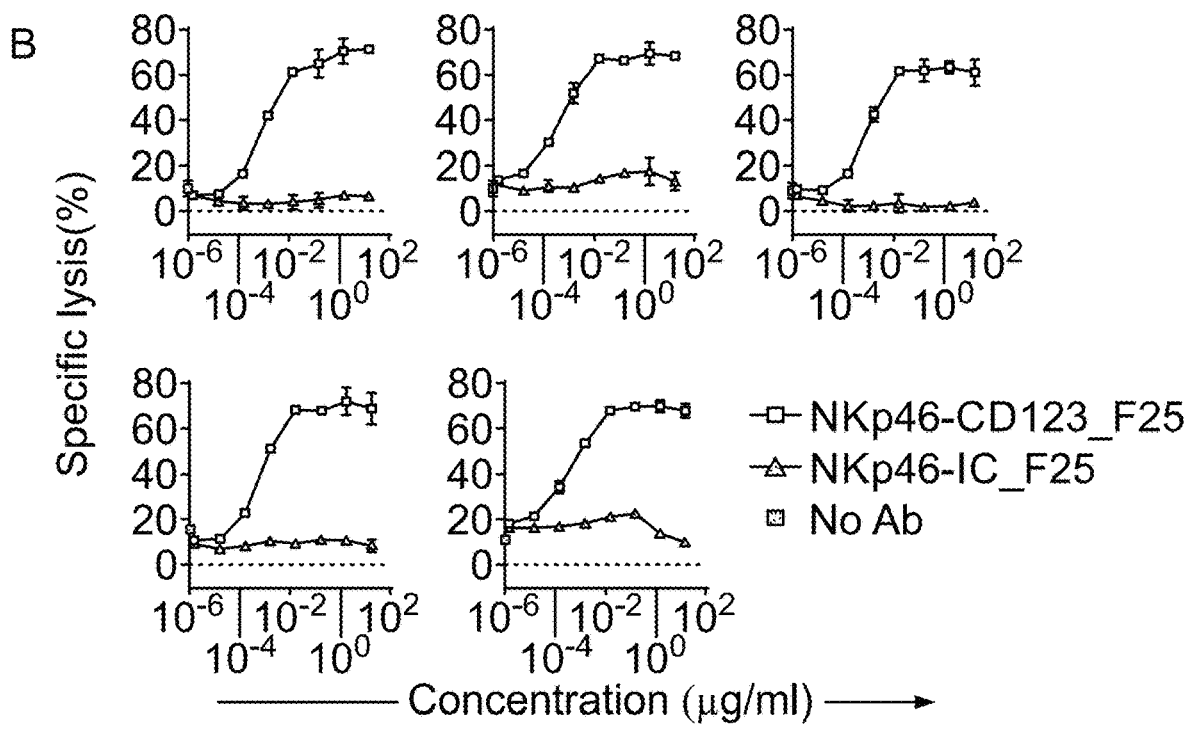
FIG. 15B reports the cytotoxicity of NKp46-CD123_F25 binding protein of the present disclosure as compared to a negative isotype control NKCE molecule not binding to CD123 (NKp46-IC_F25) against AML cell line MOLM-13. Results for five healthy NK-cell donors are shown.

Regarding experiments using MOLM-13 cells, trifunctional molecules (CD123-NKp46_F25) were more potent than the bispecific reagents activating NKp46 (CD123-NKp46_F6) or CD16a (CD123-IC_F25) separately (FIG. 15A), demonstrating potent killing activity (geometric mean EC$_{50}$ of 4.2 [95% CI: 2.7, 6.3] pM, a mean observed maximum specific lysis of 71±5%) and good consistency between healthy NK cell donors (FIG. 15B).

B.7. NK Cell Activation in Autologous Primary AML Samples by NK Cell Engagers

The properties of NKp46-CD123_F25 binding proteins of the present disclosure (NKp46-CD123_F25) to induce NK degranulation against primary CD64(+) or CD64(−) AML blasts were established in FIG. 7 through measurement of the percentage of CD107-positive NK cells.

Overall, this experiment provides evidence that the NKp46-CD123_F25 binding proteins of the present disclosure are able to activate NK cells in primary samples from AML patients in an autologous assay, e.g., with primary blasts and NK cells from the same patient.

Figure 16A:
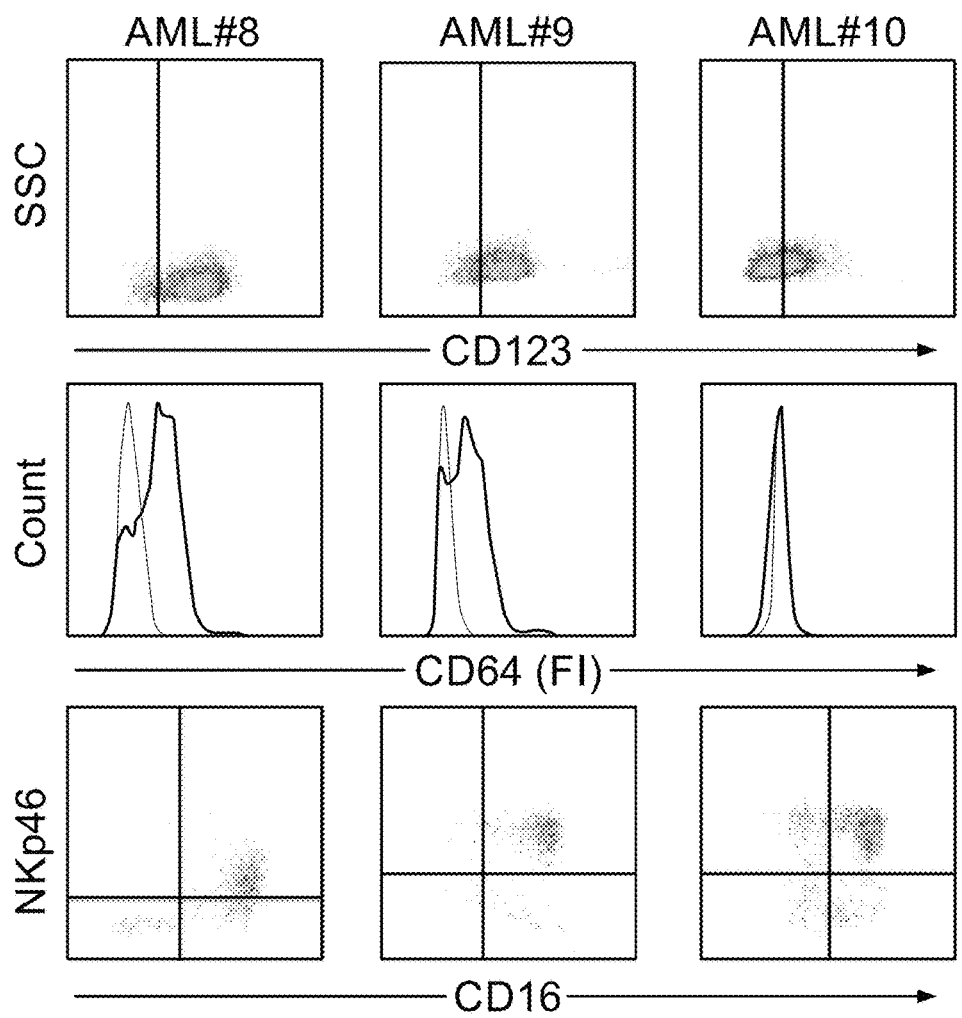
FIG. 16A is a flow cytometric analysis of NK and malignant cells from AML patients (AML #8-#10). Upper panels display the expression of CD123 on AML blasts (gated on the CD33-positive population); middle panels display the expression of CD64 (CD64 staining in black and isotype control in gray) on CD123-positive AML blasts; and lower panels display expression of NKp46 and CD16a on NK AML sample NK cells.
Figure 16B:
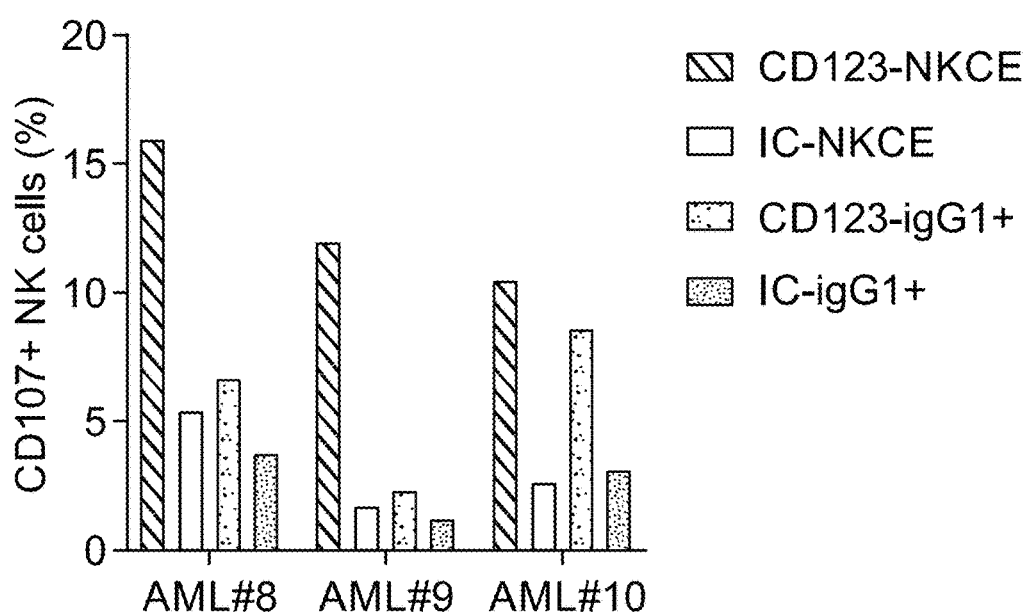
FIG. 16B is an analysis of CD107a/b expression by NK cells after the overnight treatment with NKp46-CD123_F25 (CD123-NKCE), anti-CD123 ADCC-enhanced antibody with no specificity for NKp46 (Reference-1 or CD123-IgG1+ in the graph), a control isotype NKp46-IC_F25 not binding CD123 but binding NKp46 and CD16a (600 and 120 ng/mL) (IC-NKCE) and an IgG1 isotype control (600 ng/ml) (IC-IgG1+) on PBMCs from AML patient samples expressing CD64 (AML #8 and #9) and not expressing CD64 (AML #10) at the cell surface of their blasts.

These results were further consolidated in a dedicated autologous NK-cell activation assay with two additional AML patient samples without (sample 10) and with (sample 8 and 9) CD64 expression (FIG. 16A). Again, NKp46-CD123-NKCEs mediated the autologous activation (see shift in CD107 staining) of the patients' NK cells against their own malignant cells regardless of CD64 expression status on blasts, whereas Reference-1 was active only against the CD64-negative sample (sample 10) (FIG. 16B).

Accordingly, this experiment supports the capacity of the NKp46-CD123_F25 binding protein of the present disclosure to activate NK cells ex vivo, both with respect to CD64(+) and CD64(−) AML cells.

Besides, in this autologous assay, NKp46-CD123_F25 binding protein of the present disclosure are able to engage NK cells in the presence of CD64(+) cells at a much lower concentration than what is observed in the presence of Reference-1.

In addition, mean EC$_{50}$ were also quantified for NKp46-CD123_F25 and Reference-1, in a blast killing assay using six NK healthy donors against four AML samples (2 CD64(+) and 2 CD64(−), and the results are reproduced here below.

|  | Mean $EC_{50}$ CD64(−) AML blasts +/− SD (pM) | Mean $EC_{50}$ CD64(+) AML blasts +/− SD (pM) |
| --- | --- | --- |
| NKp46-CD123_25 | 27.9 +/− 14.1 | 18.6 +/− 1.9 |
| Reference-1 | 48.0 +/− 36.3 | inactive |

Overall, these experiments again demonstrate that the blast killing activity of the NKp46-CD123_F25 binding proteins related to the present disclosure is superior to the Reference-1 antibody, even for CD64(−) AML samples, with Reference-1 being inactive against CD64(+) AML blasts.

B.8. NKp46-CD123 NK Cell Engagers Induce Anti-Tumor Activity Against MOLM-13 Human AML Injected in a SCID Mouse Model FIG. 8 reports dose-dependent anti-tumor activity with a muNKp46-huCD123_F25 binding protein (muNKp46-huCD123_F25) inducing 50% mice survival at 0.5 mg/kg, 70 days after tumor implantation, using a SCID mouse model. More specifically, the control group treated showed an MST of 27.5 days and 5% of long-term survivors.

X-axis marks the number of days after tumor implantation, consisting of an intravenous injection of human MOLM-13, including a single compound administration on day one by the intraperitoneal (i.p.) route. Y-axis marks the percentage of survival based on ten mice for the treated group and twenty mice for the control group. *** marks a p value <0.001 vs. control group.

The group treated with muNKp46-huCD123_F25 at 0.5 mg/kg showed a MST of 66 days, an increased lifespan of 140% and 50% of long term survivors, muNKp46-huCD123_F25 at 0.5 mg/kg was statistically significantly active as compared to the control group (p<0.0001). For the dose of 0.25 mg/kg, the group showed an MST of 36 days, an increased lifespan of 31% and 10% of long-term survivors, muNKp46-huCD123_F25 inducing at 0.25 mg/kg was not statistically different to the control group. For the dose of 0.05 mg/kg, the group showed an MST of 33 days, an increased lifespan of 20% and no long-term survivors, muNKp46-huCD123_F25 at 0.05 mg/kg was not statistically different to the control group.

The NKp46-CD123_F25 binding protein related to the present disclosure showed a dose-dependent anti-tumor in-vivo activity with a robust activity at 0.5 mg/kg. Those results are summarized in the following Table 3:

TABLE 3

| Group | Long term survivors | Median Survival Time in days | Increase of lifespan |
| --- | --- | --- | --- |
| F25 at 0.5 mg/kg | 50% | 66 | 140% |
| F25 at 0.25 mg/kg | 10% | 36 | 31% |
| F25 at 0.05 mg/kg | 0% | 33 | 20% |
| Control | 5% | 27.5 | — |

Hence, this confirms that the NK cell engagers are efficient for the treatment of proliferative disorders in-vivo in an animal model.

Additionally, for further evaluation of efficacy, the experiment described above and reported in FIG. 8 was repeated but including a 5 mg/kg of muNKp46-huCD123_F25 NKCE or control as well as with an additional group administered that was Reference-1. The results are presented in FIG. 18.

Figure 8:
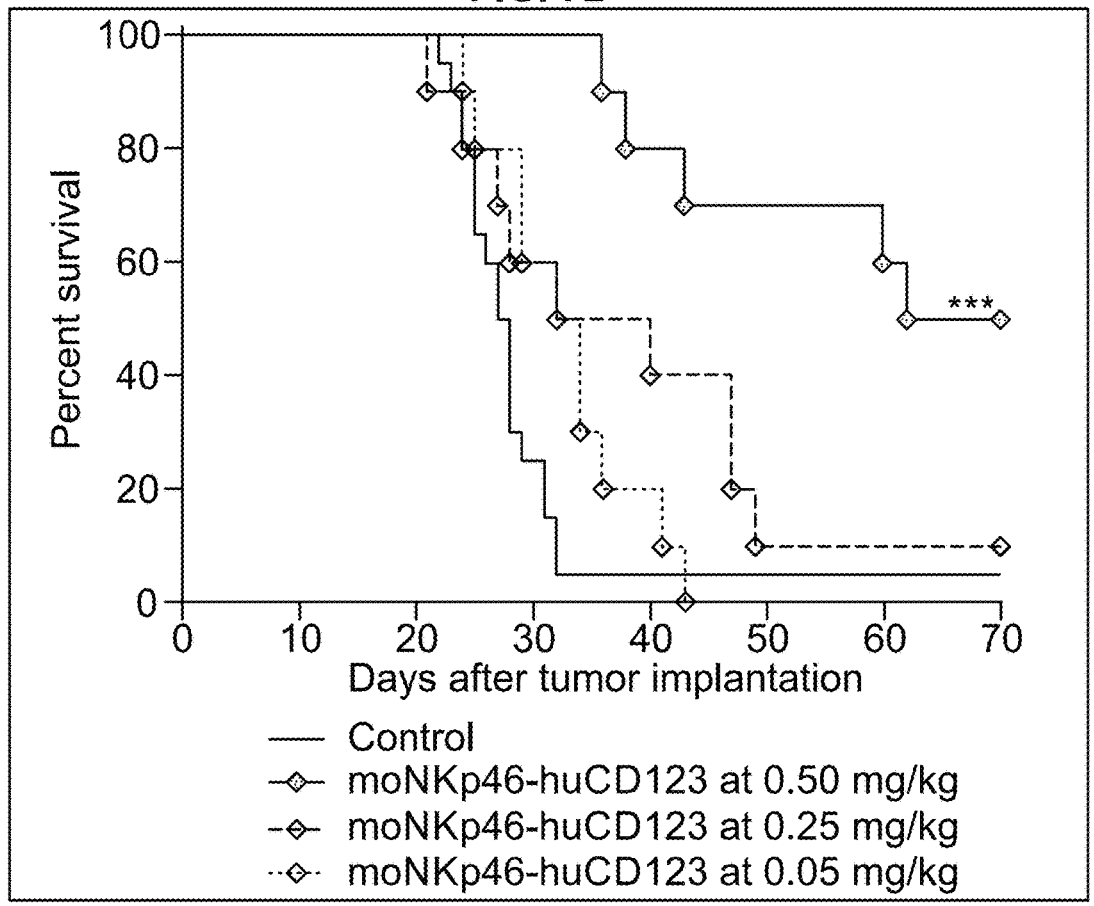
FIG. 8 reports dose-dependent anti-tumor activity with the muNKp46-huCD123_F25 binding protein (carrying anti-murineNKp46 and anti-humanCD123 binding domains and also known as moNKp46-huCD123) against MOLM-13 human cells in a Severe Combined ImmunoDeficient mice (SCID) mouse model.
Figure 18:
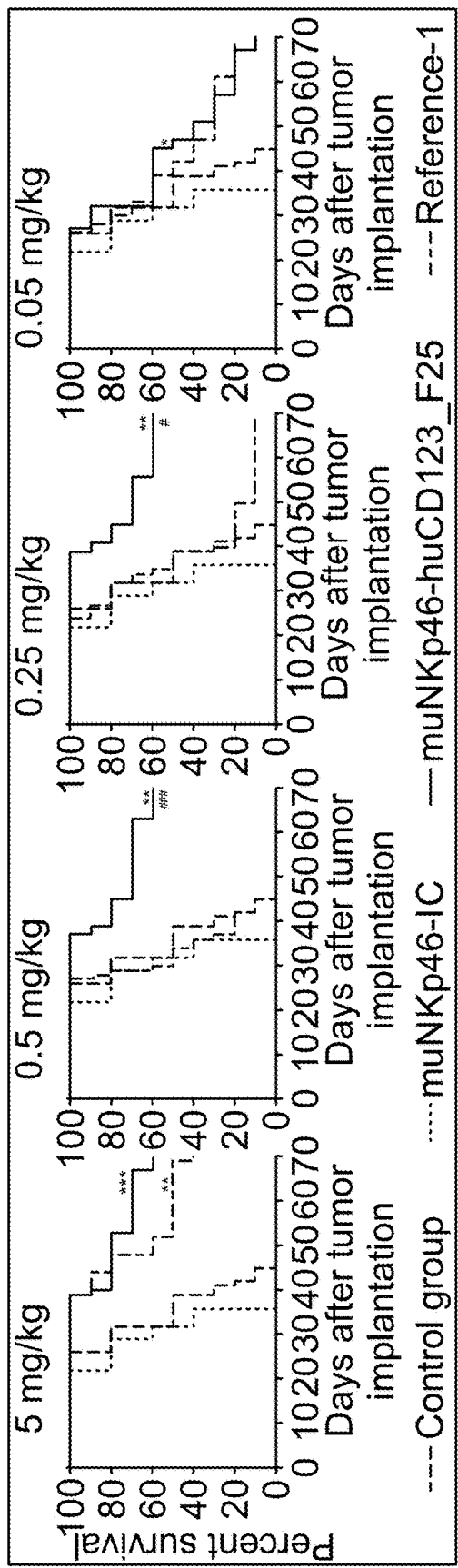
FIG. 18 shows the activity of the surrogate muNKp46-huCD123_F25 bispecific antibody (also known as moNKp46-huCD123) against disseminated human AML, MOLM-13, in SCID mice. MOLM-13 cells were injected intravenously at day 0 in a single administration. Treatments were administered on day 1 post tumor implantation by intraperitoneal route. An isotype control antibody binding muNKp46 and murine FcγRs but not huCD123 (muNKp46-IC) was administered at 0.5 mg/kg. muNKp46-huCD123_F25 and Reference-1 were administered at 5, 0.5, 0.25 and 0.05 mg/kg. The control group was left untreated. Graphs represent Kaplan-Meier curves for animals treated by muNKp46-huCD123_F25 bispecific antibody, Reference-1 and controls at 5, 0.5, 0.25 and 0.05 mg/kg. *: p<0.001 vs control group; : p<0.01 vs control group; *: p<0.05 vs control group; ###: p<0.001 vs Reference-1; #: p<0.05 vs Reference-1. n=5 to 10 mice/group.

Consistent with the FIG. 8 study, in the FIG. 18 study the surrogate muNKp46-huCD123_F25 induced a statistically significant activity at the doses of 5, 0.5, 0.25 and 0.05 mg/kg in human MOLM-13 disseminated model, with an ILS compared to control of 100% and 60% of long-term survivors for the doses of 5, 0.5 and 0.25 mg/kg and an ILS of 30% and 10% of long-term survivors for the dose of 0.05 mg/kg.

Reference-1 induced a statistically significant activity at the dose of 5 mg/kg in human MOLM-13 disseminated model, with an ILS of 70% and 40% of long-term survivors. It was not active at the doses of 0.5, 0.25 and 0.05 mg/kg.

The muNKp46-huCD123_F25 was statistically significantly more active than Reference-1 at the doses of 0.5 and 0.25 mg/kg.

Tabular results for FIG. 18 are summarized as follows:

| Group | Long term survivors | Median Survival Time in days | Increase of lifespan |
| --- | --- | --- | --- |
| muNKp46-huCD123_F25 at 5 mg/kg | 60% | >70 | >97% |
| muNKp46-huCD123_F25 at 0.5 mg/kg | 60% | >70 | >97% |
| muNKp46-huCD123_F25 at 0.25 mg/kg | 60% | >70 | >97% |
| muNKp46-huCD123_F25 at 0.05 mg/kg | 10% | 46 | 30% |
| Reference-1 at 5 mg/kg | 40% | 60.5 | 70% |
| Reference 1 at 0.5 mg/kg | 0% | 32 | 0% |
| Referenc 1 at 0.25 mg/kg | 10% | 37 | 4% |
| Reference 1 at 0.05 mg/kg | 20% | 40.5 | 14% |
| Control | 0% | 35.5 | — |

In conclusion, muNKp46-huCD123_F25 surrogate showed a dose-dependent activity with a robust activity from 0.25 mg/kg. These data demonstrated the benefit of co-engaging NK cells with NKp46/FcγRs leading to an improved in vivo efficacy relative to an anti-CD123 antibody (Reference-1).

B.9. NKp46-CD123 NK Cell Engagers Induce Anti-Tumor Activity In Vivo in Non-Human Primates The absence of pro-inflammatory cytokine release of NKCE in human PBMCs in vitro was further confirmed in two dedicated pharmacokinetic, pharmacodynamic and safety studies performed on NHPs. Cynomolgus monkeys were selected as a relevant species for preclinical pharmacokinetics, pharmacodynamics and toxicological studies on (1) the basis of their tissue distributions of NKp46 and CD123, which are similar to those in humans (Walzer et al. PNAS; 2007; 104:3384-3398 and ChiChili et al. Sci Transl Med; 2015; 7:289) and (2) because the antibodies and Fc fragment constituting the CD123-NKCE molecule bind to cynomolgus antigens and FcγRs with affinities similar to those for human molecules as shown in the Table 4 below. Specifically, CD16a (FcγRIIIA) has a monovalent $K_D$ of 0.46±0.01 μM and 2.61±0.09 μM for its 158V and 158F isoforms, respectively, and anti-NKp46 and anti-CD123 antibody moieties bind to human NKp46 and human CD123 with monovalent KD of 16.3±2.9 nM and 0.40±0.04 nM, respectively.

TABLE 4

| | $K_D$ (nM) Mean +/− SD (n = 3) | |
|---|---|---|
| | NKp46-CD123_F25 | Human IgG1 control |
| Human molecules | | |
| CD123 | 0.40 ± 0.02 | NA |
| Nkp46 | 16.6 ± 1.1 | NA |
| Human FcRn | 109 +/− 28 | 94 +/− 25 |
| Human FcγRI | 0.2 +/− 0.0 | 0.2 +/− 0.0 |
| Human FcγRIIa | 1222 +/− 99 | 1574 +/− 108 |
| Human FcγRIIb | 3196 +/− 375 | 4232 +/− 483 |
| Human FcγRIIIaF | 2606 +/− 91 | 2820 +/− 58 |
| Human FcγRIIIaV | 462 +/− 12 | 575 +/− 16 |
| Human FcγRIIIb | 6688 +/− 413 | 7541 +/− 838 |
| Cynomolgus molecules | | |
| CD123 | 1.2317 ± 0.132 | NA |
| NKp46 | 29.038.9 ± 1.74 | NA |
| Cynomolgus FcRn | 282 +/− 41 | 237 +/− 22 |
| Cynomolgus FcγRI | 12 +/− 1 | 18 +/− 2 |
| Cynomolgus FcγRIIa | 5177 +/− 290 | 6336 +/− 377 |
| Cynomolgus FcγRIIb | 1891 +/− 130 | 2320 +/− 165 |
| Cynomolgus FcγRIII | 466 +/− 36 | 580 +/− 56 |

Displayed results in table 4 were performed at 25° C. pH5.6; default condition: 25° C. pH7.4.
NA: not applicable.
SD: standard deviation.
$K_D$: Dissociation constant.

Figure 9A:
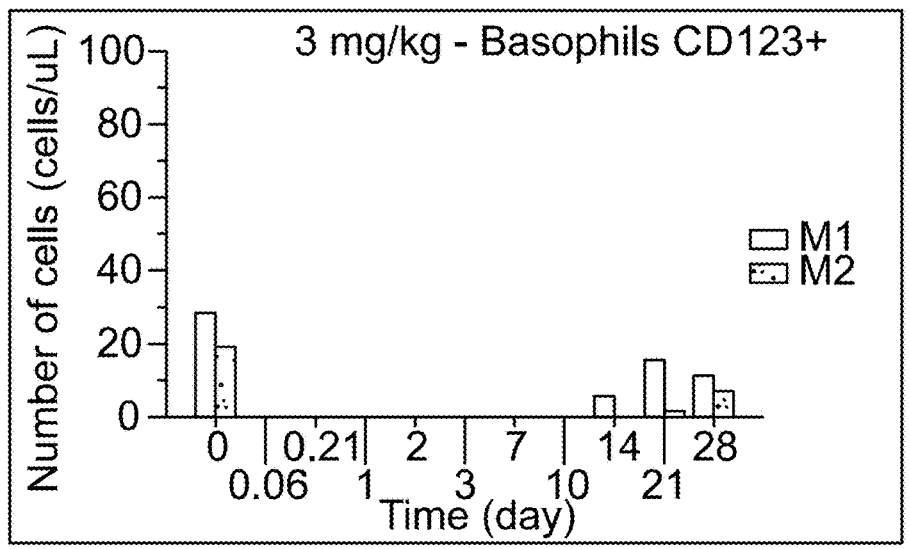
FIG. 9A-FIG. 9C report the CD123-positive basophil depletion for up to 28 days after the administration NKp46-CD123_F25 binding protein of the present disclosure in non-human primates (M1, M2, M3, M4 and M6) at 3000 μg/kg or 3 mg/kg (FIG. 9A), at 3 μg/kg (FIG. 9B), and at 0.5 μg/kg (FIG. 9C).
Figure 9B:
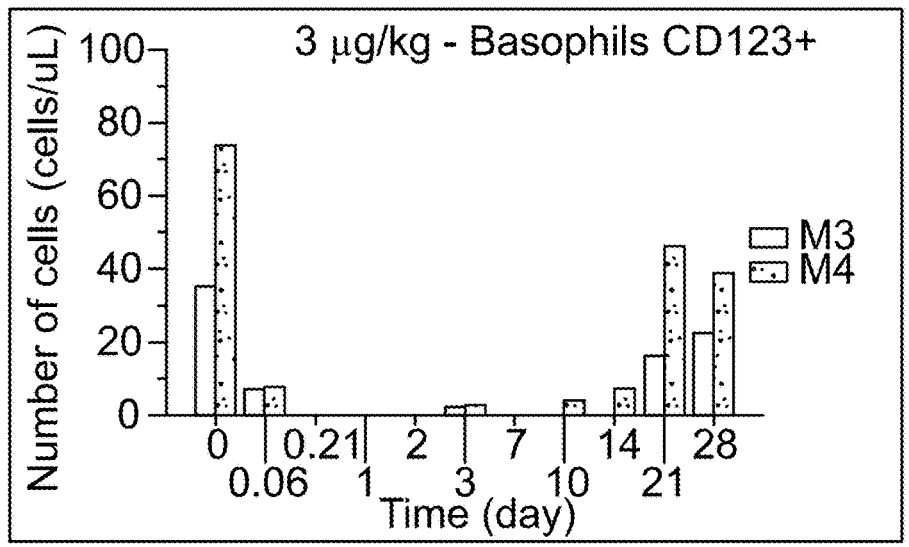
Figure 9C:
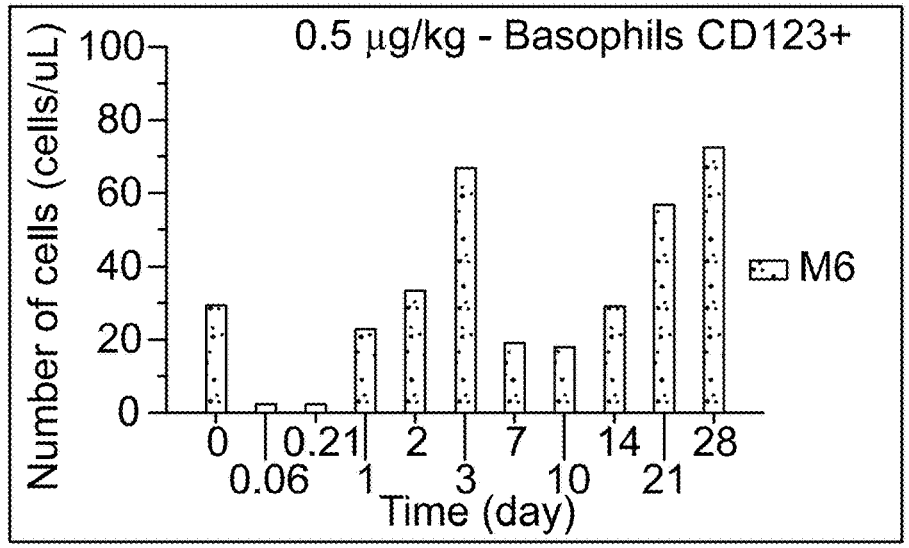

FIG. 9 further shows a complete and sustained CD123-positive basophil depletion at 3 µg/kg for up to 20 days after the injection of the NKp46-CD123_F25 binding protein related to the present disclosure (NKp46-CD123_F25), and up to 5 hours at 0.5 µg/kg for non-human primates.

Accordingly, this result demonstrates that the in vitro, ex vivo and in vivo results previously obtained, including those observed in the SCID mouse model, can be extrapolated to non-human primates for NK cell engagers.

Overall, CD123-positive immune cell depletion is a hallmark of in vivo activity of the NKp46-CD123_F25 binding proteins in non-human primate. It is found that rapid and sustained depletion of CD123-positive basophils is observed, which occurs at about 1.5 hours from start of infusion, and is maintained up to Day 7, with cell number returning to baseline on Day 28.

Figure 10A:
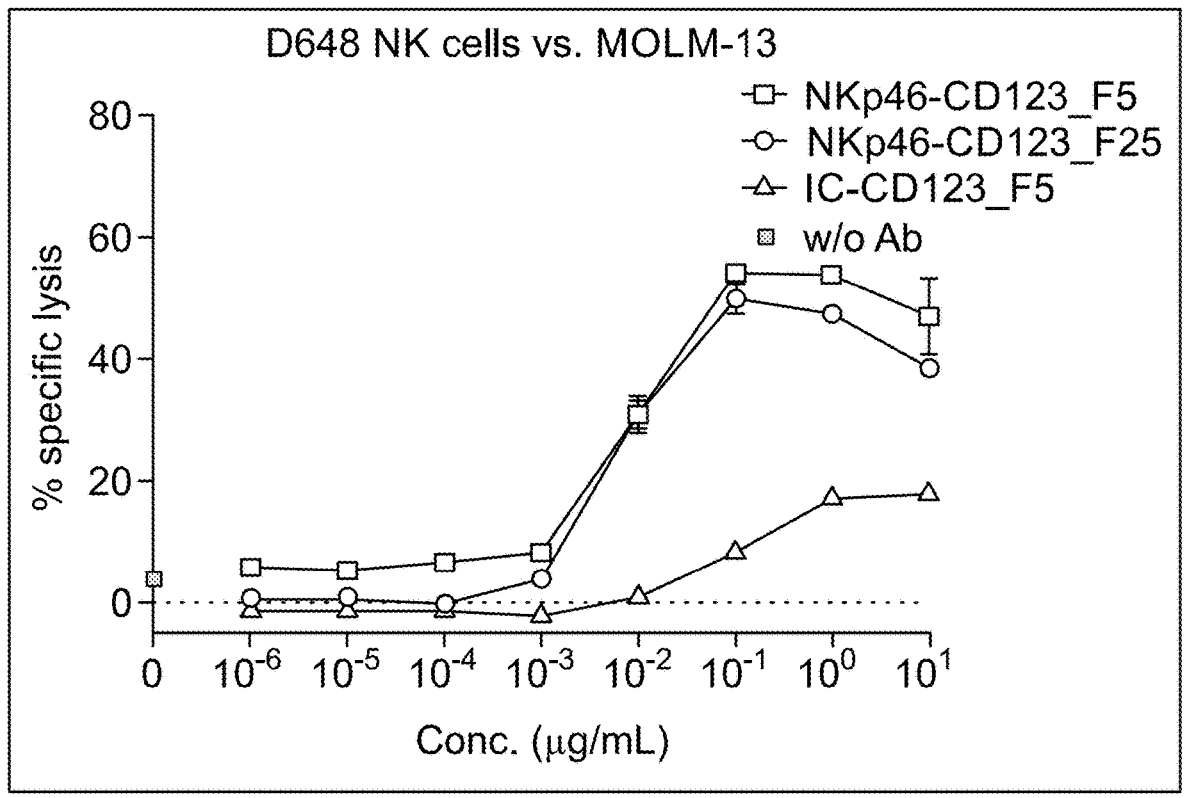
FIG. 10A-FIG. 10B reports the in-vitro cytotoxicity of two NKp46-CD123 NKCE Fc-competent binding proteins (the NKp46-CD123_F25 of the present disclosure and NKp46-CD123_F5) and a control variant of format F5 binding CD123 and CD16a but not binding NKp46 (CD123-IC_F5) against two AML cell lines, MOLM-13 (FIG. 10A) and THP-1 (FIG. 10B) in presence of NK cell healthy donor sample (D648).
Figure 10B:
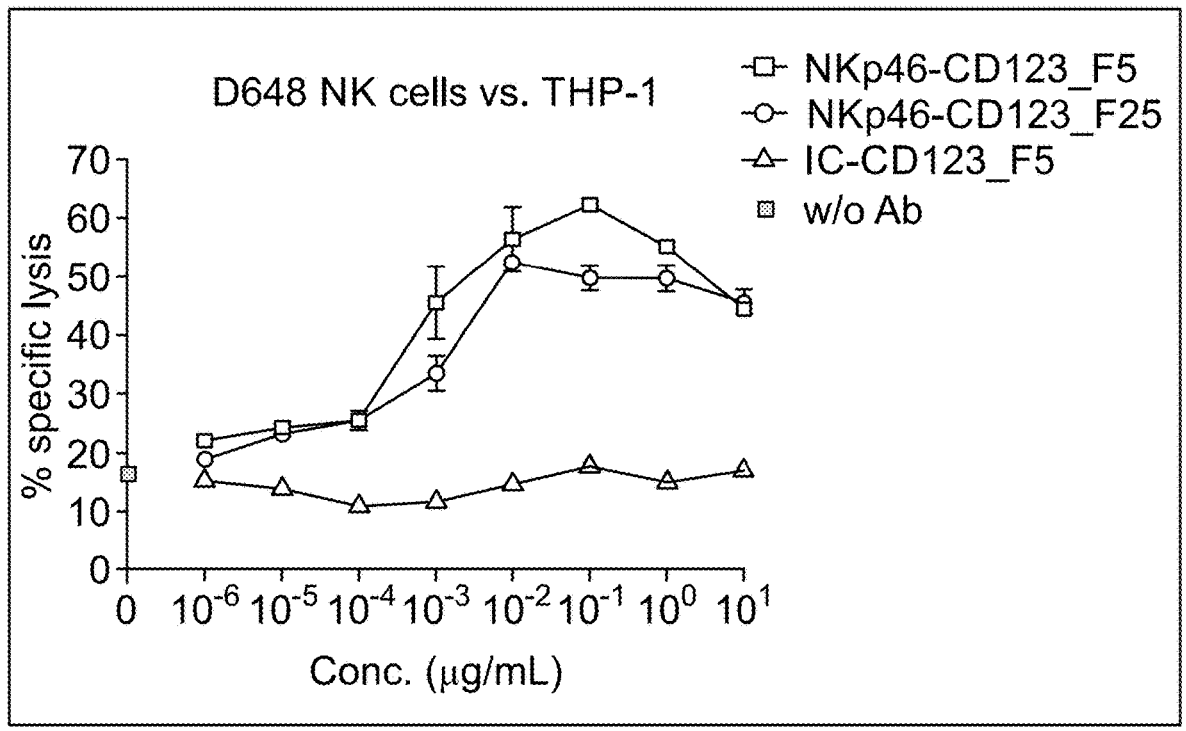

B.10. Comparison of Fc-Competent Formats, Respectively F5 vs. 25 Formats in a Cytotoxicity Assay FIGS. 10A and 10B illustrate that NKp46-CD123_F25 and NKp46-CD123_F5 binding proteins show the same cytotoxic activity against both MOLM-13 and THP-1 AML cell lines, by engaging NK cells from healthy donors (D648).

The main difference between MOLM-13 and THP-1 cells relates to their level of expression of the CD64 marker. MOLM-13 cells do not express CD64(−), whereas THP-1 cells express high level of CD64(+). Both cells express CD32a.

Thus, this example reports the variation of specific lysis for three distinct binding proteins: (i) a NKp46-CD123_F5 binding protein in the F5 format (NKp46-CD123_F5), (ii) a NKp46-CD123_F25 binding protein in the F25 format (NKp46-CD123_F25), and (iii) a negative isotype control variant of format F5 binding CD123 only (CD123-IC_F5).

Overall, those results demonstrate that cytotoxic activity is maintained with two Fc competent NKp46-CD123 binding proteins in F5 and F25 formats. In contrast, the negative controls do not lead to detectable cytotoxic activity.

B.11. NKp46-CD123 NKCEs-Induced CD123-Positive Basophil Depletion is Associated to Low Cytokine Release when Compared to T-Cells Engager Tool Potent cytotoxicity may be associated with toxicity in patients. To investigate the cytokine release from human PBMCs induced by CD123-NKCE in vitro, as a predictive assay of potential cytokine release syndrome (CRS) in patients, the following experiment was performed.

Human PBMCs (N=10 samples) were cultured for 20 hours in the presence of a NKp46-CD123_F25 (CD123-NKCE; dose of 0.1, 1, or 10 µg/mL; 0.68-68 nM), a negative isotype control variant of format F25 binding NKp46 only (NKp46-IC_F25; dose of 0.1, 1 or 10 µg/mL; 0.68-68 nM), or with an anti-CD123 T-cell engager antibody tool with specificity for CD3 and no specificity for NKp46 (CD123-TCE, Reference-1; 0.1 µg/mL; 1.6 nM) over a concentration gradient ($10^{-3}$ to $10^1$ µg/mL).

Figure 11:
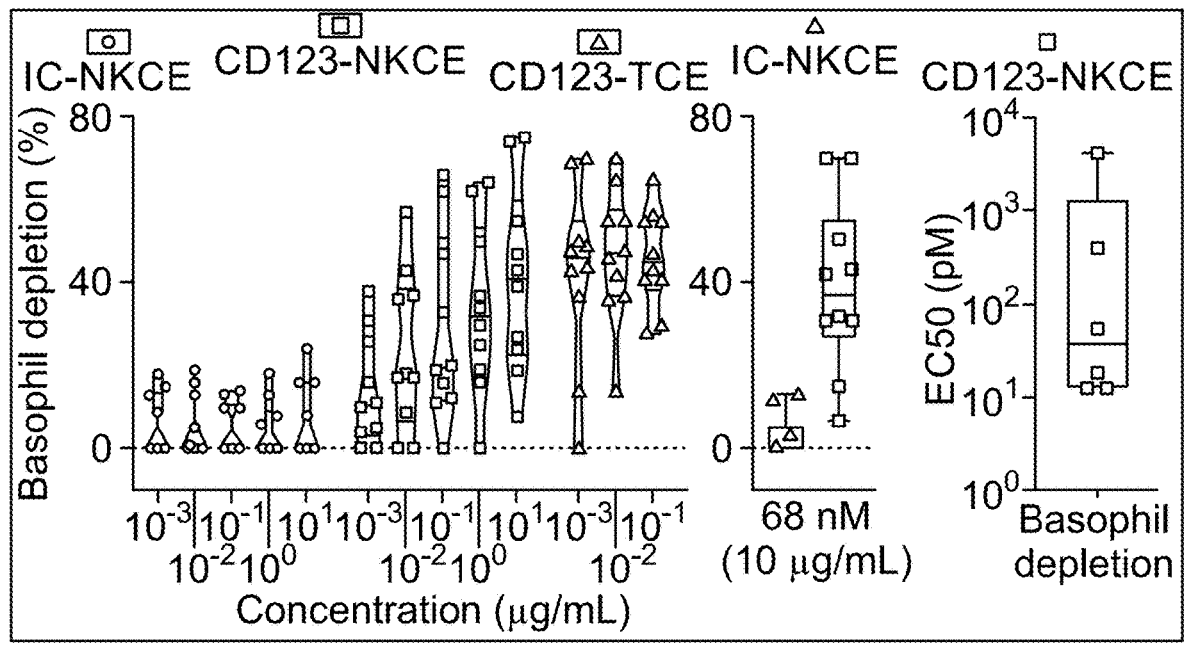
FIG. 11 left panel reports CD123-positive basophil depletion in healthy donor PBMCs (N=10) in vitro induced by the treatment with NKp46-CD123_F25 (CD123-NKCE; dose range 0.001 to 10 µg/mL), NKCE isotype control NKp46-IC_F25 (IC-NKCE; not binding CD123 but binding NKp46 and CD16a) (dose range 0.001 to 10 µg/mL), or CD3-CD123 bispecific T-cell engager (CD123-TCE tool; 0.001 to 0.1 µg/mL). Central panel reports NKp46-CD123_F25 maximum depletion activity at the highest dose tested (10 µg/mL, 68 nM). Right panel reports the $EC_{50}$ (pM) for CD123-positive basophil depletion calculated from NKp46-CD123_F25 dose responses for the PBMCs of six healthy donors.
Figure 12:
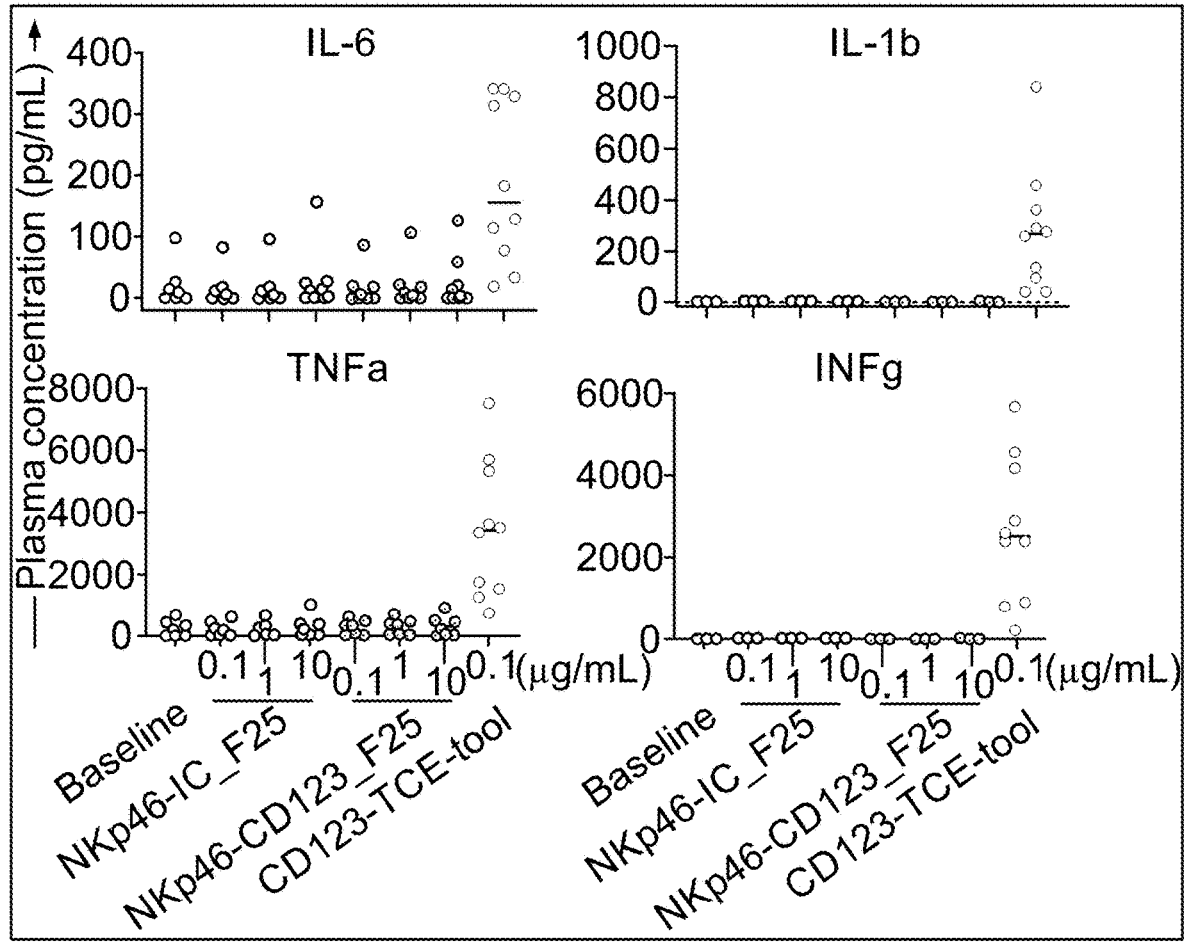
FIG. 12 displays the IL-1β, TNF-α, IFN-γ (written as INFg on the graph), and IL-6 cytokine release in vitro by healthy donor PBMCs (N=10) following the treatment with NKp46-CD123_F25, NKCE isotype control NKp46-IC_F25 (not binding CD123 but binding NKp46 and CD16a) at doses of 0.1, 1 and 10 µg/mL or a bispecific T Cell Engager tool (TCE tool) co-targeting CD123 and CD3 binding sites at dose of 0.1 µg/mL.
Figure 13A:
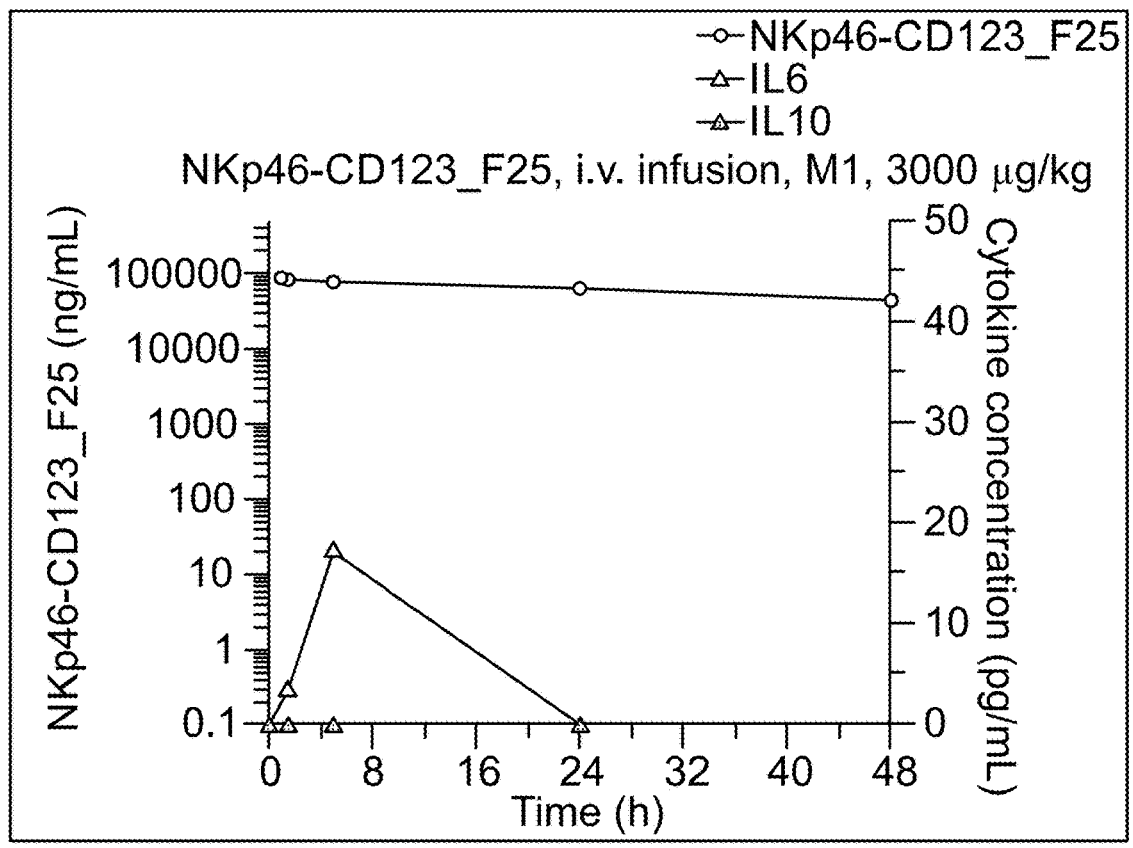
FIG. 13A-FIG. 13F show the individual IL-6 and IL-10 plasma concentration versus time profiles in correlation with NKp46-CD123_F25 binding protein concentrations at 3000 µg/kg (FIG. 13A and FIG. 13B), 3 µg/kg (FIG. 13C and FIG. 13D), 0.5 µg/kg (FIG. 13E) and <0.5 µg/kg (FIG. 13F) for 6 male Cynomolgus monkeys (M1 to M6).
Figure 13B:
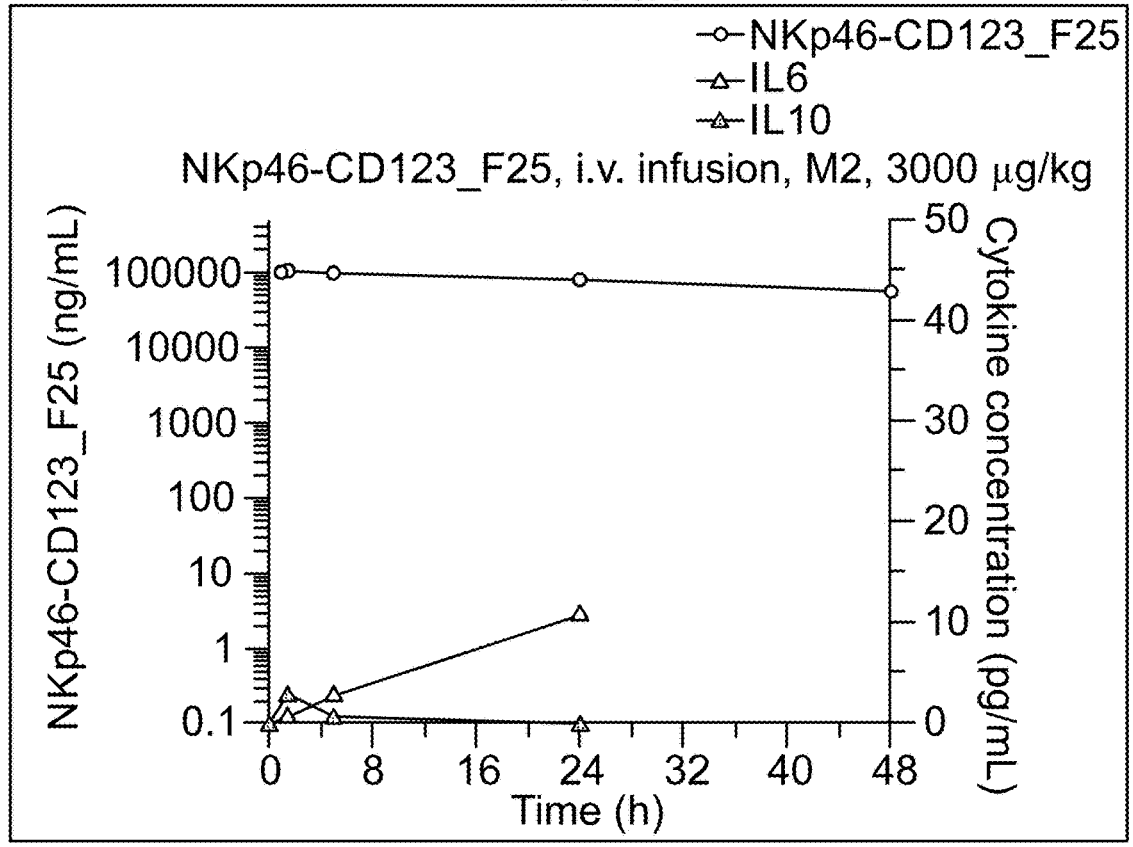
Figure 13C:
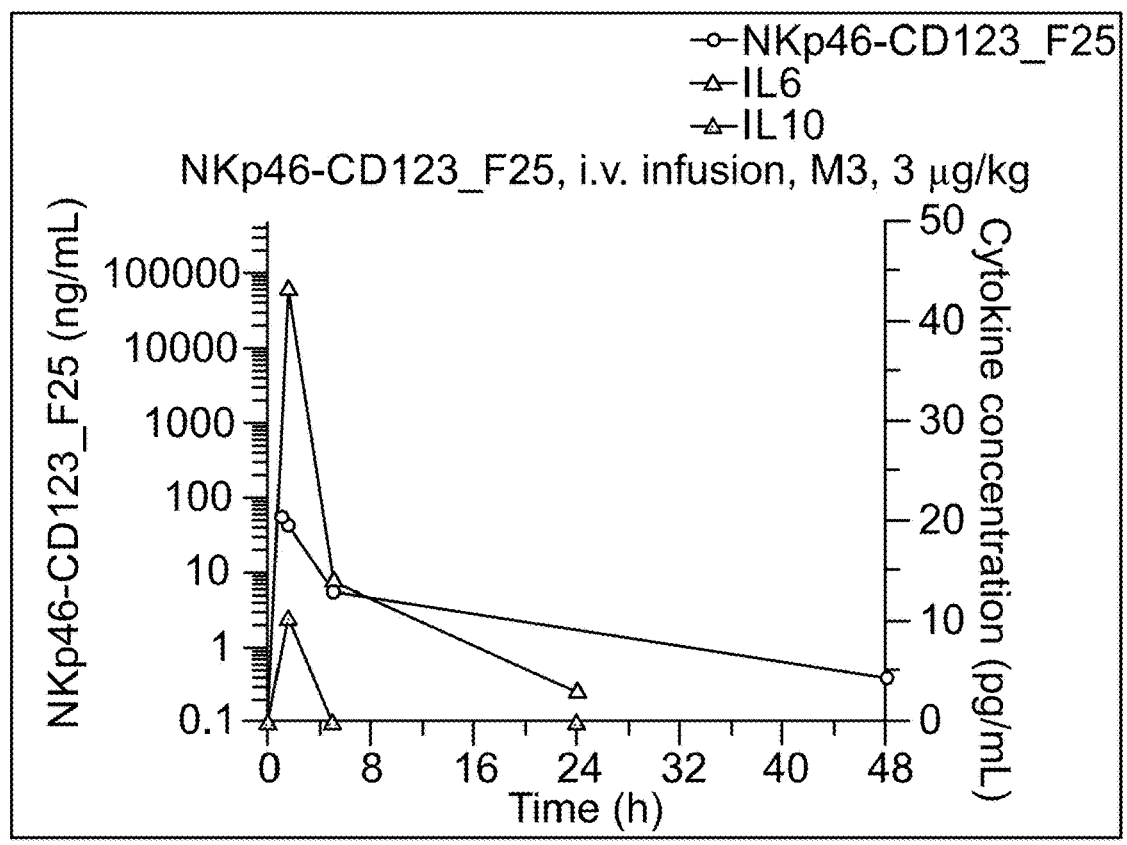
Figure 13D:
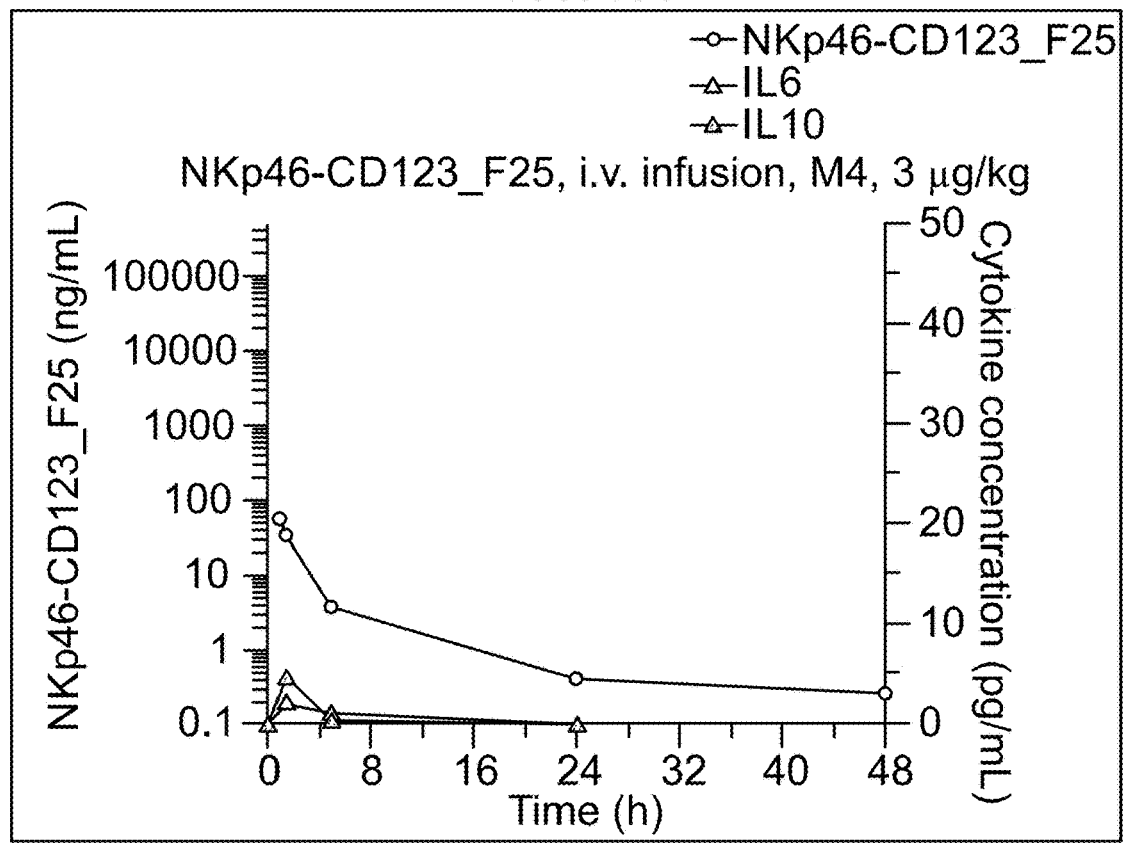
Figure 13E:
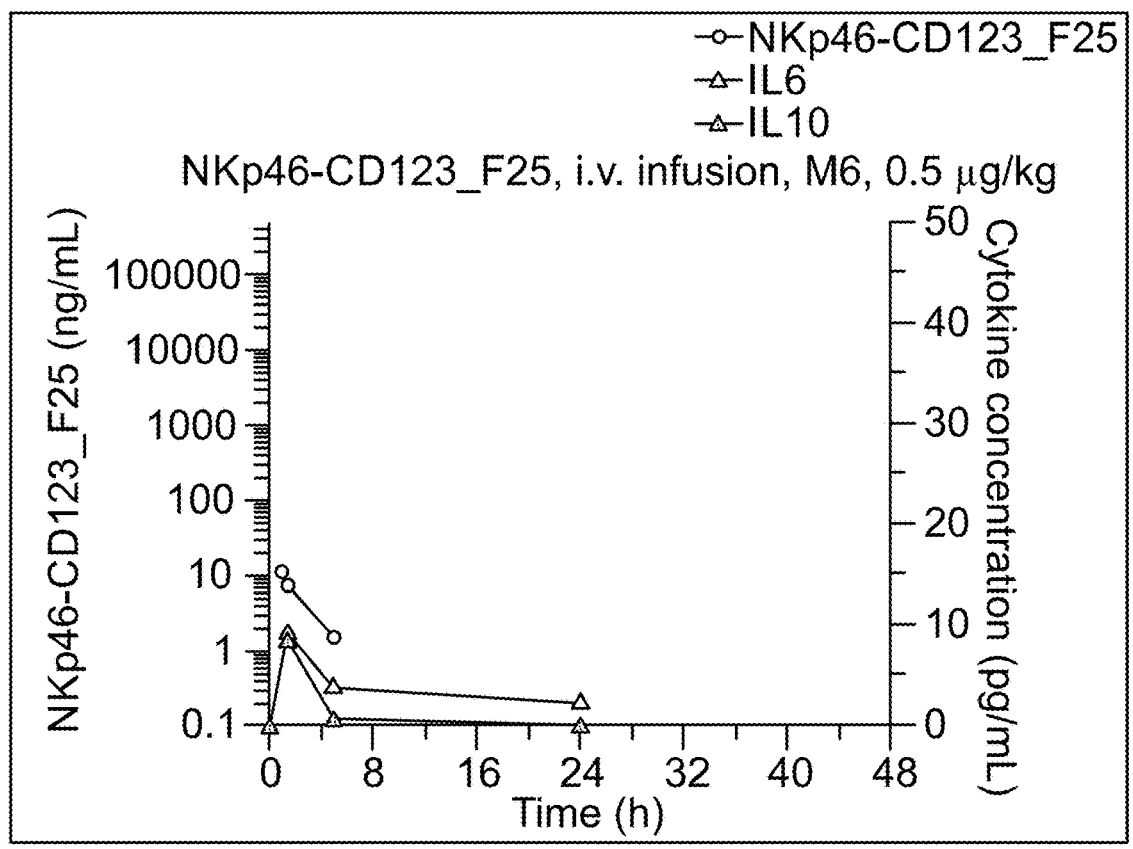
Figure 13F:
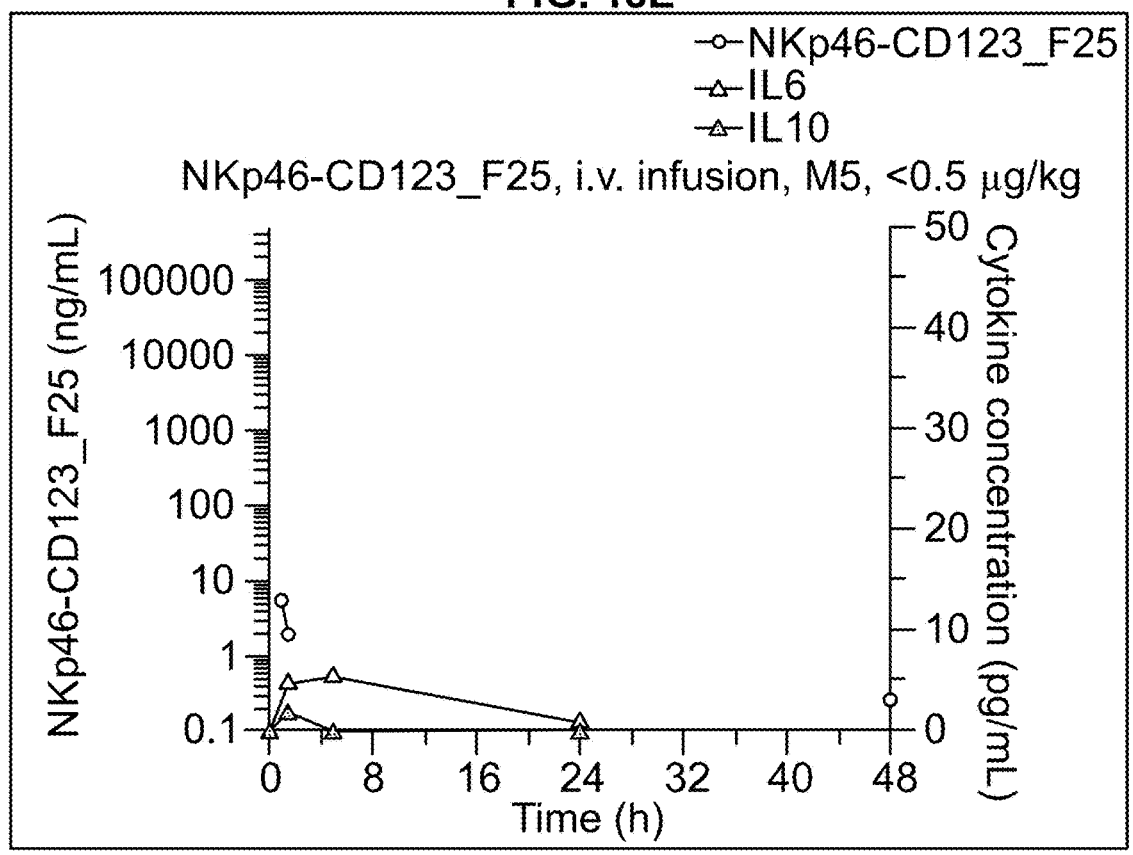

Amongst human PBMCs, CD123 is constitutively expressed on a subset of circulating basophils and plasmacytoid dendritic cells (pDC). Given that basophils have higher CD123+ expression than pDCs, the percent depletion of basophils was monitored for each treatment group indicated above. FIG. 11 shows the treatment of human PBMCs with CD123-NKCE promoted a dose-dependent partial depletion of CD123+ basophils with a median maximum depletion of 37% [31; 50], and a geometric mean $EC_{50}$ value of 38 pM (95% CI [12.9; 401]), calculated with six of 10 donor samples. In contrast, basophil depletion did not occur in a considerable amount in the presence of a F25 binding molecule lacking a CD123 binding site (NKp46-IC_F25). From the human PBMCs treatment groups indicated above, the supernatant was collected to quantify the amount of cytokine release. FIG. 12 demonstrates that the in vitro IL-6, and IL-1β pro-inflammatory cytokine and TNF-α and IFN-γ cytokine release associated to the administration of the NKp46-CD123_F25 binding protein related to the present disclosure (NKp46-CD123_F25) was much lower than the corresponding IL-6 release associated with the administration of a positive control known to induce cytokine release syndrome (CRS), Reference-1, at a 100-fold lower dose (0.1 µg/ml).

CD123-NKCE induced much lower levels of cytokine release than CD123-TCE, even at concentrations 42-times higher.

FIGS. 11 and 12 demonstrate that the treatment of PBMCs with CD123-NKCEs promoted a depletion of CD123+ basophils but induced much lower levels of IL-6, IL-1β, TNF-α and IFN-γ release than treatment with CD3-CD123 antibody molecule.

In conclusion, the NKp46-CD123_F25 binding protein related to the present disclosure (NKp46-CD123_F25) has shown its ability to engage primary NK cells to target and kill CD123+ primary normal mononuclear blood cells associated with minor cytokine release and may have a better benefit/risk profile than TCEs for the treatment of AML.

Regardless of the dose level and up to a high dose of 3 mg/kg, FIG. 13A-13F show that very low cytokine release (IL6 and IL10) was observed in all treated animals (male Cynomolgus monkeys) after the start of the injection of NKp46-CD123_F25 binding protein related to the present disclosure (NKp46-CD123_F25), without any associated clinical signs. No IL-2 nor IFNγ cytokine release were detected. More particularly, transient IL6 and IL10 peaks are detected in non-human primates after a single intravenous injection of F25 constructs at 3 mg/kg. This transient peak occurs from 1 hour to 5 hours and returns to baseline within 1 or 2 days.

Also, those very low levels of IL-6 and IL-10 cytokine release are not associated with clinical signs up to 3 mg/kg dose. This indicates that such NK cell engagers possess a good safety profile in non-human primates.

B.12. NKp46-CD123 NK Cell Engagers Promote NK-Cell Activation In Vitro that is Commensurate with Cytokine/Chemokine Production Flow cytometric analysis corresponding to FIG. 17 demonstrate that NKp46-CD123_F25 binding proteins promoted NK-cell activation only when CD123 expressing target cells are present.

Primary donor NK cells (N=3) incubated in the presence of NKp46-CD123_F25 displayed higher expression levels of NK cell activation markers, CD107 and CD69, as well as cytokines, TNF-α, IFN-γ, and chemokine, MIP-1β, in a dose-dependent manner, when MOLM-13 target cells were present (FIG. 17, comparing NK alone vs NK+MOLM-13 condition).

Overall, this experiment provides evidence that the NKp46-CD123_F25 binding proteins of the present disclosure activate and commensurately promote cytokine/chemokine production in primary NK cells towards CD123+ AML cells with no off-target activation of NK cells.

B. 13. NK Cells are the Effector Lymphocyte Subset Responsible for the Antitumor Activity of NKp46-CD123_F25

To test whether the efficacy of the NKp46-CD123_F25 depended on NK cells anti-tumor activity against MOLM-13 human AML injected in a SCID mouse model, mice underwent an NK cell depletion regimen during the experimental set-up outlined in B.8.

Figure 19:
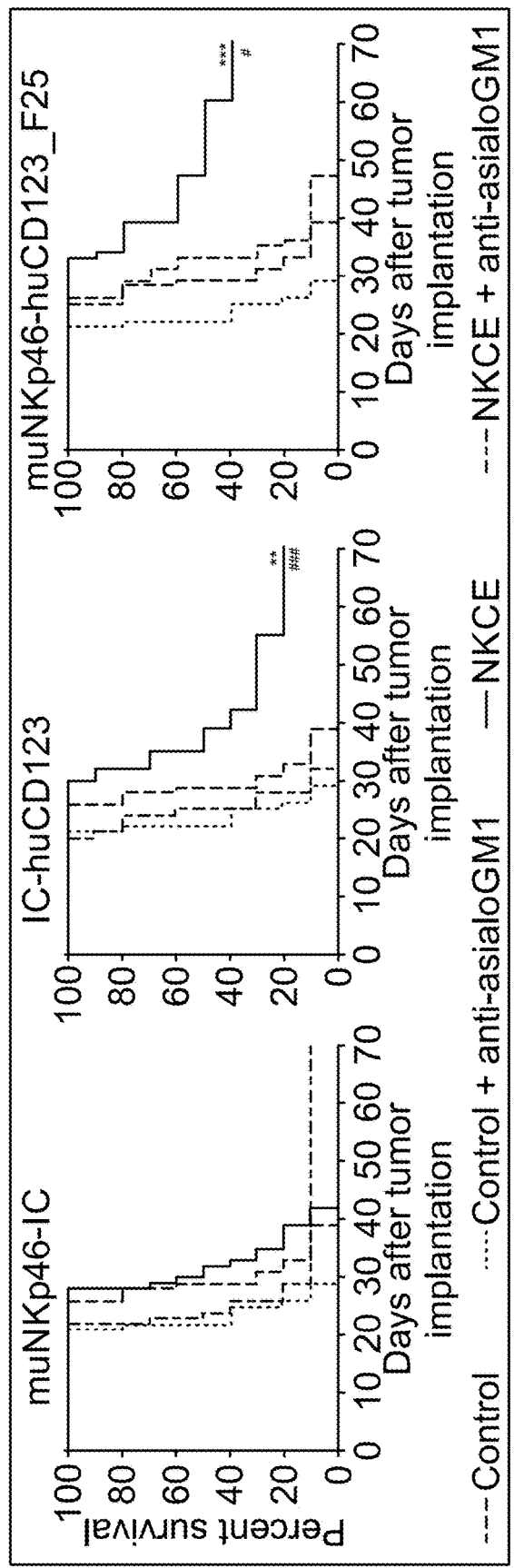
FIG. 19 evaluates the impact of NK depletion on the in vivo efficacy of surrogate muNKp46-huCD123_F25 bispecific antibody in SCID mice bearing disseminated human MOLM-13 tumor cells. NK depletion was induced by 2 intraperitoneal administrations of anti-asialo GM1 serum one day before tumor cell implantation and at day 5 after implantation. MOLM-13 cells were injected intravenously at day 0 in a single administration. Treatments were administered intraperitoneally on day 1 post tumor implantation. Controls including an isotype control antibody binding muNKp46 and murine FcγRs but not huCD123 (muNKp46-IC) and a second isotype control antibody binding huCD123 and murine FcγRs but not murine NKp46 (IC-huCD123) were also evaluated. Graphs represent Kaplan-Meier curves for animals treated by muNKp46-huCD123_F25 bispecific antibody and controls (muNKp46-IC, IC-huCD123) at 0.5, 0.25 and 0.05 mg/kg. n=10 mice/group. *: p<0.001 vs control group; : p<0.01 vs control group; ###: p<0.001 vs same treatment+NK depletion; #: p<0.05 vs same treatment+NK depletion.

The results are presented on FIG. 18 and FIG. 19 and corresponding tabular results are shown in table 5 below.

TABLE 5

| Group | Long term survivors | Median Survival Time in days | Increase of lifespan |
|---|---|---|---|
| muNKp46-IC | 0% | 31 | 7% |
| muNKp46-IC + anti-aGM1 | 10% | 23.5 | ≤0% |
| IC-huCD123 | 20% | 37 | 28% |
| IC-huCD123 + anti-aGM1 | 0% | 25 | ≤0% |
| muNKp46-huCD123_F25 | 40% | 53.5 | 84% |
| muNKp46-huCD123_F25 + anti-aGM1 | 0% | 33 | 14% |
| Control | 0% | 29 | — |

The control group treated showed a median survival time (MST) of 29 days and no long-term survivors.

The muNKp46-IC isotype control did not show activity with an ILS of 7% and no long-term survivors. No impact of the NK depletion is observed on the group treated with muNKp46-IC isotype control with no increased lifespan and 10% of long-term survivors. The IC-huCD123 isotype control was statistically significantly active with an ILS of 28% and 20% of long-term survivors. A statistically significant impact of the depletion was observed on the group treated with IC-huCD123 isotype control with no increased lifespan and no long-term survivors.

The muNKp46-huCD123_F25 was statistically significantly active with an ILS of 84% and 40% of long-term survivors. A statistically significant impact of the depletion was observed on the group treated with muNKp46-huCD123_F25 with an ILS of 14% and no long-term survivors.

In conclusion, the NK depletion impacted the anti-tumoral activity of muNKp46-huCD123_F25 confirming the NK involvement as effector cells in muNKp46-huCD123_F25 NKCE in vivo efficacy.

B. 14. NKp46-CD123 NK Cell Engagers are Safe and Efficient in NHPs

To confirm the safety profile of the Nkp46-CD123 cell engagers in the NHP study conducted in FIG. 9 and FIG. 13 interrogating the pharmacokinetics and pharmacodynamics of CD123-NKCEs administered by a single i.v. injection of a high (3 mg/kg) or low (3 μg/kg and 0.5 μg/kg) doses in male cynomolgus monkeys (2 animals each for the 3 mg/kg and 3 μg/kg doses and 1 animal for the 0.5 μg/kg dose).

Treatment with CD123-NKCE promoted a sustained and complete depletion of $CD123^+$ cells in the blood of all monkeys, for more than 10 days, at both the 3 mg/kg and 3 μg/kg doses (as exemplified for $CD123^+$ basophils and total $CD123^+$ cells in FIG. 20A and FIG. 20B), with only very small amounts (<50 μg/mL) of the pro-inflammatory cytokines IL-6 and IL-10 released (FIG. 20C) without any associated clinical signs.

A transient and partial depletion of $CD123^+$ cells was observed in the monkey treated at the lowest dose (0.5 μg/kg, data not shown), but 3 μg/kg was considered to be the lowest effective dose in this species. The PK profiles of the two monkeys treated at the highest dose (3 mg/kg) were marked by an anti-drug antibody (ADA) response (data not shown) occurring 12-14 days after treatment (FIG. 20D) and associated with the recovery of $CD123^+$ cells from the blood at later timepoints.

The preclinical safety profile of CD123-NKCE was further interrogated through an exploratory repeat-dose toxicity study in which four monkeys (2/sex/dose) were treated weekly, for four weeks, at a dose of 3 mg/kg/administration or 0.1 mg/kg/administration, administered by intravenous infusion for one hour (FIG. 21). In all monkeys (except one of the monkeys, monkey M5, male No. 5; FIG. 21), exposure to CD123-NKCEs lasted for at least two weeks, at both tested doses, with the presence of Anti-Drug Antibody (ADA) detected (data not shown) from the third administration (Day 15) (Table 6).

Table 6 below displays individual CD123-NKCE plasma concentration values after a weekly repeat 1-hour intravenous infusion at 0.1 and 3 mg/kg/administration for 4 weeks (on Days 1, 8, 15 and 22) to cynomolgus monkeys.

TABLE 6

| | | Concentration in plasma (ng/mL) | | | | | | | |
|---|---|---|---|---|---|---|---|---|---|
| | | 0.1 mg/kg/administration | | | | 3 mg/kg/administration | | | |
| Day | Sampling | M1♂ | M2♂ | F3♀ | F4♀ | M5♂ | M6♂ | F7♀ | F8♀ |
| 1 | Predose | <LLOQ | <LLOQ | <LLOQ | <LLOQ | 2.27 | <LLOQ | <LLOQ | <LLOQ |
| 1 | 1 h | 1750 | 1200 | 1550 | 1870 | 37000 | 68700 | 100000 | 46200## |
| 1 | 1.5 h | 1100 | 1520 | 1390 | 1750 | 78600 | 67000 | 98600 | 48300## |

TABLE 6-continued

| | | Concentration in plasma (ng/mL) | | | | | | | |
|---|---|---|---|---|---|---|---|---|---|
| | | 0.1 mg/kg/administration | | | | 3 mg/kg/administration | | | |
| Day | Sampling | M1♂ | M2♂ | F3♀ | F4♀ | M5♂ | M6♂ | F7♀ | F8♀ |
| 1 | 5 h | 736 | 1350 | 986 | 469 | 64100 | 72200 | 76300 | 47500## |
| 2 | 24 h | 160 | 381 | 250 | 448 | 221000# | 30800 | 55200 | 41500## |
| 4 | 72 h | 1.66 | 9.17 | 7.83 | 14.8 | 31600 | 31100 | 27500 | 29100## |
| 8 | 168 h/Predose | <LLOQ | 0.484 | 0.698 | 1.18 | 16000 | 17300 | 20100 | 37800 |
| 8 | 1 h | 1340 | 3.32 | 1980 | 1610 | 92000 | 91900 | 137000 | 87500 |
| 8 | 1.5 h | 1250 | 29.6 | 1680 | 1460 | 89900 | 88400 | 110000 | 82500 |
| 8 | 5 h | 892 | 132 | 1280 | 1210 | 38600 | 72900 | 74800 | 88300 |
| 9 | 24 h | 239 | 78.2 | 554 | 512 | 64500 | 61200 | 46100 | 65200 |
| 11 | 72 h | 1.17 | 35.7 | 43.8 | 20.8 | 46300 | 47100 | 23000 | 30500 |
| 15 | 168 h/Predose | <LLOQ | <LLOQ | 2.45 | <LLOQ | 45000 | 51.8 | <LLOQ | <LLOQ |
| 15 | 1 h | 19.3 | 205 | 256 | 5.61 | 124000 | 21600 | 2310 | 11900 |
| 15 | 1.5 h | 5.53 | 105 | 190 | 3.30 | 75900 | 33600 | 497 | 9800 |
| 15 | 5 h | <LLOQ | 22.2 | 157 | <LLOQ | 85400 | 10600 | 246 | 1170 |
| 16 | 24 h | <LLOQ | 0.333 | 35.1 | <LLOQ | 51700 | 300 | <LLOQ | 37.9 |
| 18 | 72 h | US | US | US | US | US | US | US | US |
| 22 | 168 h/Predose | <LLOQ | <LLOQ | <LLOQ | <LLOQ | 9120 | <LLOQ | <LLOQ | 1.09 |
| 22 | 1 h | 0.998 | <LLOQ | <LLOQ | <LLOQ | 61600 | 365 | <LLOQ | 149 |
| 22 | 1.5 h | <LLOQ | <LLOQ | <LLOQ | <LLOQ | 55500 | 228 | <LLOQ | 53.7 |
| 22 | 5 h | <LLOQ | <LLOQ | <LLOQ | <LLOQ | 44000 | 26.3 | <LLOQ | <LLOQ |
| 23 | 24 h | <LLOQ | <LLOQ | <LLOQ | <LLOQ | 26100 | <LLOQ | <LLOQ | <LLOQ |
| 25 | 72 h | US | US | US | US | US | US | US | US |
| 29 | 168 h | <LLOQ | <LLOQ | <LLOQ | <LLOQ | 110 | <LLOQ | <LLOQ | 0.525 # |

Values are rounded to 3 significant figures.
LLOQ (Lower Limit Of Quantification) 0.250 ng/mL;
aberrant value excluded for TK analysis;
US: unscheduled sampling;
Given as indicative due to a technical issue during 1-hour infusion on Day 1 (i.e., 50% of the dose received subcutaneously)

Transient minimal increases in IL-6 concentration were observed after each weekly administration, for both doses (Table 7 maximum levels of 25 and 160 µg/mL for doses of 0.1 and 3 mg/kg/administration, respectively). Table 7 displays individual IL-6 plasma concentration values after a weekly repeat 1-hour intravenous infusion of CD123-NKCE at 0.1 and 3 mg/kg/administration for 4 weeks (on Days 1, 8, 15 and 22) to cynomolgus monkeys.

TABLE 7

| | Sampling | IL-6 concentration in plasma (pg/mL) | | | | | | | |
|---|---|---|---|---|---|---|---|---|---|
| | Time pre or | 0.1 mg/kg/administration | | | | 3 mg/kg/administration | | | |
| Day | post dose | M1♂ | M2♂ | F3♀ | F4♀ | M5♂ | M6♂ | F7♀ | F8♀ |
| 1 | Predose | <LLOQ | <LLOQ | 0.84 | 0.54 | <LLOQ | <LLOQ | <LLOQ | 2.09 |
| 1 | 1 h | 1.52 | 1.92 | 3.12 | 4.65 | 1.49 | 1.61 | 2.63 | 7.99 |
| 1 | 1.5 h | 2.99 | 4.54 | 5.09 | 6.79 | 2.17 | 2.98 | 5.61 | 14.37 |
| 1 | 5 h | 1.83 | 3.00 | 3.17 | 3.55 | 1.57 | 8.92 | 11.41 | 15.86 |
| 2 | 24 h | <LLOQ | <LLOQ | 0.66 | 1.98 | 0.79 | 1.96 | 2.15 | 1.61 |
| 8 | 168 h/Predose | <LLOQ | <LLOQ | <LLOQ | <LLOQ | 0.73 | 1.63 | 1.52 | 0.57 |
| 8 | 1 h | 1.42 | 2.12 | 5.04 | 2.60 | 1.65 | 2.35 | 2.74 | 4.48 |
| 8 | 1.5 h | 2.97 | 18.84 | 9.85 | 2.46 | 1.90 | 2.5 | 3.92 | 8.50 |
| 8 | 5 h | 2.15 | 18.89 | 7.69 | 1.39 | 1.53 | 38.04 | 2.34 | 2.71 |
| 9 | 24 h | 0.92 | 4.23 | 1.18 | 1.56 | 0.68 | 3.98 | 11.58 | 1.03 |
| 15 | 168 h/Predose | <LLOQ | <LLOQ | <LLOQ | <LLOQ | <LLOQ | <LLOQ | 0.62 | 1.58 |
| 15 | 1 h | 1.20 | 1.98 | 2.93 | 1.63 | 2.17 | 3.14 | 7.67 | 68.51 |
| 15 | 1.5 h | 1.47 | 1.88 | 5.72 | 1.65 | 2.35 | 5.02 | 12.19 | 85.36 |
| 15 | 5 h | 2.33 | 1.33 | 1.57 | 1.33 | 5.53 | 2.01 | 4.09 | 7.11 |
| 16 | 24 h | <LLOQ | <LLOQ | 1.48 | 6.47 | 2.76 | <LLOQ | 1.40 | 0.71 |
| 22 | 168 h/Predose | <LLOQ | <LLOQ | <LLOQ | <LLOQ | 1.16 | <LLOQ | 1.34 | 1.11 |
| 22 | 1 h | 2.22 | 2.79 | 1.35 | 4.07 | 3.12 | 123.36 | 27.39 | 150.97 |
| 22 | 1.5 h | 3.54 | 3.52 | 2.23 | 5.08 | 2.83 | 121.88 | 51.43 | 159.71 |
| 22 | 5 h | 2.68 | 4.42 | 2.89 | 22.72 | 2.56 | 4.07 | 6.35 | 22.23 |
| 23 | 24 h | <LLOQ | 1.53 | <LLOQ | 0.81 | 4.52 | <LLOQ | 1.10 | 1.29 |
| 29 | 168 h | 0.79 | <LLOQ | <LLOQ | <LLOQ | 0.74 | <LLOQ | 0.69 | |

LLOQ (Lower Limit Of Quantification): 0.53 pg/mL

In particular, no significant IL-6 release was observed in monkey M5 treated at the high dose (3 mg/kg/administration) which did not exhibit ADA response and was exposed to CD123-NKCE throughout the study (FIG. 21A and FIG. 21B), whereas strong PD effects of CD123$^+$ cell depletion were observed in both blood and bone marrow of this monkey (Table 8 and FIG. 21C).

Table 8 displays the individual absolute counts of basophils and total CD123-positive cells in blood and bone marrow after a weekly repeat 1-hour intravenous infusion of CD123-NKCE at 0.1 and 3 mg/kg/administration for 4 weeks to cynomolgus monkeys.

treatment with CD123-NKCE were observed, whatever the dose. No compound-related adverse effects on hematological, coagulation, clinical chemistry, or urinary parameters were observed either. Microscopic examination of the tissues sampled revealed no evidence of organ targeting, and all observations noted were considered to lie within the background range of variation and to be unrelated to the administration of the CD123-NKCE.

Overall, these results thus constitute proof-of-principle for the efficacy of CD123-NKCE in vivo, with no signs of toxicity.

| Day | Sampling Time | 0.1 mg/kg/administration | | | | 3 mg/kg/administration | | | |
|---|---|---|---|---|---|---|---|---|---|
| | | M1♂ | M2♂ | F3♀ | F4♀ | M5♂ | M6♂ | F7♀ | F8♀ |
| Absolute count of CD123-positive basophils in blood (cells/μL) | | | | | | | | | |
| | Predose | 1.16 | 2.79 | 8.60 | 2.25 | 5.65 | 11.6 | 15.1 | <DL |
| 1 | 1.5 h | <DL | <DL | <DL | <DL | <DL | <DL | <DL | <DL |
| 1 | 5 h | <DL | <DL | <DL | <DL | <DL | <DL | <DL | <DL |
| 2 | | <DL | <DL | <DL | <DL | <DL | <DL | <DL | <DL |
| 4 | | <DL | <DL | <DL | <DL | <DL | <DL | <DL | <DL |
| 9 | | <DL | <DL | <DL | <DL | <DL | <DL | <DL | <DL |
| 15 | 1.5 h | <DL | <DL | <DL | <DL | <DL | <DL | <DL | <DL |
| 16 | | 1.90 | <DL | <DL | <DL | <DL | <DL | 1.87 | <DL |
| 23 | | 1.56 | <DL | <DL | 7.61 | <DL | 10.4 | 34.7 | 9.58 |
| 29 | | 11.8 | 3.30 | <DL | 34.5 | <DL | 24.9 | 62.3 | 17.0 |
| 50 | | 4.19 | nd | 6.30 | nd | 13.1 | nd | 12.9 | nd |
| Absolute count of total CD123-positive cells in blood (cells/μL) | | | | | | | | | |
| | Predose | 6.26 | 6.32 | 21.9 | 4.02 | 9.72 | 22.8 | 19.3 | 1.59 |
| 1 | 1.5 h | 5.90 | 1.83 | 3.01 | 3.74 | 1.50 | <DL | 1.18 | 1.24 |
| 1 | 5 h | 4.06 | 1.40 | <DL | 1.90 | <DL | <DL | <DL | <DL |
| 2 | | 3.79 | 2.00 | <DL | 2.47 | <DL | 2.08 | 2.30 | 1.48 |
| 4 | | 10.3 | 1.95 | 2.47 | 2.43 | 1.54 | 1.32 | 1.84 | 2.80 |
| 9 | | 1.44 | <DL | <DL | <DL | <DL | <DL | <DL | <DL |
| 15 | 1.5 h | 5.77 | 2.16 | 2.40 | 3.25 | 1.15 | 8.14 | 12.9 | 12.3 |
| 16 | | 17.7 | 3.77 | 2.97 | 6.42 | 1.43 | 7.16 | 10.2 | 8.91 |
| 23 | | 18.5 | 8.33 | 9.52 | 12.2 | 1.28 | 58.5 | 49.7 | 32.4 |
| 29 | | 33.9 | 18.2 | 29.5 | 47.0 | 4.15 | 82.9 | 72.1 | 38.1 |
| 50 | | 8.81 | nd | 14.5 | nd | 16.8 | nd | 17.3 | nd |
| Absolute count of CD123-positive basophils in bone marrow (cells/μL) | | | | | | | | | |
| | Predose | 439 | 11.5 | 30.2 | 30.0 | 21.4 | 14.7 | 155 | 21.3 |
| 9 | | <DL | <DL | <DL | <DL | <DL | <DL | <DL | <DL |
| 29 | | 74.5 | 25.6 | 50.2 | 89.2 | <DL | 50.0 | 235.6 | 131 |
| 50 | | 54.0 | nd | 185 | nd | 29.6 | nd | 43.9 | nd |
| Absolute count of total CD123-positive cells in bone marrow (cells/μL) | | | | | | | | | |
| | Predose | 914 | 19.8 | 45.9 | 51.1 | 61.6 | 28.9 | 218 | 41.6 |
| 9 | | 5.85 | <DL | <DL | <DL | <DL | <DL | <DL | <DL |
| 29 | | 140 | 49.6 | 192 | 142 | 68.4 | 98.1 | 311 | 200.8 |
| 50 | | 112 | nd | 402 | nd | 50.9 | nd | 71.6 | nd |

DL (detection limit): 1.15 cells/μL (blood) or 2.10 cells/μL (bone marrow);
nd: not done In all the other animals, a sustained depletion of CD123-expressing cells was observed in the blood 1.5 hours after the first administration and up to 24 hours after the 3$^{rd}$ administration, with a rebound (above baseline) observed on days 22 to 29 (Table 8). Moreover, all the treated monkeys presented a complete depletion of CD123-positive cells from the bone marrow on day 9 (24 hours after the second administration), for both doses (Table 8; values below the detection limit on day 9 for most of animals), with a restoration of CD123-positive populations at day 29, one week after the last administration.

No clinical signs, changes in body weight or body temperature, and no effects on ECG potentially attributable to B. 15. NKp46-CD123 NK Cell Engager Tumor Cell Killing with Healthy Donor NK Cells NKp46-CD123_F25 and its isotype control IC-CD123_F6 were tested in an in vitro tumor cell killing assay with NK cells taken from 2 different healthy donors (HD).

NK Cells Purification and AML Cell Line

Human peripheral blood mononuclear cells (PBMC) from anonymous healthy donors (HD) were isolated by Ficoll density gradient centrifugation. NK cells were purified from these PBMCs with MACSxpress® Whole Blood NK cells isolation kit (Miltenyi Biotec). The NK cells were rested overnight in RPMI1640 (Gibco) supplemented with 10% SVF (BioWest) and 1% L-Glutamine (Gibco).

THP1 cells (CD123+. CD64+) were chosen for this study based on their expression of CD123. Before the experiment, THP1 cells were infected with Incucyte® Nuclight Green Lentivirus (Sartorius) to express the Green Fluorescent Protein (GFP).

NK Functional Assay in Presence of NKp46-CD123_F25 Over Time

NK cells and THP1 GFP target cells were incubated in presence of NKp46-CD123_F25 or its isotype control IC-CD123_F6 at 0.1, 1, 10 and 100 ng/mL at 37° C. The ratio effector:target cells was 1:1. The medium used was the same as for NK cell culture. The target cells were monitored by florescence imaging over 74 h using Incucyte Live Cell Analysis system (EssenBioscience). The number of live target cells was quantified using IncucyteS3 software (2020B version).

Conclusion

As shown in FIG. 22, NKp46-CD123_F25 at different concentrations (1, 10 and 100 ng/mL) enhances the cytotoxic activity of HD NK cells against THP1 GFP AML cells over time at the effector:target cells ratio of 1:1.

---

The invention claimed is:

1. A binding protein comprising a first and a second antigen binding domain (ABD) and all or part of an immunoglobulin Fc region or variant thereof, wherein each of said ABD comprises an immunoglobulin heavy chain variable domain (VH) and an immunoglobulin light chain variable domain (VL), wherein each VH and VL comprises three complementary determining regions (CDR-1 to CDR-3); and wherein:
(i) the first ABD binds specifically to human CD123 and comprises:
  a VH1 comprising a CDR-H1, H2 and H3 comprising the amino acid sequences of SEQ ID NO: 1 to 3 respectively or comprising the amino acid sequences of SEQ ID NO: 4 to 6 respectively, and
  a VL1 comprising a CDR-L1, L2 and L3 comprising the amino acid sequences of SEQ ID NO: 7 to 9 respectively or comprising the amino acid sequences of SEQ ID NO: 10 to 12 respectively;
(ii) the second ABD binds specifically to human NKp46 and comprises:
  a VH2 comprising a CDR-H1, 2 and 3 comprising:
  the amino acid sequences of SEQ ID NO: 13 to 15 respectively;
  the amino acid sequences of SEQ ID NO: 16 to 18 respectively;
  the amino acid sequences of SEQ ID NO: 19 to 21 respectively;
  the amino acid sequences of SEQ ID NO: 22 to 24 respectively; or
  the amino acid sequences of SEQ ID NO: 16, 25 and 26 respectively;
  and
  a VL2 comprising a CDR-L1, 2 and 3 comprising:
  the amino acid sequences of SEQ ID NO: 27 to 29 respectively;
  the amino acid sequences of SEQ ID NO: 30 to 32 respectively;
  the amino acid sequences of SEQ ID NO: 33 to 35 respectively;
  the amino acid sequences of SEQ ID NO: 36 to 38 respectively; or
  the amino acid sequences SEQ ID NO: 39, 31 and 40 respectively;
  and wherein all or part of the immunoglobulin Fc region or variant thereof binds to a human Fc-γ receptor.

2. The binding protein according to claim 1, comprising three polypeptide chains (I), (II) and (III) that form two ABDs, as defined below:

light chain variable domain 1A ($V_{1A}$)-light chain
constant domain 1A ($C_{1A}$)-Hinge$_1$($C_H2$-$C_H3$)$_A$    (I)

heavy chain variable domain 1B ($V_{1B}$)-heavy chain
constant domain 1B ($C_{1B}$)-Hinge$_2$-($C_H2$-$C_H3$)$_B$-
$L_1$-heavy chain variable domain 2A ($V_{2A}$)-
heavy chain constant domain 2A ($C_{2A}$)-Hinge$_3$    (II)

light chain variable domain 2B ($V_{2B}$)-light chain
constant domain 2B ($C_{2B}$)    (III)

wherein:
$V_{1A}$ and $V_{1B}$ form a binding pair $V_1$ ($V_{H1}/V_{L1}$);
$V_{2A}$ and $V_{2B}$ form a binding pair $V_2$ ($V_{H2}/V_{L2}$);
$C_{1A}$ and $C_{1B}$ form a pair $C_1$ ($C_H1/C_L$) and $C_{2A}$ and $C_{2B}$ form a pair $C_2$ ($C_H1/C_L$) wherein $C_H1$ is an immunoglobulin heavy chain constant domain 1 and $C_L$ is an immunoglobulin light chain constant domain;
Hinge$_1$, Hinge$_2$ and Hinge$_3$ are identical or different and comprise all or part of an immunoglobulin hinge region;
($C_H2$-$C_H3$)$_A$ and ($C_H2$-$C_H3$)$_B$ are identical or different, and comprise an immunoglobulin heavy chain constant domain 2 ($C_H2$) and an immunoglobulin heavy chain constant domain 3 ($C_H3$);
$L_1$ is an amino acid linker.

3. The binding protein according to claim 2 wherein:
$C_{1B}$ is an immunoglobulin heavy chain constant domain 1 ($C_H1$);
$C_{2A}$ is an immunoglobulin heavy chain constant domain 1 ($C_H1$);
$C_L$ comprises an immunoglobulin kappa light chain constant domain (Cκ);
($C_H2$-$C_H3$)$_A$ comprises the amino acid sequence of SEQ ID NO: 69;
($C_H2$-$C_H3$)$_B$ comprises the amino acid sequence of SEQ ID NO: 70;
Hinge$_1$ comprises the amino acid sequence of SEQ ID NO:74;
Hinge$_2$ comprises the amino acid sequence of SEQ ID NO:75;
Hinge$_3$ comprises the amino acid sequence of SEQ ID NO: 77;
$L_1$ comprises the amino acid sequence of SEQ ID NO: 76.

4. The binding protein according to claim 2, comprising at least two polypeptide chains linked by at least one disulfide bridge.

5. The binding protein according to claim 4, wherein the polypeptide chains (I) and (II) are linked by at least one disulfide bridge between $C_{1A}$ and Hinge$_2$ and/or wherein the polypeptide chains (II) and (III) are linked by at least one disulfide bridge between Hinge$_3$ and $C_{2B}$.

6. The binding protein according to claim 2, wherein $V_{1A}$ is $V_{L1}$ and $V_{1B}$ is $V_{H1}$.

7. The binding protein according to claim 2, wherein $V_{2A}$ is $V_{H2}$ and $V_{2B}$ is $V_{L2}$.

8. The binding protein according to claim 2, wherein:
polypeptide (I) consists of the amino acid sequence of SEQ ID NO: 64;
polypeptide (II) consists of the amino acid sequence of SEQ ID NO: 65; and
polypeptide (III) consists of the amino acid sequence of SEQ ID NO: 66.

9. The binding protein according to claim 1, wherein the residue N297 of the Fc region or variant thereof according to EU numbering comprises a N-linked glycosylation, wherein the Fc region or variant thereof is a human Fc region or variant thereof of an IgG1, IgG2, IgG3, or IgG4 isotype.

10. The binding protein according to claim 1, wherein the all or part of the Fc region or variant thereof binds to a human CD16A (FcγRIII) polypeptide.

11. The binding protein according to claim 1, wherein:
(a) $V_{H1}$ comprises a CDR-H1 comprising the amino acid sequence of SEQ ID NO: 1; a CDR-H2 comprising the amino acid sequence of SEQ ID NO: 2; a CDR-H3 comprising the amino acid sequence of SEQ ID NO: 3;
$V_{L1}$ comprises a CDR-L1 comprising the amino acid sequence of SEQ ID NO: 7; a CDR-L2 comprising the amino acid sequence of SEQ ID NO: 8; a CDR-L3 comprising the amino acid sequence of SEQ ID NO: 9;
$V_{H2}$ comprises a CDR-H1 comprising the amino acid sequence of SEQ ID NO: 13; a CDR-H2 comprising the amino acid sequence of SEQ ID NO: 14; a CDR-H3 comprising the amino acid sequence of SEQ ID NO:

15; V$_{L2}$ comprises a CDR-L1 comprising the amino acid sequence of SEQ ID NO: 27; a CDR-L2 comprising the amino acid sequence of SEQ ID NO: 28; a CDR-L3 comprising the amino acid sequence of SEQ ID NO: 29;

(b) V$_{H1}$ comprises a CDR-H1 comprising the amino acid sequence of SEQ ID NO: 1; a CDR-H2 comprising the amino acid sequence of SEQ ID NO: 2; a CDR-H3 comprising the amino acid sequence of SEQ ID NO: 3; V$_{L1}$ comprises a CDR-L1 comprising the amino acid sequence of SEQ ID NO: 7; a CDR-L2 comprising the amino acid sequence of SEQ ID NO: 8; a CDR-L3 comprising the amino acid sequence of SEQ ID NO: 9; V$_{H2}$ comprises a CDR-H1 comprising the amino acid sequence of SEQ ID NO: 16; a CDR-H2 comprising the amino acid sequence of SEQ ID NO: 17; a CDR-H3 comprising the amino acid sequence of SEQ ID NO: 18; V$_{L2}$ comprises a CDR-L1 comprising the amino acid sequence of SEQ ID NO: 30; a CDR-L2 comprising the amino acid sequence of SEQ ID NO: 31; a CDR-L3 comprising the amino acid sequence of SEQ ID NO: 32;

(c) V$_{H1}$ comprises a CDR-H1 comprising the amino acid sequence of SEQ ID NO: 1; a CDR-H2 comprising the amino acid sequence of SEQ ID NO: 2; a CDR-H3 comprising the amino acid sequence of SEQ ID NO: 3; V$_{L1}$ comprises a CDR-L1 comprising the amino acid sequence of SEQ ID NO: 7; a CDR-L2 comprising the amino acid sequence of SEQ ID NO: 8; a CDR-L3 comprising the amino acid sequence of SEQ ID NO: 9; V$_{H2}$ comprises a CDR-H1 comprising the amino acid sequence of SEQ ID NO: 19; a CDR-H2 comprising the amino acid sequence of SEQ ID NO: 20; a CDR-H3 comprising the amino acid sequence of SEQ ID NO: 21; V$_{L2}$ comprises a CDR-L1 comprising the amino acid sequence of SEQ ID NO: 33; a CDR-L2 comprising the amino acid sequence of SEQ ID NO: 34; a CDR-L3 comprising the amino acid sequence of SEQ ID NO: 35;

(d) V$_{H1}$ comprises a CDR-H1 comprising the amino acid sequence of SEQ ID NO: 1; a CDR-H2 comprising the amino acid sequence of SEQ ID NO: 2; a CDR-H3 comprising the amino acid sequence of SEQ ID NO: 3; V$_{L1}$ comprises a CDR-L1 comprising the amino acid sequence of SEQ ID NO: 7; a CDR-L2 comprising the amino acid sequence of SEQ ID NO: 8; a CDR-L3 comprising the amino acid sequence of SEQ ID NO: 9; V$_{H2}$ comprises a CDR-H1 comprising the amino acid sequence of SEQ ID NO: 22; a CDR-H2 comprising the amino acid sequence of SEQ ID NO: 23; a CDR-H3 comprising the amino acid sequence of SEQ ID NO: 24; V$_{L2}$ comprises a CDR-L1 comprising the amino acid sequence of SEQ ID NO: 36; a CDR-L2 comprising the amino acid sequence of SEQ ID NO: 37; a CDR-L3 comprising the amino acid sequence of SEQ ID NO: 38;

(e) V$_{H1}$ comprises a CDR-H1 comprising the amino acid sequence of SEQ ID NO: 1; a CDR-H2 comprising the amino acid sequence of SEQ ID NO: 2; a CDR-H3 comprising the amino acid sequence of SEQ ID NO: 3; V$_{L1}$ comprises a CDR-L1 comprising the amino acid sequence of SEQ ID NO: 7; a CDR-L2 comprising the amino acid sequence of SEQ ID NO: 8; a CDR-L3 comprising the amino acid sequence of SEQ ID NO: 9; V$_{H2}$ comprises a CDR-H1 comprising the amino acid sequence of SEQ ID NO: 16; a CDR-H2 comprising the amino acid sequence of SEQ ID NO: 25; a CDR-H3 comprising the amino acid sequence of SEQ ID NO: 26; V$_{L2}$ comprises a CDR-L1 comprising the amino acid sequence of SEQ ID NO: 39; a CDR-L2 comprising the amino acid sequence of SEQ ID NO: 31; a CDR-L3 comprising the amino acid sequence of SEQ ID NO: 40;

(f) V$_{H1}$ comprises a CDR-H1 comprising the amino acid sequence of SEQ ID NO: 4; a CDR-H2 comprising the amino acid sequence of SEQ ID NO: 5; a CDR-H3 comprising the amino acid sequence of SEQ ID NO: 6; V$_{L1}$ comprises a CDR-L1 comprising the amino acid sequence of SEQ ID NO: 10; a CDR-L2 comprising the amino acid sequence of SEQ ID NO: 11; a CDR-L3 comprising the amino acid sequence of SEQ ID NO: 12; V$_{H2}$ comprises a CDR-H1 comprising the amino acid sequence of SEQ ID NO: 13; a CDR-H2 comprising the amino acid sequence of SEQ ID NO: 14; a CDR-H3 comprising the amino acid sequence of SEQ ID NO: 15; V$_{L2}$ comprises a CDR-L1 comprising the amino acid sequence of SEQ ID NO: 27; a CDR-L2 comprising the amino acid sequence of SEQ ID NO: 28; a CDR-L3 comprising the amino acid sequence of SEQ ID NO: 29;

(g) V$_{H1}$ comprises a CDR-H1 comprising the amino acid sequence of SEQ ID NO: 4; a CDR-H2 comprising the amino acid sequence of SEQ ID NO: 5; a CDR-H3 comprising the amino acid sequence of SEQ ID NO: 6; V$_{L1}$ comprises a CDR-L1 comprising the amino acid sequence of SEQ ID NO: 10; a CDR-L2 comprising the amino acid sequence of SEQ ID NO: 11; a CDR-L3 comprising the amino acid sequence of SEQ ID NO: 12; V$_{H2}$ comprises a CDR-H1 comprising the amino acid sequence of SEQ ID NO: 16; a CDR-H2 comprising the amino acid sequence of SEQ ID NO: 17; a CDR-H3 comprising the amino acid sequence of SEQ ID NO: 18; V$_{L2}$ comprises a CDR-L1 comprising the amino acid sequence of SEQ ID NO: 30; a CDR-L2 comprising the amino acid sequence of SEQ ID NO: 31; a CDR-L3 comprising the amino acid sequence of SEQ ID NO: 32;

(h) V$_{H1}$ comprises a CDR-H1 comprising the amino acid sequence of SEQ ID NO: 4; a CDR-H2 comprising the amino acid sequence of SEQ ID NO: 5; a CDR-H3 comprising the amino acid sequence of SEQ ID NO: 6; V$_{L1}$ comprises a CDR-L1 comprising the amino acid sequence of SEQ ID NO: 10; a CDR-L2 comprising the amino acid sequence of SEQ ID NO: 11; a CDR-L3 comprising the amino acid sequence of SEQ ID NO: 12; V$_{H2}$ comprises a CDR-H1 comprising the amino acid sequence of SEQ ID NO: 19; a CDR-H2 comprising the amino acid sequence of SEQ ID NO: 20; a CDR-H3 comprising the amino acid sequence of SEQ ID NO: 21; V$_{L2}$ comprises a CDR-L1 comprising the amino acid sequence of SEQ ID NO: 33; a CDR-L2 comprising the amino acid sequence of SEQ ID NO: 34; a CDR-L3 comprising the amino acid sequence of SEQ ID NO: 35;

(i) V$_{H1}$ comprises a CDR-H1 comprising the amino acid sequence of SEQ ID NO: 4; a CDR-H2 comprising the amino acid sequence of SEQ ID NO: 5; a CDR-H3 comprising the amino acid sequence of SEQ ID NO: 6; V$_{L1}$ comprises a CDR-L1 comprising the amino acid sequence of SEQ ID NO: 10; a CDR-L2 comprising the amino acid sequence of SEQ ID NO: 11; a CDR-L3 comprising the amino acid sequence of SEQ ID NO: 12; V$_{H2}$ comprises a CDR-H1 comprising the amino acid sequence of SEQ ID NO: 22; a CDR-H2 comprising the amino acid sequence of SEQ ID NO: 23; a CDR-H3 comprising the amino acid sequence of SEQ ID NO: 24; $V_{L2}$ comprises a CDR-L1 comprising the amino acid sequence of SEQ ID NO: 36; a CDR-L2 comprising the amino acid sequence of SEQ ID NO: 37; a CDR-L3 comprising the amino acid sequence of SEQ ID NO: 38; or
(j) $V_{H1}$ comprises a CDR-H1 comprising the amino acid sequence of SEQ ID NO: 4; a CDR-H2 comprising the amino acid sequence of SEQ ID NO: 5; a CDR-H3 comprising the amino acid sequence of SEQ ID NO: 6; $V_{L1}$ comprises a CDR-L1 comprising the amino acid sequence of SEQ ID NO: 10; a CDR-L2 comprising the amino acid sequence of SEQ ID NO: 11; a CDR-L3 comprising the amino acid sequence of SEQ ID NO: 12; $V_{H2}$ comprises a CDR-H1 comprising the amino acid sequence of SEQ ID NO: 16; a CDR-H2 comprising the amino acid sequence of SEQ ID NO: 25; a CDR-H3 comprising the amino acid sequence of SEQ ID NO: 26; $V_{L2}$ comprises a CDR-L1 comprising the amino acid sequence of SEQ ID NO: 39; a CDR-L2 comprising the amino acid sequence of SEQ ID NO: 31; a CDR-L3 comprising the amino acid sequence of SEQ ID NO: 40.

12. The binding protein according to claim 1, wherein:
(a) $V_{H1}$ and $V_{L1}$ comprise the amino acid sequences of SEQ ID NO: 41 and 43 respectively or comprise the amino acid sequences of SEQ ID NO: 42 and 44 respectively;
and/or
(b) $V_{H2}$ and $V_{L2}$ corresponds to comprise
the amino acid sequences of SEQ ID NO: 45 and 53 respectively;
the amino acid sequences of SEQ ID NO: 46 and 54 respectively;
the amino acid sequences of SEQ ID NO: 47 and 55 respectively;
the amino acid sequences of SEQ ID NO: 48 and 56 respectively;
the amino acid sequences of SEQ ID NO: 49 and 57 respectively;
the amino acid sequences of SEQ ID NO: 50 and 58 respectively;
the amino acid sequences of SEQ ID NO: 51 and 59 respectively; or
the amino acid sequences of SEQ ID NO: 52 and 60 respectively.

13. The binding protein according to claim 12, wherein:
(a) $V_{H1}$ comprises the amino acid sequence of SEQ ID NO: 41; $V_{L1}$ comprises the amino acid sequence of SEQ ID NO: 43; $V_{H2}$ comprises the amino acid sequence of SEQ ID NO: 45; $V_{L2}$ comprises the amino acid sequence of SEQ ID NO: 53;
(b) $V_{H1}$ comprises the amino acid sequence of SEQ ID NO: 41; $V_{L1}$ comprises the amino acid sequence of SEQ ID NO: 43; $V_{H2}$ comprises the amino acid sequence of SEQ ID NO: 46; $V_{L2}$ comprises the amino acid sequence of SEQ ID NO: 54;
(c) $V_{H1}$ comprises the amino acid sequence of SEQ ID NO: 41; $V_{L1}$ comprises the amino acid sequence of SEQ ID NO: 43; $V_{H2}$ comprises the amino acid sequence of SEQ ID NO: 47; $V_{L2}$ comprises the amino acid sequence of SEQ ID NO: 55;
(d) $V_{H1}$ comprises the amino acid sequence of SEQ ID NO: 41; $V_{L1}$ comprises the amino acid sequence of SEQ ID NO: 43; $V_{H2}$ comprises the amino acid sequence of SEQ ID NO: 48; $V_{L2}$ comprises the amino acid sequence of SEQ ID NO: 56;
(e) $V_{H1}$ comprises the amino acid sequence of SEQ ID NO: 41; $V_{L1}$ comprises the amino acid sequence of SEQ ID NO: 43; $V_{H2}$ comprises the amino acid sequence of SEQ ID NO: 49; $V_{L2}$ comprises the amino acid sequence of SEQ ID NO: 57;
(f) $V_{H1}$ comprises the amino acid sequence of SEQ ID NO: 41; $V_{L1}$ comprises the amino acid sequence of SEQ ID NO: 43; $V_{H2}$ comprises the amino acid sequence of SEQ ID NO: 50; $V_{L2}$ comprises the amino acid sequence of SEQ ID NO: 58;
(g) $V_{H1}$ comprises the amino acid sequence of SEQ ID NO: 41; $V_{L1}$ comprises the amino acid sequence of SEQ ID NO: 43; $V_{H2}$ comprises the amino acid sequence of SEQ ID NO: 51; $V_{L2}$ comprises the amino acid sequence of SEQ ID NO: 59;
(h) $V_{H1}$ comprises the amino acid sequence of SEQ ID NO: 41; $V_{L1}$ comprises the amino acid sequence of SEQ ID NO: 43; $V_{H2}$ comprises the amino acid sequence of SEQ ID NO: 52; VL2 comprises the amino acid sequence of SEQ ID NO: 60;
(i) $V_{H1}$ comprises the amino acid sequence of SEQ ID NO: 42; $V_{L1}$ comprises the amino acid sequence of SEQ ID NO: 44; $V_{H2}$ comprises the amino acid sequence of SEQ ID NO: 45; $V_{L2}$ comprises the amino acid sequence of SEQ ID NO: 53;
(j) $V_{H1}$ comprises the amino acid sequence of SEQ ID NO: 42; $V_{L1}$ comprises the amino acid sequence of SEQ ID NO: 44; $V_{H2}$ comprises the amino acid sequence of SEQ ID NO: 46; $V_{L2}$ comprises the amino acid sequence of SEQ ID NO: 54;
(k) $V_{H1}$ comprises the amino acid sequence of SEQ ID NO: 42; $V_{L1}$ comprises the amino acid sequence of SEQ ID NO: 44; $V_{H2}$ comprises the amino acid sequence of SEQ ID NO: 47; $V_{L2}$ comprises the amino acid sequence of SEQ ID NO: 55;
(l) $V_{H1}$ comprises the amino acid sequence of SEQ ID NO: 42; $V_{L1}$ comprises the amino acid sequence of SEQ ID NO: 44; $V_{H2}$ comprises the amino acid sequence of SEQ ID NO: 48; $V_{L2}$ comprises the amino acid sequence of SEQ ID NO: 56;
(m) $V_{H1}$ comprises the amino acid sequence of SEQ ID NO: 42; $V_{L1}$ comprises the amino acid sequence of SEQ ID NO: 44; $V_{H2}$ comprises the amino acid sequence of SEQ ID NO: 49; $V_{L2}$ comprises the amino acid sequence of SEQ ID NO: 57;
(n) $V_{H1}$ comprises the amino acid sequence of SEQ ID NO: 42; $V_{L1}$ comprises the amino acid sequence of SEQ ID NO: 44; $V_{H2}$ comprises the amino acid sequence of SEQ ID NO: 50; $V_{L2}$ comprises the amino acid sequence of SEQ ID NO: 58;
(o) $V_{H1}$ comprises the amino acid sequence of SEQ ID NO: 42; $V_{L1}$ comprises the amino acid sequence of SEQ ID NO: 44; $V_{H2}$ comprises the amino acid sequence of SEQ ID NO: 51; $V_{L2}$ comprises the amino acid sequence of SEQ ID NO: 59;
(p) $V_{H1}$ comprises the amino acid sequence of SEQ ID NO: 42; $V_{L1}$ comprises the amino acid sequence of SEQ ID NO: 44; $V_{H2}$ comprises the amino acid sequence of SEQ ID NO: 52; $V_{L2}$ comprises the amino acid sequence of SEQ ID NO: 60.

14. A pharmaceutical composition comprising the binding protein according to claim 1 and a pharmaceutically acceptable carrier.

15. A binding protein comprising a first and a second antigen binding domain (ABD) and all or part of an immunoglobulin Fc region or variant thereof, wherein each of said ABD comprises an immunoglobulin heavy chain variable domain (VH) and an immunoglobulin light chain variable domain (VL), wherein each VH and VL comprises three complementary determining regions (CDR-1 to CDR-3); and wherein:
- (i) the first ABD binds specifically to human CD123 and comprises a $V_{H1}$ comprising the amino acid sequence of SEQ ID NO: 41 and a $V_{L1}$ comprising the amino acid sequence of SEQ ID NO: 43: and
- (ii) the second ABD binds specifically to human NKp46 and comprises a $V_{H2}$ comprising the amino acid sequence of SEQ ID NO: 45 and a $V_{L2}$ comprising the amino acid sequence of SEQ ID NO: 53.

16. The binding protein according to claim 15, wherein the residue N297 of the Fc region or variant thereof according to EU numbering comprises a N-linked glycosylation, wherein the Fc region or variant thereof is a human Fc region or variant thereof of an IgG1, IgG2, IgG3, or IgG4 isotype.

17. The binding protein according to claim 15, wherein the all or part of the Fc region or variant thereof binds to a human CD16A (FcγRIII) polypeptide.

18. A pharmaceutical composition comprising the binding protein according to claim 15 and a pharmaceutically acceptable carrier.

19. A binding protein comprising three polypeptide chains (I), (II) and (III) that form a first and a second antigen binding domain (ABD), wherein:
- polypeptide (I) consists of the amino acid sequence of SEQ ID NO: 64;
- polypeptide (II) consists of the amino acid sequence of SEQ ID NO: 65; and
- polypeptide (III) consists of the amino acid sequence of SEQ ID NO: 66.

20. A pharmaceutical composition comprising the binding protein according to claim 19 and a pharmaceutically acceptable carrier.

21. A binding protein comprising three polypeptide chains (I), (II) and (III) that form a first and a second antigen binding domain (ABD), wherein:
- polypeptide (I) comprising the amino acid sequence of SEQ ID NO: 64;
- polypeptide (II) comprising the amino acid sequence of SEQ ID NO: 65; and
- polypeptide (III) comprising the amino acid sequence of SEQ ID NO: 66.

22. A pharmaceutical composition comprising the binding protein according to claim 21 and a pharmaceutically acceptable carrier.

* * * * *

SEQUENCE LISTING

```
<160> NUMBER OF SEQ ID NOS: 107

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Tyr Ser Phe Thr Asp Tyr Tyr Met Lys
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Asp Ile Ile Pro Ser Ser Gly Ala Thr Phe
1               5                   10

<210> SEQ ID NO 3
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ser His Leu Leu Arg Ala Ser Trp Phe Ala Tyr
1               5                   10

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Phe Thr Phe Ser His Tyr Asn
1               5

<210> SEQ ID NO 5
<211> LENGTH: 8
<212> TYPE: PRT
<213> ORGANISM: Artificial Sequence
<220> FEATURE:
```

-continued

<223> OTHER INFORMATION: Description of Artificial Sequence: Synthetic
      peptide

<400> SEQUENCE: 5

Ile Thr Tyr Asp Asp His Ser Thr
1               5

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ala Arg Leu Val Asn Tyr Ala Phe Ala Tyr
1               5                   10

<210> SEQ ID NO 7
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Glu Ser Ser Gln Ser Leu Leu Ser Ser Gly Asn Gln Lys Asn Tyr Leu
1               5                   10                  15

Thr

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Trp Ala Ser Thr Arg Glu Ser
1               5

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gln Asn Asp Tyr Ser Tyr Pro Tyr Thr
1               5

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gln Thr Val Gly Asn Asn
1               5

<210> SEQ ID NO 11
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Tyr Ala Ser
1

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gln Arg Met Tyr Asn Ser Pro Thr
1               5

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Asp Tyr Val Ile Asn
1               5

<210> SEQ ID NO 14
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Glu Ile Tyr Pro Gly Ser Gly Thr Asn Tyr Tyr Asn Glu Lys Phe Lys
1               5                   10                  15

Ala

<210> SEQ ID NO 15
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Arg Gly Arg Tyr Gly Leu Tyr Ala Met Asp Tyr
1               5                   10

<210> SEQ ID NO 16
<211> LENGTH: 6
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 16

Ser Asp Tyr Ala Trp Asn
1               5

<210> SEQ ID NO 17
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Tyr Ile Thr Tyr Ser Gly Ser Thr Ser Tyr Asn Pro Ser Leu Glu Ser
1               5                   10                  15

<210> SEQ ID NO 18
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gly Gly Tyr Tyr Gly Ser Ser Trp Gly Val Phe Ala Tyr
1               5                   10

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Glu Tyr Thr Met His
1               5

<210> SEQ ID NO 20
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gly Ile Ser Pro Asn Ile Gly Gly Thr Ser Tyr Asn Gln Lys Phe Lys
1               5                   10                  15

Gly

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Arg Gly Gly Ser Phe Asp Tyr
1               5

<210> SEQ ID NO 22
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ser Phe Thr Met His
1               5

<210> SEQ ID NO 23
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Tyr Ile Asn Pro Ser Ser Gly Tyr Thr Glu Tyr Asn Gln Lys Phe Lys
1               5                   10                  15

Asp

<210> SEQ ID NO 24
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gly Ser Ser Arg Gly Phe Asp Tyr
1               5

<210> SEQ ID NO 25
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Tyr Ile Thr Tyr Ser Gly Ser Thr Asn Tyr Asn Pro Ser Leu Lys Ser
1               5                   10                  15

<210> SEQ ID NO 26
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Cys Trp Asp Tyr Ala Leu Tyr Ala Met Asp Cys
1               5                   10

<210> SEQ ID NO 27
<211> LENGTH: 11
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 27

Arg Ala Ser Gln Asp Ile Ser Asn Tyr Leu Asn
1               5                   10

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Tyr Thr Ser Arg Leu His Ser
1               5

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gln Gln Gly Asn Thr Arg Pro Trp Thr
1               5

<210> SEQ ID NO 30
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Arg Val Ser Glu Asn Ile Tyr Ser Tyr Leu Ala
1               5                   10

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Asn Ala Lys Thr Leu Ala Glu
1               5

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gln His His Tyr Gly Thr Pro Trp Thr
1               5

<210> SEQ ID NO 33
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Arg Ala Ser Gln Ser Ile Ser Asp Tyr Leu His
1               5                   10

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Tyr Ala Ser Gln Ser Ile Ser
1               5

<210> SEQ ID NO 35
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gln Asn Gly His Ser Phe Pro Leu Thr
1               5

<210> SEQ ID NO 36
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Arg Ala Ser Glu Asn Ile Tyr Ser Asn Leu Ala
1               5                   10

<210> SEQ ID NO 37
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Ala Ala Thr Asn Leu Ala Asp
1               5

<210> SEQ ID NO 38
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gln His Phe Trp Gly Thr Pro Arg Thr
1               5

<210> SEQ ID NO 39
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Arg Thr Ser Glu Asn Ile Tyr Ser Tyr Leu Ala
1               5                   10

<210> SEQ ID NO 40
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gln His His Tyr Asp Thr Pro Leu Thr
1               5

<210> SEQ ID NO 41
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asp Tyr
                20                  25                  30

Tyr Met Lys Trp Ala Arg Gln Met Pro Gly Lys Gly Leu Glu Trp Met
            35                  40                  45

Gly Asp Ile Ile Pro Ser Ser Gly Ala Thr Phe Tyr Asn Gln Lys Phe
        50                  55                  60

Lys Gly Gln Val Thr Ile Ser Ala Asp Lys Ser Ile Ser Thr Thr Tyr
65                  70                  75                  80

Leu Gln Trp Ser Ser Leu Lys Ala Ser Asp Thr Ala Met Tyr Tyr Cys
                85                  90                  95

Ala Arg Ser His Leu Leu Arg Ala Ser Trp Phe Ala Tyr Trp Gly Gln
            100                 105                 110

Gly Thr Met Val Thr Val Ser Ser
        115                 120

<210> SEQ ID NO 42
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide -continued

<400> SEQUENCE: 42

```
Glu Val Gln Leu Val Glu Ser Gly Gly Gly Leu Val Gln Pro Gly Arg
1               5                   10                  15

Ser Leu Lys Leu Ser Cys Ala Ala Ser Gly Phe Thr Phe Ser His Tyr
            20                  25                  30

Asn Met Ala Trp Val Arg Gln Ala Pro Lys Lys Gly Leu Glu Trp Val
        35                  40                  45

Ala Thr Ile Thr Tyr Asp Asp His Ser Thr Tyr Tyr Arg Asp Ser Val
    50                  55                  60

Lys Gly Arg Phe Thr Ile Ser Arg Asp Thr Ala Lys Ser Thr Leu Tyr
65                  70                  75                  80

Leu Gln Met Asp Ser Leu Arg Ser Glu Asp Thr Ala Thr Tyr Tyr Cys
                85                  90                  95

Ala Arg Leu Val Asn Tyr Ala Phe Ala Tyr Trp Gly Gln Gly Thr Leu
            100                 105                 110

Val Thr Val Ser Ser
        115
```

<210> SEQ ID NO 43
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

```
Asp Ile Val Met Thr Gln Ser Pro Asp Ser Leu Ala Val Ser Leu Gly
1               5                   10                  15

Glu Arg Ala Thr Ile Asn Cys Glu Ser Ser Gln Ser Leu Leu Ser Ser
            20                  25                  30

Gly Asn Gln Lys Asn Tyr Leu Thr Trp Tyr Gln Gln Lys Pro Gly Gln
        35                  40                  45

Pro Pro Lys Pro Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ser Tyr Pro Tyr Thr Phe Gly Gln Gly Thr Lys Leu Glu Ile
            100                 105                 110

Lys
```

<210> SEQ ID NO 44
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

```
Asn Ile Val Met Thr Gln Ser Pro Lys Ser Met Ser Ile Ser Val Gly
1               5                   10                  15

Asp Arg Val Thr Met Asn Cys Lys Ala Ser Gln Thr Val Gly Asn Asn
            20                  25                  30
```

```
Ile Ala Trp Tyr Gln Gln Lys Pro Gly Leu Ser Pro Gln Leu Leu Ile
            35                  40                  45

Asp Tyr Ala Ser Asn Arg Tyr Thr Gly Val Pro Asn Arg Phe Thr Gly
        50                  55                  60

Gly Gly Tyr Gly Thr Asp Phe Ile Leu Thr Ile Asn Ser Val Gln Ala
65                  70                  75                  80

Glu Asp Ala Ala Phe Tyr Tyr Cys Gln Arg Met Tyr Asn Ser Pro Thr
                85                  90                  95

Phe Gly Gly Gly Thr Lys Leu Glu Leu Lys
            100                 105

<210> SEQ ID NO 45
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Asp Tyr
            20                  25                  30

Val Ile Asn Trp Val Arg Gln Ala Pro Gly Gln Gly Leu Glu Trp Met
        35                  40                  45

Gly Glu Ile Tyr Pro Gly Ser Gly Thr Asn Tyr Asn Glu Lys Phe
    50                  55                  60

Lys Ala Lys Ala Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Arg Tyr Gly Leu Tyr Ala Met Asp Tyr Trp Gly Gln
            100                 105                 110

Gly Thr Thr Val Thr Val Ser Ser
        115                 120

<210> SEQ ID NO 46
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Gln Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Val Ile Asn Trp Gly Lys Gln Arg Ser Gly Gln Gly Leu Glu Trp Ile
        35                  40                  45

Gly Glu Ile Tyr Pro Gly Ser Gly Thr Asn Tyr Asn Glu Lys Phe
    50                  55                  60

Lys Ala Lys Ala Thr Leu Thr Ala Asp Lys Ser Ser Asn Ile Ala Tyr
65                  70                  75                  80

Met Gln Leu Ser Ser Leu Thr Ser Glu Asp Ser Ala Val Tyr Phe Cys
                85                  90                  95
```

```
Ala Arg Arg Gly Arg Tyr Gly Leu Tyr Ala Met Asp Tyr Trp Gly Gln
            100                 105                 110

Gly Thr Ser Val Thr Val Ser Ser
        115                 120

<210> SEQ ID NO 47
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Glu Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30

Tyr Ala Trp Asn Trp Ile Arg Gln Phe Pro Gly Asn Lys Leu Glu Trp
        35                  40                  45

Met Gly Tyr Ile Thr Tyr Ser Gly Ser Thr Ser Tyr Asn Pro Ser Leu
    50                  55                  60

Glu Ser Arg Ile Ser Ile Thr Arg Asp Thr Ser Thr Asn Gln Phe Phe
65                  70                  75                  80

Leu Gln Leu Asn Ser Val Thr Thr Glu Asp Thr Ala Thr Tyr Tyr Cys
                85                  90                  95

Ala Arg Gly Gly Tyr Tyr Gly Ser Ser Trp Gly Val Phe Ala Tyr Trp
            100                 105                 110

Gly Gln Gly Thr Leu Val Thr Val Ser Ala
        115                 120

<210> SEQ ID NO 48
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Glu Tyr
            20                  25                  30

Thr Met His Trp Val Lys Gln Ser His Gly Lys Ser Leu Glu Trp Ile
        35                  40                  45

Gly Gly Ile Ser Pro Asn Ile Gly Gly Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Arg Gly Gly Ser Phe Asp Tyr Trp Gly Gln Gly Thr Thr Leu
            100                 105                 110

Thr Val Ser Ser
        115

<210> SEQ ID NO 49
```

```
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Gln Val Gln Leu Gln Gln Ser Ala Val Glu Leu Ala Arg Pro Gly Ala
1               5                   10                  15

Ser Val Lys Met Ser Cys Lys Ala Ser Gly Tyr Thr Phe Thr Ser Phe
            20                  25                  30

Thr Met His Trp Val Lys Gln Arg Pro Gly Gln Gly Leu Glu Trp Ile
        35                  40                  45

Gly Tyr Ile Asn Pro Ser Ser Gly Tyr Thr Glu Tyr Asn Gln Lys Phe
    50                  55                  60

Lys Asp Lys Thr Thr Leu Thr Ala Asp Lys Ser Ser Ser Thr Ala Tyr
65                  70                  75                  80

Met Gln Leu Asp Ser Leu Thr Ser Asp Ser Ala Val Tyr Tyr Cys
                85                  90                  95

Val Arg Gly Ser Ser Arg Gly Phe Asp Tyr Trp Gly Gly Thr Leu
                100                 105                 110

Val Thr Val Ser Ala
        115

<210> SEQ ID NO 50
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Ser Ser Asp
            20                  25                  30

Tyr Ala Trp Asn Trp Ile Arg Gln Pro Pro Gly Lys Gly Leu Glu Trp
        35                  40                  45

Ile Gly Tyr Ile Thr Tyr Ser Gly Ser Thr Ser Tyr Asn Pro Ser Leu
    50                  55                  60

Glu Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Gly Tyr Tyr Gly Ser Ser Trp Gly Val Phe Ala Tyr Trp
                100                 105                 110

Gly Gln Gly Thr Leu Val Thr Val Ser Ser
        115                 120

<210> SEQ ID NO 51
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 51

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Phe
            20                  25                  30

Thr Met His Trp Val Arg Gln Ala Pro Gly Gln Gly Leu Glu Trp Ile
        35                  40                  45

Gly Tyr Ile Asn Pro Ser Ser Gly Tyr Thr Glu Tyr Asn Gln Lys Phe
    50                  55                  60

Lys Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Val Arg Gly Ser Ser Arg Gly Phe Asp Tyr Trp Gly Gln Gly Thr Leu
            100                 105                 110

Val Thr Val Ser Ser
        115

<210> SEQ ID NO 52
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Ser Ser Asp
            20                  25                  30

Tyr Ala Trp Asn Trp Ile Arg Gln Pro Pro Gly Lys Gly Leu Glu Trp
        35                  40                  45

Ile Gly Tyr Ile Thr Tyr Ser Gly Ser Thr Asn Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Cys Trp Asp Tyr Ala Leu Tyr Ala Met Asp Cys Trp Gly Gln
            100                 105                 110

Gly Thr Thr Val Thr Val Ser Ser
        115                 120

<210> SEQ ID NO 53
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

```
Leu Asn Trp Tyr Gln Gln Lys Pro Gly Lys Ala Pro Lys Leu Leu Ile
            35                  40                  45

Tyr Tyr Thr Ser Arg Leu His Ser Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Phe Cys Gln Gln Gly Asn Thr Arg Pro Trp
                 85                  90                  95

Thr Phe Gly Gly Gly Thr Lys Val Glu Ile Lys
                100                 105
```

<210> SEQ ID NO 54
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

```
Asp Ile Gln Met Thr Gln Thr Thr Ser Ser Leu Ser Ala Ser Leu Gly
 1               5                  10                  15

Asp Arg Val Thr Ile Ser Cys Arg Ala Ser Gln Asp Ile Ser Asn Tyr
            20                  25                  30

Leu Asn Trp Tyr Gln Lys Pro Asp Gly Thr Val Lys Leu Leu Ile
            35                  40                  45

Tyr Tyr Thr Ser Arg Leu His Ser Gly Val Pro Ser Arg Phe Ser Gly
 50                  55                  60

Ser Gly Ser Gly Thr Asp Tyr Ser Leu Thr Ile Asn Asn Leu Glu Gln
 65                  70                  75                  80

Glu Asp Ile Ala Thr Tyr Phe Cys Gln Gln Gly Asn Thr Arg Pro Trp
                 85                  90                  95

Thr Phe Gly Gly Gly Thr Lys Leu Glu Ile Lys
                100                 105
```

<210> SEQ ID NO 55
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

```
Asp Ile Gln Met Thr Gln Ser Pro Ala Ser Leu Ser Ala Ser Val Gly
 1               5                  10                  15

Glu Thr Val Thr Ile Thr Cys Arg Val Ser Glu Asn Ile Tyr Ser Tyr
            20                  25                  30

Leu Ala Trp Tyr Gln Gln Lys Gln Gly Lys Ser Pro Gln Leu Leu Val
            35                  40                  45

Tyr Asn Ala Lys Thr Leu Ala Glu Gly Val Pro Ser Arg Phe Ser Gly
 50                  55                  60

Ser Gly Ser Gly Thr Gln Phe Ser Leu Lys Ile Asn Ser Leu Gln Pro
 65                  70                  75                  80

Glu Asp Phe Gly Ser Tyr Tyr Cys Gln His His Tyr Gly Thr Pro Trp
                 85                  90                  95

Thr Phe Gly Gly Gly Thr Lys Leu Glu Ile Lys
                100                 105
```

```
<210> SEQ ID NO 56
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
                20                  25                  30

Leu His Trp Tyr Gln Gln Lys Ser His Glu Ser Pro Arg Leu Leu Ile
            35                  40                  45

Lys Tyr Ala Ser Gln Ser Ile Ser Gly Ile Pro Ser Arg Phe Ser Gly
50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Ser Phe Pro Leu
                85                  90                  95

Thr Phe Gly Ala Gly Thr Lys Leu Glu Leu Lys
            100                 105

<210> SEQ ID NO 57
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Asp Ile Gln Met Ile Gln Ser Pro Ala Ser Leu Ser Val Ser Val Gly
1               5                   10                  15

Glu Thr Val Thr Ile Thr Cys Arg Ala Ser Glu Asn Ile Tyr Ser Asn
                20                  25                  30

Leu Ala Trp Phe Gln Gln Lys Gln Gly Lys Ser Pro Gln Leu Leu Val
            35                  40                  45

Tyr Ala Ala Thr Asn Leu Ala Asp Gly Val Pro Ser Arg Phe Ser Gly
50                  55                  60

Ser Gly Ser Gly Thr Gln Tyr Ser Leu Lys Ile Asn Ser Leu Gln Ser
65                  70                  75                  80

Glu Asp Phe Gly Ile Tyr Tyr Cys Gln His Phe Trp Gly Thr Pro Arg
                85                  90                  95

Thr Phe Gly Gly Gly Thr Lys Leu Glu Ile Lys
            100                 105

<210> SEQ ID NO 58
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Asp Ile Gln Met Thr Gln Ser Pro Ser Ser Leu Ser Ala Ser Val Gly
1               5                   10                  15
```

Asp Arg Val Thr Ile Thr Cys Arg Val Ser Glu Asn Ile Tyr Ser Tyr
            20                  25                  30

Leu Ala Trp Tyr Gln Gln Lys Pro Gly Lys Ala Pro Lys Leu Leu Val
        35                  40                  45

Tyr Asn Ala Lys Thr Leu Ala Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Gly Thr Pro Trp
                85                  90                  95

Thr Phe Gly Gly Gly Thr Lys Val Glu Ile Lys
            100                 105

<210> SEQ ID NO 59
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Phe Gln Gln Lys Pro Gly Lys Ala Pro Lys Leu Leu Val
        35                  40                  45

Tyr Ala Ala Thr Asn Leu Ala Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln His Phe Trp Gly Thr Pro Arg
                85                  90                  95

Thr Phe Gly Gly Gly Thr Lys Val Glu Ile Lys
            100                 105

<210> SEQ ID NO 60
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Asp Ile Gln Met Thr Gln Ser Pro Ser Ser Leu Ser Ala Ser Val Gly
1               5                   10                  15

Asp Arg Val Thr Ile Thr Cys Arg Thr Ser Glu Asn Ile Tyr Ser Tyr
            20                  25                  30

Leu Ala Trp Cys Gln Gln Lys Pro Gly Lys Ala Pro Lys Leu Leu Ile
        35                  40                  45

Tyr Asn Ala Lys Thr Leu Ala Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Asp Thr Pro Leu
                85                  90                  95

```
Thr Phe Gly Gln Gly Thr Lys Leu Glu Ile Lys
            100                 105
```

<210> SEQ ID NO 61
<211> LENGTH: 467
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

```
Met Ser Val Pro Thr Gln Val Leu Gly Leu Leu Leu Trp Leu Thr
1               5                   10                  15

Asp Ala Arg Cys Asp Ile Val Met Thr Gln Ser Pro Asp Ser Leu Ala
                20                  25                  30

Val Ser Leu Gly Glu Arg Ala Thr Ile Asn Cys Glu Ser Ser Gln Ser
            35                  40                  45

Leu Leu Ser Ser Gly Asn Gln Lys Asn Tyr Leu Thr Trp Tyr Gln Gln
    50                  55                  60

Lys Pro Gly Gln Pro Pro Lys Pro Leu Ile Tyr Trp Ala Ser Thr Arg
65                  70                  75                  80

Glu Ser Gly Val Pro Asp Arg Phe Ser Gly Ser Gly Ser Gly Thr Asp
                85                  90                  95

Phe Thr Leu Thr Ile Ser Ser Leu Gln Ala Glu Asp Val Ala Val Tyr
            100                 105                 110

Tyr Cys Gln Asn Asp Tyr Ser Tyr Pro Tyr Thr Phe Gly Gln Gly Thr
        115                 120                 125

Lys Leu Glu Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335
```

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
            355                 360                 365

Tyr Thr Leu Pro Pro Ser Arg Glu Glu Met Thr Lys Asn Gln Val Ser
            370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
            435                 440                 445

His Glu Ala Leu His Asn His Tyr Thr Gln Lys Ser Leu Ser Leu Ser
            450                 455                 460

Pro Gly Lys
465

<210> SEQ ID NO 62
<211> LENGTH: 700
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Met Glu Trp Ser Trp Val Phe Leu Phe Phe Leu Ser Val Thr Thr Gly
1               5                   10                  15

Val His Ser Glu Val Gln Leu Val Gln Ser Gly Ala Glu Val Lys Lys
            20                  25                  30

Pro Gly Glu Ser Leu Lys Ile Ser Cys Lys Gly Ser Gly Tyr Ser Phe
        35                  40                  45

Thr Asp Tyr Tyr Met Lys Trp Ala Arg Gln Met Pro Gly Lys Gly Leu
    50                  55                  60

Glu Trp Met Gly Asp Ile Ile Pro Ser Ser Gly Ala Thr Phe Tyr Asn
65                  70                  75                  80

Gln Lys Phe Lys Gly Gln Val Thr Ile Ser Ala Asp Lys Ser Ile Ser
                85                  90                  95

Thr Thr Tyr Leu Gln Trp Ser Ser Leu Lys Ala Ser Asp Thr Ala Met
            100                 105                 110

Tyr Tyr Cys Ala Arg Ser His Leu Leu Arg Ala Ser Trp Phe Ala Tyr
        115                 120                 125

Trp Gly Gln Gly Thr Met Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

```
Thr Val Pro Ser Ser Ser Leu Gly Thr Gln Thr Tyr Ile Cys Asn Val
    210                 215                 220

Asn His Lys Pro Ser Asn Thr Lys Val Asp Lys Arg Val Glu Pro Lys
225                 230                 235                 240

Ser Cys Asp Lys Thr His Thr Cys Pro Pro Cys Pro Ala Pro Glu Leu
                    245                 250                 255

Leu Gly Gly Pro Ser Val Phe Leu Phe Pro Pro Lys Pro Lys Asp Thr
                260                 265                 270

Leu Met Ile Ser Arg Thr Pro Glu Val Thr Cys Val Val Val Asp Val
            275                 280                 285

Ser His Glu Asp Pro Glu Val Lys Phe Asn Trp Tyr Val Asp Gly Val
        290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
                340                 345                 350

Pro Ile Glu Lys Thr Ile Ser Lys Ala Lys Gly Gln Pro Arg Glu Pro
            355                 360                 365

Gln Val Tyr Thr Leu Pro Pro Ser Arg Glu Glu Met Thr Lys Asn Gln
        370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
                420                 425                 430

Thr Val Asp Lys Ser Arg Trp Gln Gln Gly Asn Val Phe Ser Cys Ser
            435                 440                 445

Val Met His Glu Ala Leu His Asn His Tyr Thr Gln Lys Ser Leu Ser
450                 455                 460

Leu Ser Pro Gly Ser Thr Gly Ser Gln Val Gln Leu Val Gln Ser Gly
465                 470                 475                 480

Ala Glu Val Lys Lys Pro Gly Ser Ser Val Lys Val Ser Cys Lys Ala
                485                 490                 495

Ser Gly Tyr Thr Phe Ser Asp Tyr Val Ile Asn Trp Val Arg Gln Ala
                500                 505                 510

Pro Gly Gln Gly Leu Glu Trp Met Gly Glu Ile Tyr Pro Gly Ser Gly
            515                 520                 525

Thr Asn Tyr Tyr Asn Glu Lys Phe Lys Ala Lys Ala Thr Ile Thr Ala
        530                 535                 540

Asp Lys Ser Thr Ser Thr Ala Tyr Met Glu Leu Ser Ser Leu Arg Ser
545                 550                 555                 560

Glu Asp Thr Ala Val Tyr Tyr Cys Ala Arg Arg Gly Arg Tyr Gly Leu
                565                 570                 575

Tyr Ala Met Asp Tyr Trp Gly Gln Gly Thr Thr Val Thr Val Ser Ser
                580                 585                 590

Ala Ser Thr Lys Gly Pro Ser Val Phe Pro Leu Ala Pro Ser Ser Lys
            595                 600                 605

Ser Thr Ser Gly Gly Thr Ala Ala Leu Gly Cys Leu Val Lys Asp Tyr
        610                 615                 620
```

```
Phe Pro Glu Pro Val Thr Val Ser Trp Asn Ser Gly Ala Leu Thr Ser
625                 630                 635                 640

Gly Val His Thr Phe Pro Ala Val Leu Gln Ser Ser Gly Leu Tyr Ser
            645                 650                 655

Leu Ser Ser Val Val Thr Val Pro Ser Ser Ser Leu Gly Thr Gln Thr
        660                 665                 670

Tyr Ile Cys Asn Val Asn His Lys Pro Ser Asn Thr Lys Val Asp Lys
    675                 680                 685

Arg Val Glu Pro Lys Ser Cys Asp Lys Thr His Ser
690                 695                 700

<210> SEQ ID NO 63
<211> LENGTH: 234
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Met Ser Val Pro Thr Gln Val Leu Gly Leu Leu Leu Leu Trp Leu Thr
1               5                   10                  15

Asp Ala Arg Cys Asp Ile Gln Met Thr Gln Ser Pro Ser Ser Leu Ser
            20                  25                  30

Ala Ser Val Gly Asp Arg Val Thr Ile Thr Cys Arg Ala Ser Gln Asp
        35                  40                  45

Ile Ser Asn Tyr Leu Asn Trp Tyr Gln Gln Lys Pro Gly Lys Ala Pro
    50                  55                  60

Lys Leu Leu Ile Tyr Tyr Thr Ser Arg Leu His Ser Gly Val Pro Ser
65                  70                  75                  80

Arg Phe Ser Gly Ser Gly Ser Gly Thr Asp Phe Thr Phe Thr Ile Ser
                85                  90                  95

Ser Leu Gln Pro Glu Asp Ile Ala Thr Tyr Phe Cys Gln Gln Gly Asn
            100                 105                 110

Thr Arg Pro Trp Thr Phe Gly Gly Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 64
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 64

Asp Ile Val Met Thr Gln Ser Pro Asp Ser Leu Ala Val Ser Leu Gly
1               5                   10                  15

Glu Arg Ala Thr Ile Asn Cys Glu Ser Ser Gln Ser Leu Leu Ser Ser
            20                  25                  30

Gly Asn Gln Lys Asn Tyr Leu Thr Trp Tyr Gln Gln Lys Pro Gly Gln
        35                  40                  45

Pro Pro Lys Pro Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ser Tyr Pro Tyr Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
            405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
            435                 440                 445

<210> SEQ ID NO 65
<211> LENGTH: 681
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asp Tyr
            20                  25                  30

Tyr Met Lys Trp Ala Arg Gln Met Pro Gly Lys Gly Leu Glu Trp Met
        35                  40                  45

Gly Asp Ile Ile Pro Ser Ser Gly Ala Thr Phe Tyr Asn Gln Lys Phe
50                  55                  60

Lys Gly Gln Val Thr Ile Ser Ala Asp Lys Ser Ile Ser Thr Thr Tyr
65                  70                  75                  80

Leu Gln Trp Ser Ser Leu Lys Ala Ser Asp Thr Ala Met Tyr Tyr Cys
                85                  90                  95

Ala Arg Ser His Leu Leu Arg Ala Ser Trp Phe Ala Tyr Trp Gly Gln
            100                 105                 110

Gly Thr Met Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

```
Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Ser Thr Gly Ser Gln Val Gln Leu Val Gln Ser Gly Ala Glu Val
450                 455                 460

Lys Lys Pro Gly Ser Ser Val Lys Val Ser Cys Lys Ala Ser Gly Tyr
465                 470                 475                 480

Thr Phe Ser Asp Tyr Val Ile Asn Trp Val Arg Gln Ala Pro Gly Gln
            485                 490                 495

Gly Leu Glu Trp Met Gly Glu Ile Tyr Pro Gly Ser Gly Thr Asn Tyr
            500                 505                 510

Tyr Asn Glu Lys Phe Lys Ala Lys Ala Thr Ile Thr Ala Asp Lys Ser
            515                 520                 525

Thr Ser Thr Ala Tyr Met Glu Leu Ser Ser Leu Arg Ser Glu Asp Thr
530                 535                 540

Ala Val Tyr Tyr Cys Ala Arg Arg Gly Arg Tyr Gly Leu Tyr Ala Met
545                 550                 555                 560

Asp Tyr Trp Gly Gln Gly Thr Thr Val Thr Val Ser Ser Ala Ser Thr
            565                 570                 575

Lys Gly Pro Ser Val Phe Pro Leu Ala Pro Ser Ser Lys Ser Thr Ser
            580                 585                 590

Gly Gly Thr Ala Ala Leu Gly Cys Leu Val Lys Asp Tyr Phe Pro Glu
            595                 600                 605

Pro Val Thr Val Ser Trp Asn Ser Gly Ala Leu Thr Ser Gly Val His
            610                 615                 620

Thr Phe Pro Ala Val Leu Gln Ser Ser Gly Leu Tyr Ser Leu Ser Ser
625                 630                 635                 640

Val Val Thr Val Pro Ser Ser Ser Leu Gly Thr Gln Thr Tyr Ile Cys
            645                 650                 655

Asn Val Asn His Lys Pro Ser Asn Thr Lys Val Asp Lys Arg Val Glu
            660                 665                 670

Pro Lys Ser Cys Asp Lys Thr His Ser
            675                 680
```

<210> SEQ ID NO 66
<211> LENGTH: 214
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 66

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln Gln Gly Asn Thr Arg Pro Trp
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 67
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

```
<210> SEQ ID NO 68
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val

<210> SEQ ID NO 69
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190
```

```
Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 70
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly
    210                 215

<210> SEQ ID NO 71
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45
```

Val Asp Gly Val Glu Val His Asn Ala Lys Thr Lys Pro Arg Glu Glu
        50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
                100                 105                 110

<210> SEQ ID NO 72
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
                20                  25                  30

Tyr Pro Ser Asp Ile Ala Val Glu Trp Glu Ser Asn Gly Gln Pro Glu
                35                  40                  45

Asn Asn Tyr Lys Thr Thr Pro Pro Val Leu Asp Ser Asp Gly Ser Phe
            50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
                100                 105

<210> SEQ ID NO 73
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
                20                  25                  30

Tyr Pro Ser Asp Ile Ala Val Glu Trp Glu Ser Asn Gly Gln Pro Glu
                35                  40                  45

Asn Asn Tyr Lys Thr Thr Pro Pro Val Leu Asp Ser Asp Gly Ser Phe
            50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly
                100                 105

<210> SEQ ID NO 74

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Asp Lys Thr His Thr Cys Pro Pro Cys Pro
1               5                   10

<210> SEQ ID NO 75
<211> LENGTH: 15
<212> TYPE: PRT
<213> ORGANISM: Homo sapiens

<400> SEQUENCE: 75

Glu Pro Lys Ser Cys Asp Lys Thr His Thr Cys Pro Pro Cys Pro
1               5                   10                  15

<210> SEQ ID NO 76
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Ser Thr Gly Ser
1

<210> SEQ ID NO 77
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Glu Pro Lys Ser Cys Asp Lys Thr His Ser
1               5                   10

<210> SEQ ID NO 78
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Glu Pro Lys Ser Cys Asp Lys Thr His
1               5

<210> SEQ ID NO 79
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Glu Pro Lys Ser Cys Asp Lys Thr His Thr
1               5                   10
```

<210> SEQ ID NO 80
<211> LENGTH: 20
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 80
cuugaggugu caugcgugga                                           20

<210> SEQ ID NO 81
<211> LENGTH: 20
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 81
aagcaucgcu acacaucagc                                           20

<210> SEQ ID NO 82
<211> LENGTH: 45
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 82
tacgactcac aagcttgccg ccaccatgtc ttccacactc cctgc               45

<210> SEQ ID NO 83
<211> LENGTH: 57
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 83
ccgccccgac tctagatcaa tggtgatggt ggtgatgatt ctgggcagtg tgatccc   57

<210> SEQ ID NO 84
<211> LENGTH: 255
<212> TYPE: PRT
<213> ORGANISM: Homo sapiens

<400> SEQUENCE: 84

Met Ser Ser Thr Leu Pro Ala Leu Leu Cys Val Gly Leu Cys Leu Ser
1               5                   10                  15

Gln Arg Ile Ser Ala Gln Gln Thr Leu Pro Lys Pro Phe Ile Trp
            20                  25                  30

Ala Glu Pro His Phe Met Val Pro Lys Glu Lys Gln Val Thr Ile Cys
        35                  40                  45

Cys Gln Gly Asn Tyr Gly Ala Val Glu Tyr Gln Leu His Phe Glu Gly
    50                  55                  60

Ser Leu Phe Ala Val Asp Arg Pro Lys Pro Pro Glu Arg Ile Asn Lys
65                  70                  75                  80

Val Lys Phe Tyr Ile Pro Asp Met Asn Ser Arg Met Ala Gly Gln Tyr
                85                  90                  95

```
Ser Cys Ile Tyr Arg Val Gly Glu Leu Trp Ser Pro Ser Asn Leu
            100                 105                 110

Leu Asp Leu Val Val Thr Glu Met Tyr Asp Thr Pro Thr Leu Ser Val
            115                 120                 125

His Pro Gly Pro Glu Val Ile Ser Gly Glu Lys Val Thr Phe Tyr Cys
130                 135                 140

Arg Leu Asp Thr Ala Thr Ser Met Phe Leu Leu Lys Glu Gly Arg
145                 150                 155                 160

Ser Ser His Val Gln Arg Gly Tyr Gly Lys Val Gln Ala Glu Phe Pro
                165                 170                 175

Leu Gly Pro Val Thr Thr Ala His Arg Gly Thr Tyr Arg Cys Phe Gly
            180                 185                 190

Ser Tyr Asn Asn His Ala Trp Ser Phe Pro Ser Glu Pro Val Lys Leu
            195                 200                 205

Leu Val Thr Gly Asp Ile Glu Asn Thr Ser Leu Ala Pro Glu Asp Pro
            210                 215                 220

Thr Phe Pro Ala Asp Thr Trp Gly Thr Tyr Leu Leu Thr Thr Glu Thr
225                 230                 235                 240

Gly Leu Gln Lys Asp His Ala Leu Trp Asp His Thr Ala Gln Asn
                245                 250                 255

<210> SEQ ID NO 85
<211> LENGTH: 262
<212> TYPE: PRT
<213> ORGANISM: Macaca fascicularis

<400> SEQUENCE: 85

Met Ser Ser Thr Leu Arg Ala Leu Leu Cys Leu Gly Leu Cys Leu Ser
1               5                   10                  15

Gln Arg Ile Ser Ala Pro Lys Gln Thr Leu Pro Lys Pro Ile Ile Arg
            20                  25                  30

Ala Glu Ser Thr Tyr Met Val Pro Lys Glu Lys Gln Ala Thr Leu Cys
        35                  40                  45

Cys Gln Gly Ser Tyr Gly Ala Val Glu Tyr Gln Leu His Phe Glu Gly
    50                  55                  60

Ser Leu Phe Ala Val Glu Arg Pro Lys Pro Pro Glu Arg Ile Asn Gly
65                  70                  75                  80

Val Lys Phe His Ile Pro Asp Met Asn Ser Arg Lys Ala Gly Arg Tyr
                85                  90                  95

Ser Cys Ile Tyr Arg Val Gly Glu Leu Trp Ser Glu Arg Ser Asp Leu
            100                 105                 110

Leu Asp Leu Val Val Thr Glu Met Tyr Asp Thr Pro Thr Leu Ser Val
            115                 120                 125

His Pro Gly Pro Glu Val Thr Ser Gly Glu Lys Val Thr Phe Tyr Cys
130                 135                 140

Arg Leu Asp Thr Ala Thr Ser Met Phe Leu Leu Lys Glu Gly Arg
145                 150                 155                 160

Ser Arg Asp Val Gln Arg Ser Tyr Gly Lys Val Gln Ala Glu Phe Pro
                165                 170                 175

Met Gly Pro Val Thr Thr Ala His Arg Gly Ser Tyr Arg Cys Phe Gly
            180                 185                 190

Ser Tyr Asn Asn Tyr Ala Trp Ser Phe Pro Ser Glu Pro Val Lys Leu
            195                 200                 205
```

```
Leu Val Thr Gly Asp Ile Glu Asn Thr Ser Leu Ala Pro Thr Asp Pro
            210                 215                 220

Thr Phe Pro Asp Ser Trp Asp Thr Cys Leu Leu Thr Arg Glu Thr Gly
225                 230                 235                 240

Leu Gln Lys Asp Leu Ala Leu Trp Asp His Thr Ala Gln Asn Asp Tyr
            245                 250                 255

Lys Asp Asp Asp Lys
            260

<210> SEQ ID NO 86
<211> LENGTH: 287
<212> TYPE: PRT
<213> ORGANISM: Homo sapiens

<400> SEQUENCE: 86

Thr Lys Glu Asp Pro Asn Pro Pro Ile Thr Asn Leu Arg Met Lys Ala
1               5                   10                  15

Lys Ala Gln Gln Leu Thr Trp Asp Leu Asn Arg Asn Val Thr Asp Ile
            20                  25                  30

Glu Cys Val Lys Asp Ala Asp Tyr Ser Met Pro Ala Val Asn Asn Ser
        35                  40                  45

Tyr Cys Gln Phe Gly Ala Ile Ser Leu Cys Glu Val Thr Asn Tyr Thr
    50                  55                  60

Val Arg Val Ala Asn Pro Pro Phe Ser Thr Trp Ile Leu Phe Pro Glu
65                  70                  75                  80

Asn Ser Gly Lys Pro Trp Ala Gly Ala Glu Asn Leu Thr Cys Trp Ile
            85                  90                  95

His Asp Val Asp Phe Leu Ser Cys Ser Trp Ala Val Gly Pro Gly Ala
            100                 105                 110

Pro Ala Asp Val Gln Tyr Asp Leu Tyr Leu Asn Val Ala Asn Arg Arg
        115                 120                 125

Gln Gln Tyr Glu Cys Leu His Tyr Lys Thr Asp Ala Gln Gly Thr Arg
    130                 135                 140

Ile Gly Cys Arg Phe Asp Asp Ile Ser Arg Leu Ser Ser Gly Ser Gln
145                 150                 155                 160

Ser Ser His Ile Leu Val Arg Gly Arg Ser Ala Ala Phe Gly Ile Pro
            165                 170                 175

Cys Thr Asp Lys Phe Val Val Phe Ser Gln Ile Glu Ile Leu Thr Pro
            180                 185                 190

Pro Asn Met Thr Ala Lys Cys Asn Lys Thr His Ser Phe Met His Trp
        195                 200                 205

Lys Met Arg Ser His Phe Asn Arg Lys Phe Arg Tyr Glu Leu Gln Ile
    210                 215                 220

Gln Lys Arg Met Gln Pro Val Ile Thr Glu Gln Val Arg Asp Arg Thr
225                 230                 235                 240

Ser Phe Gln Leu Leu Asn Pro Gly Thr Tyr Thr Val Gln Ile Arg Ala
            245                 250                 255

Arg Glu Arg Val Tyr Glu Phe Leu Ser Ala Trp Ser Thr Pro Gln Arg
            260                 265                 270

Phe Glu Cys Asp Gln Glu Glu Gly Ala Asn Thr Arg Ala Trp Arg
        275                 280                 285

<210> SEQ ID NO 87
<211> LENGTH: 254
<212> TYPE: PRT
```

<213> ORGANISM: Homo sapiens

<400> SEQUENCE: 87

Met Trp Gln Leu Leu Leu Pro Thr Ala Leu Leu Leu Val Ser Ala
1               5                   10                  15

Gly Met Arg Thr Glu Asp Leu Pro Lys Ala Val Val Phe Leu Glu Pro
            20                  25                  30

Gln Trp Tyr Arg Val Leu Glu Lys Asp Ser Val Thr Leu Lys Cys Gln
        35                  40                  45

Gly Ala Tyr Ser Pro Glu Asp Asn Ser Thr Gln Trp Phe His Asn Glu
    50                  55                  60

Ser Leu Ile Ser Ser Gln Ala Ser Ser Tyr Phe Ile Asp Ala Ala Thr
65                  70                  75                  80

Val Asp Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
            100                 105                 110

Ala Pro Arg Trp Val Phe Lys Glu Glu Asp Pro Ile His Leu Arg Cys
        115                 120                 125

His Ser Trp Lys Asn Thr Ala Leu His Lys Val Thr Tyr Leu Gln Asn
    130                 135                 140

Gly Lys Gly Arg Lys Tyr Phe His His Asn Ser Asp Phe Tyr Ile Pro
145                 150                 155                 160

Lys Ala Thr Leu Lys Asp Ser Gly Ser Tyr Phe Cys Arg Gly Leu Val
                165                 170                 175

Gly Ser Lys Asn Val Ser Ser Glu Thr Val Asn Ile Thr Ile Thr Gln
            180                 185                 190

Gly Leu Ala Val Ser Thr Ile Ser Ser Phe Phe Pro Pro Gly Tyr Gln
        195                 200                 205

Val Ser Phe Cys Leu Val Met Val Leu Leu Phe Ala Val Asp Thr Gly
    210                 215                 220

Leu Tyr Phe Ser Val Lys Thr Asn Ile Arg Ser Ser Thr Arg Asp Trp
225                 230                 235                 240

Lys Asp His Lys Phe Lys Trp Arg Lys Asp Pro Gln Asp Lys
                245                 250

<210> SEQ ID NO 88
<211> LENGTH: 254
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 88

Met Trp Gln Leu Leu Leu Pro Thr Ala Leu Leu Leu Val Ser Ala
1               5                   10                  15

Gly Met Arg Thr Glu Asp Leu Pro Lys Ala Val Val Phe Leu Glu Pro
            20                  25                  30

Gln Trp Tyr Arg Val Leu Glu Lys Asp Ser Val Thr Leu Lys Cys Gln
        35                  40                  45

Gly Ala Tyr Ser Pro Glu Asp Asn Ser Thr Gln Trp Phe His Asn Glu
    50                  55                  60

Ser Leu Ile Ser Ser Gln Ala Ser Ser Tyr Phe Ile Asp Ala Ala Thr
65                  70                  75                  80

Val Asp Asp Ser Gly Glu Tyr Arg Cys Gln Thr Asn Leu Ser Thr Leu
            85                  90                  95

Ser Asp Pro Val Gln Leu Glu Val His Ile Gly Trp Leu Leu Leu Gln
            100                 105                 110

Ala Pro Arg Trp Val Phe Lys Glu Glu Asp Pro Ile His Leu Arg Cys
            115                 120                 125

His Ser Trp Lys Asn Thr Ala Leu His Lys Val Thr Tyr Leu Gln Asn
        130                 135                 140

Gly Lys Gly Arg Lys Tyr Phe His His Asn Ser Asp Phe Tyr Ile Pro
145                 150                 155                 160

Lys Ala Thr Leu Lys Asp Ser Gly Ser Tyr Phe Cys Arg Gly Leu Phe
                165                 170                 175

Gly Ser Lys Asn Val Ser Ser Glu Thr Val Asn Ile Thr Ile Thr Gln
            180                 185                 190

Gly Leu Ala Val Ser Thr Ile Ser Ser Phe Phe Pro Pro Gly Tyr Gln
        195                 200                 205

Val Ser Phe Cys Leu Val Met Val Leu Leu Phe Ala Val Asp Thr Gly
    210                 215                 220

Leu Tyr Phe Ser Val Lys Thr Asn Ile Arg Ser Ser Thr Arg Asp Trp
225                 230                 235                 240

Lys Asp His Lys Phe Lys Trp Arg Lys Asp Pro Gln Asp Lys
                245                 250

<210> SEQ ID NO 89
<211> LENGTH: 45
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 89
tacgactcac aagcttgccg ccaccatgtc ttccacactc cgtgc                    45

<210> SEQ ID NO 90
<211> LENGTH: 62
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 90
ccgccccgac tctagatcac ttgtcatcgt catctttgta atcattctgg gcagtgtggt    60
cc                                                                   62

<210> SEQ ID NO 91
<211> LENGTH: 441
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 91

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Arg Ser Tyr
            20                  25                  30

```
Leu Ala Trp Tyr Gln Gln Lys Pro Gly Gln Ala Pro Arg Leu Leu Phe
            35                  40                  45

Ser Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Tyr Arg Tyr Ser Pro Arg
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys Asp Lys Thr His Thr Cys Pro Pro Cys Pro
210                 215                 220

Ala Pro Glu Leu Leu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Lys Phe Asn Trp Tyr
            260                 265                 270

Val Asp Gly Val Glu Val His Asn Ala Lys Thr Lys Pro Arg Glu Glu
            275                 280                 285

Gln Tyr Asn Ser Thr Tyr Arg Val Val Ser Val Leu Thr Val Leu His
290                 295                 300

Gln Asp Trp Leu Asn Gly Lys Glu Tyr Lys Cys Lys Val Ser Asn Lys
305                 310                 315                 320

Ala Leu Pro Ala Pro Ile Glu Lys Thr Ile Ser Lys Ala Lys Gly Gln
                325                 330                 335

Pro Arg Glu Pro Gln Val Tyr Thr Leu Pro Pro Ser Arg Glu Glu Met
            340                 345                 350

Thr Lys Asn Gln Val Ser Leu Thr Cys Leu Val Lys Gly Phe Tyr Pro
            355                 360                 365

Ser Asp Ile Ala Val Glu Trp Glu Ser Asn Gly Gln Pro Glu Asn Asn
            370                 375                 380

Tyr Lys Thr Thr Pro Pro Val Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
            420                 425                 430

Lys Ser Leu Ser Leu Ser Pro Gly Lys
            435                 440
```

<210> SEQ ID NO 92
<211> LENGTH: 678
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 92

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asn Tyr
            20                  25                  30

Ala Met His Trp Val Arg Gln Ala Pro Gly Lys Gly Leu Glu Trp Val
        35                  40                  45

Ser Gly Ile Ser Arg Ser Ser Gly Asp Ile Asp Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Gly Gly Val Gly Ser Phe Asp Thr Trp Gly Gln Gly Thr Met
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365
```

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
            405                 410                 415

Trp Gln Gln Gly Asn Val Phe Ser Cys Ser Val Met His Glu Ala Leu
        420                 425                 430

His Asn His Tyr Thr Gln Lys Ser Leu Ser Leu Ser Pro Gly Ser Thr
    435                 440                 445

Gly Ser Gln Val Gln Leu Val Gln Ser Gly Ala Glu Val Lys Lys Pro
450                 455                 460

Gly Ser Ser Val Lys Val Ser Cys Lys Ala Ser Gly Tyr Thr Phe Ser
465                 470                 475                 480

Asp Tyr Val Ile Asn Trp Val Arg Gln Ala Pro Gly Gln Gly Leu Glu
            485                 490                 495

Trp Met Gly Glu Ile Tyr Pro Gly Ser Gly Thr Asn Tyr Tyr Asn Glu
        500                 505                 510

Lys Phe Lys Ala Lys Ala Thr Ile Thr Ala Asp Lys Ser Thr Ser Thr
    515                 520                 525

Ala Tyr Met Glu Leu Ser Ser Leu Arg Ser Glu Asp Thr Ala Val Tyr
530                 535                 540

Tyr Cys Ala Arg Arg Gly Arg Tyr Gly Leu Tyr Ala Met Asp Tyr Trp
545                 550                 555                 560

Gly Gln Gly Thr Thr Val Thr Val Ser Ser Ala Ser Thr Lys Gly Pro
            565                 570                 575

Ser Val Phe Pro Leu Ala Pro Ser Ser Lys Ser Thr Ser Gly Gly Thr
        580                 585                 590

Ala Ala Leu Gly Cys Leu Val Lys Asp Tyr Phe Pro Glu Pro Val Thr
    595                 600                 605

Val Ser Trp Asn Ser Gly Ala Leu Thr Ser Gly Val His Thr Phe Pro
610                 615                 620

Ala Val Leu Gln Ser Ser Gly Leu Tyr Ser Leu Ser Ser Val Val Thr
625                 630                 635                 640

Val Pro Ser Ser Ser Leu Gly Thr Gln Thr Tyr Ile Cys Asn Val Asn
            645                 650                 655

His Lys Pro Ser Asn Thr Lys Val Asp Lys Arg Val Glu Pro Lys Ser
        660                 665                 670

Cys Asp Lys Thr His Ser
        675

<210> SEQ ID NO 93
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
                50                  55                  60

Ser Gly Ser Gly Thr Asp Phe Thr Phe Thr Ile Ser Ser Leu Gln Pro
 65                  70                  75                  80

Glu Asp Ile Ala Thr Tyr Phe Cys Gln Gln Gly Asn Thr Arg Pro Trp
                 85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 94
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Asp Ile Val Met Thr Gln Ser Pro Asp Ser Leu Ala Val Ser Leu Gly
1               5                   10                  15

Glu Arg Ala Thr Ile Asn Cys Glu Ser Ser Gln Ser Leu Leu Ser Ser
            20                  25                  30

Gly Asn Gln Lys Asn Tyr Leu Thr Trp Tyr Gln Gln Lys Pro Gly Gln
        35                  40                  45

Pro Pro Lys Pro Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ser Tyr Pro Tyr Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

```
Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
                260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Arg Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
    435                 440                 445

<210> SEQ ID NO 95
<211> LENGTH: 680
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asp Tyr
            20                  25                  30

Tyr Met Lys Trp Ala Arg Gln Met Pro Gly Lys Gly Leu Glu Trp Met
        35                  40                  45

Gly Asp Ile Ile Pro Ser Ser Gly Ala Thr Phe Tyr Asn Gln Lys Phe
    50                  55                  60

Lys Gly Gln Val Thr Ile Ser Ala Asp Lys Ser Ile Ser Thr Thr Tyr
65                  70                  75                  80
```

```
Leu Gln Trp Ser Ser Leu Lys Ala Ser Asp Thr Ala Met Tyr Tyr Cys
                85                  90                  95

Ala Arg Ser His Leu Leu Arg Ala Ser Trp Phe Ala Tyr Trp Gly Gln
            100                 105                 110

Gly Thr Met Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Ser Thr Gly Ser Glu Val Gln Leu Val Glu Ser Gly Gly Gly Leu
    450                 455                 460

Val Lys Pro Gly Gly Ser Leu Lys Leu Ser Cys Ala Ala Ser Gly Phe
465                 470                 475                 480

Thr Phe Ser Asp Tyr Gly Met His Trp Val Arg Gln Ala Pro Glu Lys
                485                 490                 495
```

Gly Leu Glu Trp Val Ala Tyr Ile Ser Ser Gly Ser Thr Ile Tyr
            500                 505                 510

Tyr Ala Asp Thr Val Lys Gly Arg Phe Thr Ile Ser Arg Asp Asn Ala
            515                 520                 525

Lys Asn Thr Leu Phe Leu Gln Met Thr Ser Leu Arg Ser Glu Asp Thr
            530                 535                 540

Ala Met Tyr Tyr Cys Ala Arg Gly Thr Thr Ile Phe Asn Tyr Phe Glu
545                 550                 555                 560

Tyr Trp Gly Gln Gly Thr Ser Val Thr Val Ser Ser Ala Ser Thr Lys
                565                 570                 575

Gly Pro Ser Val Phe Pro Leu Ala Pro Ser Ser Lys Ser Thr Ser Gly
            580                 585                 590

Gly Thr Ala Ala Leu Gly Cys Leu Val Lys Asp Tyr Phe Pro Glu Pro
            595                 600                 605

Val Thr Val Ser Trp Asn Ser Gly Ala Leu Thr Ser Gly Val His Thr
            610                 615                 620

Phe Pro Ala Val Leu Gln Ser Ser Gly Leu Tyr Ser Leu Ser Ser Val
625                 630                 635                 640

Val Thr Val Pro Ser Ser Ser Leu Gly Thr Gln Thr Tyr Ile Cys Asn
                645                 650                 655

Val Asn His Lys Pro Ser Asn Thr Lys Val Asp Lys Arg Val Glu Pro
            660                 665                 670

Lys Ser Cys Asp Lys Thr His Ser
            675                 680

<210> SEQ ID NO 96
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Glu Ile Pro Pro Thr Phe Gly Ala Gly Thr Lys Leu Glu Leu
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 97
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Asp Ile Val Met Thr Gln Ser Pro Asp Ser Leu Ala Val Ser Leu Gly
1               5                   10                  15

Glu Arg Ala Thr Ile Asn Cys Glu Ser Ser Gln Ser Leu Leu Ser Ser
            20                  25                  30

Gly Asn Gln Lys Asn Tyr Leu Thr Trp Tyr Gln Gln Lys Pro Gly Gln
        35                  40                  45

Pro Pro Lys Pro Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ser Tyr Pro Tyr Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

```
Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 98
<211> LENGTH: 680
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asp Tyr
            20                  25                  30

Tyr Met Lys Trp Ala Arg Gln Met Pro Gly Lys Gly Leu Glu Trp Met
        35                  40                  45

Gly Asp Ile Ile Pro Ser Ser Gly Ala Thr Phe Tyr Asn Gln Lys Phe
    50                  55                  60

Lys Gly Gln Val Thr Ile Ser Ala Asp Lys Ser Ile Ser Thr Thr Tyr
65                  70                  75                  80

Leu Gln Trp Ser Ser Leu Lys Ala Ser Asp Thr Ala Met Tyr Tyr Cys
                85                  90                  95

Ala Arg Ser His Leu Leu Arg Ala Ser Trp Phe Ala Tyr Trp Gly Gln
            100                 105                 110

Gly Thr Met Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205
```

```
Pro Ser Asn Thr Lys Val Asp Lys Arg Val Glu Pro Lys Ser Cys Asp
    210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
        275                 280                 285
Asn Ala Lys Thr Lys Pro Arg Glu Glu Gln Tyr Asn Ser Thr Tyr Arg
290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Glu Glu Met Thr Lys Asn Gln Val Ser Leu
        355                 360                 365
Thr Cys Leu Val Lys Gly Phe Tyr Pro Ser Asp Ile Ala Val Glu Trp
370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly Ser Thr Gly Ser Gln Val Gln Leu Val Gln Ser Gly Ala Glu Val
450                 455                 460
Lys Lys Pro Gly Ser Ser Val Lys Val Ser Cys Lys Ala Ser Gly Tyr
465                 470                 475                 480
Thr Phe Ser Asp Tyr Val Ile Asn Trp Val Arg Gln Ala Pro Gly Gln
                485                 490                 495
Gly Leu Glu Trp Met Gly Glu Ile Tyr Pro Gly Ser Gly Thr Asn Tyr
            500                 505                 510
Tyr Asn Glu Lys Phe Lys Ala Lys Ala Thr Ile Thr Ala Asp Lys Ser
        515                 520                 525
Thr Ser Thr Ala Tyr Met Glu Leu Ser Ser Leu Arg Ser Glu Asp Thr
530                 535                 540
Ala Val Tyr Tyr Cys Ala Arg Arg Gly Arg Tyr Gly Leu Tyr Ala Met
545                 550                 555                 560
Asp Tyr Trp Gly Gln Gly Thr Thr Val Thr Val Ser Ser Arg Thr Val
                565                 570                 575
Ala Ala Pro Ser Val Phe Ile Phe Pro Pro Ser Asp Glu Gln Leu Lys
            580                 585                 590
Ser Gly Thr Ala Ser Val Val Cys Leu Leu Asn Asn Phe Tyr Pro Arg
        595                 600                 605
Glu Ala Lys Val Gln Trp Lys Val Asp Asn Ala Leu Gln Ser Gly Asn
610                 615                 620
```

Ser Gln Glu Ser Val Thr Glu Gln Asp Ser Lys Asp Ser Thr Tyr Ser
625                 630                 635                 640

Leu Ser Ser Thr Leu Thr Leu Ser Lys Ala Asp Tyr Glu Lys His Lys
            645                 650                 655

Val Tyr Ala Cys Glu Val Thr His Gln Gly Leu Ser Ser Pro Val Thr
            660                 665                 670

Lys Ser Phe Asn Arg Gly Glu Cys
        675                 680

<210> SEQ ID NO 99
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln Gln Gly Asn Thr Arg Pro Trp
                85                  90                  95

Thr Phe Gly Gly Gly Thr Lys Val Glu Ile Lys Ala Ser Thr Lys Gly
            100                 105                 110

Pro Ser Val Phe Pro Leu Ala Pro Ser Ser Lys Ser Thr Ser Gly Gly
        115                 120                 125

Thr Ala Ala Leu Gly Cys Leu Val Lys Asp Tyr Phe Pro Glu Pro Val
130                 135                 140

Thr Val Ser Trp Asn Ser Gly Ala Leu Thr Ser Gly Val His Thr Phe
145                 150                 155                 160

Pro Ala Val Leu Gln Ser Ser Gly Leu Tyr Ser Leu Ser Ser Val Val
                165                 170                 175

Thr Val Pro Ser Ser Ser Leu Gly Thr Gln Thr Tyr Ile Cys Asn Val
            180                 185                 190

Asn His Lys Pro Ser Asn Thr Lys Val Asp Lys Arg Val Glu Pro Lys
        195                 200                 205

Ser Cys Asp Lys Thr His Ser
    210                 215

<210> SEQ ID NO 100
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Asp Ile Val Met Thr Gln Ser Pro Asp Ser Leu Ala Val Ser Leu Gly
1               5                   10                  15

-continued

Glu Arg Ala Thr Ile Asn Cys Glu Ser Ser Gln Ser Leu Leu Ser Ser
                20                  25                  30

Gly Asn Gln Lys Asn Tyr Leu Thr Trp Tyr Gln Lys Pro Gly Gln
 35                  40                  45

Pro Pro Lys Pro Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ser Tyr Pro Tyr Thr Phe Gly Gln Gly Thr Lys Leu Glu Ile
                100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
                180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
                260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

-continued

```
His Asn His Tyr Thr Gln Lys Ser Leu Ser Leu Ser Pro Gly Lys
        435                 440                 445

<210> SEQ ID NO 101
<211> LENGTH: 679
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asp Tyr
            20                  25                  30

Tyr Met Lys Trp Ala Arg Gln Met Pro Gly Lys Gly Leu Glu Trp Met
        35                  40                  45

Gly Asp Ile Ile Pro Ser Ser Gly Ala Thr Phe Tyr Asn Gln Lys Phe
    50                  55                  60

Lys Gly Gln Val Thr Ile Ser Ala Asp Lys Ser Ile Ser Thr Thr Tyr
65                  70                  75                  80

Leu Gln Trp Ser Ser Leu Lys Ala Ser Asp Thr Ala Met Tyr Tyr Cys
                85                  90                  95

Ala Arg Ser His Leu Leu Arg Ala Ser Trp Phe Ala Tyr Trp Gly Gln
            100                 105                 110

Gly Thr Met Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335
```

Lys Thr Ile Ser Lys Ala Lys Gly Gln Pro Arg Glu Pro Gln Val Tyr
                340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Ser Thr Gly Ser Glu Val Gln Leu Val Gln Ser Gly Ala Glu Val
450                 455                 460

Lys Lys Ser Gly Glu Ser Leu Lys Ile Ser Cys Lys Gly Ser Gly Tyr
465                 470                 475                 480

Ser Phe Thr Ser Tyr Trp Ile Gly Trp Val Arg Gln Met Pro Gly Lys
                485                 490                 495

Gly Leu Glu Trp Met Gly Ile Phe Tyr Pro Gly Asp Ser Ser Thr Arg
            500                 505                 510

Tyr Ser Pro Ser Phe Gln Gly Gln Val Thr Ile Ser Ala Asp Lys Ser
        515                 520                 525

Val Asn Thr Ala Tyr Leu Gln Trp Ser Ser Leu Lys Ala Ser Asp Thr
    530                 535                 540

Ala Met Tyr Tyr Cys Ala Arg Arg Arg Asn Trp Gly Asn Ala Phe Asp
545                 550                 555                 560

Ile Trp Gly Gln Gly Thr Met Val Thr Val Ser Ser Arg Thr Val Ala
                565                 570                 575

Ala Pro Ser Val Phe Ile Phe Pro Pro Ser Asp Glu Gln Leu Lys Ser
            580                 585                 590

Gly Thr Ala Ser Val Val Cys Leu Leu Asn Asn Phe Tyr Pro Arg Glu
        595                 600                 605

Ala Lys Val Gln Trp Lys Val Asp Asn Ala Leu Gln Ser Gly Asn Ser
    610                 615                 620

Gln Glu Ser Val Thr Glu Gln Asp Ser Lys Asp Ser Thr Tyr Ser Leu
625                 630                 635                 640

Ser Ser Thr Leu Thr Leu Ser Lys Ala Asp Tyr Glu Lys His Lys Val
                645                 650                 655

Tyr Ala Cys Glu Val Thr His Gln Gly Leu Ser Ser Pro Val Thr Lys
            660                 665                 670

Ser Phe Asn Arg Gly Glu Cys
        675

<210> SEQ ID NO 102
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 102

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Thr
                85                  90                  95

Trp Thr Phe Gly Gln Gly Thr Lys Val Glu Ile Lys Ala Ser Thr Lys
            100                 105                 110

Gly Pro Ser Val Phe Pro Leu Ala Pro Ser Ser Lys Ser Thr Ser Gly
        115                 120                 125

Gly Thr Ala Ala Leu Gly Cys Leu Val Lys Asp Tyr Phe Pro Glu Pro
    130                 135                 140

Val Thr Val Ser Trp Asn Ser Gly Ala Leu Thr Ser Gly Val His Thr
145                 150                 155                 160

Phe Pro Ala Val Leu Gln Ser Ser Gly Leu Tyr Ser Leu Ser Ser Val
                165                 170                 175

Val Thr Val Pro Ser Ser Ser Leu Gly Thr Gln Thr Tyr Ile Cys Asn
            180                 185                 190

Val Asn His Lys Pro Ser Asn Thr Lys Val Asp Lys Arg Val Glu Pro
        195                 200                 205

Lys Ser Cys Asp Lys Thr His Ser
    210                 215

<210> SEQ ID NO 103
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Arg Ser Tyr
            20                  25                  30

Leu Ala Trp Tyr Gln Gln Lys Pro Gly Gln Ala Pro Arg Leu Leu Phe
        35                  40                  45

Ser Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Tyr Arg Tyr Ser Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125
```

```
Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 104
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asn Tyr
            20                  25                  30

Ala Met His Trp Val Arg Gln Ala Pro Gly Lys Gly Leu Glu Trp Val
        35                  40                  45

Ser Gly Ile Ser Arg Ser Ser Gly Asp Ile Asp Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Gly Gly Val Gly Ser Phe Asp Thr Trp Gly Gln Gly Thr Met
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Asp Val
225                 230                 235                 240

Phe Leu Phe Pro Pro Lys Pro Lys Asp Thr Leu Met Ile Ser Arg Thr
                245                 250                 255
```

```
Pro Glu Val Thr Cys Val Val Asp Val Ser His Glu Asp Pro Glu
            260                 265                 270
Val Lys Phe Asn Trp Tyr Val Asp Gly Val Glu Val His Asn Ala Lys
        275                 280                 285
Thr Lys Pro Arg Glu Glu Gln Tyr Asn Ser Thr Tyr Arg Val Val Ser
    290                 295                 300
Val Leu Thr Val Leu His Gln Asp Trp Leu Asn Gly Lys Glu Tyr Lys
305                 310                 315                 320
Cys Lys Val Ser Asn Lys Ala Leu Pro Ala Pro Glu Lys Thr Ile
                325                 330                 335
Ser Lys Ala Lys Gly Gln Pro Arg Glu Pro Gln Val Tyr Thr Leu Pro
            340                 345                 350
Pro Ser Arg Glu Glu Met Thr Lys Asn Gln Val Ser Leu Thr Cys Leu
        355                 360                 365
Val Lys Gly Phe Tyr Pro Ser Asp Ile Ala Val Glu Trp Glu Ser Asn
    370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
            420                 425                 430
His Asn His Tyr Thr Gln Lys Ser Leu Ser Leu Ser Pro Gly Lys
        435                 440                 445

<210> SEQ ID NO 105
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 105
auguaugucc cagaaaccug                                                    20

<210> SEQ ID NO 106
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 106
aagcauauga ccccaaggcu                                                    20

<210> SEQ ID NO 107
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 107

His His His His His His
1               5
```